US008329399B2

(12) United States Patent
Siu et al.

(10) Patent No.: US 8,329,399 B2
(45) Date of Patent: Dec. 11, 2012

(54) ENDOMETRIAL BIOMARKERS

(76) Inventors: K. W. Michael Siu, Toronto (CA);
Terence J. Colgan, Toronto (CA);
Alexander J. Romaschin, Toronto (CA);
Leroi V. De Souza, North York (CA)

( * ) Notice: Subject to any disclaimer, the term of this patent is extended or adjusted under 35 U.S.C. 154(b) by 0 days.

(21) Appl. No.: 12/447,398

(22) PCT Filed: Oct. 26, 2007

(86) PCT No.: PCT/CA2007/001935
§ 371 (c)(1),
(2), (4) Date: Dec. 21, 2009

(87) PCT Pub. No.: WO2008/049239
PCT Pub. Date: May 2, 2008

(65) Prior Publication Data
US 2010/0172838 A1 Jul. 8, 2010

Related U.S. Application Data

(60) Provisional application No. 60/854,782, filed on Oct. 27, 2006.

(51) Int. Cl.
*C12Q 1/68* (2006.01)
(52) U.S. Cl. .................................................. 435/6.1
(58) Field of Classification Search .................. None
See application file for complete search history.

(56) References Cited

U.S. PATENT DOCUMENTS

| | | | |
|---|---|---|---|
| 2004/0096915 | A1 | 5/2004 | Diamandis et al. |
| 2004/0115745 | A1 | 6/2004 | Lou et al. |
| 2004/0203012 | A1 | 10/2004 | Diamandis et al. |
| 2005/0176002 | A1 | 8/2005 | Yousef et al. |
| 2005/0287528 | A1 | 12/2005 | Diamandis et al. |
| 2006/0073525 | A1 | 4/2006 | Yousef et al. |
| 2006/0134120 | A1 | 6/2006 | Diamandis et al. |
| 2006/0159616 | A1 | 7/2006 | Diamandis et al. |
| 2006/0223059 | A1 | 10/2006 | Yousef et al. |
| 2008/0226554 | A1 | 9/2008 | Colgan et al. |

FOREIGN PATENT DOCUMENTS

| | | | |
|---|---|---|---|
| WO | WO 0146259 A1 * | 6/2001 | |
| WO | WO 02/09573 | 2/2002 | |
| WO | WO 2005/061725 | 7/2005 | |
| WO | WO 2006/116873 | 11/2006 | |
| WO | WO 2007/081767 | 7/2007 | |

OTHER PUBLICATIONS

Hebbar et al. (BMC Cancer. Sep. 27, 2005;5:124).*
ACE, "Microarray profiling of progesterone-regulated endometrial genes during the rhesus monkey secretory phase", Reproductive Biology and Endocrinology, 2:54-62, Jul. 2004.
Bell, "Pregnancy-associated endometrial $\alpha_2$-globulin, the major secretory protein of the luteal phase and first trimester pregnancy endometrium, is not glycosylated prolactin but related to β-lactoglobulins", J. of Clinical Endocrinology & Metabolism, 65(5):1067-1071, Nov. 1987.
Bouchard, "Proteins with whey-acidic-protein motifs and cancer", The Lancet Oncology, 7(2):167-174, Feb. 2006.
Buckley, "Normal endometrium and non-proliferative conditions of the endometrium", Obstetrical and Gynaecological Pathology, 5th ed., pp. 391-44 (London: Elsevier Science Limited, 2003).
Byrjalsen, "Human endometrial proteins with cyclic changes in the expression during the normal menstrual cycle: characterization by protein sequence analysis", Human Reproduction, 10(10):2760-2766, Oct. 1995.
Canadian Cancer Statistics 2006. National Cancer Institute of Canada: ISSN 0835-2976, 1-112, Apr. 2006.
Cao, "Distinctive gene expression profiles by cDNA microarrays in endometrioid and serous carcinomas of the endometrium", International Journal of Gynecologic Pathology, 23(4):321-329, Oct. 2004.
Chen, "Characterization of human mucin 5B gene expression in airway epithelium and the genomic clone of the amino-terminal and 5'-flanking region", American Journal of Respiratory Cell and Molecular Biology, 25(5):542-553, Nov. 2001.
Condeelis, "Macrophages: obligate partners for tumor cell migration, invasion, and metastasis", Cell, 124(2):263-266, Jan. 2006.
Craig, "The use of proteotypic peptide libraries for protein identification", Rapid Communications in Mass Spectrometry, 19(13):1844-1850, Jul. 15, 2005.
Davies, "Identification of a novel mechanism of NF-Kβ inactivation by progesterone through progesterone receptors in Hec50co poorly differentiated endometrial cancer cells: induction of A20 and ABIN-2", Gynecologic Oncology, 94(2):463-470, Aug. 2004.
DeSouza, "Proteomic analysis of the proliferative and secretory phases of the human endometrium: protein identification and differential protein expression", Proteomics, 5(1):270-281, Jan. 2005.
DeSouza, "Search for cancer markers from endometrial tissues using differentially labeled tags iTRAQ and cICAT with multidimensional liquid chromatography and tandem mass spectrometry", Journal of Proteome Research, 4:377-386, Mar.-Apr. 2005.
Di Carlo, "The intriguing role of polymorphonuclear neutrophils in antitumor reactions", Blood, 97(2):339-345, Jan. 15, 2001.
Dombrauckas, "Structural basis for tumor pyruvate kinase M2 allosteric regulation and catalysis", Biochemistry, 44(27):9417-9429, Jul. 2005.
Galgano, "Comprehensive analysis of HE4 expression in normal and malignant human tissues", Modern Pathology, 19(6):847-853, Jun. 2006: E-pub Apr. 7, 2006.
Gygi, "Quantitative analysis of complex protein mixtures using isotope-coded affinity tags", Nature Biotechnology, 17(10):994-999, Oct. 1999.
Gleave, "Use of antisense oligonucleotides targeting the antiapoptotic gene, clusterin/testosterone-repressed prostate message 2, to enhance androgen sensitivity and chemosensitivity in prostate cancer", Urology, 58(2 Suppl 1A):39-49, Aug. 2001.
Guo, "Direct analysis of laser capture microdissected endometrial carcinoma and epithelium by matrix-assisted laser desorption/ionization mass spectrometry", Rapid Communications in Mass Spectrometry, 19(19):2762-2766, Oct. 15, 2005.

(Continued)

*Primary Examiner* — Christopher M. Babic
(74) *Attorney, Agent, or Firm* — Ainslie Little; Blake, Cassels & Graydon LLP

(57) ABSTRACT

Methods for detecting endometrial diseases or an endometrium phase in a subject are described comprising measuring endometrial markers or polynucleotides encoding the markers in a sample from the subject. The invention also provides localization or imaging methods for endometrial diseases, and kits for carrying out the methods of the invention. The invention also contemplates therapeutic applications for endometrial diseases employing endometrial markers, polynucleotides encoding the markers, and/or binding agents for the markers.

11 Claims, 3 Drawing Sheets

OTHER PUBLICATIONS

Figure 1:
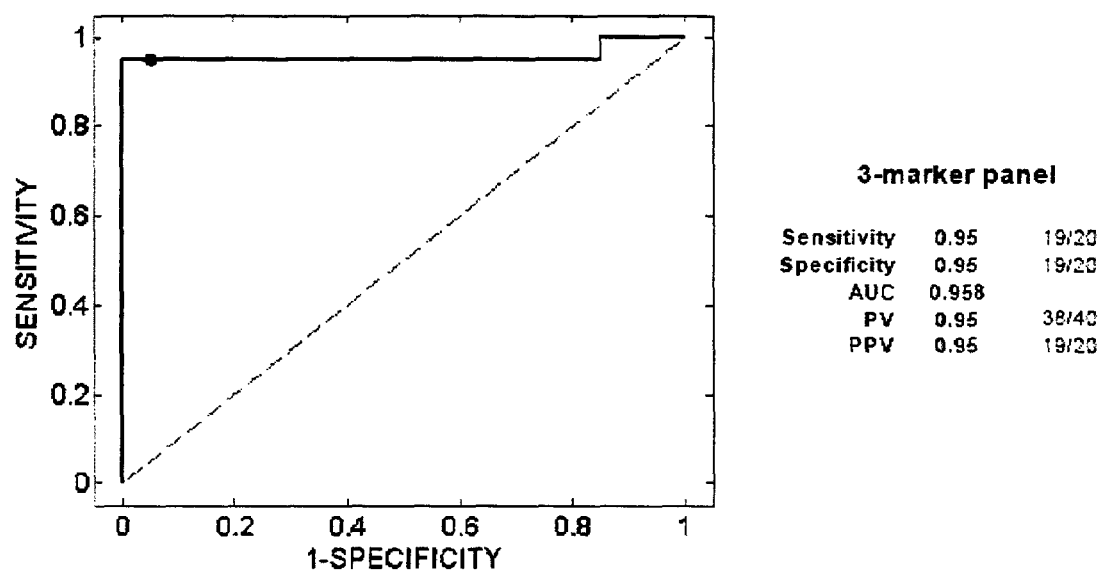

Hardardóttir, "Endotoxin and cytokines increase hepatic messenger RNA levels and serum concentrations of apolipoprotein J (clusterin) in Syrian hamsters", The Journal of Clinical Investigation, 94(3):1304-1309, Sep. 1994.

Hellström, "The HE4 (WFDC2) protein is a biomarker for ovarian carcinoma", Cancer Research, 63(13):3695-3700, Jul. 2003.

Hempen, "Transcriptional regulation of the human polymeric Ig receptor gene: analysis of basal promoter elements", The Journal of Immunology, 169(4):1912-1921, Aug. 2002.

Huang, "α1-antitrypsin inhibits angiogenesis and tumor growth", International Journal of Cancer, 112(6):1042-1048, Dec. 2004.

Joseph, "Creatine kinase activity and isoenzymes in lung, colon and liver carcinomas", British Journal of Cancer, 76(5):600-605, 1997.

Kang, "Overexpression of clusterin in human hepatocellular carcinoma", Human Pathology, 35(11):1340-1346, Nov. 2004.

Krüger, "Value of clusterin immunoreactivity as a predictive factor in muscle-invasive urothelial bladder carcinoma", Urology, 67(1):105-109, Jan. 2006.

Kuster, "Scoring proteomes with proteotypic peptide probes", Nature Reviews: Molecular Cell Biology, 6(7):577-583, Jul. 2005.

Lalitkumar, "Placental protein 14 in endometrium during menstrual cycle and effect of early luteal phase mifepristone administration on its expression in implantation stage endometrium in the rhesus monkey", Human Reproduction, 13(12):3478-3486, Dec. 1998.

Mazurek, "Pyruvate kinase type M2 and its role in tumor growth and spreading", Seminars in Cancer Biology, 15(4):300-308, Aug. 2005.

Mutter, "Global expression changes of constitutive and hormonally regulated genes during endometrial neoplastic transformation", Gynecologic Oncology 83(2):177-185, Nov. 2001.

Pallares, "Abnormalities in the NF-Kβ family and related proteins in endometrial carcinoma", Journal of Pathology, 204(5):569-577, Dec. 2004.

Pepe, "Evaluating technologies for classification and prediction in medicine", Statistics in Medicine, 24(24):3687-3696, Dec. 2005.

Pilette, "Secretory component is cleaved by neutrophil serine proteinases but its epithelial production is increased by neutrophils through NF-Kβ- and p38 mitogen-activated protein kinase-dependent mechanisms", American Journal of Respiratory Cell and Molecular Biology, 28(4):485-498, Apr. 2003.

Rincheval-Arnold, "Up-regulation of polymeric immunoglobulin receptor mRNA in mammary epithelial cells by IFN-gamma", Molecular and Cellular Endocrinology 194(1-2):95-105, Aug. 2002.

Ronquist, "Prostasome-derived proteins capable of eliciting an immune response in prostate cancer patient", International Journal of Cancer, 119(4):847-853, Aug. 2006.

Sarkar, "Vitamin A is required for regulation of polymeric immunoglobulin receptor (pIgR) expression by interleukin-4 and interferon-γ in a human intestinal epithelial cell line", The Journal of Nutrition, 128(7):1063-1069, Jul. 1998.

Satyaswaroop, "Creatine kinase activity in human endometrium: relative distribution in isolated glands and stroma", American Journal of Obstetrics & Gynecology—Home, 146(2):159-162, May 1983.

Schjerven, "Mechanism of IL-4-mediated up-regulation of the polymeric Ig receptor: role of STATE6 in cell type-specific delayed transcriptional response", The Journal of Immunology, 165(7):3898-3906, Oct. 2000.

Schneider, "Improved sensitivity in the diagnosis of gastro-intestinal tumors by fuzzy logic-based tumor marker profiles including the tumor M2-PK", Anticancer Research, 25(3A):1507-1515, May-Jun. 2005.

Shamamian, "Activation of progelatinase A (MMP-2) by neutrophil elastase, cathepsin G, and proteinase-3: a role for inflammatory cells in tumor invasion and angiogenesis", Journal of Cellular Physiology, 189(2):197-206, Nov. 2001.

Shibata, "Placental leucine aminopeptidase (P-LAP) expression is associated with chemosensitivity in human endometrial carcinoma", Gynecologic Oncology, 95(2):307-313, Nov. 2004.

So, "Knockdown of the cytoprotective chaperone, clusterin, chemosensitizes human breast cancer cells both in vitro and in vivo", Molecular Cancer Therapeutics, 4(12):1837-1849, Dec. 2005.

Takenouchi-Ohkubo, "Role of nuclear factor-Kβ in the expression by tumor necrosis factor-α of the human polymeric immunoglobulin receptor (pIgR) gene", Immunogenetics, 51(4-5):289-295, Apr. 2000.

Ugurel, "Tumor type M2 pyruvate kinase (TuM2-PK) as a novel plasma tumor marker in melanoma", International Journal of Cancer, 117(5):825-830, Dec. 2005.

Yang, "Protein expression profiling of endometrial malignancies reveals a new tumor marker: chaperonin 10", Journal of Proteomic Research, 3(3):636-643, May-Jun. 2004.

Young, "Calcium regulation of actin filament capping and monomer binding by macrophage capping protein", The Journal of Biological Chemistry, 269(19):13997-14002, May 1994.

Yu, "Overexpression of MUC5 genes is associated with early post-operative metastasis in non-small-cell lung cancer", International Journal of Cancer (Pred. Oncol.), 69(6):457-465, Dec. 20, 1996.

Zierau, "Tamoxifen exerts agonistic effects on clusterin and complement C3 gene expression in RUCA-I primary xenografts and metastases but not normal uterus", Endocrine-Related Cancer, 11(4):823-830, Dec. 2004.

Zorn, "Gene expression profiles of serous, endometrioid, and clear cell subtypes of ovarian and endometrial cancer", Clinical Cancer Research, 11(18):6422-6430, Sep. 15, 2005.

Abdul-Rahman, "Expression of high-abundance proteins in sera of patients with endometrial and cervical cancers: analysis using 2-DE with silver staining and lectin detection methods", Electrophoresis, 28(12):1989-1996, Jun. 2007.

Dong, "Melanoma cell extravasation under flow conditions is modulated by leukocytes and endogenously produced interleukin 8", Molecular & Cellular Biomechanics, 2(3):145-160, Sep. 2005.

Ferguson, "Stratification of intermediate-risk endometrial cancer patients into groups at high risk or low risk for recurrence based on tumor gene expression profiles", Clinical Cancer Research, 11(6):2252-2257, Mar. 15, 2005.

Hebbar, "Differential expression of MUC genes in endometrial and cervical tissues and tumors", BMC Cancer. 5:124-135, Sep. 27, 2005.

Li, "Is the measurement of placental protein-14 and CA-125 in plasma and uterine flushings useful in the evaluation of peri-menopausal and post-menopausal bleeding?", Human Reproduction, 13(10):2895-2901, Oct. 1998.

Norderhaug, "Regulation of the formation and external transport of secretory immunoglobulins", Critical Reviews™ in Immunology, 19(5-6):481-508, 1999.

Reid-Nicholson, "Immunophenotypic diversity of endometrial adenocarcinomas: implications for differential diagnosis", Modern Pathology, 19(8):1091-1100, Epub Apr. 28, 2006, Aug. 2006.

Drapkin R., et al, Human Epididymis Protein 4 (HE4) is a Secreted Glycoprotein that is Overexpressed by Serous and Endometrioid Ovarian Carcinomas, Cancer Research, vol. 65, No. 6, pp. 2162-2169, Mar. 15, 2005.

Li H., et al, Identification of Candidate Biomarker Proteins Released by Human Endometrial and Cervical Cancer Cells Using Two-Dimensional Liquid Chromatography/Tandem Mass Spectrometry, Journal of Proteome Research, vol. 6, No. 7, pp. 2615-2622, May 25, 2007.

Ono K., et al, Identification by cDNA Microarray of Genes Involved in Ovarian Carcinogenesis, Cancer Research, vol. 60, pp. 5007-5011, Sep. 15, 2000.

Extended European Search Report for corresponding EP Application No. 07816085, dated Sep. 28, 2010 including supplementary EP search report completed Sep. 15, 2010 and EP search opinion.

International Preliminary Report on Patentability dated Apr. 28, 2009 in the corresponding International Patent Application No. PCT/CA2007/001935.

Office Action dated Mar. 19, 2010, issued in U.S. Appl. No. 10/584,207.

Response to Office Action dated Jun. 18, 2010, submitted in U.S. Appl. No. 10/584,207.

Office Action dated Sep. 2, 2010, issued in U.S. Appl. No. 10/584,207.

Li et al, Is the measurement of placental protein-14 and CA-125 in plasma and uterine flushings useful in the evaluation of perimenopausal and postmenopausal bleeding?, Human Reproduction, 13(10):2895-2901 (Oct. 1998).

* cited by examiner

ENDOMETRIAL BIOMARKERS

This application is a national stage of International Patent Application No. PCT/CA2007/001935, filed Oct. 26, 2007, which claims the benefit of the priority of U.S. Provisional Patent Application No. 60/854,782, filed Oct. 27, 2006.

FIELD OF THE INVENTION

The invention relates to endometrial markers, methods for assessing the status of an endometrial tissue, and methods for the detection, diagnosis, prediction, and therapy of an endometrial disease.

BACKGROUND OF THE INVENTION

Differential tagging with isotopic reagents, such as isotope-coded affinity tags (ICAT) (1) or the more recent variation that uses isobaric tagging reagents, iTRAQ (Applied Biosystems, Foster City, Calif.), followed by multidimensional liquid chromatography (LC) and tandem mass spectrometry (MS/MS) analysis is a powerful methodology in the search of biomarkers for various disease states.

Endometrial carcinoma (EmCa), a cancer of the lining of the uterus, is the fourth most common cancer in Canadian women (4). Current methods of diagnosis rely on invasive techniques—biopsy and curettage—and no screening is available. A panel of biomarkers that helps in early diagnosis would, therefore, be useful, especially for highrisks groups, e.g., women who are on Tamoxifen treatment or have hereditary nonpolyposis colorectal cancer syndrome. Although the eventual diagnostic testing for such biomarkers would be most facile from bodily fluids, such as blood or urine, the iTRAQ experiments performed thus far have been on resected EmCa from uterine tissues (hysterectomy specimens) (2, 3). The rationale for this approach is that the concentration of any biomarker is most likely highest in the cancerous tissue itself, and not when diluted in the bodily fluids, thus facilitating discovery. In addition, the use of the cancerous tissue reduces the intrinsic need to demonstrate that any differentially expressed protein detected does indeed originate from the endometrial cancer. By contrast, the origins of differentially expressed protein in the blood could include a variety of potential sites other than the actual tumor. The use of homogenized tissues yields a heterogeneous sample with the proteome being contributed by the stroma, vasculature, blood, and malignant/benign epithelium. This heterogeneity may attenuate, and even mask, the variation in protein expression levels characteristic of cancerous epithelial cells. One remedy for this drawback is the use of laser capture microdissection (LCM) to procure the specific, malignant epithelial cells from the samples (5). This approach, however, is not practical, when $10^3$-$10^4$ cells per sample are required for current proteomic techniques, in a global biomarker discovery strategy. Thus far, the types of differentially expressed proteins discovered (2, 3) are primarily medium- to high-abundance proteins, as universal detection methods, including the MS/MS technologies that were employed, are much more efficient in detecting major rather than minor components in a complex mixture.

A strategy in the search of EmCa markers requires a comparison between the cancerous endometrium and the two major phases, proliferative and secretory, of the normal reproductive-aged endometrium (3, 6). The multiplexing ability afforded by the iTRAQ reagents, which are available in four different tags or flavors, is well suited for such a simultaneous comparison, especially in view of the fact that endometrial carcinoma itself can have two distinct morphologic and physiologic types. Type I cancers are endometrioid in histologic typing, well-differentiated, and estrogen-dependent; and have typically a better prognosis. By contrast, Type II carcinomas are serous and clear cell carcinomas, hormone-independent, and aggressive; and have generally a poorer clinical outcome (7).

SUMMARY OF THE INVENTION

Applicants have identified markers associated with the endometrium, and in particular with proliferative endometrium, secretory endometrium and diseased endometrial tissue. Thus, the invention relates to novel markers for the endometrium, and in particular markers of endometrial disease, and compositions comprising same.

In an aspect, the invention provides marker sets that distinguish the endometrium or phases thereof, or endometrial diseases, and uses therefor. A marker set may comprise a plurality of polypeptides and/or polynucleotides encoding such polypeptides comprising or consisting of at least one marker listed in Table 1 and optionally 2, 3, 4, 5, 6, 7, 8, 9, 10, 11, 12, 13, 14, or 15 of the markers listed in Table 2. In specific aspects, the markers consist of at least 2, 3, 4 or 5 polypeptides listed in Table 1. In an aspect the protein marker sets comprise or consist of protein clusters, or proteins in pathways comprising markers listed in Table 1 and optionally in Table 2.

The markers identified in Table 1 and optionally Table 2, including but not limited to native-sequence polypeptides, isoforms, chimeric polypeptides, all homologs, fragments, and precursors of the markers, including modified forms of the polypeptides and derivatives are referred to and defined herein as "endometrial marker(s)". Polynucleotides encoding endometrial markers are referred to and defined herein as "endometrial polynucleotide marker(s)", "polynucleotides encoding endometrial markers", or "polynucleotides encoding the marker(s)". The endometrial markers and endometrial polynucleotide markers are sometimes collectively referred to herein as "marker(s)". Markers of endometrial cancer are referred to herein as "endometrial cancer markers", "endometrial cancer polynucleotide markers", and "polynucleotides encoding endometrial cancer markers".

Endometrial markers listed in Table 1 and optionally Table 2, and polynucleotides encoding the markers, have application in the determination of the status or phase of the endometrium and in the detection of an endometrial disease such as endometrial cancer. Thus, the markers can be used for diagnosis, monitoring (i.e. monitoring progression or therapeutic treatment), prognosis, treatment, or classification of an endometrial disease (e.g. endometrial cancer), or as markers before surgery or after relapse. The invention also contemplates methods for assessing the status of an endometrial tissue, and methods for the diagnosis and therapy of an endometrial disease.

The markers characteristic of different stages or phases of endometrium may be used to identify the physiologic stage or phase of the endometrium within the physiologic cycle. In an aspect, the endometrial markers may be used to assess and manage reproductive disorders and infertility. In particular, endometrial markers associated with the secretory phase or proliferative phase may be used to determine if an endometrium is at the optimum stage or phase for embryo implantation.

In an embodiment, the endometrial marker is characteristic of the secretory phase, and includes the marker WFDC2 and optionally one or more of glutamate receptor subunit zeta 1 [GenBank Accession NOs. NP_000823, NP_015566, and NP_067544], macrophage migration inhibitory factor [SEQ ID NO. 49], GSK-3 binding protein FRAT1 [GenBank Accession NO. NP_005470], myosin light chain kinase 2 [GenBank Accession No. NP_149109], tropomyosin 1 alpha chain [GeneBank Accession NOs. NP_000357, NP_001018004, NP_001018005, NP_001018006, NP_001018007, NP_001018008, and NP_001018020], and/or polynucleotides encoding the polypeptides.

In accordance with methods of the invention, endometrium can be assessed or characterized, for example, by detecting the presence in the sample of (a) an endometrial marker or fragment thereof; (b) a metabolite which is produced directly or indirectly by an endometrial marker; (c) a transcribed nucleic acid or fragment thereof having at least a portion with which an endometrial polynucleotide marker is substantially identical; and/or (c) a transcribed nucleic acid or fragment thereof, wherein the nucleic acid hybridizes with an endometrial polynucleotide marker.

The levels of endometrial markers or endometrial polynucleotide markers in a sample may be determined by methods as described herein and generally known in the art. The expression levels may be determined by isolating and determining the level of nucleic acid transcribed from each endometrial polynucleotide. Alternatively or additionally, the levels of endometrial markers translated from mRNA transcribed from an endometrial polynucleotide marker may be determined.

In an aspect, the invention provides a method for characterizing or classifying an endometrial sample comprising detecting a difference in the expression of a first plurality of endometrial markers or endometrial polynucleotide markers relative to a control, the first plurality of markers comprising or consisting of at least 2, 3, 4, or 5 of the markers corresponding to the markers listed in Table 1, and optionally 2, 3, 4, 5, 6, 7, 8, 9, 10, 11, 12, 13, 14, or 15 of the markers listed in Table 2. In specific aspects, the plurality of markers consists of at least 3, 4 or 5 of the markers listed in Table 1.

In an aspect, a method is provided for characterizing an endometrium by detecting endometrial markers or endometrial polynucleotide markers associated with an endometrium stage or phase, or endometrial disease in a subject comprising:
(a) obtaining a sample from a subject;
(b) detecting or identifying in the sample endometrial markers or endometrial polynucleotide markers; and
(c) comparing the detected amount with an amount detected for a standard.

In an embodiment of the invention, a method is provided for detecting endometrial cancer markers or endometrial cancer polynucleotide markers associated with endometrial cancer in a patient comprising:
(a) obtaining a sample from a patient;
(b) detecting in the sample endometrial cancer markers or endometrial cancer polynucleotide markers; and
(c) comparing the detected amount with an amount detected for a standard.

The term "detect" or "detecting" includes assaying, imaging or otherwise establishing the presence or absence of the target endometrial markers or polynucleotides encoding the markers, subunits thereof, or combinations of reagent bound targets, and the like, or assaying for, imaging, ascertaining, establishing, or otherwise determining one or more factual characteristics of an endometrium phase or endometrial disease including cancer, metastasis, stage, or similar conditions. The term encompasses diagnostic, prognostic, and monitoring applications for the endometrial markers and polynucleotides encoding the markers.

The invention also provides a method of assessing whether a patient is afflicted with or has a pre-disposition for endometrial disease, in particular endometrial cancer, the method comprising comparing:
(a) levels of endometrial markers or polynucleotides encoding endometrial markers associated with the endometrial disease in a sample from the patient; and
(b) normal levels of endometrial markers or polynucleotides encoding endometrial markers associated with the endometrial disease in samples of the same type obtained from control patients not afflicted with the disease, wherein altered levels of the endometrial markers or the polynucleotides relative to the corresponding normal levels of endometrial markers or polynucleotides is an indication that the patient is afflicted with endometrial disease.

In an aspect of a method of the invention for assessing whether a patient is afflicted with or has a pre-disposition for endometrial cancer, higher levels of endometrial cancer markers (e.g., WFDC2, clusterin) in a sample relative to the corresponding normal levels is an indication that the patient is afflicted with endometrial cancer.

In another aspect of a method of the invention for assessing whether a patient is afflicted with or has a pre-disposition for endometrial cancer, lower levels of endometrial cancer markers (e.g., mucin 5B) in a sample relative to the corresponding normal levels is an indication that the patient is afflicted with endometrial cancer.

In a further aspect, a method for screening a subject for endometrial disease is provided comprising (a) obtaining a biological sample from a subject; (b) detecting the amount of endometrial markers associated with the disease in said sample; and (c) comparing said amount of endometrial markers detected to a predetermined standard, where detection of a level of endometrial markers that differs significantly from the standard indicates endometrial disease.

In an embodiment, a significant difference between the levels of endometrial marker levels in a patient and normal levels is an indication that the patient is afflicted with or has a predisposition to endometrial disease.

In a particular embodiment the amount of endometrial marker(s) (e.g., WFDC2, clusterin, Cap-G) detected is greater than that of a standard and is indicative of endometrial disease, in particular endometrial cancer. In another particular embodiment the amount of endometrial marker(s) (e.g., mucin 5B) detected is lower than that of a standard and is indicative of endometrial disease, in particular endometrial cancer.

In aspects of the methods of the invention, the methods are non-invasive for detecting endometrium phase or endometrial disease which in turn allow for diagnosis of a variety of conditions or diseases associated with the endometrium.

In particular, the invention provides a non-invasive non-surgical method for detection, diagnosis or prediction of endometrial disease in a subject comprising: obtaining a sample of blood, plasma, serum, urine or saliva or a tissue sample from the subject; subjecting the sample to a procedure to detect endometrial markers or endometrial polynucleotide markers in the blood, plasma, serum, urine, saliva or tissue; detecting, diagnosing, and predicting endometrial disease by comparing the levels of endometrial markers or endometrial polynucleotide markers to the levels of marker(s) or polynucleotide(s) obtained from a control subject with no endometrial disease.

In an embodiment, endometrial disease is detected, diagnosed, or predicted by determination of increased levels of markers (e.g one or more Table 1 upregulated markers, and optionally one or more Table 2 up-regulated markers) when compared to such levels obtained from the control.

In another embodiment, endometrial disease is detected, diagnosed, or predicted by determination of decreased levels of markers (e.g. mucin 5B and optionally one or more Table 2 down-regulated markers) when compared to such levels obtained from the control.

The invention also provides a method for assessing the aggressiveness or indolence of an endometrial disease in particular cancer (e.g. staging), the method comprising comparing:
  (a) levels of endometrial markers or polynucleotides encoding endometrial markers associated with the endometrial disease in a patient sample; and
  (b) normal levels of the endometrial markers or the polynucleotides in a control sample.

In an embodiment, a significant difference between the levels in the sample and the normal levels is an indication that the endometrial disease, in particular cancer, is aggressive or indolent. In a particular embodiment, the levels of endometrial markers are higher than normal levels. In another particular embodiment, the levels of endometrial markers are lower than normal levels.

In an embodiment, a method is provided for diagnosing and/or monitoring Type II endometrial cancer comprising comparing:
  (a) levels of Cap-G or polynucleotides encoding Cap-G in a sample from the patient; and
  (b) normal levels of Cap-G or polynucleotides encoding same in samples of the same type obtained from control patients not afflicted with endometrial cancer or having a different stage of endometrial cancer, wherein altered levels of Cap-G or polynucleotides encoding same compared with the corresponding normal levels is an indication that the patient is afflicted with Type II endometrial cancer.

In an embodiment, a method is provided for diagnosing and/or monitoring Type I endometrial cancer comprising comparing
  (a) levels of WFDC2 or polynucleotides encoding WFDC2 in a sample from the patient; and
  (b) normal levels of WFDC2 or polynucleotides encoding same in samples of the same type obtained from control patients not afflicted with endometrial cancer or having a different stage of endometrial cancer, wherein altered levels of WFDC2 or polynucleotides encoding same compared with the corresponding normal levels is an indication that the patient is afflicted with Type I endometrial cancer.

In an aspect, the invention provides a method for determining whether a cancer has metastasized or is likely to metastasize in the future, the method comprising comparing:
  (a) levels of endometrial cancer markers or polynucleotides encoding endometrial cancer markers in a patient sample; and
  (b) normal levels (or non-metastatic levels) of the endometrial cancer markers or polynucleotides in a control sample.

In an embodiment, a significant difference between the levels in the patient sample and the normal levels is an indication that the cancer has metastasized or is likely to metastasize in the future.

In another aspect, the invention provides a method for monitoring the progression of endometrial disease, in particular endometrial cancer in a patient the method comprising:

(a) detecting endometrial markers or polynucleotides encoding the markers associated with the disease in a sample from the patient at a first time point;
  (b) repeating step (a) at a subsequent point in time; and
  (c) comparing the levels detected in (a) and (b), and therefrom monitoring the progression of the endometrial disease.

The invention contemplates a method for determining the effect of an environmental factor on the endometrium or phase thereof, or endometrial disease comprising comparing endometrial polynucleotide markers or endometrial markers in the presence and absence of the environmental factor.

The invention also provides a method for assessing the potential efficacy of a test agent for inhibiting endometrial disease, and a method of selecting an agent for inhibiting endometrial disease.

The invention contemplates a method of assessing the potential of a test compound to contribute to an endometrial disease comprising:
  (a) maintaining separate aliquots of endometrial diseased cells in the presence and absence of the test compound; and
  (b) comparing the levels of endometrial markers or polynucleotides encoding the markers associated with the disease in each of the aliquots.

A significant difference between the levels of endometrial markers or polynucleotides encoding the markers in an aliquot maintained in the presence of (or exposed to) the test compound relative to the aliquot maintained in the absence of the test compound, indicates that the test compound potentially contributes to endometrial disease.

The invention further relates to a method of assessing the efficacy of a therapy for inhibiting endometrial disease in a patient. A method of the invention comprises comparing: (a) levels of endometrial markers or polynucleotides encoding the markers associated with disease in a first sample from the patient obtained from the patient prior to providing at least a portion of the therapy to the patient; and (b) levels of endometrial markers or polynucleotides encoding the markers associated with disease in a second sample obtained from the patient following therapy.

In an embodiment, a significant difference between the levels of endometrial markers or polynucleotides encoding the markers in the second sample relative to the first sample is an indication that the therapy is efficacious for inhibiting endometrial disease.

In a particular embodiment, the method is used to assess the efficacy of a therapy for inhibiting endometrial disease (e.g. endometrial cancer), where lower levels of endometrial markers or polynucleotides encoding same in the second sample relative to the first sample, is an indication that the therapy is efficacious for inhibiting the disease.

The "therapy" may be any therapy for treating endometrial disease, in particular endometrial cancer, including but not limited to therapeutics, radiation, immunotherapy, gene therapy, and surgical removal of tissue. Therefore, the method can be used to evaluate a patient before, during, and after therapy.

Certain methods of the invention employ binding agents (e.g. antibodies) that specifically recognize endometrial markers.

In an embodiment, the invention provides methods for determining the presence or absence of endometrial disease, in particular endometrial cancer, in a patient, comprising the steps of (a) contacting a biological sample obtained from a patient with one or more binding agent that specifically binds to one or more endometrial markers associated with the disease; and (b) detecting in the sample an amount of marker that binds to the binding agent, relative to a predetermined standard or cut-off value, and therefrom determining the presence or absence of endometrial disease in the patient.

In another embodiment, the invention relates to a method for diagnosing and monitoring an endometrial disease, in particular endometrial cancer, in a subject by quantitating one or more endometrial markers associated with the disease in a biological sample from the subject comprising (a) reacting the biological sample with one or more binding agent specific for the endometrial markers (e.g. an antibody) that are directly or indirectly labelled with a detectable substance; and (b) detecting the detectable substance.

In another aspect the invention provides a method of using an antibody to detect expression of one or more endometrial marker in a sample, the method comprising: (a) combining antibodies specific for one or more endometrial marker with a sample under conditions which allow the formation of antibody:marker complexes; and (b) detecting complex formation, wherein complex formation indicates expression of the marker in the sample. Expression may be compared with standards and is diagnostic of an endometrial disease, in particular endometrial cancer.

Embodiments of the methods of the invention involve (a) reacting a biological sample from a subject with antibodies specific for one or more endometrial markers which are directly or indirectly labelled with an enzyme; (b) adding a substrate for the enzyme wherein the substrate is selected so that the substrate, or a reaction product of the enzyme and substrate forms fluorescent complexes; (c) quantitating one or more endometrial markers in the sample by measuring fluorescence of the fluorescent complexes; and (d) comparing the quantitated levels to levels obtained for other samples from the subject patient, or control subjects.

In another embodiment the quantitated levels are compared to levels quantitated for control subjects (e.g. normal or benign) without an endometrial disease (e.g. cancer) wherein an increase in endometrial marker levels compared with the control subjects is indicative of endometrial disease.

In a further embodiment the quantitated levels are compared to levels quantitated for control subjects (e.g. normal or benign) without an endometrial disease (e.g. cancer) wherein a decrease in endometrial marker levels compared with the control subjects is indicative of endometrial disease.

A particular embodiment of the invention comprises the following steps
  (a) incubating a biological sample with first antibodies specific for one or more endometrial cancer markers which are directly or indirectly labeled with a detectable substance, and second antibodies specific for one or more endometrial cancer markers which are immobilized;
  (b) detecting the detectable substance thereby quantitating endometrial cancer markers in the biological sample; and
  (c) comparing the quantitated endometrial cancer markers with levels for a predetermined standard.

The standard may correspond to levels quantitated for samples from control subjects without endometrial cancer (normal or benign), with a different disease stage, or from other samples of the subject. In an embodiment, increased levels of endometrial cancer markers as compared to the standard may be indicative of endometrial cancer. In another embodiment, lower levels of endometrial cancer markers as compared to a standard may be indicative of endometrial cancer.

Endometrial marker levels can be determined by constructing an antibody microarray in which binding sites comprise immobilized, preferably monoclonal, antibodies specific to a substantial fraction of marker-derived endometrial marker proteins of interest.

Other methods of the invention employ one or more polynucleotides capable of hybridizing to one or more polynucleotides encoding endometrial markers. Thus, methods can be used to monitor an endometrial disease (e.g. cancer) by detecting endometrial polynucleotide markers associated with the disease.

Thus, the present invention relates to a method for diagnosing and monitoring an endometrial disease (e.g. endometrial cancer) in a sample from a subject comprising isolating nucleic acids, preferably mRNA, from the sample; and detecting endometrial marker polynucleotides associated with the disease in the sample. The presence of different levels of endometrial marker polynucleotides in the sample compared to a standard or control may be indicative of endometrium phase, disease, disease stage, and/or a negative or positive prognosis (e.g., longer progression-free and overall survival).

In embodiments of the invention, endometrial cancer marker polynucleotide positive tumors (e.g. higher levels of the polynucleotides compared to a control normal or benign sample) are a negative diagnostic indicator. Positive tumors can be indicative of endometrial cancer, advanced stage disease, lower progression-free survival, and/or overall survival.

In other embodiments of the invention, endometrial cancer marker polynucleotide negative tumors (e.g. lower levels of the polynucleotides compared to a control normal or benign tissue) are a negative diagnostic indicator. Negative tumors can be indicative of endometrial cancer, advanced stage disease, lower progression-free survival, and/or overall survival.

The invention provides methods for determining the presence or absence of an endometrial disease in a subject comprising detecting in the sample levels of nucleic acids that hybridize to one or more polynucleotides encoding endometrial markers associated with the disease, comparing the levels with a predetermined standard or cut-off value, and therefrom determining the presence or absence of endometrial disease in the subject. In an embodiment, the invention provides methods for determining the presence or absence of endometrial cancer in a subject comprising (a) contacting a sample obtained from the subject with oligonucleotides that hybridize to one or more polynucleotides encoding endometrial cancer markers; and (b) detecting in the sample a level of nucleic acids that hybridize to the polynucleotides relative to a predetermined cut-off value, and therefrom determining the presence or absence of endometrial cancer in the subject.

Within certain embodiments, the amount of polynucleotides that are mRNA are detected via polymerase chain reaction using, for example, oligonucleotide primers that hybridize to one or more polynucleotides encoding endometrial markers, or complements of such polynucleotides. Within other embodiments, the amount of mRNA is detected using a hybridization technique, employing oligonucleotide probes that hybridize to one or more polynucleotides encoding endometrial markers, or complements thereof.

When using mRNA detection, the method may be carried out by combining isolated mRNA with reagents to convert to cDNA according to standard methods; treating the converted cDNA with amplification reaction reagents (such as cDNA PCR reaction reagents) in a container along with an appropriate mixture of nucleic acid primers; reacting the contents of the container to produce amplification products; and analyzing the amplification products to detect the presence of one or more endometrial polynucleotide markers in the sample.

For mRNA the analyzing step may be accomplished using Northern Blot analysis to detect the presence of endometrial polynucleotide markers. The analysis step may be further accomplished by quantitatively detecting the presence of endometrial polynucleotide markers in the amplification product, and comparing the quantity of marker detected against a panel of expected values for the known presence or absence of the markers in normal and malignant tissue derived using similar primers.

Therefore, the invention provides a method wherein mRNA is detected by (a) isolating mRNA from a sample and combining the mRNA with reagents to convert it to cDNA; (b) treating the converted cDNA with amplification reaction reagents and nucleic acid primers that hybridize to one or more endometrial polynucleotide markers to produce amplification products; (d) analyzing the amplification products to detect an amount of mRNA encoding the endometrial markers; and (e) comparing the amount of mRNA to an amount detected against a panel of expected values for normal and diseased tissue (e.g. malignant tissue) derived using similar nucleic acid primers.

In particular embodiments of the invention, the methods described herein utilize the endometrial polynucleotide markers placed on a microarray so that the expression status of each of the markers is assessed simultaneously.

In a particular aspect, the invention provides an endometrial microarray comprising a defined set of genes (i.e., at least 2, 3 4, or 5 genes listed in Table 1 and optionally at least 5 to 10 genes listed in Table 2) whose expression is significantly altered by endometrium phase or endometrial disease. The invention further relates to the use of the microarray as a prognostic tool to predict endometrium phase or endometrial disease. In an embodiment, the endometrial microarray discriminates between endometrial disease resulting from different etiologies.

In an embodiment, the invention provides for oligonucleotide arrays comprising marker sets described herein. The microarrays provided by the present invention may comprise probes to markers able to distinguish endometrium phase or disease. In particular, the invention provides oligonucleotide arrays comprising probes to a subset or subsets of at least 5 to 10 gene markers up to a full set of markers which distinguish endometrium phase or endometrial disease.

The invention also contemplates a method comprising administering to cells or tissues imaging agents that carry labels for imaging and bind to endometrial markers and optionally other markers of an endometrial disease, and then imaging the cells or tissues.

In an aspect the invention provides an in vivo method comprising administering to a subject an agent that has been constructed to target one or more endometrial markers.

In a particular embodiment, the invention contemplates an in vivo method comprising administering to a mammal one or more agent that carries a label for imaging and binds to one or more endometrial marker, and then imaging the mammal.

According to a particular aspect of the invention, an in vivo method for imaging endometrial cancer is provided comprising:
 (a) injecting a patient with an agent that binds to one or more endometrial cancer marker, the agent carrying a label for imaging the endometrial cancer;
 (b) allowing the agent to incubate in vivo and bind to one or more endometrial cancer marker associated with the endometrial cancer; and
 (c) detecting the presence of the label localized to the endometrial cancer.

In an embodiment of the invention the agent is an antibody which recognizes an endometrial cancer marker. In another embodiment of the invention the agent is a chemical entity which recognizes an endometrial cancer marker.

An agent carries a label to image an endometrial marker and optionally other markers. Examples of labels useful for imaging are radiolabels, fluorescent labels (e.g fluorescein and rhodamine), nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed.

The invention also contemplates the localization or imaging methods described herein using multiple markers for an endometrial disease (e.g. endometrial cancer).

The invention also relates to kits for carrying out the methods of the invention. In an embodiment, a kit is for assessing whether a patient is afflicted with an endometrial disease (e.g. endometrial cancer) and it comprises reagents for assessing one or more endometrial markers or polynucleotides encoding the markers.

The invention further provides kits comprising marker sets described herein. In an aspect the kit contains a microarray ready for hybridization to target endometrial oligonucleotide markers, plus software for the data analyses.

The invention also provides a diagnostic composition comprising an endometrial marker or a polynucleotide encoding the marker. A composition is also provided comprising a probe that specifically hybridizes to endometrial polynucleotide markers, or a fragment thereof, or an antibody specific for endometrial markers or a fragment thereof. In another aspect, a composition is provided comprising one or more endometrial polynucleotide marker specific primer pairs capable of amplifying the polynucleotides using polymerase chain reaction methodologies. The probes, primers or antibodies can be labeled with a detectable substance.

Still further the invention relates to therapeutic applications for endometrial diseases, in particular endometrial cancer, employing endometrial markers and polynucleotides encoding the markers, and/or binding agents for the markers.

In an aspect, the invention relates to compositions comprising markers or parts thereof associated with an endometrial disease, or antibodies specific for endometrial markers associated with an endometrial disease, and a pharmaceutically acceptable carrier, excipient, or diluent. A method for treating or preventing an endometrial disease, in particular endometrial cancer, in a patient is also provided comprising administering to a patient in need thereof, markers or parts thereof associated with an endometrial disease, antibodies specific for endometrial markers associated with an endometrial disease, or a composition of the invention. In an aspect the invention provides a method of treating a patient afflicted with or at risk of developing an endometrial disease (e.g. endometrial cancer) comprising inhibiting expression of endometrial markers.

In an aspect, the invention provides antibodies specific for endometrial markers associated with a disease (e.g. endometrial cancer) that can be used therapeutically to destroy or inhibit the disease (e.g. the growth of endometrial cancer marker expressing cancer cells), or to block endometrial marker activity associated with a disease. In an aspect, endometrial cancer markers may be used in various immunotherapeutic methods to promote immune-mediated destruction or growth inhibition of tumors expressing endometrial cancer markers.

The invention also contemplates a method of using endometrial markers or parts thereof, or antibodies specific for endometrial markers in the preparation or manufacture of a medicament for the prevention or treatment of an endometrial disease e.g. endometrial cancer.

Another aspect of the invention is the use of endometrial markers, peptides derived therefrom, or chemically produced (synthetic) peptides, or any combination of these molecules, for use in the preparation of vaccines to prevent an endometrial disease and/or to treat an endometrial disease.

The invention contemplates vaccines for stimulating or enhancing in a subject to whom the vaccine is administered production of antibodies directed against one or more endometrial markers.

The invention also provides a method for stimulating or enhancing in a subject production of antibodies directed against one or more endometrial marker. The method comprises administering to the subject a vaccine of the invention in a dose effective for stimulating or enhancing production of the antibodies.

The invention further provides a method for treating, preventing, or delaying recurrence of an endometrial disease (e.g. endometrial cancer). The method comprises administering to the subject a vaccine of the invention in a dose effective for treating, preventing, or delaying recurrence of an endometrial disease (e.g. endometrial cancer).

The invention contemplates the methods, compositions, and kits described herein using additional markers associated with an endometrial disease (e.g. endometrial cancer). The methods described herein may be modified by including reagents to detect the additional markers, or polynucleotides for the markers.

In particular, the invention contemplates the methods described herein using multiple markers for an endometrial cancer. Therefore, the invention contemplates a method for analyzing a biological sample for the presence of endometrial cancer markers and polynucleotides encoding the markers, and other markers that are specific indicators of cancer, in particular endometrial cancer. The methods described herein may be modified by including reagents to detect the additional markers, or nucleic acids for the additional markers.

In embodiments of the invention the methods, compositions and kits use one or more of the markers listed in Table 1, in particular WFDC2, clusterin and mucin 5B, and optionally one or more listed in Table 2. In another embodiment, the method uses a panel of markers selected from the markers listed in Table 1, and optionally one or more listed in Table 2 in particular a panel comprising two, three or four or more of the markers in Table 1.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE TABLES AND DRAWINGS

The invention will now be described in relation to the Tables and drawings:
Table Legends
Table 1: Differentially expressed proteins in endometrial malignancies/cancer.

Table 2: Differentially expressed proteins in endometrial malignancies/cancer.

Table 3: Average iTRAQ ratios for normal proliferative, normal secretory, Type I and Type II EmCa samples. Ratios in the first panel are from the comparison between the normal proliferative samples. In any given row of this panel, the ratios were normalized to the average normal proliferative ratio. The only exception to this was Cpn 10, which was not observed in the second set of normal proliferative sample comparisons. In this case the ratios reported are relative to the first normal proliferative sample in the set i.e. P1 and P7. The ratios for the rest of the panels (i.e. secretory, Type I and Type II) were relative to the average normal proliferative level. In instances where the average normal proliferative level could not be calculated across all ten normal proliferative samples, the values reported were relative to the corresponding normal proliferative sample in the individual set. (ND: not detected; NO: not quantified). Ratios deemed to signify differential expression are bolded and shown in a larger font.

Table 4: Individual ratios from each of the three runs on the RP column used to calculate the average ratios for PK reported in Table 3: P. proliferative; S, secretory; I, Type I EmCa; and II, Type II EmCa.

Table 5: Cross-validation of biomarker panel using a two-thirds/one-thirds split. The panel of three potential markers, PK, Cpn10, and AAT, were tested using 10 random splits on which the logistic regression predictor was trained and tested. The high number of true positives (pos) and negatives (negs), and low number of false positives and negatives for each test set when compared with the training set validates the biomarker panel.

Figure Legends

FIG. 1: Receiver operating characteristic curve resulting from a logistic regressional analysis using a panel of 3 potential biomarkers: PK, Cpn 10, and AAT.

Figure 2:
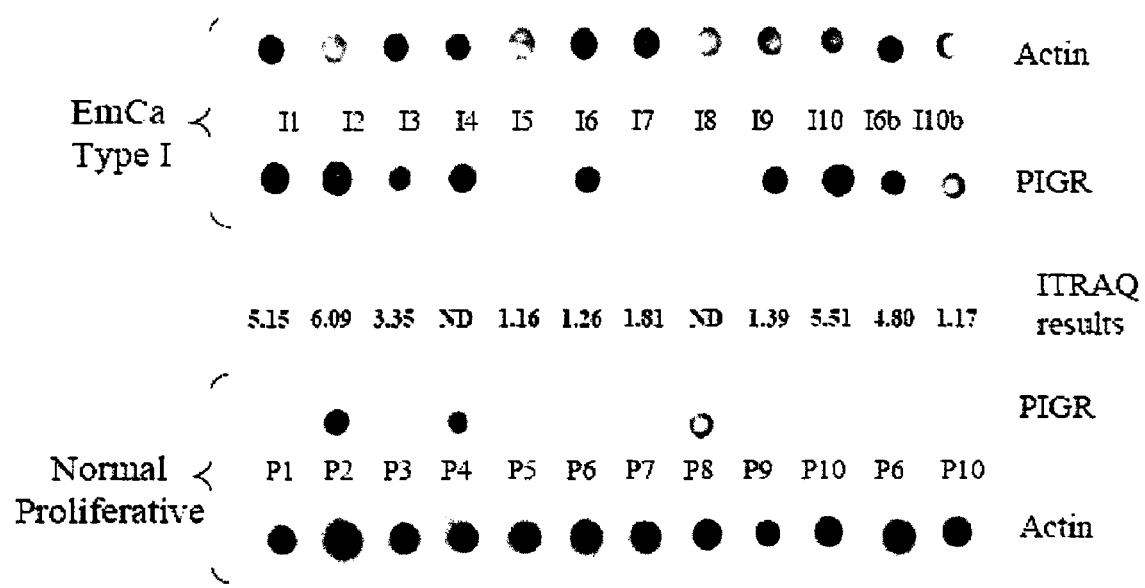

FIG. 2: (a) Dot Blot analysis of β-actin and PIGR. The panel in the middle shows the average of the iTRAQ ratios obtained for PIGR in the twelve pairs of samples in the dot blots. The ratios shown are not normalized to the average normal proliferative sample level in order to show the correlation between the iTRAQ and dot blot results. β-Actin blots performed in duplicate for the same set of samples is shown above and below the Type I and normal proliferative samples respectively. The sample numbers between the actin and PIGR blots correspond to the iTRAQ sample set numbers. The iTRAQ ratios reported in the middle panel for I6b and I10b are relative to the P6 and P10 samples respectively. Despite higher loading in general in the normal proliferative samples as is evident from the β-actin blots, the PIGR levels were higher in most Type I samples and correlate well with the iTRAQ result in the center panel.

Figure 3:
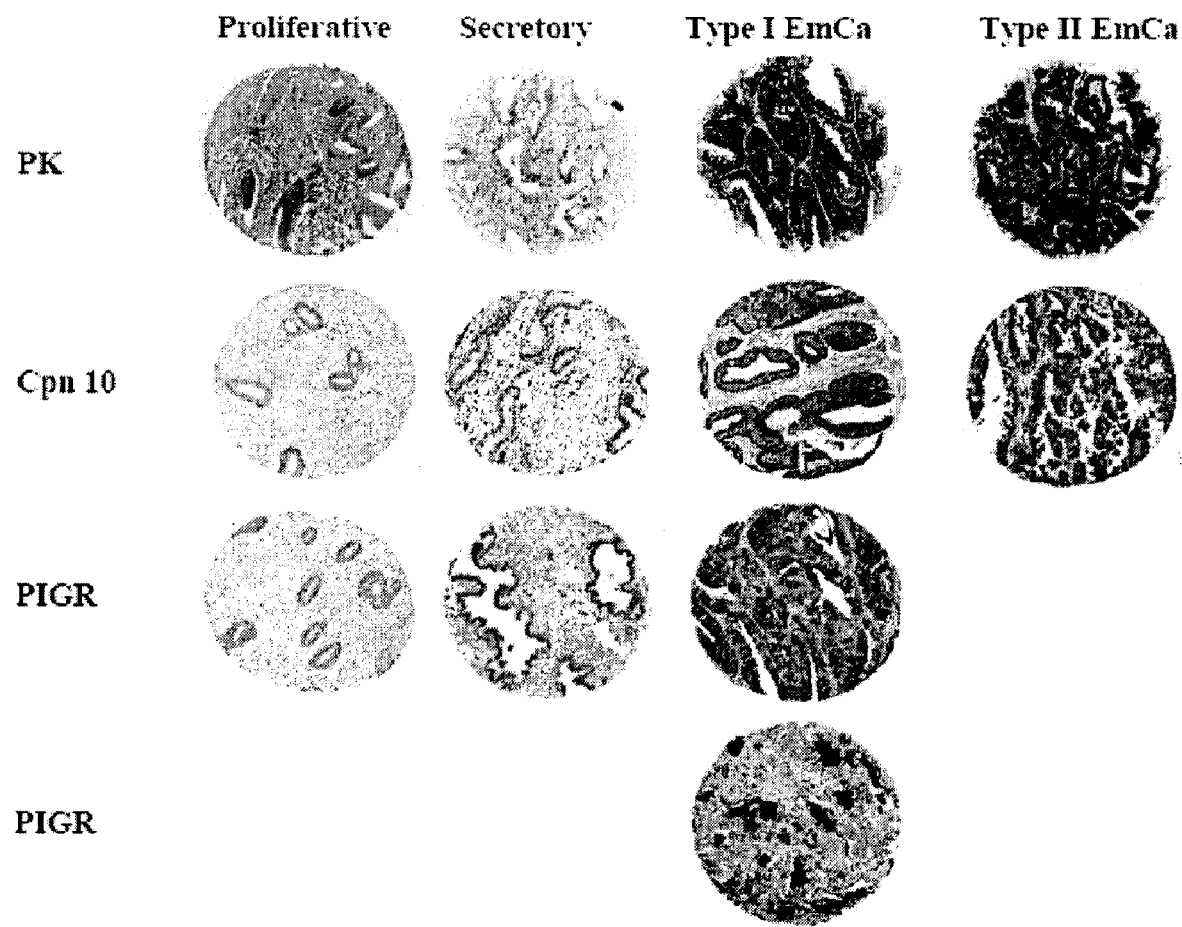

FIG. 3. Immunohistochemical validation of iTRAQ-discovered potential cancer markers using antibodies targeted to PK, Cpn10, and PIGR. Positive staining is brown and is most intense in EmCa samples.

DETAILED DESCRIPTION OF THE INVENTION

Methods are provided for characterizing the stage or phase of endometrium, detecting the presence of an endometrial disease (e.g. endometrial cancer) in a sample, the absence of a disease (e.g. endometrial cancer) in a sample, the stage or grade of the disease, and other characteristics of endometrial diseases that are relevant to prevention, diagnosis, characterization, and therapy of endometrial diseases such as cancer in a patient, for example, the benign or malignant nature of an endometrial cancer, the metastatic potential of an endometrial cancer, assessing the histological type of neoplasm associated with an endometrial cancer, the indolence or aggressiveness of an endometrial cancer, and other characteristics of endometrial diseases that are relevant to prevention, diagnosis, characterization, and therapy of endometrial diseases such as cancer in a patient. Methods are also provided for assessing the efficacy of one or more test agents for inhibiting an endometrial disease, assessing the efficacy of a therapy for an endometrial disease, monitoring the progression of an endometrial disease, selecting an agent or therapy for inhibiting an endometrial disease, treating a patient afflicted with an endometrial disease, inhibiting an endometrial disease in a patient, and assessing the disease (e.g. carcinogenic) potential of a test compound.

Glossary

For convenience, certain terms employed in the specification, examples, and appended claims are collected here.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. Thus, for example, reference to a composition or method comprising "an endometrial marker" includes two or more endometrial markers. The term "about" means plus or minus 0.1 to 50%, 5-50%, or 10-40%, preferably 10-20%, more preferably 10% or 15%, of the number to which reference is being made.

"Endometrial disease" refers to any disorder, disease, condition, syndrome or combination of manifestations or symptoms recognized or diagnosed as a disorder of the endometrium, including but not limited to hyperplasia and cancer precursors, endometrial cancer or carcinoma, endometriosis, reproductive disorders, and infertility.

"Endometrial cancer" or "endometrial carcinoma" includes malignant endometrial disease including but not limited to endometrioid, mucinous, and serous adenocarcinomas, adenosquamous carcinomas, clear cell carcinomas, uterine sarcomas including stromal sarcomas, malignant mixed Mullerian tumors (carcinosarcomas), and leiomyosarcomas.

The terms "sample", "biological sample", and the like mean a material known or suspected of expressing or containing one or more endometrial polynucleotide markers or one or more endometrial markers. A test sample can be used directly as obtained from the source or following a pretreatment to modify the character of the sample. The sample can be derived from any biological source, such as tissues, extracts, or cell cultures, including cells (e.g. tumor cells), cell lysates, and physiological fluids, such as, for example, whole blood, plasma, serum, saliva, ocular lens fluid, cerebral spinal fluid, sweat, urine, milk, ascites fluid, synovial fluid, peritoneal fluid, lavage fluid, and the like. The sample can be obtained from animals, preferably mammals, most preferably humans. The sample can be treated prior to use, such as preparing plasma from blood, diluting viscous fluids, and the like. Methods of treatment can involve filtration, distillation, extraction, concentration, inactivation of interfering components, the addition of reagents, and the like.

In embodiments of the invention the sample is a mammalian tissue sample. In a particular embodiment, the tissue is endometrial tissue.

In another embodiment the sample is a human physiological fluid. In a particular embodiment, the sample is human serum.

The samples that may be analyzed in accordance with the invention include polynucleotides from clinically relevant sources, preferably expressed RNA or a nucleic acid derived therefrom (cDNA or amplified RNA derived from cDNA that incorporates an RNA polymerase promoter). The target polynucleotides can comprise RNA, including, without limitation total cellular RNA, poly(A)$^+$ messenger RNA (mRNA) or fraction thereof, cytoplasmic mRNA, or RNA transcribed from cDNA (i.e., cRNA; see, for example, Linsley & Schelter, U.S. patent application Ser. No. 09/411,074, or U.S. Pat. Nos. 5,545,522, 5,891,636, or 5,716,785). Methods for preparing total and poly(A)$^+$ RNA are well known in the art, and are described generally, for example, in Sambrook et al., (1989, Molecular Cloning—A Laboratory Manual ($2^{nd}$ Ed.), Vols. 1-3, Cold Spring Harbor Laboratory, Cold Spring Harbor, N.Y.) and Ausubel et al, eds. (1994, Current Protocols in Molecular Biology, vol. 2, Current Protocols Publishing, New York). RNA may be isolated from eukaryotic cells by procedures involving lysis of the cells and denaturation of the proteins contained in the cells. Additional steps may be utilized to remove DNA. Cell lysis may be achieved with a nonionic detergent, followed by microcentrifugation to remove the nuclei and hence the bulk of the cellular DNA. (See Chirgwin et al., 1979, Biochemistry 18:5294-5299). Poly(A)+RNA can be selected using oligo-dT cellulose (see Sambrook et al., 1989, *Molecular Cloning—A Laboratory Manual* (2nd Ed.), Vols. 1-3, Cold Spring Harbor Laboratory, Cold Spring Harbor, N.Y.). In the alternative, RNA can be separated from DNA by organic extraction, for example, with hot phenol or phenol/chloroform/isoamyl alcohol.

It may be desirable to enrich mRNA with respect to other cellular RNAs, such as transfer RNA (tRNA) and ribosomal RNA (rRNA). Most mRNAs contain a poly(A) tail at their 3' end allowing them to be enriched by affinity chromatography, for example, using oligo(dT) or poly(U) coupled to a solid support, such as cellulose or Sephadex™ (see Ausubel et al., eds., 1994, *Current Protocols in Molecular Biology*, vol. 2, Current Protocols Publishing, New York). Bound poly(A)+ mRNA is eluted from the affinity column using 2 mM EDTA/ 0.1% SDS.

A sample of RNA can comprise a plurality of different mRNA molecules each with a different nucleotide sequence. In an aspect of the invention, the mRNA molecules in the RNA sample comprise at least 100 different nucleotide sequences.

Target polynucleotides can be detectably labeled at one or more nucleotides using methods known in the art. The label is preferably uniformly incorporated along the length of the RNA, and more preferably, is carried out at a high degree of efficiency. The detectable label can be a luminescent label, fluorescent label, bio-luminescent label, chemi-luminescent label, radiolabel, and colorimetric label. In a particular embodiment, the label is a fluorescent label, such as a fluorescein, a phosphor, a rhodamine, or a polymethine dye derivative. Commercially available fluorescent labels include, for example, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.).

Target polynucleotides from a patient sample can be labeled differentially from polynucleotides of a standard. The standard can comprise target polynucleotides from normal individuals (i.e., those not afflicted with or pre-disposed to endometrial disease), in particular pooled from samples from normal individuals. The target polynucleotides can be derived from the same individual, but taken at different time points, and thus indicate the efficacy of a treatment by a change in expression of the markers, or lack thereof, during and after the course of treatment.

The terms "subject", "individual" and "patient" refer to a warm-blooded animal such as a mammal. In particular, the terms refer to a human. A subject, individual or patient may be afflicted with or suspected of having or being pre-disposed to endometrial disease or a condition as described herein. The terms also includes domestic animals bred for food or as pets, including horses, cows, sheep, poultry, fish, pigs, cats, dogs, and zoo animals.

Methods herein for administering an agent or composition to subjects/individuals/patients contemplate treatment as well as prophylactic use. Typical subjects for treatment include persons susceptible to, suffering from or that have suffered a condition or disease described herein. In particular, suitable subjects for treatment in accordance with the invention are persons that are susceptible to, suffering from or that have suffered endometrial cancer.

The term "endometrial marker" refers to a marker associated with normal or diseased endometrial tissue and comprises or consists of one or more of the polypeptides listed in Table 1, in particular WFDC2, clusterin, and/or mucin 5B, and optionally one or more of the polypeptides listed in Table 2. The term includes native-sequence polypeptides, isoforms, chimeric polypeptides, complexes, all homologs, fragments, precursors, and modified forms and derivatives of the markers.

An endometrial marker may be associated with a stage or phase of endometrial tissue such as the secretory or proliferative phase. Examples of endometrial markers associated with the secretory phase are WFDC2, and optionally one or more of glutamate receptor subunit zeta 1 [GenBank Accession NOs. NP_000823, NP_015566, and NP_067544], macrophage migration inhibitory factor [SEQ ID NO. 49], GSK-3 binding protein FRAT1 [GenBank Accession NO. NP_005470], myosin light chain kinase 2 [GenBank Accession No. NP_149109], and tropomyosin 1 alpha chain [GeneBank Accession NOs. NP_000357, NP_001018004, NP_001018005, NP_001018006, NP_001018007, NP_001018008, and NP_001018020].

An endometrial marker may be associated with an endometrial disease, in particular it may be an endometrial cancer marker. The term "endometrial cancer marker" includes a marker associated with endometrial cancer, in particular a marker listed in Table 1, and optionally a marker listed in Table 2.

In an aspect of the invention, an endometrial cancer marker is WAP four-disulfide core domain 2 (WFDC2). The terms "WAP four-disulfide core domain 2", "WFDC2" "WFDC2 polypeptide" and "WFDC2 protein" include human WAP four-disulfide core domain 2, in particular the native-sequence polypeptide, isoforms, chimeric polypeptides, all homologs, fragments, precursors, complexes, and modified forms and derivatives of human WAP four-disulfide core domain 2. The amino acid sequence for native human WAP four-disulfide core domain 2 includes the amino acid sequences referenced in NCBI Gene ID: 10406, including GenBank Accession Nos. CAG33258, NP_006094, NP_542772, NP_542773, and NP_542774, and the exemplary sequences shown in SEQ ID NOs. 1 to 4.

In an aspect of the invention, an endometrial cancer marker is clusterin. The terms "clusterin", "clusterin polypeptide" and "clusterin protein" include human clusterin, in particular the native-sequence polypeptide, isoforms, chimeric polypeptides, all homologs, fragments, precursors, complexes, and modified forms and derivatives of human clusterin. The amino acid sequence for native human clusterin includes the amino acid sequences referenced in NCBI Gene ID: 1191, including GenBank Accession Nos. NP_001822, and NP_976084, and the exemplary sequences shown in SEQ ID NOs. 10 and 11.

In an aspect of the invention, an endometrial cancer marker is mucin 5B. The terms "mucin 5B", "mucin 5B polypeptide" and "mucin 5B protein" include human mucin 5B, in particular the native-sequence polypeptide, isoforms, chimeric polypeptides, all homologs, fragments, precursors, complexes, and modified forms and derivatives of human mucin 5B. The amino acid sequence for native human mucin 5B includes the amino acid sequences referenced in NCBI Gene ID: 4587, including GenBank Accession Nos. AAG33673, AAG33673.1, CAA06167.1, AAC51344.1, CAA70926.1, CAA96577.1, AAC67545.1, AAF64523.1, AAB35930.1, AAB61398.1, AAC51343.1, AAB65151.1, CAA52408.1, CAA52910.1, Q14879, Q93043, Q9HC84, Q9NYE4, and the exemplary sequence shown in SEQ ID NO. 14.

In an aspect of the invention, an endometrial cancer marker is leucine aminopeptidase 3 or LAP3. The terms "leucine aminopeptidase 3", "LAP3", "LAP3 polypeptide" and "LAP3 protein" include human LAP3, in particular the native-sequence polypeptide, isoforms, chimeric polypeptides, all homologs, fragments, precursors, complexes, and modified forms and derivatives of human LAP3. The amino acid sequence for native human LAP3 includes the amino acid sequences referenced in NCBI Gene ID: 51056, including GenBank Accession No. NP_056991 and the exemplary sequence shown in SEQ ID NO. 15.

In an aspect of the invention, an endometrial cancer marker is macrophage capping protein or CAP-G. The terms "macrophage capping protein", "CAP-G", "CAP-G polypeptide" and "CAP-G protein" include human CAP-G, in particular the native-sequence polypeptide, isoforms, chimeric polypeptides, all homologs, fragments, precursors, complexes, and modified forms and derivatives of human CAP-G. The amino acid sequence for native human CAP-G includes the amino acid sequences referenced in NCBI Gene ID: 822, including GenBank Accession Nos. NP_001738 and the exemplary sequence shown in SEQ ID NO. 17.

In an aspect of the invention, an endometrial cancer marker is progestagen-associated endometrial protein (PAEP). The terms "progestagen-associated endometrial protein", "PAEP", "PAEP polypeptide" and "PAEP protein" include human PAEP, in particular the native-sequence polypeptide, isoforms, chimeric polypeptides, all homologs, fragments, precursors, complexes, and modified forms and derivatives of human PAEP. The amino acid sequence for native human PAEP includes the amino acid sequences referenced in NCBI Gene ID: 5047 including GenBank Accession Nos. NP_002562 and NP_001018059, and the exemplary sequence shown in SEQ ID NO. 19.

A "native-sequence polypeptide" comprises a polypeptide having the same amino acid sequence of a polypeptide derived from nature. Such native-sequence polypeptides can be isolated from nature or can be produced by recombinant or synthetic means. The term specifically encompasses naturally occurring truncated or secreted forms of a polypeptide, polypeptide variants including naturally occurring variant forms (e.g. alternatively spliced forms or splice variants), and naturally occurring allelic variants.

The term "polypeptide variant" means a polypeptide having at least about 45%, 50%, 55%, 60%, 65%, 70%, 75%, 80%, 85%, 90%, 95%, 97%, 98%, or 99% amino acid sequence identity, particularly at least about 70-80%, more particularly at least about 85%, still more particularly at least about 90%, most particularly at least about 95% amino acid sequence identity with a native-sequence polypeptide. Particular polypeptide variants have at least 70-80%, 85%, 90%, 95% amino acid sequence identity to the sequences identified in Table 1 or 2. Such variants include, for instance, polypeptides wherein one or more amino acid residues are added to, or deleted from, the N- or C-terminus of the full-length or mature sequences of the polypeptide, including variants from other species, but excludes a native-sequence polypeptide. In aspects of the invention variants retain the immunogenic activity of the corresponding native-sequence polypeptide.

Percent identity of two amino acid sequences, or of two nucleic acid sequences is defined as the percentage of amino acid residues or nucleotides in a candidate sequence that are identical with the amino acid residues in a polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various conventional ways, for instance, using publicly available computer software including the GCG program package (Devereux J. et al., Nucleic Acids Research 12(1): 387, 1984); BLASTP, BLASTN, and FASTA (Atschul, S. F. et al. J. Molec. Biol. 215: 403-410, 1990). The BLAST X program is publicly available from NCBI and other sources (BLAST Manual, Altschul, S. et al. NCBI NLM NIH Bethesda, Md. 20894; Altschul, S. et al. J. Mol. Biol. 215: 403-410, 1990). Skilled artisans can determine appropriate parameters for measuring alignment, including any algorithms needed to achieve maximal alignment over the full length of the sequences being compared. Methods to determine identity and similarity are codified in publicly available computer programs.

An allelic variant may also be created by introducing substitutions, additions, or deletions into a polynucleotide encoding a native polypeptide sequence such that one or more amino acid substitutions, additions, or deletions are introduced into the encoded protein. Mutations may be introduced by standard methods, such as site-directed mutagenesis and PCR-mediated mutagenesis. In an embodiment, conservative substitutions are made at one or more predicted non-essential amino acid residues. A "conservative amino acid substitution" is one in which an amino acid residue is replaced with an amino acid residue with a similar side chain. Amino acids with similar side chains are known in the art and include amino acids with basic side chains (e.g. Lys, Arg, His), acidic side chains (e.g. Asp, Glu), uncharged polar side chains (e.g. Gly, Asp, Glu, Ser, Thr, Tyr and Cys), nonpolar side chains (e.g. Ala, Val, Leu, Iso, Pro, Trp), beta-branched side chains (e.g. Thr, Val, Iso), and aromatic side chains (e.g. Tyr, Phe, Trp, His). Mutations can also be introduced randomly along part or all of the native sequence, for example, by saturation mutagenesis. Following mutagenesis the variant polypeptide can be recombinantly expressed and the activity of the polypeptide may be determined.

Polypeptide variants include polypeptides comprising amino acid sequences sufficiently identical to or derived from the amino acid sequence of a native polypeptide which include fewer amino acids than the full length polypeptides. A portion of a polypeptide can be a polypeptide which is for example, 10, 15, 20, 25, 30, 35, 40, 45, 50, 60, 70, 80, 90, 100 or more amino acids in length. Portions in which regions of a polypeptide are deleted can be prepared by recombinant techniques and can be evaluated for one or more functional activities such as the ability to form antibodies specific for a polypeptide.

A naturally occurring allelic variant may contain conservative amino acid substitutions from the native polypeptide sequence or it may contain a substitution of an amino acid from a corresponding position in a polypeptide homolog, for example, a murine polypeptide.

An endometrial marker may be part of a chimeric or fusion protein. A "chimeric protein" or "fusion protein" comprises all or part (preferably biologically active) of an endometrial marker operably linked to a heterologous polypeptide (i.e., a polypeptide other than an endometrial marker). Within the fusion protein, the term "operably linked" is intended to indicate that an endometrial marker and the heterologous polypeptide are fused in-frame to each other. The heterologous polypeptide can be fused to the N-terminus or C-terminus of an endometrial marker. A useful fusion protein is a GST fusion protein in which an endometrial marker is fused to the C-terminus of GST sequences. Another example of a fusion protein is an immunoglobulin fusion protein in which all or part of an endometrial marker is fused to sequences derived from a member of the immunoglobulin protein family. Chimeric and fusion proteins can be produced by standard recombinant DNA techniques.

A modified form of a polypeptide referenced herein includes modified forms of the polypeptides and derivatives of the polypeptides, including post-translationally modified forms such as glycosylated, phosphorylated, acetylated, methylated or lapidated forms of the polypeptides. For example, an N-terminal methionine may be cleaved from a polypeptide, and a new N-terminal residue may or may not be acetylated. In particular, for chaperonin 10 the first residue, methionine, can be cleaved and the second first residue, alanine can be N-acetylated.

Endometrial markers may be prepared by recombinant or synthetic methods, or isolated from a variety of sources, or by any combination of these and similar techniques.

"Endometrial polynucleotide marker(s)", polynucleotides encoding the marker(s)", and "polynucleotides encoding endometrial markers" refer to polynucleotides that encode endometrial markers including native-sequence polypeptides, polypeptide variants including a portion of a polypeptide, an isoform, precursor, complex, a chimeric polypeptide, or modified forms and derivatives of the polypeptides. An endometrial polynucleotide marker comprises or consists of one or more of the polynucleotides encoding the polypeptides listed in Table 1 and optionally one or more of the polynucleotides encoding the polypeptides listed in Table 2. In particular, endometrial polynucleotide markers comprise or consist essentially of the polynucleotides encoding WFDC2, clusterin, mucin 5B, leucine aminopeptidase 3 (LAP3), macrophage capping protein (CAP-G), and/or progestagen-associated endometrial protein (PAEP).

In an aspect, a polynucleotide of the invention encodes WFDC2, more particularly a polynucleotide sequence referenced in NCBI Gene ID. 10406, more particularly GenBank Accession Nos. NM_006103, NM_080734, NM_080735, or NM_080736 [and see for example SEQ ID NOs. 5, 6, 7, 8 or 9], or a fragment thereof.

In an aspect, a polynucleotide of the invention encodes clusterin more particularly a polynucleotide sequence referenced in NCBI Gene ID. 1191, more particularly GenBank Accession Nos. NM_001831 or NM_203339 [and see for example SEQ ID NOs. 12 or 13], or fragment thereof.

In an aspect, a polynucleotide of the invention encodes mucin 5B more particularly a polynucleotide sequence referenced in NCBI Gene ID. 4587, more particularly GenBank Accession Nos. AJ004862.1, U78554.1, Y09788.2, Z72496.1, AF086604.1, AF253321.1, S80993.1, U63836.1, U78551.1, U95031.1, X74370.1, or X74955.1, or a fragment thereof.

In an aspect, a polynucleotide of the invention encodes LAP3 more particularly a polynucleotide sequence referenced in NCBI Gene ID. 5106, more particularly GenBank Accession No. NP_015907 [and see for example SEQ ID NO. 16], or a fragment thereof.

In an aspect, a polynucleotide of the invention encodes CAP-G more particularly a polynucleotide sequence referenced in NCBI Gene ID. 822, more particularly GenBank Accession No. NP_001747 [and see for example SEQ ID NO. 18], or a fragment thereof.

In an aspect, a polynucleotide of the invention encodes PAEP more particularly a polynucleotide sequence referenced in NCBI Gene ID. 5047, more particularly GenBank Accession Nos. NM_001018049 or NM_00257 [and see for example SEQ ID NO. 20 or 21], or a fragment thereof.

Endometrial polynucleotide markers include complementary nucleic acid sequences, and nucleic acids that are substantially identical to these sequences (e.g. having at least about 45%, 50%, 55%, 60%, 65%, 70%, 75%, 80%, 85%, 90%, 95%, 97%, 98%, or 99% sequence identity).

Endometrial polynucleotide markers also include sequences that differ from a native sequence due to degeneracy in the genetic code. As one example, DNA sequence polymorphisms within the nucleotide sequence of an endometrial marker may result in silent mutations that do not affect the amino acid sequence. Variations in one or more nucleotides may exist among individuals within a population due to natural allelic variation. DNA sequence polymorphisms may also occur which lead to changes in the amino acid sequence of a polypeptide.

Endometrial polynucleotide markers also include nucleic acids that hybridize under stringent conditions, preferably high stringency conditions to an endometrial polynucleotide marker, in particular an endometrial cancer polynucleotide marker. Appropriate stringency conditions which promote DNA hybridization are known to those skilled in the art, or can be found in Current Protocols in Molecular Biology, John Wiley & Sons, N.Y. (1989), 6.3.1-6.3.6. For example, 6.0× sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

Endometrial polynucleotide markers also include truncated nucleic acids or nucleic acid fragments and variant forms of the nucleic acids that arise by alternative splicing of an mRNA corresponding to a DNA.

The endometrial polynucleotide markers are intended to include DNA and RNA (e.g. mRNA) and can be either double stranded or single stranded. A polynucleotide may, but need not, include additional coding or non-coding sequences, or it may, but need not, be linked to other molecules and/or carrier or support materials. The polynucleotides for use in the methods of the invention may be of any length suitable for a particular method. In certain applications the term refers to antisense polynucleotides (e.g. mRNA or DNA strand in the reverse orientation to sense cancer polynucleotide markers).

"Statistically different levels", "significantly altered levels", or "significant difference" in levels of markers in a patient sample compared to a control or standard (e.g. normal levels or levels in other samples from a patient) may represent levels that are higher or lower than the standard error of the detection assay. In particular embodiments, the levels may be 1.5, 2, 3, 4, 5, or 6 times higher or lower than the control or standard.

"Microarray" and "array," refer to nucleic acid or nucleotide arrays or protein or peptide arrays that can be used to detect biomolecules associated with endometrium or a phase thereof or endometrial disease, for instance to measure gene expression. A variety of arrays are made in research and manufacturing facilities worldwide, some of which are available commercially. By way of example, spotted arrays and in situ synthesized arrays are two kinds of nucleic acid arrays that differ in the manner in which the nucleic acid materials are placed onto the array substrate. A widely used in situ synthesized oligonucleotide array is GeneChip™ made by Affymetrix, Inc. Oligonucleotide probes that are 20- or 25-base long can be synthesized in silico on the array substrate. These arrays can achieve high densities (e.g., more than 40,000 genes per $cm^2$). Generally spotted arrays have lower densities, but the probes, typically partial cDNA molecules, are much longer than 20- or 25-mers. Examples of spotted cDNA arrays include LifeArray made by Incyte Genomics and DermArray made by IntegriDerm (or Invitrogen). Pre-synthesized and amplified cDNA sequences are attached to the substrate of spotted arrays. Protein and peptide arrays also are known (see for example, Zhu et al., *Science* 293:2101 (2001).

"Binding agent" refers to a substance such as a polypeptide or antibody that specifically binds to one or more endometrial markers. A substance "specifically binds" to one or more endometrial markers if is reacts at a detectable level with one or more endometrial markers, and does not react detectably with peptides containing an unrelated or different sequence. Binding properties may be assessed using an ELISA, which may be readily performed by those skilled in the art (see for example, Newton et al, Develop. Dynamics 197: 1-13, 1993).

A binding agent may be a ribosome, with or without a peptide component, an aptamer, an RNA molecule, or a polypeptide. A binding agent may be a polypeptide that comprises one or more endometrial marker sequence, a peptide variant thereof, or a non-peptide mimetic of such a sequence. By way of example, a WFDC2 sequence may be a peptide portion of a WFDC2 that is capable of modulating a function mediated by WFDC2.

An aptamer includes a DNA or RNA molecule that binds to nucleic acids and proteins. An aptamer that binds to a protein (or binding domain) of an endometrial marker or an endometrial polynucleotide marker can be produced using conventional techniques, without undue experimentation. (For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)).

Antibodies for use in the present invention include but are not limited to monoclonal or polyclonal antibodies, immunologically active fragments (e.g. a Fab or (Fab)$_2$ fragments), antibody heavy chains, humanized antibodies, antibody light chains, genetically engineered single chain $F_v$ molecules (Ladner et al, U.S. Pat. No. 4,946,778), chimeric antibodies, for example, antibodies which contain the binding specificity of murine antibodies, but in which the remaining portions are of human origin, or derivatives, such as enzyme conjugates or labeled derivatives.

Antibodies including monoclonal and polyclonal antibodies, fragments and chimeras, may be prepared using methods known to those skilled in the art. Isolated native or recombinant endometrial markers may be utilized to prepare antibodies. (See, for example, Kohler et al. (1975) Nature 256:495-497; Kozbor et al. (1985) J. Immunol Methods 81:31-42; Cote et al. (1983) Proc Natl Acad Sci 80:2026-2030; and Cole et al. (1984) Mol Cell Biol 62:109-120 for the preparation of monoclonal antibodies; Huse et al. (1989) Science 246:1275-1281 for the preparation of monoclonal Fab fragments; and, Pound (1998) Immunochemical Protocols, Humana Press, Totowa, N.J. for the preparation of phagemid or B-lymphocyte immunoglobulin libraries to identify antibodies). Antibodies specific for an endometrial marker may also be obtained from scientific or commercial sources.

In an embodiment of the invention, antibodies are reactive against an endometrial marker if they bind with a $K_a$ of greater than or equal to $10^{-7}$ M.

Markers

The invention provides a set of markers correlated with endometrium or phase thereof, or endometrial disease. In an aspect, the invention provides a set of markers identified as useful for detection, diagnosis, prevention and therapy of endometrial disease comprising or consisting of one or more of the markers listed in Table 1. In another aspect, the invention provides the endometrial marker WFDC2 and optionally markers in Table 2 for detection and diagnosis of an endometrium phase. The invention also provides a method of using endometrial markers listed in Table 1, and optionally in Table 2, to distinguish an endometrium phase or to distinguish endometrial disease.

In an embodiment, the markers comprise or consist of WAP four-disulfide core domain 2 (WFDC2), mucin 5B, and/or clusterin.

In an embodiment, the markers comprise or consist of WAP four-disulfide core domain 2 (WFDC2), mucin 5B, and clusterin.

In an embodiment, the markers comprise or consist of mucin 5B and/or clusterin

In an embodiment, the markers comprise or consist of WAP four-disulfide core domain 2 (WFDC2), mucin 5B, clusterin, and/or progestagen-associated endometrial protein (PAEP or PP14).

In an embodiment, the markers comprise or consist of WAP four-disulfide core domain 2 (WFDC2), mucin 5B, clusterin, and progestagen-associated endometrial protein (PAEP or PP14).

In an embodiment, the markers comprise or consist of mucin 5B, clusterin, and progestagen-associated endometrial protein (PAEP or PP14).

In an embodiment, the markers comprise or consist of WAP four-disulfide core domain 2 (WFDC2), mucin 5B, clusterin, LAP3 and CAP-G.

In an embodiment, the markers comprise or consist of mucin 5B, clusterin, LAP3 and CAP-G.

In an embodiment, the markers comprise or consist of LAP3 and CAP-G.

In an embodiment, the markers comprise or consist of WFDC2, clusterin, mucin 5B, pyruvate kinase M1/M2 (PK), chaperonin 10 (Cpn10) and α-1-antitrypsin (ATT) and optionally 2, 3, 4 or more other markers listed in Table 1 and Table 2.

In an embodiment, the markers comprise or consist of clusterin, mucin 5B, pyruvate kinase M1/M2 (PK), chaperonin 10 (Cpn10) and α-1-antitrypsin (ATT) and optionally 2, 3, 4 or more other markers listed in Table 1 and Table 2.

In an embodiment, the markers comprise or consist of WFDC2, clusterin, mucin 5B, pyruvate kinase M1/M2 (PK), chaperonin 10 (Cpn10), α-1-antitrypsin, polymeric-immunoglobulin receptor (PIGR), macrophage migration inhibitory factor (MIF), creatine kinase B chain (CKB), and/or progestagen-associated endometrial protein (PAEP or PP14).

In an embodiment, the markers comprise or consist of clusterin, mucin 5B, pyruvate kinase M1/M2 (PK), chaperonin 10 (Cpn10), α-1-antitrypsin, polymeric-immunoglobulin receptor (PIGR), macrophage migration inhibitory factor (MIF), creatine kinase (CKB), and/or progestagen-associated endometrial protein (PAEP or PP14).

In embodiments of the invention, a marker is provided which is selected from the group consisting of the polypeptides set forth in Table 1 which polypeptides are up-regulated biomarkers in endometrial cancer and optionally at least 2, 3, 4, 5, 6, 7, 8, 9, or 10 polypeptides set forth in Table 2 which polypeptides are up-regulated biomarkers in endometrial cancer.

In embodiments of the invention, a marker is provided which is selected from the group consisting of mucin 5B in Table 1 and at least 2, 3, 4, 5, 6, 7, 8, 9, or 10 polypeptides set forth in Table 2 which polypeptides are down-regulated biomarkers in endometrial cancer.

The invention provides marker sets that distinguish endometrium phase or endometrial disease and uses therefor. In an aspect, the invention provides a method for classifying an endometrium phase or endometrial disease comprising detecting a difference in the expression of a first plurality of endometrial markers or endometrial polynucleotide markers relative to a control, the first plurality of endometrial markers or endometrial polynucleotide markers comprising or consisting of at least 2, 3, 4, or 5 of the markers listed in Table 1. In specific aspects, the plurality of markers consists of WFDC2, clusterin, and mucin 5B and at least 5 to 10 of the markers listed in Table 2. In specific aspects, a control comprises markers derived from a pool of samples from individual patients with no endometrial disease, or individuals with a known endometrium phase.

Any of the markers provided herein may be used alone or with other markers of endometrium phase or endometrial disease, or with markers for other phenotypes or conditions.

Detection Methods

A variety of methods can be employed for the diagnostic and prognostic evaluation of endometrial disease or endometrial status involving one or more endometrial markers and polynucleotides encoding the markers, and the identification of subjects with a predisposition to endometrial diseases or that are receptive to in vitro fertilization and embryo transfer procedures. Such methods may, for example, utilize endometrial polynucleotide markers, and fragments thereof, and binding agents (e.g. antibodies) against one or more endometrial markers, including peptide fragments. In particular, the polynucleotides and antibodies may be used, for example, for (1) the detection of the presence of endometrial polynucleotide marker mutations, or the detection of either over- or under-expression of endometrial marker mRNA relative to a non-disorder state or different endometrium phase, or the qualitative or quantitative detection of alternatively spliced forms of endometrial polynucleotide marker transcripts which may correlate with certain conditions or susceptibility toward such conditions; and (2) the detection of either an over- or an under-abundance of one or more endometrial markers relative to a non-disorder state or a different endometrium phase or the presence of a modified (e.g., less than full length) endometrial marker which correlates with a disorder state or a progression toward a disorder state, or a particular endometrium phase.

The invention contemplates a method for detecting the phase of an endometrial tissue, in particular a secretory endometrial tissue, comprising producing a profile of levels of one or more endometrial marker associated with a known endometrium phase and/or polynucleotides encoding the markers, and optionally other markers associated with the endometrium phase in cells from a patient, and comparing the profile with a reference to identify a profile for the test cells indicative of the endometrium phase. In an aspect, the endometrial markers comprise WFDC2, and optionally one or more of glutamate receptor subunit zeta 1, macrophage migration inhibitory factor, FRAT1, myosin light chain kinase 2, tropomyosin 1 alpha chain, or fragments thereof.

The invention also contemplates a method for detecting an endometrial disease, in particular an endometrial cancer, comprising producing a profile of levels of one or more endometrial marker associated with an endometrial disease and/or polynucleotides encoding the markers, and other markers associated with endometrial disease in cells from a patient, and comparing the profile with a reference to identify a profile for the test cells indicative of disease. In an aspect, the endometrial markers are one or more of WFDC2, clusterin, and/or mucin 5B and optionally one or more of LAP3, CAP-G, PAEP, chaperonin 10, calgranulin A, calgranulin B, polymeric-immunoglobulin receptor (precursor), phosphatidylethanolamine-binding protein, acidic leucine-rich nuclear phosphoprotein 32 family member A, heat shock 70 kDa protein 6, macrophage migration inhibitory factor, calgizzarin (S100C protein), triosephosphate isomerase, alpha-1-antitrypsin precursor, creatine kinase B chain, (B-CK), pyruvate, M1 or M2 isozyme, transgelin (smooth muscle protein 22-alpha), and heterologous nuclear ribonucleoprotein D0.

The methods described herein may be used to evaluate the probability of the presence of malignant or pre-malignant cells, for example, in a group of cells freshly removed from a host. Such methods can be used to detect tumors, quantitate their growth, and help in the diagnosis and prognosis of endometrial disease. The methods can be used to detect the presence of cancer metastasis, as well as confirm the absence or removal of all tumor tissue following surgery, cancer chemotherapy, and/or radiation therapy. They can further be used to monitor cancer chemotherapy and tumor reappearance.

The methods described herein can be adapted for diagnosing and monitoring endometrial tissue status or an endometrial disease by detecting one or more endometrial markers or polynucleotides encoding the markers in biological samples from a subject. These applications require that the amount of markers or polynucleotides quantitated in a sample from a subject being tested be compared to a predetermined standard or cut-off value. The standard may correspond to levels quantitated for another sample or an earlier sample from the subject, or levels quantitated for a control sample. Levels for control samples from healthy subjects, different endometrial tissue phases, or subjects with an endometrial disease may be established by prospective and/or retrospective statistical studies. Healthy subjects who have no clinically evident disease or abnormalities may be selected for statistical studies. Diagnosis may be made by a finding of statistically different levels of detected endometrial markers associated with disease or polynucleotides encoding same, compared to a control sample or previous levels quantitated for the same subject.

The methods described herein may also use multiple markers for an endometrial disease, in particular endometrial cancer. Therefore, the invention contemplates a method for analyzing a biological sample for the presence of one or more endometrial markers and polynucleotides encoding the markers, and other markers that are specific indicators of an endometrial disease. The methods described herein may be modified by including reagents to detect the additional markers, or polynucleotides for the markers.

Nucleic Acid Methods/Assays

As noted herein an endometrial disease or phase may be detected based on the level of endometrial polynucleotide markers in a sample. Techniques for detecting polynucleotides such as polymerase chain reaction (PCR) and hybridization assays are well known in the art.

Probes may be used in hybridization techniques to detect endometrial polynucleotide markers. The technique generally involves contacting and incubating nucleic acids (e.g. recombinant DNA molecules, cloned genes) obtained from a sample from a patient or other cellular source with a probe under conditions favorable for the specific annealing of the probes to complementary sequences in the nucleic acids. After incubation, the non-annealed nucleic acids are removed, and the presence of nucleic acids that have hybridized to the probe if any are detected.

Nucleotide probes for use in the detection of nucleic acid sequences in samples may be constructed using conventional methods known in the art. Suitable probes may be based on nucleic acid sequences encoding at least 5 sequential amino acids from regions of an endometrial polynucleotide marker, preferably they comprise 10-200, more particularly 10-30, 10-40, 20-50, 40-80, 50-150, 80-120 nucleotides in length.

The probes may comprise DNA or DNA mimics (e.g., derivatives and analogues) corresponding to a portion of an organism's genome, or complementary RNA or RNA mimics. Mimics are polymers comprising subunits capable of specific, Watson-Crick-like hybridization with DNA, or of specific hybridization with RNA. The nucleic acids can be modified at the base moiety, at the sugar moiety, or at the phosphate backbone.

DNA can be obtained using standard methods such as polymerase chain reaction (PCR) amplification of genomic DNA or cloned sequences. (See, for example, in Innis et al., eds., 1990, PCR Protocols: A Guide to Methods and Applications, Academic Press Inc., San Diego, Calif.). Computer programs known in the art can be used to design primers with the required specificity and optimal amplification properties, such as Oligo version 5.0 (National Biosciences). Controlled robotic systems may be useful for isolating and amplifying nucleic acids.

A nucleotide probe may be labeled with a detectable substance such as a radioactive label that provides for an adequate signal and has sufficient half-life such as $^{32}P$, $^{3}H$, $^{14}C$ or the like. Other detectable substances that may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect endometrial polynucleotide markers, preferably in human cells. The nucleotide probes may also be useful in the diagnosis of an endometrial disease involving one or more endometrial polynucleotide markers, in monitoring the progression of such disorder, or monitoring a therapeutic treatment.

The detection of endometrial polynucleotide markers may involve the amplification of specific gene sequences using an amplification method such as polymerase chain reaction (PCR), followed by the analysis of the amplified molecules using techniques known to those skilled in the art. Suitable primers can be routinely designed by one of skill in the art.

By way of example, at least two oligonucleotide primers may be employed in a PCR based assay to amplify a portion of a polynucleotide encoding one or more endometrial marker derived from a sample, wherein at least one of the oligonucleotide primers is specific for (i.e. hybridizes to) a polynucleotide encoding the endometrial marker. The amplified cDNA is then separated and detected using techniques well known in the art, such as gel electrophoresis.

In order to maximize hybridization under assay conditions, primers and probes employed in the methods of the invention generally have at least about 60%, preferably at least about 75%, and more preferably at least about 90% identity to a portion of a polynucleotide encoding an endometrial marker; that is, they are at least 10 nucleotides, and preferably at least 20 nucleotides in length. In an embodiment the primers and probes are at least about 10-40 nucleotides in length.

Hybridization and amplification techniques described herein may be used to assay qualitative and quantitative aspects of endometrial polynucleotide marker expression. For example, RNA may be isolated from a cell type or tissue known to express an endometrial polynucleotide marker and tested utilizing the hybridization (e.g. standard Northern analyses) or PCR techniques referred to herein.

The primers and probes may be used in the above-described methods in situ i.e directly on tissue sections (fixed and/or frozen) of patient tissue obtained from biopsies or resections.

In an aspect of the invention, a method is provided employing reverse transcriptase-polymerase chain reaction (RT-PCR), in which PCR is applied in combination with reverse transcription. Generally, RNA is extracted from a sample tissue using standard techniques (for example, guanidine isothiocyanate extraction as described by Chomcynski and Sacchi, Anal. Biochem. 162:156-159, 1987) and is reverse transcribed to produce cDNA. The cDNA is used as a template for a polymerase chain reaction. The cDNA is hybridized to a set of primers, at least one of which is specifically designed against an endometrial marker sequence. Once the primer and template have annealed a DNA polymerase is employed to extend from the primer, to synthesize a copy of the template. The DNA strands are denatured, and the procedure is repeated many times until sufficient DNA is generated to allow visualization by ethidium bromide staining and agarose gel electrophoresis.

Amplification may be performed on samples obtained from a subject with a suspected endometrial disease and an individual who is not afflicted with an endometrial disease. The reaction may be performed on several dilutions of cDNA spanning at least two orders of magnitude. A statistically significant difference in expression in several dilutions of the subject sample as compared to the same dilutions of the non-disease sample may be considered positive for the presence of an endometrial disease.

In an embodiment, the invention provides methods for determining the presence or absence of an endometrial disease in a subject comprising (a) contacting a sample obtained from the subject with oligonucleotides that hybridize to endometrial polynucleotide markers; and (b) detecting in the sample a level of nucleic acids that hybridize to the polynucleotides relative to a predetermined cut-off value, and therefrom determining the presence or absence of an endometrial disease in the subject. In an aspect, the endometrial disease is cancer and the endometrial markers are one or more of WFDC2, clusterin, and mucin 5B and optionally one or more of LAP3, CAP-G, PAEP, chaperonin 10, calgranulin A, calgranulin B, polymeric-immunoglobulin receptor (precursor), phosphatidylethanolamine-binding protein, acidic leucine-rich nuclear phosphoprotein 32 family member A, heat shock 70 kDa protein 6, macrophage migration inhibitory factor, calgizzarin (S100C protein), triosephosphate isomerase, alpha-1-antitrypsin precursor, creatine kinase B chain, (B-CK), pyruvate, M1 or M2 isozyme, transgelin (smooth muscle protein 22-alpha), and heterologous nuclear ribonucleoprotein D0. In an embodiment, the endometrial disease is cancer and the endometrial markers are one or more of WFDC2, clusterin, and mucin 5B and optionally one or more of chaperonin 10, polymeric-immunoglobulin receptor (precursor), macrophage migration inhibitory factor, alpha-1-antitrypsin, creatine kinase B chain, (B-CK), and pyruvate kinase M1 or M2 isozyme. In another embodiment, the endometrial disease is cancer and the endometrial markers are one or more of WFDC2, clusterin, mucin 5B, LAP3 and/or CAP-G, PAEP, and optionally one or more of chaperonin 10, polymeric-immunoglobulin receptor (precursor), macrophage migration inhibitory factor, alpha-1-antitrypsin, creatine kinase B chain, (B-CK), and pyruvate kinase M1 or M2 isozyme. In another embodiment, the endometrial disease is cancer and the endometrial markers are WFDC2, clusterin, and mucin 5B, and optionally one or more of chaperonin 10, polymeric-immunoglobulin receptor (precursor), macrophage migration inhibitory factor, alpha-1-antitrypsin, creatine kinase B chain, (B-CK), and pyruvate kinase M1 or M2 isozyme. In another embodiment, the endometrial disease is cancer and the endometrial markers are WFDC2, clusterin, mucin 5B, chaperonin 10, alpha-1-antitrypsin, and pyruvate kinase M1 or M2 isozyme.

In another embodiment, the invention provides methods for determining uterine receptivity of a subject to in vitro fertilization comprising (a) contacting a sample obtained from the subject with oligonucleotides that hybridize to endometrial polynucleotide markers associated with an endometrial tissue phase (e.g. secretory phase); and (b) detecting in the sample a level of nucleic acids that hybridize to the polynucleotides relative to a predetermined cut-off value, wherein the presence or absence of the endometrial marker polynucleotides as compared to non-receptive controls indicates uterine receptivity. In an aspect, the endometrial markers are WFDC2 and optionally one or more of glutamate receptor subunit zeta 1, macrophage migration inhibitory factor, FRAT1, myosin light chain kinase 2, tropomyosin 1 alpha chain, or fragments thereof.

The invention provides a method wherein an endometrial marker mRNA is detected by (a) isolating mRNA from a sample and combining the mRNA with reagents to convert it to cDNA; (b) treating the converted cDNA with amplification reaction reagents and nucleic acid primers that hybridize to one or more endometrial marker polynucleotides, to produce amplification products; (d) analyzing the amplification products to detect amounts of mRNA encoding endometrial polynucleotide markers; and (e) comparing the amount of mRNA to an amount detected against a panel of expected values for normal and malignant tissue derived using similar nucleic acid primers.

Endometrial cancer marker-positive samples or alternatively higher levels in patients compared to a control (e.g. non-cancerous tissue) may be indicative of late stage disease, and/or that the patient is not responsive to chemotherapy. Alternatively, negative samples or lower levels compared to a control (e.g. non-cancerous tissue or negative samples) may be indicative of progressive disease and shorter overall survival.

In another embodiment, the invention provides methods for determining the presence or absence of endometrial cancer in a subject comprising (a) contacting a sample obtained from the subject with oligonucleotides that hybridize to one or more endometrial cancer polynucleotide markers; and (b) detecting in the sample levels of nucleic acids that hybridize to the polynucleotides relative to a predetermined cut-off value, and therefrom determining the presence or absence of endometrial cancer in the subject. In an embodiment, the endometrial cancer polynucleotide markers encode one or more polypeptides listed in Table 1. In particular, the endometrial markers are one or more of WFDC2, clusterin, mucin 5B, LAP3, CAP-G, and/or PAEP, and optionally one or more of chaperonin 10, calgranulin A, calgranulin B, polymeric-immunoglobulin receptor (precursor), phosphatidylethanolamine-binding protein, acidic leucine-rich nuclear phosphoprotein 32 family member A, heat shock 70 kDa protein 6, macrophage migration inhibitory factor, calgizzarin (S100C protein), triosephosphate isomerase, alpha-1-antitrypsin precursor, creatine kinase B chain, (B-CK), pyruvate, M1 or M2 isozyme, transgelin (smooth muscle protein 22-alpha), and heterologous nuclear ribonucleoprotein D0, or fragments thereof.

In particular, the invention provides a method wherein WFDC2, clusterin, and/or mucin 5B mRNA is detected by (a) isolating mRNA from a sample and combining the mRNA with reagents to convert it to cDNA; (b) treating the converted cDNA with amplification reaction reagents and nucleic acid primers that hybridize to a polynucleotide encoding WFDC2, clusterin, and/or mucin 5B, to produce amplification products; (d) analyzing the amplification products to detect an amount of mRNA encoding WFDC2, clusterin, and/or mucin 5B; and (e) comparing the amount of mRNA to an amount detected against a panel of expected values for normal and malignant tissue derived using similar nucleic acid primers.

Endometrial cancer marker-positive samples or alternatively higher levels, in particular significantly higher levels of WFDC2 and/or clusterin polynucleotides in patients compared to a control (e.g. normal or benign) are indicative of endometrial cancer. Negative samples or lower levels (e.g., of mucin 5B polynucleotides) compared to a control (e.g. normal or benign) may also be indicative of progressive disease and poor overall survival.

Oligonucleotides or longer fragments derived from an endometrial cancer polynucleotide marker may be used as targets in a microarray. The microarray can be used to simultaneously monitor the expression levels of large numbers of genes and to identify genetic variants, mutations, and polymorphisms. The information from the microarray may be used to determine gene function, to understand the genetic basis of a disorder, to diagnose a disorder, and to develop and monitor the activities of therapeutic agents.

The preparation, use, and analysis of microarrays are well known to a person skilled in the art. (See, for example, Brennan, T. M. et al. (1995) U.S. Pat. No. 5,474,796; Schena, et al. (1996) Proc. Natl. Acad. Sci. 93:10614-10619; Baldeschweiler et al. (1995), PCT Application WO95/251116; Shalon, D. et al. (I 995) PCT application WO95/35505; Heller, R. A. et al. (1997) Proc. Natl. Acad. Sci. 94:2150-2155; and Heller, M. J. et al. (1997) U.S. Pat. No. 5,605,662.)

Thus, the invention also includes an array comprising one or more endometrial polynucleotide markers (in particular the markers listed in Table 1) and optionally other markers (e.g. markers listed in Table 2). The array can be used to assay expression of endometrial polynucleotide markers in the array. The invention allows the quantitation of expression of one or more endometrial polynucleotide markers.

Microarrays typically contain at separate sites nanomolar quantities of individual genes, cDNAs, or ESTs on a substrate (e.g. nitrocellulose or silicon plate), or photolithographically prepared glass substrate. The arrays are hybridized to cDNA probes using conventional techniques with gene-specific primer mixes. The target polynucleotides to be analyzed are isolated, amplified and labeled, typically with fluorescent labels, radiolabels or phosphorous label probes. After hybridization is completed, the array is inserted into the scanner, where patterns of hybridization are detected. Data are collected as light emitted from the labels incorporated into the target, which becomes bound to the probe array. Probes that completely match the target generally produce stronger signals than those that have mismatches. The sequence and position of each probe on the array are known, and thus by complementarity, the identity of the target nucleic acid applied to the probe array can be determined.

Microarrays are prepared by selecting polynucleotide probes and immobilizing them to a solid support or surface. The probes may comprise DNA sequences, RNA sequences, copolymer sequences of DNA and RNA, DNA and/or RNA analogues, or combinations thereof. The probe sequences may be full or partial fragments of genomic DNA, or they may be synthetic oligonucleotide sequences synthesized either enzymatically in vivo, enzymatically in vitro (e.g., by PCR), or non-enzymatically in vitro.

The probe or probes used in the methods of the invention can be immobilized to a solid support or surface which may be either porous or non-porous. For example, the probes can be attached to a nitrocellulose or nylon membrane or filter covalently at either the 3' or the 5' end of the polynucleotide probe. The solid support may be a glass or plastic surface. In an aspect of the invention, hybridization levels are measured to microarrays of probes consisting of a solid support on the surface of which are immobilized a population of polynucleotides, such as a population of DNA or DNA mimics, or, alternatively, a population of RNA or RNA mimics. A solid support may be a nonporous or, optionally, a porous material such as a gel.

In accordance with embodiments of the invention, a microarray is provided comprising a support or surface with an ordered array of hybridization sites or "probes" each representing one of the markers described herein. The microarrays can be addressable arrays, and in particular positionally addressable arrays. Each probe of the array is typically located at a known, predetermined position on the solid support such that the identity of each probe can be determined from its position in the array. In preferred embodiments, each probe is covalently attached to the solid support at a single site.

Microarrays used in the present invention are preferably (a) reproducible, allowing multiple copies of a given array to be produced and easily compared with each other; (b) made from materials that are stable under hybridization conditions; (c) small, (e.g., between 1 $cm^2$ and 25 $cm^2$, between 12 $cm^2$ and 13 $cm^2$, or 3 $cm^2$; and (d) comprise a unique set of binding sites that will specifically hybridize to the product of a single gene in a cell (e.g., to a specific mRNA, or to a specific cDNA derived therefrom). However, it will be appreciated that larger arrays may be used particularly in screening arrays, and other related or similar sequences will cross hybridize to a given binding site.

In accordance with an aspect of the invention, the microarray is an array in which each position represents one of the markers described herein (e.g. the markers listed in Table 1 and optionally Table 2). Each position of the array can comprise a DNA or DNA analogue based on genomic DNA to which a particular RNA or cDNA transcribed from a genetic marker can specifically hybridize. A DNA or DNA analogue can be a synthetic oligomer or a gene fragment. In an embodiment, probes representing each of the endometrial markers and endometrial polynucleotide markers is present on the array. In a preferred embodiment, the array comprises at least 5 of the endometrial polynucleotide markers.

Probes for the microarray can be synthesized using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 10 and about 500 bases, 20-100 bases, or 40-70 bases in length. Synthetic nucleic acid probes can include non-natural bases, such as, without limitation, inosine. Nucleic acid analogues such as peptide nucleic acid may be used as binding sites for hybridization. (see, e.g., Egholm et al., 1993, Nature 363:566-568; U.S. Pat. No. 5,539,083).

Probes can be selected using an algorithm that takes into account binding energies, base composition, sequence complexity, cross-hybridization binding energies, and secondary structure (see Friend et al., International Patent Publication WO 01/05935, published Jan. 25, 2001).

Positive control probes, (e.g., probes known to be complementary and hybridize to sequences in the target polynucleotides), and negative control probes, (e.g., probes known to not be complementary and hybridize to sequences in the target polynucleotides) are typically included on the array. Positive controls can be synthesized along the perimeter of the array or synthesized in diagonal stripes across the array. A reverse complement for each probe can be next to the position of the probe to serve as a negative control.

The probes can be attached to a solid support or surface, which may be made from glass, plastic (e.g., polypropylene, nylon), polyacrylamide, nitrocellulose, gel, or other porous or nonporous material. The probes can be printed on surfaces such as glass plates (see Schena et al., 1995, Science 270: 467-470). This method may be particularly useful for preparing microarrays of cDNA (See also, DeRisi et al., 1996, Nature Genetics 14:457-460; Shalon et al., 1996, Genome Res. 6:639-645; and Schena et al., 1995, Proc. Natl. Acad. Sci. U.S.A. 93:10539-11286).

High-density oligonucleotide arrays containing thousands of oligonucleotides complementary to defined sequences, at defined locations on a surface can be produced using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270) or other methods for rapid synthesis and deposition of defined oligonucleotides (Blanchard et al., Biosensors & Bioelectronics 11:687-690). Using these methods oligonucleotides (e.g., 60-mers) of known sequence are synthesized directly on a surface such as a derivatized glass slide. The array produced may be redundant, with several oligonucleotide molecules per RNA.

Microarrays can be made by other methods including masking (Maskos and Southern, 1992, Nuc. Acids. Res. 20:1679-1684). In an embodiment, microarrays of the present invention are produced by synthesizing polynucleotide probes on a support wherein the nucleotide probes are attached to the support covalently at either the 3' or the 5' end of the polynucleotide.

The invention provides microarrays comprising a disclosed marker set. In one embodiment, the invention provides a microarray for distinguishing endometrial disease samples comprising a positionally-addressable array of polynucleotide probes bound to a support, the polynucleotide probes comprising a plurality of polynucleotide probes of different nucleotide sequences, each of the different nucleotide sequences comprising a sequence complementary and hybridizable to a plurality of genes, the plurality consisting of at least 2, 3, 4, 5, or 6 of the genes corresponding to the markers listed in Table 1 and optionally at least 2 to 18, 5 to 16, or 10 to 15 of the genes corresponding to the markers listed in Table 2. An aspect of the invention provides microarrays comprising at least 4, 5, or 6 of the polynucleotides encoding the markers listed in Table 1.

The invention provides gene marker sets that distinguish endometrium phase or endometrial disease and uses therefor. In an aspect, the invention provides a method for classifying an endometrium phase or disease comprising detecting a difference in the expression of a first plurality of genes relative to a control, the first plurality of genes consisting of at least 3, 4, 5, or 6 of the genes encoding the markers listed in Table 1. In specific aspects, the plurality of genes consists of at least 4 or 5 of the genes encoding the markers listed in Table 1 and optionally at least 2 to 18, 5 to 16, or 10 to 15 of the genes corresponding to the markers listed in Table 2. In another specific aspect, the control comprises nucleic acids derived from a pool of samples from individual control patients.

The invention provides a method for classifying an endometrium phase or endometrial disease by calculating the similarity between the expression of at least 3, 4, 5, or 6 polynucleotides encoding markers listed in Table 1 in a sample to the expression of the same markers in a control pool, comprising the steps of:

(a) labeling nucleic acids derived from a sample, with a first fluorophore to obtain a first pool of fluorophore-labeled nucleic acids;

(b) labeling with a second fluorophore a first pool of nucleic acids derived from two or more endometrial disease samples, and a second pool of nucleic acids derived from two or more control samples;

(c) contacting the first fluorophore-labeled nucleic acid and the first pool of second fluorophore-labeled nucleic acid with a first microarray under conditions such that hybridization can occur, and contacting the first fluorophore-labeled nucleic acid and the second pool of second fluorophore-labeled nucleic acid with a second microarray under conditions such that hybridization can occur, detecting at each of a plurality of discrete loci on the first microarray a first flourescent emission signal from the first fluorophore-labeled nucleic acid and a second fluorescent emission signal from the first pool of second fluorophore-labeled genetic matter that is bound to the first microarray and detecting at each of the marker loci on the second microarray the first fluorescent emission signal from the first fluorophore-labeled nucleic acid and a third fluorescent emission signal from the second pool of second fluorophore-labeled nucleic acid;

(d) determining the similarity of the sample to patient and control pools by comparing the first fluorescence emission signals and the second fluorescence emission signals, and the first emission signals and the third fluorescence emission signals; and (e) classifying the sample as endometrial disease where the first fluorescence emission signals are more similar to the second fluorescence emission signals than to the third fluorescent emission signals, and classifying the sample as non-endometrial disease where the first fluorescence emission signals are more similar to the third fluorescence emission signals than to the second fluorescent emission signals, wherein the first microarray and the second microarray are similar to each other, exact replicas of each other, or are identical, and wherein the similarity is defined by a statistical method such that the cell sample and control are similar where the p value of the similarity is less than 0.01.

In aspects of the invention, the array can be used to monitor the time course of expression of one or more endometrial polynucleotide markers in the array. This can occur in various biological contexts such as tumor progression.

The array is also useful for ascertaining differential expression patterns of endometrial polynucleotide markers, and optionally other markers, in normal and abnormal cells. This may provide a battery of nucleic acids that could serve as molecular targets for diagnosis or therapeutic intervention.

Protein Methods

Binding agents may be used for a variety of diagnostic and assay applications. There are a variety of assay formats known to the skilled artisan for using a binding agent to detect a target molecule in a sample. (For example, see Harlow and Lane, Antibodies: A Laboratory Manual, Cold Spring Harbor Laboratory, 1988). In general, the presence or absence of an endometrial disease (e.g. cancer) or an endometrium phase in a subject may be determined by (a) contacting a sample from the subject with a binding agent; (b) detecting in the sample a level of polypeptide that binds to the binding agent; and (c) comparing the level of polypeptide with a predetermined standard or cut-off value.

In particular embodiments of the invention, the binding agent is an antibody. Antibodies specifically reactive with one or more endometrial marker, or derivatives, such as enzyme conjugates or labeled derivatives, may be used to detect one or more endometrial marker in various samples (e.g. biological materials). They may be used as diagnostic or prognostic reagents and they may be used to detect abnormalities in the level of expression of one or more endometrial marker, or abnormalities in the structure, and/or temporal, tissue, cellular, or subcellular location of one or more endometrial marker. Antibodies may also be used to screen potentially therapeutic compounds in vitro to determine their effects on disorders (e.g. endometrial cancer) involving one or more endometrial markers, and other conditions. In vitro immunoassays may also be used to assess or monitor the efficacy of particular therapies.

In an aspect, the invention provides a method for monitoring or diagnosing an endometrial disease (e.g. cancer) in a subject by quantitating one or more endometrial markers in a biological sample from the subject comprising reacting the sample with antibodies specific for one or more endometrial markers, which are directly or indirectly labeled with detectable substances and detecting the detectable substances. In a particular embodiment of the invention, endometrial markers are quantitated or measured.

In an aspect of the invention, a method for detecting an endometrial disease (e.g. cancer) is provided comprising:
(a) obtaining a sample suspected of containing one or more endometrial markers associated with an endometrial disease;
(b) contacting said sample with antibodies that specifically bind to the endometrial markers under conditions effective to bind the antibodies and form complexes;
(c) measuring the amount of endometrial markers present in the sample by quantitating the amount of the complexes; and
(d) comparing the amount of endometrial markers present in the samples with the amount of endometrial markers in a control, wherein a change or significant difference in the amount of endometrial markers in the sample compared with the amount in the control is indicative of an endometrial disease.

In an embodiment, the invention contemplates a method for monitoring the progression of an endometrial disease (e.g. cancer) in an individual, comprising:
(a) contacting antibodies which bind to one or more endometrial markers with a sample from the individual so as to form complexes comprising the antibodies and one or more endometrial markers in the sample;
(b) determining or detecting the presence or amount of complex formation in the sample;
(c) repeating steps (a) and (b) at a point later in time; and
(d) comparing the result of step (b) with the result of step (c), wherein a difference in the amount of complex formation is indicative of disease, disease stage, and/or progression of the disease in said individual.

The amount of complexes may also be compared to a value representative of the amount of the complexes from an individual not at risk of, or afflicted with, an endometrial disease at different stages. A significant difference in complex formation may be indicative of advanced disease e.g. advanced endometrial cancer, or an unfavourable prognosis.

In aspects of the invention for diagnosis and monitoring of endometrial cancer, the endometrial markers are one or more of WFDC2, clusterin, mucin 5B, LAP3, CAP-G, and PAEP, more particularly WFDC2, clusterin, and/or mucin 5B, and optionally one or more of chaperonin 10, calgranulin A, calgranulin B, polymeric-immunoglobulin receptor (precursor), phosphatidylethanolamine-binding protein, acidic leucine-rich nuclear phosphoprotein 32 family member A, heat shock 70 kDa protein 6, macrophage migration inhibitory factor, calgizzarin (S100C protein), triosephosphate isomerase, alpha-1-antitrypsin precursor, creatine kinase B chain, (B-CK), pyruvate kinase M1 or M2 isozyme, transgelin (smooth muscle protein 22-alpha), and heterologous nuclear ribonucleoprotein D0, more particularly chaperonin 10, alpha-1-antitrypsin precursor and pyruvate kinase M1 or M2 isozyme, or fragments thereof.

In embodiments of the methods of the invention, WFDC2 and/or clusterin is detected in samples and higher levels, in particular significantly higher levels compared to a control (normal or benign) is indicative of endometrial cancer.

In aspects of the invention for characterizing endometrium phase the endometrial markers comprise WFDC2 and one or more of glutamate receptor subunit zeta 1, macrophage migration inhibitory factor, FRAT1, myosin light chain kinase 2, tropomyosin 1 alpha chain, and fragments thereof.

In another embodiment, the invention provides methods for determining uterine receptivity of a subject to in vitro fertilization comprising (a) contacting a sample obtained from the subject with antibodies that bind to one or more endometrial marker associated with a certain endometrium phase (e.g. secretory phase); and (b) detecting in the sample a level of endometrial marker relative to a predetermined cut-off value, wherein the presence or absence of the endometrial marker as compared to non-receptive controls indicates uterine receptivity. In a particular embodiment, the markers comprise WFDC2, clusterin, and/or mucin 5B and optionally one or more of glutamate receptor subunit zeta 1, macrophage migration inhibitory factor, FRAT1, myosin light chain kinase 2, tropomyosin 1 alpha chain, and fragments thereof, more particularly WFDC2, glutamate receptor subunit zeta 1 or a fragment thereof, and/or macrophage migration inhibitory factor.

Antibodies may be used in any known immunoassays that rely on the binding interaction between antigenic determinants of one or more endometrial marker and the antibodies.

Immunoassay procedures for in vitro detection of antigens in fluid samples are also well known in the art. [See for example, Paterson et al., Int. J. Can. 37:659 (1986) and Burchell et al., Int. J. Can. 34:763 (1984) for a general description of immunoassay procedures]. Qualitative and/or quantitative determinations of one or more endometrial marker in a sample may be accomplished by competitive or non-competitive immunoassay procedures in either a direct or indirect format. Detection of one or more endometrial marker using antibodies can be done utilizing immunoassays which are run in either the forward, reverse or simultaneous modes. Examples of immunoassays are radioimmunoassays (RIA), enzyme immunoassays (e.g. ELISA), immunofluorescence, immunoprecipitation, latex agglutination, hemagglutination, histochemical tests, and sandwich (immunometric) assays. These terms are well understood by those skilled in the art. A person skilled in the art will know, or can readily discern, other immunoassay formats without undue experimentation.

According to an embodiment of the invention, an immunoassay for detecting one or more endometrial markers in a biological sample comprises contacting binding agents that specifically bind to endometrial markers in the sample under conditions that allow the formation of first complexes comprising a binding agent and endometrial markers and determining the presence or amount of the complexes as a measure of the amount of endometrial markers contained in the sample. In a particular embodiment, the binding agents are labeled differently or are capable of binding to different labels.

Antibodies may be used to detect and quantify one or more endometrial markers in a sample in order to diagnose and treat pathological states. In particular, the antibodies may be used in immunohistochemical analyses, for example, at the cellular and sub-subcellular level, to detect one or more endometrial markers, to localize them to particular endometrial cells and tissues (e.g. tumor cells and tissues), and to specific subcellular locations, and to quantitate the level of expression.

Immunohistochemical methods for the detection of antigens in tissue samples are well known in the art. For example, immunohistochemical methods are described in Taylor, Arch. Pathol. Lab. Med. 102:112 (1978). Briefly, in the context of the present invention, a tissue sample obtained from a subject suspected of having an endometrial-related problem is contacted with antibodies, preferably monoclonal antibodies recognizing one or more endometrial markers. The site at which the antibodies are bound is determined by selective staining of the sample by standard immunohistochemical procedures. The same procedure may be repeated on the same sample using other antibodies that recognize one or more endometrial markers. Alternatively, a sample may be contacted with antibodies against one or more endometrial markers simultaneously, provided that the antibodies are labeled differently or are able to bind to a different label. The tissue sample may be normal endometrial tissue, a cancer tissue or a benign tissue.

An antibody microarray in which binding sites comprise immobilized, preferably monoclonal, antibodies specific to a substantial fraction of marker-derived endometrial markers of interest can be utilized in the present invention. Antibody arrays can be prepared using methods known in the art [(see for example, Zhu et al., Science 293:2101 (2001) and reference 20].

Antibodies specific for one or more endometrial marker may be labelled with a detectable substance and localised in biological samples based upon the presence of the detectable substance. Examples of detectable substances include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or colorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

One of the ways an antibody can be detectably labeled is to link it directly to an enzyme. The enzyme when later exposed to its substrate will produce a product that can be detected. Examples of detectable substances that are enzymes are horseradish peroxidase, beta-galactosidase, luciferase, alkaline phosphatase, acetylcholinesterase, malate dehydrogenase, ribonuclease, urease, catalase, glucose-6-phosphate, staphylococcal nuclease, delta-5-steroid isomerase, yeast alcohol dehydrogenase, alpha-glycerophosphate, triose phosphate isomerase, asparaginase, glucose oxidase, and acetylcholine esterase.

For increased sensitivity in an immunoassay system a fluorescence-emitting metal atom such as Eu (europium) and other lanthanides can be used. These can be attached to the desired molecule by means of metal-chelating groups such as DTPA or EDTA.

A bioluminescent compound may also be used as a detectable substance. Bioluminescence is a type of chemiluminescence found in biological systems where a catalytic protein increases the efficiency of the chemiluminescent reaction. The presence of a bioluminescent molecule is determined by detecting the presence of luminescence. Examples of bioluminescent detectable substances are luciferin, luciferase and aequorin.

Indirect methods may also be employed in which the primary antigen-antibody reaction is amplified by the introduction of a second antibody, having specificity for the antibody reactive against one or more endometrial markers. By way of example, if the antibody having specificity against one or more endometrial marker is a rabbit IgG antibody, the second antibody may be goat anti-rabbit gamma-globulin labelled with a detectable substance as described herein.

Methods for conjugating or labelling the antibodies discussed above may be readily accomplished by one of ordinary skill in the art. (See for example Inman, Methods In Enzymology, Vol. 34, Affinity Techniques, Enzyme Purification: Part B, Jakoby and Wichek (eds.), Academic Press, New York, p. 30, 1974; and Wilchek and Bayer, "The Avidin-Biotin Complex in Bioanalytical Applications," Anal. Biochem. 171:1-32, 1988 re methods for conjugating or labelling the antibodies with enzyme or ligand binding partner).

Cytochemical techniques known in the art for localizing antigens using light and electron microscopy may be used to detect one or more endometrial markers. Generally, antibodies may be labeled with detectable substances and one or more endometrial markers may be localised in tissues and cells based upon the presence of the detectable substances.

In the context of the methods of the invention, the sample, binding agents (e.g. antibodies specific for one or more endometrial markers), or one or more endometrial markers may be immobilized on a carrier or support. Examples of suitable carriers or supports are agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, etc. The support material may have any possible configuration including spherical (e.g. bead), cylindrical (e.g. inside surface of a test tube or well, or the external surface of a rod), or flat (e.g. sheet, test strip). Thus, the carrier may be in the shape of, for example, a tube, test plate, well, beads, disc, sphere, etc. The immobilized antibody may be prepared by reacting the material with a suitable insoluble carrier using known chemical or physical methods, for example, cyanogen bromide coupling. An antibody may be indirectly immobilized using a second antibody specific for the antibody. For example, mouse antibody specific for an endometrial marker may be immobilized using sheep anti-mouse IgG Fc fragment specific antibody coated on the carrier or support.

Where a radioactive label is used as a detectable substance, one or more endometrial marker may be localized by radioautography. The results of radioautography may be quantitated by determining the density of particles in the radioautographs by various optical methods, or by counting the grains.

Time-resolved fluorometry may be used to detect a signal. For example, the method described in Christopoulos T K and Diamandis E P Anal Chem 1992:64:342-346 may be used with a conventional time-resolved fluorometer.

In accordance with an embodiment of the invention, a method is provided wherein one or more endometrial marker antibodies are directly or indirectly labelled with enzymes, substrates for the enzymes are added wherein the substrates are selected so that the substrates, or a reaction product of an enzyme and substrate, form fluorescent complexes with a lanthanide metal (e.g. europium, terbium, samarium, and dysprosium, preferably europium and terbium). A lanthanide metal is added and one or more endometrial cancer markers are quantitated in the sample by measuring fluorescence of the fluorescent complexes. Enzymes are selected based on the ability of a substrate of the enzyme, or a reaction product of the enzyme and substrate, to complex with lanthanide metals such as europium and terbium. Suitable enzymes and substrates that provide fluorescent complexes are described in U.S. Pat. No. 5,3112,922 to Diamandis. Examples of suitable enzymes include alkaline phosphatase and β-galactosidase. Preferably, the enzyme is alkaline phosphatase.

Examples of enzymes and substrates for enzymes that provide such fluorescent complexes are described in U.S. Pat. No. 5,312,922 to Diamandis. By way of example, when the antibody is directly or indirectly labelled with alkaline phosphatase the substrate employed in the method may be 4-methylumbelliferyl phosphate, 5-fluorosalicyl phosphate, or diflunisal phosphate. The fluorescence intensity of the complexes is typically measured using a time-resolved fluorometer e.g. a CyberFluor 615 Immunoanalyzer (Nordion International, Kanata, Ontario).

One or more endometrial marker antibodies may also be indirectly labelled with an enzyme. For example, the antibodies may be conjugated to one partner of a ligand binding pair, and the enzyme may be coupled to the other partner of the ligand binding pair. Representative examples include avidin-biotin, and riboflavin-riboflavin binding protein. In an embodiment, the antibodies are biotinylated, and the enzyme is coupled to streptavidin. In another embodiment, an antibody specific for endometrial marker antibody is labeled with an enzyme.

In accordance with an embodiment, the present invention provides means for determining one or more endometrial markers in a sample by measuring one or more endometrial markers by immunoassay. It will be evident to a skilled artisan that a variety of immunoassay methods can be used to measure one or more endometrial markers. In general, an immunoassay method may be competitive or noncompetitive. Competitive methods typically employ an immobilized or immobilizable antibody to one or more endometrial marker and a labeled form of one or more endometrial marker. Sample endometrial markers and labeled endometrial markers compete for binding to antibodies to endometrial markers. After separation of the resulting labeled endometrial markers that have become bound to antibodies (bound fraction) from that which has remained unbound (unbound fraction), the amount of the label in either bound or unbound fraction is measured and may be correlated with the amount of endometrial markers in the test sample in any conventional manner, e.g., by comparison to a standard curve.

In an aspect, a non-competitive method is used for the determination of one or more endometrial markers, with the most common method being the "sandwich" method. In this assay, two antibodies to endometrial markers are employed. One of the antibodies to endometrial markers is directly or indirectly labeled (sometimes referred to as the "detection antibody") and the other is immobilized or immobilizable (sometimes referred to as the "capture antibody"). The capture and detection antibodies can be contacted simultaneously or sequentially with the test sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the liquid test mixture, and the label is measured in at least a portion of the separated capture antibody phase or the remainder of the liquid test mixture. Generally it is measured in the capture antibody phase since it comprises endometrial cancer markers bound by ("sandwiched" between) the capture and detection antibodies. In an embodiment, the label may be measured without separating the capture antibodies and liquid test mixture.

In a typical two-site immunometric assay for endometrial markers, one or both of the capture and detection antibodies are polyclonal antibodies or one or both of the capture and detection antibodies are monoclonal antibodies (i.e. polyclonal/polyclonal, monoclonal/monoclonal, or monoclonal/polyclonal). The label used in the detection antibody can be selected from any of those known conventionally in the art. The label may be an enzyme or a chemiluminescent moiety, but it can also be a radioactive isotope, a fluorophor, a detectable ligand (e.g., detectable by a secondary binding by a labeled binding partner for the ligand), and the like. In a particular aspect, the antibody is labelled with an enzyme which is detected by adding a substrate that is selected so that a reaction product of the enzyme and substrate forms fluorescent complexes. The capture antibody may be selected so that it provides a means for being separated from the remainder of the test mixture. Accordingly, the capture antibody can be introduced to the assay in an already immobilized or insoluble form, or can be in an immobilizable form, that is, a form which enables immobilization to be accomplished subsequent to introduction of the capture antibody to the assay.

An immobilized capture antibody may comprise an antibody covalently or noncovalently attached to a solid phase such as a magnetic particle, a latex particle, a microtiter plate well, a bead, a cuvette, or other reaction vessel. An example of an immobilizable capture antibody is antibody which has been chemically modified with a ligand moiety, e.g., a hapten, biotin, or the like, and which can be subsequently immobilized by contact with an immobilized form of a binding partner for the ligand, e.g., an antibody, avidin, or the like. In an embodiment, the capture antibody may be immobilized using a species specific antibody for the capture antibody that is bound to the solid phase.

The above-described immunoassay methods and formats are intended to be exemplary and are not limiting.

Computer Systems

Analytic methods contemplated herein can be implemented by use of computer systems and methods described below and known in the art. Thus, the invention provides computer readable media comprising one or more endometrial markers, and/or polynucleotides encoding one or more endometrial markers, and optionally other markers (e.g. markers of endometrial cancer). "Computer readable media" refers to any medium that can be read and accessed directly by a computer, including but not limited to magnetic storage media, such as floppy discs, hard disc storage medium, and magnetic tape; optical storage media such as CD-ROM; electrical storage media such as RAM and ROM; and hybrids of these categories such as magnetic/optical storage media. Thus, the invention contemplates computer readable medium having recorded thereon markers identified for patients and controls.

"Recorded" refers to a process for storing information on computer readable medium. The skilled artisan can readily adopt any of the presently known methods for recording information on computer readable medium to generate manufactures comprising information on one or more endometrial markers, and optionally other markers.

A variety of data processor programs and formats can be used to store information on one or more endometrial markers, and/or polynucleotides encoding one or more endometrial markers, and other markers on computer readable medium. For example, the information can be represented in a word processing text file, formatted in commercially-available software such as WordPerfect and MicroSoft Word, or represented in the form of an ASCII file, stored in a database application, such as DB2, Sybase, Oracle, or the like. Any number of dataprocessor structuring formats (e.g., text file or database) may be adapted in order to obtain computer readable medium having recorded thereon the marker information.

By providing the marker information in computer readable form, one can routinely access the information for a variety of purposes. For example, one skilled in the art can use the information in computer readable form to compare marker information obtained during or following therapy with the information stored within the data storage means.

The invention provides a medium for holding instructions for performing a method for determining uterine endometrial receptivity of a patient, or whether a patient has an endometrial disease (e.g. endometrial cancer) or a pre-disposition to an endometrial disease (e.g. cancer), comprising determining the presence or absence of one or more endometrial markers, and/or polynucleotides encoding one or more endometrial markers, and optionally other markers, and based on the presence or absence of the one or more endometrial markers, and/or polynucleotides encoding one or more endometrial markers, and optionally other markers, determining uterine endometrial receptivity, endometrial disease (e.g. cancer) or a pre-disposition to an endometrial disease (e.g. cancer), and optionally recommending a procedure or treatment.

The invention also provides in an electronic system and/or in a network, a method for determining uterine endometrial receptivity of a patient, whether a subject has an endometrial disease (e.g. cancer) or a pre-disposition to an endometrial disease (e.g. cancer), comprising determining the presence or absence of one or more endometrial markers, and/or polynucleotides encoding one or more endometrial markers, and optionally other markers (e.g. cancer markers), and based on the presence or absence of the one or more endometrial markers, and/or polynucleotides encoding one or more endometrial markers, and optionally other markers, determining the uterine endometrial receptivity of the patient, whether the subject has an endometrial disease (e.g. cancer) or a pre-disposition to an endometrial disease (e.g. cancer), and optionally recommending a procedure or treatment.

The invention further provides in a network, a method for determining whether a subject is receptive to in vitro fertilization, has an endometrial disease (e.g. cancer) or a pre-disposition to an endometrial disease (e.g. cancer) comprising: (a) receiving phenotypic information on the subject and information on one or more endometrial markers, and/or polynucleotides encoding one or more endometrial markers, and optionally other markers associated with samples from the subject; (b) acquiring information from the network corresponding to the one or more endometrial markers, and/or polynucleotides encoding one or more endometrial markers, and optionally other markers; and (c) based on the phenotypic information and information on the one or more endometrial markers, and/or polynucleotides encoding one or more endometrial markers, and optionally other markers, determining whether the subject is receptive to in vitro fertilization, has an endometrial disease (e.g. cancer) or a pre-disposition to an endometrial disease (e.g. cancer); and (d) optionally recommending a procedure or treatment.

The invention still further provides a system for identifying selected records that identify a diseased endometrial cell or tissue (e.g. cancer cell or tissue) or an endometrium phase. A system of the invention generally comprises a digital computer; a database server coupled to the computer; a database coupled to the database server having data stored therein, the data comprising records of data comprising one or more endometrial markers, and/or polynucleotides encoding one or more endometrial markers, and optionally other endometrial markers, and a code mechanism for applying queries based upon a desired selection criteria to the data file in the database to produce reports of records which match the desired selection criteria.

In an aspect of the invention a method is provided for detecting endometrial cancer tissue or cells using a computer having a processor, memory, display, and input/output devices, the method comprising the steps of:

(a) creating records of one or more endometrial cancer markers, and/or polynucleotides encoding one or more endometrial cancer markers, and optionally other markers of cancer identified in a sample suspected of containing endometrial cancer cells or tissue;

(b) providing a database comprising records of data comprising one or more endometrial cancer markers, and/or polynucleotides encoding one or more endometrial cancer markers, and optionally other markers of cancer; and (c) using a code mechanism for applying queries based upon a desired selection criteria to the data file in the database to produce reports of records of step (a) which provide a match of the desired selection criteria of the database of step (b) the presence of a match being a positive indication that the markers of step (a) have been isolated from cells or tissue that are endometrial cancer cells or tissue.

The invention contemplates a business method for determining whether a subject is receptive to in vitro fertilization, has an endometrial disease (e.g. cancer) or a pre-disposition to endometrial cancer comprising: (a) receiving phenotypic information on the subject and information on one or more endometrial markers, and/or polynucleotides encoding the markers, and optionally other markers, associated with samples from the subject; (b) acquiring information from a network corresponding to one or more endometrial markers, and/or polynucleotides encoding the markers, and optionally other markers; and (c) based on the phenotypic information, information on one or more endometrial markers, and/or polynucleotides encoding the markers, and optionally other markers, and acquired information, determining whether the subject is receptive to in vitro fertilization, has an endometrial disease (e.g. cancer) or a pre-disposition to an endometrial disease (e.g. cancer); and (d) optionally recommending a procedure or treatment.

In an aspect of the invention, the computer systems, components, and methods described herein are used to monitor disease or determine the stage of disease, or determine uterine endometrial receptivity.

Imaging Methods

Binding agents, in particular antibodies, specific for one or more endometrial markers may also be used in imaging methodologies in the management of an endometrial disease or determining uterine endometrial receptivity.

In an aspect, the invention provides a method for imaging tumors associated with one or more endometrial cancer markers.

The invention also contemplates imaging methods described herein using multiple markers for an endometrial disease or endometrium phase. Preferably each agent is labeled so that it can be distinguished during the imaging.

In an embodiment the method is an in vivo method and a subject or patient is administered one or more agents that carry an imaging label and that are capable of targeting or binding to one or more endometrial markers. The agent is allowed to incubate in vivo and bind to the endometrial markers associated with endometrial cells or tissues of a particular phase or associated with diseased cells or tissues, (e.g. an endometrial tumor). The presence of the label is localized to the endometrial cells or tissues, and the localized label is detected using imaging devices known to those skilled in the art.

The agent may be an antibody or chemical entity that recognizes the endometrial markers. In an aspect of the invention the agent is a polyclonal antibody or monoclonal antibody, or fragments thereof, or constructs thereof including but not limited to, single chain antibodies, bifunctional antibodies, molecular recognition units, and peptides or entities that mimic peptides. The antibodies specific for the endometrial markers used in the methods of the invention may be obtained from scientific or commercial sources, or isolated native endometrial markers or recombinant endometrial markers may be utilized to prepare antibodies etc. as described herein.

An agent may be a peptide that mimics the epitope for an antibody specific for an endometrial marker and binds to the marker. The peptide may be produced on a commercial synthesizer using conventional solid phase chemistry. By way of example, a peptide may be prepared that includes either tyrosine, lysine, or phenylalanine to which $N_2S_2$ chelate is complexed (See U.S. Pat. No. 4,897,255). An anti-endocrine marker peptide conjugate is then combined with a radiolabel (e.g. sodium $^{99m}$Tc pertechnetate or sodium $^{188}$Re perrhenate) and it may be used to locate an endometrial marker producing cell or tissue (e.g. tumor).

The agent carries a label to image the endometrial markers. The agent may be labelled for use in radionuclide imaging. In particular, the agent may be directly or indirectly labelled with a radioisotope. Examples of radioisotopes that may be used in the present invention are the following: $^{277}$Ac, $^{211}$At, $^{128}$Ba, $^{131}$Ba, $^{7}$Be, $^{204}$Bi, $^{205}$Bi, $^{206}$Bi, $^{76}$Br, $^{77}$Br, $^{82}$Br, $^{109}$Cd, $^{47}$Ca, $^{11}$C, $^{14}$C, $^{36}$Cl, $^{48}$Cr, $^{51}$Cr, $^{62}$Cu, $^{64}$Cu, $^{67}$Cu, $^{165}$Dy, $^{155}$Eu, $^{18}$F, $^{153}$Gd, $^{66}$Ga, $^{67}$Ga, $^{68}$Ga, $^{72}$Ga, $^{198}$Au, $^{3}$H, $^{166}$Ho, $^{111}$In, $^{113m}$In, $^{115m}$In, $^{123}$I, $^{125}$I, $^{131}$I, $^{189}$Ir, $^{191m}$Ir, $^{192}$Ir, $^{194}$Ir, $^{52}$Fe, $^{55}$Fe, $^{59}$Fe, $^{177}$Lu, $^{15}$O, $^{191m-191}$Os, $^{109}$Pd, $^{32}$P, $^{33}$P, $^{42}$K, $^{226}$Ra, $^{186}$Re, $^{188}$Re, $^{82m}$Rb, $^{153}$Sm, $^{46}$Sc, $^{47}$Sc, $^{72}$Se, $^{75}$Se, $^{105}$Ag, $^{22}$Na, $^{24}$Na, $^{89}$Sr, $^{35}$S, $^{38}$S, $^{177}$Ta, $^{96}$Tc, $^{99m}$Tc, $^{201}$Tl, $^{202}$Tl, $^{113}$Sn, $^{117m}$Sn, $^{121}$Sn, $^{166}$Yb, $^{169}$Yb, $^{175}$Yb, $^{88}$Y, $^{90}$Y, $^{62}$Zn and $^{65}$Zn. Preferably the radioisotope is $^{131}$I, $^{125}$I, $^{123}$I, $^{111}$I, $^{99m}$Tc, $^{90}$Y, $^{186}$Re, $^{188}$Re, $^{32}$P, $^{153}$Sm, $^{67}$Ga, $^{201}$Tl $^{77}$Br, or $^{18}$F, and is imaged with a photoscanning device.

Procedures for labeling biological agents with the radioactive isotopes are generally known in the art. U.S. Pat. No. 4,302,438 describes tritium labeling procedures. Procedures for iodinating, tritium labeling, and $^{35}$S labeling especially adapted for murine monoclonal antibodies are described by Goding, J. W. (supra, pp 124-126) and the references cited therein. Other procedures for iodinating biological agents, such as antibodies, binding portions thereof, probes, or ligands, are described in the scientific literature [see Hunter and Greenwood, Nature 144:945 (1962), David et al., Biochemistry 13:1014-1021 (1974), and U.S. Pat. Nos. 3,867, 517 and 4,376,110]. Iodinating procedures for agents are described by Greenwood, F. et al., Biochem. J. 89:114-123 (1963); Marchalonis, J., Biochem. J. 113:299-305 (1969); and Morrison, M. et al., Immunochemistry, 289-297 (1971). $^{99m}$Tc-labeling procedures are described by Rhodes, B. et al. in Burchiel, S. et al. (eds.), Tumor Imaging: The Radioimmunochemical Detection of Cancer, New York: Masson 111-123 (1982) and the references cited therein. Labelling of antibodies or fragments with technetium-99m are also described for example in U.S. Pat. No. 5,317,091, U.S. Pat. No. 4,478,815, U.S. Pat. No. 4,478,818, U.S. Pat. No. 4,472,371, U.S. Pat. No. Re 32,417, and U.S. Pat. No. 4,311,688. Procedures suitable for $^{111}$In-labeling biological agents are described by Hnatowich, D. J. et al., J. Immul. Methods, 65:147-157 (1983), Hnatowich, D. et al., J. Applied Radiation, 35:554-557 (1984), and Buckley, R. G. et al., F.E.B.S. 166:202-204 (1984).

An agent may also be labeled with a paramagnetic isotope for purposes of an in vivo method of the invention. Examples of elements that are useful in magnetic resonance imaging include gadolinium, terbium, tin, iron, or isotopes thereof. (See, for example, Schaefer et al., (1989) JACC 14, 472-480; Shreve et al., (1986) Magn. Reson. Med. 3, 336-340; Wolf, G L., (1984) Physiol. Chem. Phys. Med. NMR 16, 93-95; Wesbey et al., (1984) Physiol. Chem. Phys. Med. NMR 16, 145-155; Runge et al., (1984) Invest. Radiol. 19, 408-415 for discussions on in vivo nuclear magnetic resonance imaging.)

In the case of a radiolabeled agent, the agent may be administered to the patient, it is localized to the cell or tissue (e.g. tumor) having an endometrial marker with which the agent binds, and is detected or "imaged" in vivo using known techniques such as radionuclear scanning using e.g., a gamma camera or emission tomography. [See for example, A. R. Bradwell et al., "Developments in Antibody Imaging", Monoclonal Antibodies for Cancer Detection and Therapy, R. W. Baldwin et al., (eds.), pp. 65-85 (Academic Press 1985)]. A positron emission transaxial tomography scanner, such as designated Pet VI located at Brookhaven National Laboratory, can also be used where the radiolabel emits positrons (e.g., $^{11}$C, $^{18}$F, $^{15}$O, and $^{13}$N).

Whole body imaging techniques using radioisotope labeled agents can be used for locating diseased cells and tissues (e.g. primary tumors and tumors which have metastasized). Antibodies specific for endometrial markers, or fragments thereof having the same epitope specificity, are bound to a suitable radioisotope, or a combination thereof, and administered parenterally. For endometrial cancer, administration preferably is intravenous. The bio-distribution of the label can be monitored by scintigraphy, and accumulations of the label are related to the presence of endometrial cancer cells. Whole body imaging techniques are described in U.S. Pat. Nos. 4,036,945 and 4,311,688. Other examples of agents useful for diagnosis and therapeutic use that can be coupled to antibodies and antibody fragments include metallothionein and fragments (see, U.S. Pat. No. 4,732,864). These agents are useful in diagnosis staging and visualization of cancer, in particular endometrial cancer, so that surgical and/or radiation treatment protocols can be used more efficiently.

An imaging agent may carry a bioluminescent or chemiluminescent label. Such labels include polypeptides known to be fluorescent, bioluminescent or chemiluminescent, or, that act as enzymes on a specific substrate (reagent), or can generate a fluorescent, bioluminescent or chemiluminescent molecule. Examples of bioluminescent or chemiluminescent labels include luciferases, aequorin, obelin, mnemiopsin, berovin, a phenanthridinium ester, and variations thereof and combinations thereof. A substrate for the bioluminescent or chemiluminescent polypeptide may also be utilized in a method of the invention. For example, the chemiluminescent polypeptide can be luciferase and the reagent luciferin. A substrate for a bioluminescent or chemiluminescent label can be administered before, at the same time (e.g., in the same formulation), or after administration of the agent.

An imaging agent may comprise a paramagnetic compound, such as a polypeptide chelated to a metal, e.g., a metalloporphyrin. The paramagnetic compound may also comprise a monocrystalline nanoparticle, e.g., a nanoparticle comprising a lanthanide (e.g., Gd) or iron oxide; or, a metal ion comprising a lanthanide. "Lanthanides" refers to elements of atomic numbers 58 to 70, a transition metal of atomic numbers 21 to 29, 42 or 44, a Gd(III), a Mn(II), or an element comprising a Fe element. Paramagnetic compounds can also comprise a neodymium iron oxide ($NdFeO_3$) or a dysprosium iron oxide ($DyFeO_3$). Examples of elements that are useful in magnetic resonance imaging include gadolinium, terbium, tin, iron, or isotopes thereof. (See, for example, Schaefer et al., (1989) JACC 14, 472-480; Shreve et al., (1986) Magn. Reson. Med. 3, 336-340; Wolf, G L., (1984) Physiol. Chem. Phys. Med. NMR 16, 93-95; Wesbey et al., (1984) Physiol. Chem. Phys. Med. NMR 16, 145-155; Runge et al., (1984) Invest. Radiol. 19, 408-415 for discussions on in vivo nuclear magnetic resonance imaging.)

An image can be generated in a method of the invention by computer assisted tomography (CAT), magnetic resonance spectroscopy (MRS) image, magnetic resonance imaging (MRI), positron emission tomography (PET), single-photon emission computed tomography (SPECT), or bioluminescence imaging (BLI) or equivalent.

Computer assisted tomography (CAT) and computerized axial tomography (CAT) systems and devices well known in the art can be utilized in the practice of the present invention. (See, for example, U.S. Pat. Nos. 6,151,377; 5,946,371; 5,446,799; 5,406,479; 5,208,581; 5,109,397). The invention may also utilize animal imaging modalities, such as Micro-CAT™ (ImTek, Inc.).

Magnetic resonance imaging (MRI) systems and devices well known in the art can be utilized in the practice of the present invention. For a description of MRI methods and devices see, for example, U.S. Pat. Nos. 6,151,377; 6,144,202; 6,128,522; 6,127,825; 6,121,775; 6,119,032; 6,115,446; 6,111,410; 602,891; 5,555,251; 5,455,512; 5,450,010; 5,378,987; 5,214,382; 5,031,624; 5,207,222; 4,985,678; 4,906,931; 4,558,279. MRI and supporting devices are commercially available for example, from Bruker Medical GMBH; Caprius; Esaote Biomedica; Fonar; GE Medical Systems (GEMS); Hitachi Medical Systems America; Intermagnetics General Corporation; Lunar Corp.; MagneVu; Marconi Medicals; Philips Medical Systems; Shimadzu; Siemens; Toshiba America Medical Systems; including imaging systems, by, e.g., Silicon Graphics. The invention may also utilize animal imaging modalities such as micro-MRIs.

Positron emission tomography imaging (PET) systems and devices well known in the art can be utilized in the practice of the present invention. For example, a method of the invention may use the system designated Pet VI located at Brookhaven National Laboratory. For descriptions of PET systems and devices see, for example, U.S. Pat. Nos. 6,151,377; 6,072,177; 5,900,636; 5,608,221; 5,532,489; 5,272,343; 5,103,098. Animal imaging modalities such as micro-PETs (Corcorde Microsystems, Inc.) can also be used in the invention.

Single-photon emission computed tomography (SPECT) systems and devices well known in the art can be utilized in the practice of the present invention. (See, for example, U.S. Pat. Nos. 6,115,446; 6,072,177; 5,608,221; 5,600,145; 5,210,421; 5,103,098.) The methods of the invention may also utilize animal imaging modalities, such as micro-SPECTs.

Bioluminescence imaging includes bioluminescence, fluorescence or chemiluminescence or other photon detection systems and devices that are capable of detecting bioluminescence, fluorescence or chemiluminescence. Sensitive photon detection systems can be used to detect bioluminescent and fluorescent proteins externally; see, for example, Contag (2000) Neoplasia 2:41-52; Zhang (1994) Clin. Exp. Metastasis 12:87-92. The methods of the invention can be practiced using any such photon detection device, or variation or equivalent thereof, or in conjunction with any known photon detection methodology, including visual imaging. By way of example, an intensified charge-coupled device (ICCD) camera coupled to an image processor may be used in the present invention. (See, e.g., U.S. Pat. No. 5,650,135). Photon detection devices are also commercially available from Xenogen, Hamamatsue.

Screening Methods

The invention also contemplates methods for evaluating test agents or compounds for their ability to inhibit an endometrial disease (e.g. cancer), potentially contribute to an endometrial disease (e.g. cancer), or inhibit or enhance an endometrium phase. Test agents and compounds include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, $F(ab)_2$, and Fab expression library fragments, and epitope-binding fragments thereof)], and small organic or inorganic molecules. The agents or compounds may be endogenous physiological compounds or natural or synthetic compounds.

The invention provides a method for assessing the potential efficacy of a test agent for inhibiting an endometrial disease (e.g. cancer) in a patient, the method comprising comparing:
- (a) levels of one or more endometrial markers, and/or polynucleotides encoding endometrial markers, and optionally other markers in a first sample obtained from a patient and exposed to the test agent; and
- (b) levels of one or more endometrial markers and/or polynucleotides encoding endometrial markers, and optionally other markers, in a second sample obtained from the patient, wherein the sample is not exposed to the test agent, wherein a significant difference in the levels of expression of one or more endometrial markers, and/or polynucleotides encoding one or more endometrial markers, and optionally the other markers, in the first sample, relative to the second sample, is an indication that the test agent is potentially efficacious for inhibiting an endometrial disease (e.g. cancer) in the patient.

The first and second samples may be portions of a single sample obtained from a patient or portions of pooled samples obtained from a patient.

In an aspect, the invention provides a method of selecting an agent for inhibiting an endometrial disease (e.g. cancer) in a patient comprising:
- (a) obtaining a sample from the patient;
- (b) separately maintaining aliquots of the sample in the presence of a plurality of test agents;
- (c) comparing one or more endometrial markers, and/or polynucleotides encoding endometrial markers, and optionally other markers, in each of the aliquots; and
- (d) selecting one of the test agents which alters the levels of one or more endometrial markers, and/or polynucleotides encoding endometrial markers, and optionally other markers in the aliquot containing that test agent, relative to other test agents.

In a further aspect, the invention provides a method of selecting an agent for inhibiting or enhancing an endometrium phase in a patient comprising:
- (a) obtaining a sample of endometrium in a selected phase (e.g. secretory or proliferative phase);
- (b) separately maintaining aliquots of the sample in the presence of a plurality of test agents;
- (c) comparing one or more endometrial markers, and/or polynucleotides encoding endometrial markers, and optionally other markers, in each of the aliquots; and
- (d) selecting one of the test agents which alters the levels of one or more endometrial markers, and/or polynucleotides encoding endometrial markers, and optionally other markers in the aliquot containing that test agent, relative to other test agents.

Still another aspect of the present invention provides a method of conducting a drug discovery business comprising:
- (a) providing one or more methods or assay systems for identifying agents that inhibit an endometrial disease (e.g. endometrial cancer) or affect an endometrium phase in a patient;
- (b) conducting therapeutic profiling of agents identified in step (a), or further analogs thereof, for efficacy and toxicity in animals; and
- (c) formulating a pharmaceutical preparation including one or more agents identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

The invention also contemplates a method of assessing the potential of a test compound to contribute to an endometrial disease (e.g. endometrial cancer) comprising:
- (a) maintaining separate aliquots of cells or tissues from a patient with an endometrial disease (e.g. cancer) in the presence and absence of the test compound; and
- (b) comparing one or more endometrial markers, and/or polynucleotides encoding endometrial markers, and optionally other markers in each of the aliquots.

A significant difference between the levels of the markers in the aliquot maintained in the presence of (or exposed to) the test compound relative to the aliquot maintained in the absence of the test compound, indicates that the test compound possesses the potential to contribute to an endometrial disease (e.g. endometrial cancer).

Kits

The invention also contemplates kits for carrying out the methods of the invention. Kits may typically comprise two or more components required for performing a diagnostic assay. Components include but are not limited to compounds, reagents, containers, and/or equipment.

The methods described herein may be performed by utilizing pre-packaged diagnostic kits comprising one or more specific endometrial marker polynucleotide or antibody described herein, which may be conveniently used, e.g., in clinical settings to screen and diagnose patients and to screen and identify those individuals exhibiting a predisposition to developing an endometrial disease.

In an embodiment, a container with a kit comprises a binding agent as described herein. By way of example, the kit may contain antibodies or antibody fragments which bind specifically to epitopes of one or more endometrial markers and optionally other markers, antibodies against the antibodies labelled with an enzyme; and a substrate for the enzyme. The kit may also contain microtiter plate wells, standards, assay diluent, wash buffer, adhesive plate covers, and/or instructions for carrying out a method of the invention using the kit.

In an aspect of the invention, the kit includes antibodies or fragments of antibodies which bind specifically to an epitope of one or more polypeptide listed in Table 1 and optionally one or more polypeptide listed in Table 2 and means for detecting binding of the antibodies to their epitope associated with tumor cells, either as concentrates (including lyophilized compositions), which may be further diluted prior to use or at the concentration of use, where the vials may include one or more dosages. Where the kits are intended for in vivo use, single dosages may be provided in sterilized containers, having the desired amount and concentration of agents. Containers that provide a formulation for direct use, usually do not require other reagents, as for example, where the kit contains a radiolabelled antibody preparation for in vivo imaging.

A kit may be designed to detect the level of polynucleotides encoding one or more endometrial polynucleotide markers in a sample. In an embodiment, the polynucleotides encode one or more polynucleotides encoding a polypeptide listed in Table 1 and optionally one or more polynucleotides listed in Table 2. Such kits generally comprise at least one oligonucleotide probe or primer, as described herein, that hybridizes to a polynucleotide encoding one or more endometrial cancer markers. Such an oligonucleotide may be used, for example, within a PCR or hybridization procedure. Additional components that may be present within the kits include a second oligonucleotide and/or a diagnostic reagent or container to facilitate detection of a polynucleotide encoding one or more endometrial cancer markers.

The invention provides a kit containing a microarray described herein ready for hybridization to target endometrial polynucleotide markers, plus software for the data analysis of the results. The software to be included with the kit comprises data analysis methods, in particular mathematical routines for marker discovery, including the calculation of correlation coefficients between clinical categories and marker expression. The software may also include mathematical routines for calculating the correlation between sample marker expression and control marker expression, using array-generated fluorescence data, to determine the clinical classification of the sample.

The reagents suitable for applying the screening methods of the invention to evaluate compounds may be packaged into convenient kits described herein providing the necessary materials packaged into suitable containers.

The invention contemplates a kit for assessing the presence of endometrial cells, wherein the kit comprises antibodies specific for one or more endometrial markers, or primers to or probes for polynucleotides encoding same, and optionally probes, primers or antibodies specific for other markers associated with an endometrial disease (e.g. cancer).

The invention relates to a kit for assessing the suitability of each of a plurality of test compounds for inhibiting an endometrial disease (e.g. endometrial cancer) in a patient. The kit comprises reagents for assessing one or more endometrial markers or polynucleotides encoding same, and optionally a plurality of test agents or compounds.

Additionally the invention provides a kit for assessing the potential of a test compound to contribute to an endometrial disease (e.g. cancer). The kit comprises endometrial diseased cells (e.g. cancer cells) and reagents for assessing one or more endometrial markers, polynucleotides encoding same, and optionally other markers associated with an endometrial disease.

Therapeutic Applications

One or more endometrial markers may be targets for immunotherapy. Immunotherapeutic methods include the use of antibody therapy, in vivo vaccines, and ex vivo immunotherapy approaches.

In one aspect, the invention provides one or more endometrial marker antibodies that may be used systemically to treat an endometrial disease associated with the marker. In particular, the endometrial disease is endometrial cancer and one or more endometrial marker antibodies may be used systemically to treat endometrial cancer. Preferably antibodies are used that target the tumor cells but not the surrounding non-tumor cells and tissue.

Thus, the invention provides a method of treating a patient susceptible to, or having a disease (e.g. cancer) that expresses one or more endometrial marker (in particular a marker up-regulated in endometrial cancer, for example, an up-regulated marker in Table 1 and optionally an up-regulated marker in Table 2), comprising administering to the patient an effective amount of an antibody that binds specifically to one or more endometrial marker.

In another aspect, the invention provides a method of inhibiting the growth of tumor cells expressing one or more endometrial cancer markers, comprising administering to a patient an antibody which binds specifically to one or more endometrial cancer markers in an amount effective to inhibit growth of the tumor cells.

One or more endometrial marker antibodies may also be used in a method for selectively inhibiting the growth of, or killing a cell expressing one or more endometrial marker (e.g. tumor cell expressing one or more endometrial cancer marker) comprising reacting one or more endometrial marker antibody immunoconjugate or immunotoxin with the cell in an amount sufficient to inhibit the growth of, or kill the cell.

By way of example, unconjugated antibodies to endometrial cancer markers may be introduced into a patient such that the antibodies bind to endometrial cancer marker expressing cancer cells and mediate growth inhibition of such cells (including the destruction thereof), and the tumor, by mechanisms which may include complement-mediated cytolysis, antibody-dependent cellular cytotoxicity, altering the physiologic function of one or more endometrial cancer markers, and/or the inhibition of ligand binding or signal transduction pathways. In addition to unconjugated antibodies to endometrial cancer markers, one or more endometrial cancer marker antibodies conjugated to therapeutic agents (e.g. immunoconjugates) may also be used therapeutically to deliver the agent directly to one or more endometrial cancer marker expressing tumor cells and thereby destroy the tumor. Examples of such agents include abrin, ricin A, Pseudomonas exotoxin, or diphtheria toxin; proteins such as tumor necrosis factor, alpha-interferon, beta-interferon, nerve growth factor, platelet derived growth factor, tissue plasminogen activator; and biological response modifiers such as lymphokines, interleukin-1, interleukin-2, interleukin-6, granulocyte macrophage colony stimulating factor, granulocyte colony stimulating factor, or other growth factors.

Cancer immunotherapy using one or more endometrial cancer marker antibodies may utilize the various approaches that have been successfully employed for cancers, including but not limited to colon cancer (Arlen et al., 1998, Crit Rev Immunol 18: 133-138), multiple myeloma (Ozaki et al., 1997, Blood 90: 3179-3186; Tsunenati et al., 1997, Blood 90: 2437-2444), gastric cancer (Kasprzyk et al., 1992, Cancer Res 52: 2771-2776), B-cell lymphoma (Funakoshi et al., 1996, J Immunther Emphasis Tumor Immunol 19: 93-101), leukemia (Zhong et al., 1996, Leuk Res 20: 581-589), colorectal cancer (Moun et al., 1994, Cancer Res 54: 6160-6166); Velders et al., 1995, Cancer Res 55: 4398-4403), and breast cancer (Shepard et al., 1991, J Clin Immunol 11: 117-127).

In the practice of a method of the invention, endometrial cancer marker antibodies capable of inhibiting the growth of cancer cells expressing endometrial cancer markers are administered in a therapeutically effective amount to cancer patients whose tumors express or overexpress one or more endometrial cancer markers. The invention may provide a specific, effective and long-needed treatment for endometrial cancer. The antibody therapy methods of the invention may be combined with other therapies including chemotherapy and radiation.

Patients may be evaluated for the presence and level of expression or overexpression of one or more endometrial markers in diseased cells and tissues (e.g. tumors), in particular using immunohistochemical assessments of tissue, quantitative imaging as described herein, or other techniques capable of reliably indicating the presence and degree of expression of one or more endometrial markers. Immunohistochemical analysis of tumor biopsies or surgical specimens may be employed for this purpose.

Endometrial marker antibodies useful in treating disease (e.g. cancer) include those that are capable of initiating a potent immune response against the disease (e.g. tumor) and those that are capable of direct cytotoxicity. In this regard, endometrial marker antibodies may elicit cell lysis by either complement-mediated or antibody-dependent cell cytotoxicity (ADCC) mechanisms, both of which require an intact Fc portion of the immunoglobulin molecule for interaction with effector cell Fc receptor sites or complement proteins.

Endometrial marker antibodies that exert a direct biological effect on tumor growth may also be useful in the practice of the invention. Such antibodies may not require the complete immunoglobulin to exert the effect. Potential mechanisms by which such directly cytotoxic antibodies may act include inhibition of cell growth, modulation of cellular differentiation, modulation of tumor angiogenesis factor profiles, and the induction of apoptosis. The mechanism by which a particular antibody exerts an anti-tumor effect may be evaluated using any number of in vitro assays designed to determine ADCC, antibody-dependent macrophage-mediated cytotoxicity (ADMMC), complement-mediated cell lysis, and others known in the art.

The anti-tumor activity of a particular endometrial cancer marker antibody, or combination of endometrial cancer marker antibodies, may be evaluated in vivo using a suitable animal model. Xenogenic cancer models, where human cancer explants or passaged xenograft tissues are introduced into immune compromised animals, such as nude or SCID mice, may be employed.

The methods of the invention contemplate the administration of single endometrial marker antibodies as well as combinations, or "cocktails", of different individual antibodies such as those recognizing different epitopes of other markers. Such cocktails may have certain advantages inasmuch as they contain antibodies that bind to different epitopes of endometrial markers and/or exploit different effector mechanisms or combine directly cytotoxic antibodies with antibodies that rely on immune effector functionality. Such antibodies in combination may exhibit synergistic therapeutic effects. In addition, the administration of one or more endometrial marker specific antibodies may be combined with other therapeutic agents, including but not limited to chemotherapeutic agents, androgen-blockers, and immune modulators (e.g., IL2, GM-CSF). The endometrial marker specific antibodies may be administered in their "naked" or unconjugated form, or may have therapeutic agents conjugated to them.

The endometrial marker specific antibodies used in the methods of the invention may be formulated into pharmaceutical compositions comprising a carrier suitable for the desired delivery method. Suitable carriers include any material which when combined with the antibodies retains the function of the antibody and is non-reactive with the subject's immune systems. Examples include any of a number of standard pharmaceutical carriers such as sterile phosphate buffered saline solutions, bacteriostatic water, and the like (see, generally, Remington's Pharmaceutical Sciences 16.sup.th Edition, A. Osal., Ed., 1980).

One or more endometrial marker specific antibody formulations may be administered via any route capable of delivering the antibodies to the a disease (e.g. tumor) site. Routes of administration include, but are not limited to, intravenous, intraperitoneal, intramuscular, intratumor, intradermal, and the like. Preferably, the route of administration is by intravenous injection. Antibody preparations may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the antibody preparation via an acceptable route of administration such as intravenous injection (IV), at an effective dose. Dosages will depend upon various factors generally appreciated by those of skill in the art, including the type of disease and the severity, grade, or stage of the disease, the binding affinity and half life of the antibodies used, the degree of endometrial marker expression in the patient, the extent of circulating endometrial markers, the desired steady-state antibody concentration level, frequency of treatment, and the influence of any chemotherapeutic agents used in combination with the treatment method of the invention. Daily doses may range from about 0.1 to 100 mg/kg. Doses in the range of 10-500 mg antibodies per week may be effective and well tolerated, although even higher weekly doses may be appropriate and/or well tolerated. A determining factor in defining the appropriate dose is the amount of a particular antibody necessary to be therapeutically effective in a particular context. Repeated administrations may be required to achieve disease inhibition or regression. Direct administration of one or more endometrial marker antibodies is also possible and may have advantages in certain situations.

Patients may be evaluated for serum cancer markers in order to assist in the determination of the most effective dosing regimen and related factors. The endometrial cancer assay methods described herein, or similar assays, may be used for quantitating circulating endometrial marker levels in patients prior to treatment. Such assays may also be used for monitoring throughout therapy, and may be useful to gauge therapeutic success in combination with evaluating other parameters such as serum levels of endometrial markers.

The invention further provides vaccines formulated to contain one or more endometrial marker or fragment thereof.

In an embodiment, the invention provides a method of vaccinating an individual against one or more endometrial marker listed in Table 1 and optionally one or more maker listed in Table 2, comprising the step of inoculating the individual with the marker or fragment thereof that lacks activity, wherein the inoculation elicits an immune response in the individual thereby vaccinating the individual against the marker.

The use in anti-cancer therapy of a tumor antigen in a vaccine for generating humoral and cell-mediated immunity is well known and, for example, has been employed in prostate cancer using human PSMA and rodent PAP immunogens (Hodge et al., 1995, Int. J. Cancer 63: 231-237; Fong et al., 1997, J. Immunol. 159: 3113-3117). These and similar methods can be practiced by employing one or more endometrial markers, or fragment thereof, or endometrial polynucleotide markers and recombinant vectors capable of expressing and appropriately presenting endometrial marker immunogens.

By way of example, viral gene delivery systems may be used to deliver one or more endometrial polynucleotide markers. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658-663). Non-viral delivery systems may also be employed by using naked DNA encoding one or more endometrial cancer marker or fragment thereof introduced into the patient (e.g., intramuscularly) to induce an anti-tumor response.

Various ex vivo strategies may also be employed. One approach involves the use of cells to present one or more endometrial marker to a patient's immune system. For example, autologous dendritic cells which express MHC class I and II, may be pulsed with one or more endometrial marker or peptides thereof that are capable of binding to MHC molecules, to thereby stimulate the patients' immune systems (See, for example, Tjoa et al., 1996, Prostate 28: 65-69; Murphy et al., 1996, Prostate 29: 371-380).

Anti-idiotypic endometrial marker specific antibodies can also be used in therapy as a vaccine for inducing an immune response to cells expressing one or more endometrial marker. The generation of anti-idiotypic antibodies is well known in the art and can readily be adapted to generate anti-idiotypic endometrial cancer marker specific antibodies that mimic an epitope on one or more endometrial cancer markers (see, for example, Wagner et al., 1997, Hybridoma 16: 33-40; Foon et al., 1995, J Clin Invest 96: 334-342; Herlyn et al., 1996, Cancer Immunol Immunother 43: 65-76). Such an antibody can be used in anti-idiotypic therapy as presently practiced with other anti-idiotypic antibodies directed against antigens associated with disease (e.g. tumor antigens).

Genetic immunization methods may be utilized to generate prophylactic or therapeutic humoral and cellular immune responses directed against cells expressing one or more endometrial cancer marker. One or more DNA molecules encoding endometrial markers, constructs comprising DNA encoding one or more endometrial markers/immunogens and appropriate regulatory sequences may be injected directly into muscle or skin of an individual, such that the cells of the muscle or skin take-up the construct and express the encoded endometrial markers/immunogens. The endometrial markers/immunogens may be expressed as cell surface proteins or be secreted. Expression of one or more endometrial markers results in the generation of prophylactic or therapeutic humoral and cellular immunity against the disease (e.g. cancer). Various prophylactic and therapeutic genetic immunization techniques known in the art may be used.

The invention further provides methods for inhibiting cellular activity (e.g., cell proliferation, activation, or propagation) of a cell expressing one or more endometrial marker. This method comprises reacting immunoconjugates of the invention (e.g., a heterogeneous or homogenous mixture) with the cell so that endometrial markers form complexes with the immunoconjugates. A subject with a neoplastic or preneoplastic condition can be treated when the inhibition of cellular activity results in cell death.

In another aspect, the invention provides methods for selectively inhibiting a cell expressing one or more endometrial marker by reacting any one or a combination of the immunoconjugates of the invention with the cell in an amount sufficient to inhibit the cell. Amounts include those that are sufficient to kill the cell or sufficient to inhibit cell growth or proliferation.

Vectors derived from retroviruses, adenovirus, herpes or vaccinia viruses, or from various bacterial plasmids, may be used to deliver polynucleotides encoding endometrial cancer markers to a targeted organ, tissue, or cell population. Methods well known to those skilled in the art may be used to construct recombinant vectors that will express antisense polynucleotides for endometrial markers. (See, for example, the techniques described in Sambrook et al (supra) and Ausubel et al (supra)).

Methods for introducing vectors into cells or tissues include those methods discussed herein and which are suitable for in vivo, in vitro and ex vivo therapy. For ex vivo therapy, vectors may be introduced into stem cells obtained from a patient and clonally propagated for autologous transplant into the same patient (See U.S. Pat. Nos. 5,399,493 and 5,437,994). Delivery by transfection and by liposome are well known in the art.

Genes encoding endometrial markers can be turned off by transfecting a cell or tissue with vectors that express high levels of a desired endometrial marker-encoding fragment. Such constructs can inundate cells with untranslatable sense or antisense sequences. Even in the absence of integration into the DNA, such vectors may continue to transcribe RNA molecules until all copies are disabled by endogenous nucleases.

Modifications of gene expression can be obtained by designing antisense molecules, DNA, RNA or PNA, to the regulatory regions of a gene encoding an endometrial marker, i.e., the promoters, enhancers, and introns. Preferably, oligonucleotides are derived from the transcription initiation site, e.g. between −10 and +10 regions of the leader sequence. The antisense molecules may also be designed so that they block translation of mRNA by preventing the transcript from binding to ribosomes. Inhibition may also be achieved using "triple helix" base-pairing methodology. Triple helix pairing compromises the ability of the double helix to open sufficiently for the binding of polymerases, transcription factors, or regulatory molecules. Therapeutic advances using triplex DNA were reviewed by Gee J E et al (In: Huber B E and B I Carr (1994) Molecular and Immunologic Approaches, Futura Publishing Co, Mt Kisco N.Y.).

Ribozymes are enzymatic RNA molecules that catalyze the specific cleavage of RNA. Ribozymes act by sequence-specific hybridization of the ribozyme molecule to complementary target RNA, followed by endonucleolytic cleavage. The invention therefore contemplates engineered hammerhead motif ribozyme molecules that can specifically and efficiently catalyze endonucleolytic cleavage of sequences encoding an endometrial marker.

Specific ribozyme cleavage sites within any potential RNA target may initially be identified by scanning the target molecule for ribozyme cleavage sites which include the following sequences, GUA, GUU and GUC. Once the sites are identified, short RNA sequences of between 15 and 20 ribonucleotides corresponding to the region of the target gene containing the cleavage site may be evaluated for secondary structural features which may render the oligonucleotide inoperable. The suitability of candidate targets may also be determined by testing accessibility to hybridization with complementary oligonucleotides using ribonuclease protection assays.

One or more endometrial markers and polynucleotides encoding the markers, and fragments thereof, may be used in the treatment of an endometrial disease (e.g. endometrial cancer) in a subject. In an aspect the endometrial markers and polynucleotides encoding the markers are endometrial cancer markers that are down-regulated in endometrial cancer, for example, mucin 5B and one or more of the down-regulated markers listed in Table 2. The markers or polynucleotides may be formulated into compositions for administration to subjects suffering from an endometrial disease. Therefore, the present invention also relates to a composition comprising one or more endometrial markers or polynucleotides encoding the markers, or a fragment thereof, and a pharmaceutically acceptable carrier, excipient or diluent. A method for treating or preventing an endometrial disease in a subject is also provided comprising administering to a patient in need thereof, one or more endometrial markers or polynucleotides encoding the markers, or a composition of the invention.

The invention further provides a method of inhibiting an endometrial disease (e.g. endometrial cancer) in a patient comprising:
  (a) obtaining a sample comprising diseased cells from the patient;
  (b) separately maintaining aliquots of the sample in the presence of a plurality of test agents;
  (c) comparing levels of one or more endometrial markers, and/or polynucleotides encoding one or more endometrial markers in each aliquot;

(d) administering to the patient at least one of the test agents which alters the levels of the endometrial markers, and/or polynucleotides encoding one or more endometrial markers in the aliquot containing that test agent, relative to the other test agents.

Endometrial markers in uterine biopsy tissue or fluid and sera may vary between known fertile and infertile women during the window of implantation, deviate in women undergoing ovarian hyperstimulation/ovulation induction, and correlate with successful initiation of pregnancy. Therefore, endometrial markers of the invention may serve as minimally or noninvasive markers of uterine receptivity for implantation.

The present invention further provides a method of determining uterine endometrial receptivity by first obtaining a serum, uterine fluid or endometrial biopsy sample from a patient and detecting the presence of an endometrial marker associated with a certain endometrium phase, wherein the presence or absence of an endometrial marker as compared to controls indicates uterine receptivity. In an embodiment, the endometrium phase is the secretory phase. Where necessary for the evaluation, repetitive samples may be collected throughout the menstrual cycle. Non-receptive controls are both women who are in the non-fertile stage of the menstrual cycle and women with known uterine dysfunction where an endometrial marker is not present or present on the endometrium throughout the menstrual cycle or certain endometrium phases.

The present invention further provides a method of monitoring the effects of ovarian hyperstimulation and/or ovulation induction protocols on uterine receptivity either for individual women receiving the treatment or for the evaluation of new protocols. In an embodiment, the method comprises: (a) obtaining a serum, uterine or fluid or endometrial biopsy sample from a patient receiving the treatments; and (b) detecting the presence of an endometrial marker of the invention present in the endometrium at the time of fertilization, early embryogenesis, and implantation; wherein presence or absence of an endometrial marker indicates receptivity. A disruption of the normal cyclic presence of an endometrial marker indicates that the treatment may adversely affect uterine receptivity. This disruption may include non-cyclic presence of an endometrial marker or an aberrant presence of an endometrial marker as compared to controls.

In an aspect the invention provides a method of determining a probability of successful implantation with an ovarian stimulation in vitro fertilization and embryo transfer procedure, comprising:
(a) determining a level of an endometrial marker in a sample obtained from a patient who has undergone an ovarian stimulation in vitro fertilization and embryo transfer procedure; and
(b) determining a probability of successful implantation based on the patient's determined endometrial marker level;
wherein a significantly different endometrial marker level relative to a standard level is associated with a decreased or increased probability of successful implantation.

The present invention further provides a method of contraception by interrupting the cyclic presence of an endometrial marker. The interruption can be to reduce or eliminate a marker present during the uterine receptivity window for implantation of the menstrual cycle and to thereby alter the cyclic presence/pattern of a marker. The interruption can utilize an antagonist of a marker. The term antagonist or antagonizing is used in its broadest sense. Antagonism can include any mechanism or treatment that results in inhibition, inactivation, blocking or reduction or alteration of cyclic presence of an endometrial marker.

An active therapeutic substance described herein may be administered in a convenient manner such as by injection (subcutaneous, intravenous, etc.), oral administration, inhalation, transdermal application, or rectal administration. Depending on the route of administration, the active substance may be coated in a material to protect the substance from the action of enzymes, acids and other natural conditions that may inactivate the substance. Solutions of an active compound as a free base or pharmaceutically acceptable salt can be prepared in an appropriate solvent with a suitable surfactant. Dispersions may be prepared in glycerol, liquid polyethylene glycols, and mixtures thereof, or in oils.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, the active substances in association with one or more pharmaceutically acceptable vehicles or diluents, and contained in buffered solutions with a suitable pH and iso-osmotic with the physiological fluids.

The compositions are indicated as therapeutic agents either alone or in conjunction with other therapeutic agents or other forms of treatment. The compositions of the invention may be administered concurrently, separately, or sequentially with other therapeutic agents or therapies.

The therapeutic activity of compositions and agents/compounds identified using a method of the invention and may be evaluated in vivo using a suitable animal model.

The following non-limiting example is illustrative of the present invention:

Example 1

Experimental Procedures

Samples and Reagents

Endometrial tissues were retrieved from an in-house, dedicated, research endometrial-tissue bank. With patient consent, samples from hysterectomy specimens had been flash-frozen in liquid nitrogen within 20 minutes of devitalizing. The patient consent forms and tissue-banking procedures were approved by the Research Ethics Boards of York University, Mount Sinai Hospital, University Health Network, and North York General Hospital. These frozen samples were sectioned and stored at $-80°$ C. The histologic diagnosis for each sample was confirmed using microscopic examination of a hematoxylin and eosin-stained frozen section of each research tissue block. The tissue from the mirror face of the histologic section was then washed three times in approximately 1 mL of phosphate-buffered saline (PBS) with a cocktail of protease inhibitors as described previously (1 mM AEBSF, 10 µM leupeptin, 1 µg/mL aprotinin, and 1 µM pepstatin) (3). The washed tissue was then homogenized in 0.5 mL PBS with protease inhibitors, using a handheld homogenizer. These homogenates were then flash frozen in liquid nitrogen and stored at $-80°$ C. until use. Samples were thawed and clarified by centrifugation and the protein concentration determined by a Bradford-type assay using Bio-Rad's protein quantification reagent (Bio-Rad, Mississauga, ON, Canada). Two hundred micrograms of each of the forty samples was then labeled individually with an iTRAQ tag. As double the manufacturer's suggested amounts (Applied Biosystems) were used two individual vials of each tag for labeling each sample were also used. Trypsin digestion and labeling were performed as per the manufacturer's protocol. Normal proliferative, normal secretory, Type I cancer, and Type II cancer samples, were labeled with the 114, 115, 116 and 117 tags, respectively. The trypsin digested and labeled samples were then mixed in sets of four with each set containing one of each type of labels, thus resulting in ten sets in total.

Strong Cation Exchange (SCX) Separation Conditions

Each set of labeled samples was then separated by SCX fractionation using an HP1050 high-performance liquid chromatography (HPLC) instrument (Agilent, Palo Alto, Calif., USA) with a 2.1-mm internal diameter (ID)×100 mm length PolyLC Polysulfoethyl A column packed with 5 µm beads with 300 Å pores (The Nest Group, Southborough, Mass., USA). A 2.1-mm ID×10-mm length guard column of the same material was fitted immediately upstream of the analytical column. Separation was performed as previously described (3). Briefly, each pooled sample set was diluted with the loading buffer (15 mM $KH_2PO_4$ in 25% acetonitrile, pH 3.0) to a total volume of 2 mL and the pH adjusted to 3.0 with phosphoric acid. Samples were then filtered using a 0.45-µm syringe filter (Millipore, Cambridge, ON, Canada) before loading onto the column. Separation was performed using a linear binary gradient over 1 hour. Buffer A was identical in composition to the loading buffer, while Buffer B was Buffer A containing 350 mM KCl. Fractions were collected every two minutes using an SF-2120 Super Fraction Collector (Advantec MFS, Dublin, Calif., USA), after an initial wait of 2 minutes to accommodate the void volume. This resulted in a total of 30 SCX fractions per sample set. These fractions were dried by speed vacuuming (Thermo Savant SC110 A, Holbrook, N.Y., USA) and resuspended in 30 µL of 0.1% formic acid each.

LC-MS/MS Run Conditions

The fractions from 6 to 25 were then analyzed by nano LC-MS/MS using the LC Packings Ultimate instrument (Amsterdam, The Netherlands) fitted with a 1-µL sample loop. Samples were loaded onto a 5-mm reverse phase (RP) C18 precolumn (LC Packings) at 50 µL per minute and washed for 4 minutes before switching the precolumn in-line with the separation column. The separation column used was either a 75-µm ID×150-mm length Pepmap RP column from LC Packings packed with 3-µm C18 beads with 100 Å pores, or an in-house equivalent packed with similar beads from Kromasil (The Nest Group). The flow rate used for separation on the RP column was 200 nL/min while the gradient was as shown in the table below.

| Time (min) | | | | | | | | |
|---|---|---|---|---|---|---|---|---|
| 0 | 10 | 15 | 125 | 145 | 150 | 160 | 162 | 188 |
| % B | 5 | 5 | 15 | 35 | 60 | 80 | 80 | 5 | Stop |

Samples were analyzed on a Q-STAR Pulsar i mass spectrometer (Applied Biosystems/MDS SCIEX, Foster City, Calif.) in Information-Dependent Acquisition (IDA) mode with the scan cycles set up to perform a 1-s MS Scan followed by 5 MS/MS scans of the 5 most abundant peaks for 2 s each. For the first set of runs, the acquisition method was set up to allow one repetition of any m/z followed by a dynamic exclusion for a period of 60 s. The method was also set up to select the smallest peaks in the MS scan that are nearest to a threshold of 10 counts on every fourth scan. The last set of runs were performed using the same method but without any repetitions and with a dynamic exclusion of 30 s. Each sample was run a minimum of 2 times and a maximum of 3 times. The last run for each sample was performed using an inclusion list populated by m/z values that corresponded to peptides that appear to be proteotypic (8, 9) for proteins that were deemed to be of interest after evaluating the results of the first set of runs. Relative protein abundances were determined using the MS/MS scans of iTRAQ-labeled peptides (3). The iTRAQ-labeled peptides fragmented under collision-induced dissociation (CID) conditions to give reporter ions at 114.1, 115.1, 116.1, and 117.1 Th. Larger, sequence-information-rich fragment ions were also produced under these conditions and gave the identity of the protein from which the peptide was analyzed. The ratios of peak areas of the iTRAQ reporter ions reflect the relative abundances of the peptides and the proteins in the samples.

Data Analysis

The software used (Applied Biosystems/MDS SCIEX) for data acquisition for the first set of runs was Analyst 1.0 SP8, while the software for the second run onwards was Analyst 1.1. Data were analyzed using ProQUANT 1.0 or 1.1, respectively, and the database searched was the Celera human database (human KBMS 20041109) provided by Applied Biosystems. Tolerance for the searches was set for 0.4 Da for the MS and 0.2 Da for the MS/MS spectra. The two parameters used to evaluate the quality of the peptide matches were the score and the confidence and are described in detail in the literature accompanying the software. Briefly, the score is a ProQUANT-generated value based on the number of ions that matches the theoretical list of fragments of the peptide in question, while the confidence, also a ProQUANT-generated value, is calculated from empirical data. The algorithm used to calculate the confidence incorporates the distance score calculated for the peptide, as well as factors such as the total number of results returned in the search. The distance score itself is calculated by determining the difference between the particular peptide's score and that of the 7th highest scoring peptide for that particular MS/MS spectrum, and is a measure of the confidence of the match. Only those peptides scoring higher than a score of 20 and a confidence of 75 were retained in the ProQUANT search. The ProQUANT results were then grouped using ProGroup viewer, which reports the lowest number of non-redundant protein identities that would account for the peptides identified along with the ratios for the relative abundance of these proteins after normalizing. Normalizing was performed by first calculating the median ratio of all proteins reported. Peptides that contribute to the protein identification but with ratios of the iTRAQ signature peaks smaller than 40 counts between the pair of labeled peaks in question were excluded from this calculation. The resulting median ratio was the normalizing factor used and was termed the applied bias. This normalizing factor is based on the assumption that most of the protein levels in the test samples should be similar to those in the control, with the exception of those that are specific to the condition of the test sample itself (i.e., malignant or benign), thus minimizing any systematic error. When the ratio for a protein from a set of constituent peptides is calculated, peptide ratios with smaller errors are weighted more heavily by the program. All peptides used for this calculation were unique to the given protein; peptides that were common to other isoforms or proteins of the same family were ignored. ProGroup also assesses the confidence of the protein identities reported. The ProGroup confidence score cut-off used was 1.3, which corresponds to a confidence limit of 95%. On occasion, the ratios of some proteins that were not automatically given by the ProGroup software were also reported, using the ratios returned by the ProQUANT searches. These were typically instances in which the confidence in the sequence of the identifying peptides were lower than the specified cut-off for reporting by ProGroup, but for which there were more confident results for the same peptides from a different sample run. Identities of these peptides were manually verified prior to inclusion. Lastly, the ratios for each of the potential markers were averaged across all the runs in which they were identified.

As mentioned previously, the ten normal proliferative samples were also compared against each other in a separate series of experiments. Samples for this second series of experiments were grouped in three sets. The first of these sets contained the proliferative samples used in the first four sets of samples in the experiments comparing the cancerous samples, i.e., P1-P4, the second set comprised proliferative samples P4-P7, and the third set P7-P10. In cases where the particular protein of interest was identified in all the three sample sets in these proliferative sample comparisons, the expression ratios were all recalculated relative to one proliferative sample, typically P1. These adjusted ratios were then used to calculate the average normal proliferative ratio, which was in turn used to normalize all the individual normal proliferative ratios themselves. This calculation was also performed on the individual expression ratios for the EmCa sample comparisons, thus permitting them to first be expressed relative to P1 and then relative to the average normal proliferative level.

Dot-Blot and Immunohistochemical Verification

Verification of the differential expression levels of potential markers discovered using iTRAQ analysis was provided by dot-blot analyses and/or immunohistochemical analyses using antibodies specific to the protein of interest. Dot-blot analysis was performed by spotting 2 μg of each homogenate on a nitrocellulose filter (BioRad); after blocking with 5% (w/v) skimmed milk in Tris-buffered saline (TBS, 20 mM Tris pH 7.5, 150 mM NaCl), each filter was probed by incubating it with a primary antibody in 5% bovine serum albumin in TBS with 0.1% Tween 20 overnight with shaking. An additional blot was probed with antibody specific for β-actin. Additionally, selected proteins identified in the iTRAQ study were verified and localized using immunohistochemistry of proliferative, secretory, and EmCa tissues fixed in 10% buffered formalin and embedded in paraffin blocks. The antibodies were applied in an appropriate dilution determined through a pilot study and immunohistochemically visualized using a diaminobenzidine chromogen. Interpretations of the immunohistochemically stained sections were conducted using a standardized microscopic review to assess positive staining (brown) for the targeted proteins in four tissue components: epithelium/carcinoma, endometrial stroma, any white blood cells, and glandular secretions. Antibodies used for these verifications were purchased from various commercial sources: β-actin, Cell Signaling Technologies (Pickering, ON, Canada); polymeric immunoglobulin receptor (PIGR), Cedarlane Laboratories (Hornby, ON, Canada); pyruvate kinase (PK) M2, ScheBo Biotech AG (Glessen, Germany); and chaperonin 10 (Cpn 10), Stressgen (Victoria, BC, Canada).

Statistical Analysis

Evaluation of differential expression in the iTRAQ analyses was performed using two statistical approaches. A preliminary evaluation of the data was carried out using a power analysis. For this, the ratios of areas of the iTRAQ reporter ions beyond which differential expression is considered significant, are given by $2 \times SD^2 \times (Z\alpha+Z\beta)^2/N^{0.5}$, where SD is the standard deviation, $(Z\alpha+Z\beta)^2$ is the power index, and N is the number of sample sets (10). The standard deviations of the cytoplasmic structural proteins, actin and β-5-tubulin, were used to estimate the variation of protein concentrations between individual patients and sets. These averaged to be ~0.3 over many iTRAQ analyses (see, e.g., Table 3). A power index of 10.5 was used for confidence limits of 95% for Type I and 90% for Type II errors (10). Thus for N=2, the ratios must be <0.51 or >1.97 to indicate differential expression; for N=10, the criteria relax to <0.70 or >1.43. The three most significant and consistent biomarkers were then chosen as explanatory input variables in a logistic regression model as a discriminator between malignant and normal samples. If p denotes the predicted probability that a case i whose observed marker values are given by the vector x(i)=(x(i, marker 1), x(i, marker 2), x(i, marker 3)) is malignant. Then the logistic regression discriminator has the form $$p(\text{case } i \text{ is malignant}|x(i)) = \exp(\alpha + \Sigma \beta j x(i,j))/[1+\exp(\alpha + \Sigma \beta j x(i,j))]$$

where the index 'i' denotes the individual sample and 'j' is a summation index that runs over the markers. Analogously, logistic regression discriminators were defined for each of the three markers individually. For a training set S of marker values x(i) (i=1, ..., n) the model parameters α and βj were determined by maximizing the multiplicative likelihood over S, using R Statistics (version 2.0.1). The discriminators were trained using the average observed iTRAQ ratios as marker observations in the malignant and benign cases. Here, the malignant cases comprise a total of 20 Type I and Type II cancer cases, while the benign cases comprise ten normal proliferative and ten normal secretory cases. Receiver Operating Characteristic (ROC) curves were calculated from the predictive scores of the parametrized logistic regression model by varying thresholds for "positive" calls between 0 and 1. Sensitivities, specificities, predictive values (PV), and positive predictive values (PPV) were calculated using a cut-off value of 0.5 on the logistic regression predictor. For any given ROC curve, the area-under-the-curve (AUC) value was determined using the Mann-Whitney statistics (11, 12).

Results

Of all the proteins identified in the across the sample sets analyzed, only a few displayed distinct trends in their levels of differential expression across any of the three categories relative to the proliferative phase. These proteins, all confidently identified with more than two peptide matches in each case, are given in Table 3, along with two structural proteins: actin and β-5-tubulin as controls. Two samples initially classified as Type II cancers (II6 and II10) were subsequently reclassified as predominantly Type I (after histological re-examination) and are shown in Table 3 as I6b and I10b. The expression ratios shown are the averages of the replicate analyses. For pyruvate kinase M1/M2, polymeric immunoglobulin receptor precursor, macrophage migration inhibitory factor (MIF), α-1-antitrypsin (AAT), creatine kinase chain B (CKB), transgelin, actin, and β-5-tubulin, the ratios are those relative to the averages of the proliferative phase samples. Observations of the other listed proteins were incomplete in the proliferative phase comparisons; for these proteins, the ratios are relative to the specific proliferative phase samples used in the pairing. Table 4 shows the details of PK results as an illustration of the typical analytical precision achievable. Due to the scope of this study, the various runs for each sample set were often temporally separated by as much as six months. The ratios determined, however, varied typically by no more than ±20%.

PCMs such as PK, PIGR, Cpn 10, MIF, AAT, CKB and transgelin were verified in this extensive study. Two proteins reported earlier (3), phosphatidylethanolamine binding protein (PEBP) and heterogenous nuclear ribonucleoprotein D0 (hnRNP D0) do not show consistent differential expression in this expanded study. Three new proteins showing differential expression in the 10 sets examined are WAP four-disulfide core domain protein 2 (WFDC2), clusterin, and mucin 5B. In addition, progestagen-associated endometrial protein, also known as PP14 and known to be selectively overexpressed in the secretory phase (13, 14), is evident.

In Table 3, ratios that are bolded were determined to indicate differential expression via a power analysis. Differential expression is not observed in every sample set. For example, eight out of 12 Type I cancer samples, six out of eight Type II cancer samples, and zero out of 10 secretory phase samples overexpress PK. Similarly, seven out of 12 Type I cancer samples, four out of eight Type II cancer samples, and two out of 10 secretory phase samples underexpress AAT; six out of 10 Type I cancer samples, four out of eight Type II cancer samples, and two out of 10 secretory phase samples overexpress PIGR. Performances of the other proteins (except the two structural proteins) are comparable. By contrast, for actin and β-5-tubulin, virtually all sample sets showed no significant differential expression.

The comparisons of the ten proliferative samples afford an estimate on the variation of the abundances of proteins across samples or individual patients. An analysis of the following nine consistently observed proteins, PIGR, PK, Cpn 10, MIF, AAT, CKB, transgelin, actin, and β-5-tubulin, in the proliferative and secretory phases (thus giving 18 cases) shows that 13 out of 18 cases have relative standard deviations (RSDs) ≦30%, three out of 18 cases have RSDs 31-40%, and two out of 18 cases have RSDs >40%. The two structural proteins, actin and β-5-tubulin, exhibit RSDs of 25-32% in the Type I and Type II EmCa samples. However, of the 14 remaining cases in the malignant samples, five out of 14 cases have RSDs ≦30%, three out of 14 cases have RSDs 31-40%, and six out of 14 cases have RSDs >40%. Thus there are typically much larger patient-to-patient variations across the malignant samples.

In a second statistical analysis strategy, all listed proteins in Table 3 were screened for their individual association with malignant or benign status using the two sample t-test. Four proteins were deemed to provide the maximal allowable number of individual components in a panel that constitute robust and reproducible results, i.e., without losing validity due to overfitting. At a t-test significance threshold of p=0.005, the following four proteins were found to be differentially expressed between cancer and normal cases: PK (p=1.24× $10^{-7}$), Cpn 10 (p=2.2×$10^{-3}$), AAT (p=8.97×$10^{-4}$), and CKB (p=2.06×$10^{-4}$). AAT is more uniformly expressed than CKB within the combined proliferative and secretory samples, and was included in a candidate panel marker together with PK and Cpn10. The performance is shown in FIG. 1. Evidently the use of the panel of three potential markers permits discrimination between cancer and normal samples, achieving an AUC of 0.96, and a sensitivity, selectivity, PV and PPV of 0.95 each. This was an improvement over the result when using the single best marker (PK), which achieved an AUC of 0.95, a sensitivity of 0.85, selectivity of 0.90, PV of 0.875 and PPV of 0.895. To assess whether the panel would be reproducible and valid in its predictive performance on independent data, two thirds/one third cross-validation were used. The set of 40 samples was split 10 times randomly into training and test sets of, respectively, 26 and 14 samples; the data from the 26 samples were used as input variables to train the logistic regression predictor. To maintain proportions and make the performance of the predictor over the random splits more comparable, the random selection was programmed such that identical absolute numbers of benign and malignant cases were assigned to training and test sets in each of the 10 data splits (i.e., 13 benign/13 malignant in each training set; 7 benign/7 malignant in each test set). Once the logistic regression discriminator was parametrically specified on a training set, it was used as a predictor to make calls for each of the 14 "independent" test cases, by using a cut-off value of 0.5. The accuracy of these calls, compared to the actual disease status of the test cases, was evaluated in terms of fractions of true positives (sensitivity) and false positives (1-specificity), for each of the ten test sets (Table 5). The similarity in performances between the training and test sets validates the predictability and ruggedness of the panel of biomarkers.

Support for the iTRAQ results was provided by dot-blot analyses of the same 40 samples. FIG. 2 shows the results of the PIGR and β-actin blots; the latter was used for normalizing the protein loading. It is evident that the relative intensities of the dots do qualitatively correlate with the ratios across the sample sets as reported in the iTRAQ analyses. Additionally, immunohistochemistry validated the overexpression of PK, PIGR, and Cpn 10 in the malignant epithelium of EmCa tissues (FIG. 3). Intense positive staining (brown) is evident in the epithelial cells of the glands in the cancer samples for PK, Cpn 10 and PIGR. By contrast, the glands of normal proliferative and secretory endometrium show absence of, or only weak, staining. For PIGR, intense staining is also evident within the lumen of the glands of one of the two Type I EmCa tissues, consistent with the expectation that this protein is cell-surface bound or secreted (15).

Discussion

Pyruvate kinase M1/M2 was demonstrated as being overexpressed in EmCa samples by both cICAT and iTRAQ methods (3). This result has been verified in this study, where PK appears to be an effective marker for differentiating between both Types I and II EmCa and normal endometrial tissues. Pyruvate kinase's significance as a cancer biomarker has increasingly been recognized. A number of studies have suggested that PK M2, in particular, is present primarily in a dimeric form in tumors and that it is useful as a biomarker in the early detection of tumors (16, 17). In fact the M2 isoform, after initial expression at the fetal stage, was reported to be prevalent only in proliferating cells and tumors (17). PK overexpression in tumor cells is understandable and can be explained on the basis of the key role that it plays in the generation of ATP in the glycolytic pathway. Under the hypoxic conditions that are typical for tumors, this pathway is a critical route by which tumors satisfy the higher energy requirements needed for proliferation (reviewed in ref. 18). Another study demonstrated that PK M2, in combination with any of three tumor markers (CEA, CA72-4, CA19-9) for gastro-intestinal cancer, results in improved sensitivity for detection of colorectal, gastric and esophageal cancers (19).

Polymeric immunoglobulin receptor precursor was previously observed to be overexpressed in EmCa and has been verified in this study (3). PIGR is part of the immune response system and is typically expressed by epithelial cells. Its primary role is the transport of dimeric IgA from the basolateral surface of the epithelium to the apical surface where they are released into exocrine secretions (20, 21). It is, therefore, plausible that the overexpression is part of the host's response to the presence of the cancerous cells themselves or to the carcinogenic stimulus. This would also suggest possible mechanistic explanations for the less aggressive nature of the Type I cancer. These possible explanations stem from the fact that the cleaved form of PIGR, known as the secretory component (SC), is a known inhibitor of the proinflammatory cytokine IL-8 and acts by forming an inactive complex with this chemokine, thereby preventing chemotaxis of polymorphonuclear neutrophils (PMN) (22). While it is generally accepted that PMNs play an anti-tumorigenic role (23), there are instances where this might not hold true. A recent study showed that melanoma cell extravasation is facilitated by PMNs and that blocking either the IL-8 receptors on PMN or neutralizing the soluble IL-8 in cell suspensions reduced extravasation of these melanoma cells (24). Thus the inhibition of PMN accumulation might reduce the potential for metastases to occur. PMNs might also facilitate tumor progression through the release of enzymes that are responsible for activation of matrix metalloproteinase-2 (MMP-2) from its inactive proMMP-2 form (25). In turn, MMP-2 is known to be involved with angiogenesis and tumor invasion (25). Consequently, the increased level of PIGR in the Type I cancer might result in the effective inhibition of angiogenesis and prevention of tumor invasion. Such a contradictory role for cells that are part of the immune response is well documented. A similar role for macrophages was recently described in a review, which demonstrated that macrophages facilitate tumor progression by enabling angiogenesis and tumor cell motility as a result of increased intravasation (26). Thus the inhibition of PMN migration by PIGR overexpression might result in the inhibition of angiogenesis, tumor invasion, and metastases thereby accounting for the less aggressive nature of the Type I cancer.

A closer examination of the factors that affect the expression levels of the potential markers is also enlightening. The factors influencing the expression levels of PIGR include induction by cytokines such as IL-4, TNFα, IFN-γ (21, 27, 28). Signaling pathways that are involved with the response to induction by such ligands include the STAT, NFκB and p38-MAPK pathways (21, 22, 27, 28). In addition, there are cofactors that are also known to be involved with upregulation of PIGR expression. One such cofactor is all-trans retinoic acid (RA), which is a metabolite of vitamin A (29). RA enhances the upregulation of PIGR expression in response to IL-4 and IFN-γ stimulations. RA and NFκB also regulate the expression levels of some of the other potential markers discovered in this study and are discussed below. It is also noteworthy that NFκB has been specifically linked with endometrial cancer by various other studies (30, 31).

WAP 4-disulfide core domain protein 2, which is also known as HE4, belongs to a family of proteins that are known to be proteinase inhibitors. WFDC2 is known to be overexpressed in a range of different cell lines including ovarian, renal, lung, colon, and breast lines. In a recent study, WFDC2 showed upregulation in mRNA levels during the secretory phase in rhesus monkeys (32). This result is consistent with the iTRAQ results that were observed in the secretory-phase samples (Table 3). The bulk of the initial studies on WFDC2 were focused on using it as a biomarker for ovarian carcinoma (34). However, an investigation on the expression levels of this protein in various human tissues using DNA microarrays, followed by validation with immunohistochemistry, has confirmed that overexpression is also observed in 90% of endometrial adenocarcinomas (34). It is noteworthy that a recent review has suggested that the overexpression of WFDC2 is a good, early marker for ovarian cancer, even better than CA125 for that purpose. However, WFDC2 did not show as high an overexpression in clear cell as opposed to epithelial ovarian carcinomas and might not prove useful for diagnosis of the former (35). This last aspect appears to mirror the results with Type II EmCa in which overexpression levels, on average, were also not as high as those in Type I EmCa-Type II endometrial cancers are serous and/or clear cell cancers (36).

Another noteworthy point is that NFκB might also play a role in regulating the expression levels of WFDC2, through a binding site identified in the promoter region of WFDC2, as well as other proteins belonging to this family (35). This link with NFκB appears to be in common between WFDC2 and PIGR above, thus suggesting a possible common means for the overexpression of both proteins.

Mucin 5B is a new potential EmCa marker found in this study. This protein has not been previously reported to be a marker for or associated with endometrial cancer. Mucins in general, however, have been associated with various cancers and have been proposed to promote tumor cell invasion and metastases (37). In the case of lung cancer, tumors of patients who were smokers showed a higher level of Mucin 5B, and these patients tended to show higher degrees of post-operative relapse (37). Furthermore, it has been demonstrated that Mucin 5B mRNA expression is enhanced by RA, a factor in common with PIGR above (38). The 5' flanking region of Mucin 5B has two NFκB binding sites, suggesting another element in common with PIGR and WFDC2 (38).

Alpha-1-antitrypsin is a secreted glycoprotein, which like WFDC2 is a protease inhibitor. In this study, the expression levels are downregulated relative to the normal proliferative samples. AAT is known to inhibit angiogenesis and tumor growth, thus underexpression would have forseeable implications for cancer (39). The precedence for such downregulation of expression levels for AAT in cancers has been discussed previously (3).

Clusterin is another new potential biomarker for EmCa found in this study. It is an anti-apoptotic glycoprotein that has been implicated in resistance to various cell-death triggers (40). Independent validation for the findings is provided by the TMA results available from the Human Protein Atlas (41). Their results show rare, moderately stained cells in the stroma, and no staining in the glandular cells or the myometrium in the normal endometrial samples. By contrast, five out of 12 endometrial cancer samples show moderate cytoplasmic staining in the epithelial cells and another four show weak staining. Overexpression of clusterin has previously been reported for various cancers, including hepatocellular, breast, prostate and urothelial bladder carcinoma (42-45). Of particular interest is a study that showed inhibition of clusterin expression aided in sensitivity to chemotherapy, thus making clusterin a useful therapeutic target (43). Moreover, another study demonstrated that Tamoxifen, a drug used to treat breast cancer, enhanced clusterin expression levels, which in turn was linked to an increased potential for metastases of breast cancer cells. This, in their view, suggests a possible mechanism for the increase of endometrial cancer in postmenopausal women undergoing Tamoxifen treatment for breast cancer (46).

The small increase observed in the levels of creatine kinase B (CKB) in the secretory phase in this study was consistent with the findings of another study that had demonstrated a similar increase in the secretory phase over the proliferative phase, using 2D gels followed by tryptic digestion and partial N-terminus sequencing (47). Additionally, other independent enzyme-activity studies showed a greater than 3-fold increase in the activity for creatine kinase B in the secretory phase over the proliferative phase (48). CKB is underexpressed in EmCa; the extent is apparently larger in Type II than Type I samples. This downregulation has also been observed in various other cancers including colon and lung adenocarcinomas as well as squamous cell carcinomas (49).

Cpn 10, calgizzarin, transgelin and MIF are all proteins previously detected as being differentially expressed in EmCa samples; these have all also been implicated in various other forms of cancer (3, 50). Macrophage capping protein (Cap-G) and leucine aminopeptidase 3 (LAP 3) were identified in a sufficient number of EmCa samples to justify inclusion in the list of differentially expression proteins in this study. They showed apparent trends in expression levels in Type II EmCa, suggesting that they might prove useful as subjects of a targeted investigation. Cap-G belongs to the gelsolin family of proteins, which upon activation by Ca2+, is responsible for capping barbed ends of actin filaments (51). Thus Cap-G affects the actin filament structure within a cell, and as non-muscle cells require to rapidly reorganize the actin filament network in order to change shape during movement, it is conceivable that Cap-G is one of the proteins involved in the mechanism by which a tumor cell metastasizes. This could be the reason that it appears to be overexpressed to a larger extent in the more aggressive Type II than in Type I EmCa. Currently, not much detail is known about the function and the distribution of expression for LAP3. Interestingly, placental leucine aminopeptidase (P-LAP) has been linked specifically with EmCa and an increased expression level of P-LAP is associated with a poor prognosis (52). However, a BLAST search between the LAP3 and P-LAP amino acid sequence returned no significant homology, thus making LAP3 a potentially novel marker for endometrial cancer.

Some commonalities appear among the various PCMs discussed above. One of these is the possible implication of PMNs. As noted individually above, PMNs and PIGR expression levels are closely linked. In fact, not only can the PIGR expression level affect PMN chemotaxis, but also PMN-expressed enzymes, such as NE and PR3, known to cleave PIGR to form SC (22). Furthermore, under specific conditions, supernatants from activated PMNs have been shown to induce PIGR expression through the NFκB pathway (22). Thus PMNs might conceivably be the potential common element that was alluded to earlier, which could elicit a response through NFκB sites in WFDC2 and PIGR as well as Mucin 5B. Another possible association between PMNs and WFDC2 is the fact that in some cell types, other proteins belonging to the WFDC family, namely, SLPI and elafin, are known to inhibit NE (22). Anti-proteinase activity by WFDC2 has not yet been demonstrated but inferred on the basis of its similarity to SLPI and elafin (35); it is, therefore, possible that WFDC2 may play a role in inhibiting PMN-expressed enzymes in the endometrium, akin to that of SLPI and elafin in the other cell types. Another antiproteinase that might have some influence on the possible role of PMNs in this context is AAT, a known inhibitor of the PMN-released enzyme NE. Lastly, it has also been proposed that one of the mechanisms by which PMNs cause the overexpression of PIGR is through the release of IL-1β (22). IL-1 is also known to cause an increase in the clusterin expression level, thus representing another link between clusterin and the aforementioned biomarkers (53).

In the study, the ten sample sets were correlated by comparing the ten proliferative samples among themselves. An alternative strategy is to pool the ten proliferative samples and compare every other sample to the proliferative pool. As shown previously, the relative expression level (ratio) for any given PCM across the ten-sample sets appears to vary with a relative standard deviation typically ≦30%. Some of this variation may reflect genuine person-to-person differences; however, a significant contribution to this observed variation must also stem from differing proportions of cancerous glands within the samples that were homogenized, or differing stages and extents of the EmCa. It may be useful to record the proportion of cancerous tissue present in each sample. Accounting for such a factor might help to reduce the range of differential expression observed within each PCM. A perhaps conceptually simplest means in addressing this issue would be to analyze laser capture microdissected (LCM-ed) cancerous glands or epithelial cells. Relative expression of PCMs would then be evaluated against similarly procured epithelial cells from normal endometrial tissues. To minimize the number of LCM-ed cells required, this analysis could conceivably be performed under multiple-reaction monitoring (MRM) mode on a triple-quadrupole or linear ion trap instrument, which has long been used for mallmolecule quantification in the pharmaceutical industry. Such monitoring would target the transitions specific to the peptides of interest from the PCMs. The increased sampling time afforded by MRM would result in superior sensitivity, thus requiring less protein or fewer cancerous cells.

TABLE 1

Differentially Expressed Proteins in Endometrial Malignancies/Cancer

| Protein | Gene name | Accession Numbers | Expression in EmCa |
|---|---|---|---|
| WAP four-disulfide core domain 2 (WFDC2) | WFDC2 | GeneID: 10406 CAG33258, NP_006094, NP_542772, NP_542773, NP_542774 (protein) NM_006103, NM_080734, NM_080735, NM_080736 (mRNA) and SEQ ID NOs. 1 to 9. | Up in secretory phase; higher levels in Type I |
| Clusterin | CLU | GeneID: 1191 NP_001822, NP_976084 (protein) NM_001831, NM_203339 (mRNA) and SEQ ID NOs. 10 to 13. | Up |
| Mucin 5B | MUC5B | GeneID: 4587 AAG33673.1, CAA06167.1, AAC51344.1, CAA70926.1, CAA96577.1, AAC67545.1, AAF64523.1, AAB35930.1, AAB61398.1, AAC51343.1, AAB65151.1, CAA52408.1, CAA52910.1, Q14879, Q93043, Q9HC84, Q9NYE4 (protein) | Under |

TABLE 1-continued

Differentially Expressed Proteins in Endometrial Malignancies/Cancer

| Protein | Gene name | Accession Numbers | Expression in EmCa |
|---|---|---|---|
| | | AC061979.17 (11065 . . . 50111), AF107890.1, AJ004862.1, U78554.1 Y09788.2, Z72496.1, AF086604.1, AF253321.1 S80993.1, U63836.1, U78551.1, U95031.1, X74370.1, X74955.1 (mRNA) and SEQ ID NO. 14. | |
| leucine aminopeptidase 3 (LAP3) | LAP3 | Gene ID. 51056 NP_056991 (protein) NM_015907 (mRNA) and SEQ ID NOs. 15 and 16. | Up |
| Macrophage capping protein; gelsolin-like capping protein (CAP-G) | CAP-G | Gene ID: 822 NP_001738 (protein) NM_001747 (mRNA) and SEQ ID NOs. 17 and 18. | Up |
| Progestagen-associated endometrial protein (PAEP) (pregnancy-associated endometrial alpha-2-globulin, placental protein 14 glycodelin) | PAEP | Gene ID: 5047 NP_002562 and NP_001018059 (protein) NM_001018049 and NM_002571 (mRNA) and SEQ ID NOs. 19, 20 and 21. | |

TABLE 2

Differentially Expressed Proteins in Endometrial Malignancies/Cancer

| Protein | Gene name | Accession Nos. | Expression in EmCa |
|---|---|---|---|
| Chaperonin 10 (Cpn10) | HSPE1 | Gene ID: 3336 Q04984 and AAH23518 NP_002148 [SEQ ID NO. 32] NM_002157 and U07550 [SEQ ID NOs. 32 and 33] | Up |
| Calgranulin A | S100A8 | GeneID: 6279 NP_002955, P05109 [SEQ ID NO. 34] A12027 [SEQ ID NO. 35] NM_002964 [SEQ ID NO. 36] | Up |
| Calgranulin B | S100A9 | Gene ID: 6280 NM_002965 (mRNA) NP_002956 (protein) P06702 [SEQ ID NO. 37] X06233 [SEQ ID NO. 38] M21064 [SEQ ID NO. 39] | Up |
| Polymeric-immunoglobulin Receptor precursor | PIGR | Gene ID: 5284 NP_002635, P01833 or Q8IZY7 [SEQ ID NO. 40] NM_002644 [SEQ ID NO. 41] | Up |
| Phosphatidylethanolamine-binding protein | PBP PEBP-1 | Gene ID: 5037 NP_002558 P30086 [SEQ ID NO. 42] (PEBP) NM_002567 [SEQ ID NO. 43] | Up |
| Acidic leucine-rich nuclear phosphoprotein 32 family member A | ANP32A | GeneID: 8125 NP_006296 P39687 [SEQ ID NO. 44] NM_006305 [SEQ ID NO. 45] | Up |
| Heat shock 70 kDa protein 6 | HSPA6 | GeneID: 3310 P17066 [SEQ ID 46] NM_002155 [SEQ ID NO. 47] X51757 [SEQ ID NO. 48] | Up |
| Macrophage migration Inhibitory factor (MIF) | MIF | GeneID: 4282 NP_002406 P14174 [SEQ ID NO. 49] NM_002415 [SEQ ID NO. 50] L19686 [SEQ ID NO. 51] | Up |

TABLE 2-continued

Differentially Expressed Proteins in Endometrial Malignancies/Cancer

| Protein | Gene name | Accession Nos. | Expression in EmCa |
|---|---|---|---|
| Calgizzarin (S100C protein) | S100A11 | GeneID: 6282<br>NP_005611<br>P31949 [SEQ ID NO. 52]<br>NM_005620 and D38583[SEQ ID NO. 53] | Up |
| Triosephosphate isomerase | TPI1 | Gene ID: 7167<br>P00938 and NP_000356[SEQ ID NO. 54]<br>NM_000365 [SEQ ID NO. 55]<br>X69723 [SEQ ID NO. 56] | Up |
| Alpha-1-antitrypsin precursor | SERPINA1 (AAT) | GeneID: 5265<br>NP_000286<br>NP_001002235<br>NP_001002236 (protein)<br>NM_001002235<br>NM_001002236 (mRNA)<br>gi/1703025<br>ITHU and P01009 [SEQ ID NO. 57]<br>NM_000295[SEQ ID NO. 58]<br>K02212 [SEQ ID NO. 59] | Under |
| Creatine kinase B (B-CK) | CKB | GeneID: 1152<br>gi/125294, NP_001814<br>P12277[SEQ ID NO. 60]<br>NM_001823 [SEQ ID NO. 61]<br>X15334 [SEQ ID NO. 62] | Under |
| Pyruvate kinase, M1 or M2 isozyme | PKM2 | GeneID: 5315<br>NM_002654<br>NM_182470<br>NM_182471 (mRNA)<br>NP_002645<br>NP_872270<br>NP_872271 (protein)<br>gi/20178296; gi/125604;<br>P14618, KPY1_HUMAN [SEQ ID NO. 63]<br>X56494 [SEQ ID NO. 64] | Up |
| Transgelin (smooth muscle protein 22-alpha) | TAGLN | GeneID: 6876<br>NM_001001522<br>NM_003186 (mRNA)<br>NP_001001522<br>NP_003177 (proteint)<br>gi/3123283<br>Q01995 [SEQ ID NO. 65]<br>D84342 [SEQ ID NO. 66] | Under |
| Heterologous nuclear ribonucleoprotein D | hnRPD | GeneID: 3184<br>NM_001003810<br>NM_002138<br>NM_031369<br>NM_031370 (mRNA)<br>NP_001003810<br>NP_002129<br>NP_112737<br>NP_112738 (protein)<br>ROD_HUMAN (Q14103) [SEQ ID NO. 67]<br>AF026126 [SEQ ID NO. 68] | Up |
| Actin | ACT gamma 1<br>ACT gamma 2 | Gene ID. 71 (gamma 1)<br>NP_001605 (protein)<br>NM_001614 (mRNA)<br>Gene ID. 72 (gamma 2)<br>NP_001606 (protein)<br>NM_001615 (mRNA)<br>[SEQ ID NOs. 28, 29, 30, and 31.] | |
| Beta-5 tubulin | TUBB | Gene ID. 203068<br>NP_821133 (protein)<br>NM_178014 (mRNA)<br>[SEQ ID NOs. 26 and 27.] | |
| Hn RNP-DO | RALY | GeneID: 22913<br>NP_031393, NP_057951 (protein) | |

TABLE 2-continued

Differentially Expressed Proteins in Endometrial Malignancies/Cancer

| Protein | Gene name | Accession Nos. | Expression in EmCa |
|---|---|---|---|
| | | NM_016732 NM_007367(mRNA) [SEQ ID NOs. 22, 23, 24, and 25.] | |

TABLE 3

Normal proliferative samples

| Protein Name | P1 | P2 | P3 | P4 | P5 | P6 | P7 | P8 | P9 | P10 | Avg |
|---|---|---|---|---|---|---|---|---|---|---|---|
| PP14 | ND | ND | ND | ND | ND | ND | 1.20 | 0.04 | 0.70 | 1.19 | 1.00 |
| PIGR | 0.92 | 0.51 | 1.02 | 1.96 | 0.88 | 0.84 | 0.84 | 0.88 | 0.85 | 0.89 | 1.00 |
| PK | 1.19 | 0.99 | 0.99 | 1.15 | 1.20 | 0.97 | 0.88 | 0.84 | 0.93 | 0.87 | 1.00 |
| WFDC2 | 0.73 | 1.69 | 0.74 | 0.93 | ND | ND | ND | ND | ND | ND | 1.00 |
| Clusterin | ND | ND | ND | 1.10 | 1.16 | 0.88 | 1.02 | 0.81 | 1.10 | 0.94 | 1.00 |
| Mucin 5B | ND | ND | ND | ND | ND | ND | ND | ND | ND | ND | |
| Calgizzarin | ND | ND | ND | ND | ND | ND | ND | ND | ND | ND | |
| Cpn 10 | 1.00 | 0.64 | 0.60 | 0.59 | ND | ND | 1.00 | | 1.26 | 1.13 | 1.17 |
| MIF | 1.69 | 1.12 | 1.02 | 1.18 | 0.35 | 0.37 | 0.65 | | 0.81 | 0.81 | 1.00 |
| AAT | 0.91 | 0.93 | 1.07 | 0.96 | 1.09 | 1.07 | 1.20 | 0.92 | 1.11 | 0.81 | 1.00 |
| CKB | 0.04 | 0.00 | 0.00 | 1.07 | 1.21 | 1.30 | 0.33 | 1.17 | 0.34 | 0.84 | 1.00 |
| Transgelin | 0.83 | 0.61 | 0.89 | 1.26 | 1.06 | 1.64 | 1.24 | 0.93 | 0.83 | 0.61 | 1.00 |
| Actin | 1.25 | 0.99 | 0.88 | 1.02 | 1.04 | 0.94 | 1.04 | 0.86 | 0.95 | 0.93 | 1.00 |
| Beta-5-tubulin | 0.91 | 0.99 | 1.13 | 0.86 | 1.11 | 1.03 | 0.92 | 0.76 | 1.11 | 1.18 | 1.00 |
| PEBP | 1.85 | 0.81 | 0.83 | 0.99 | 0.91 | 0.32 | 0.64 | ND | ND | ND | 1.00 |
| HnRNP D0 | 1.04 | 0.28 | 1.24 | 0.33 | 1.11 | 1.03 | 0.89 | 1.05 | 1.02 | 0.38 | 1.00 |
| LAP3 | 1.03 | 0.32 | 1.07 | 1.20 | 1.05 | 1.00 | 0.90 | 0.98 | 0.65 | 1.15 | 1.00 |
| CAP-G | ND | ND | ND | 0.80 | 0.92 | 0.37 | 0.99 | 1.84 | 0.89 | 0.38 | 1.00 |

Normal secretory samples

| Protein Name | S1 | S2 | S3 | S4 | S5 | S6 | S7 | S8 | S9 | S10 | Avg |
|---|---|---|---|---|---|---|---|---|---|---|---|
| PP14 | | | 1.42 | | | | ND | 2.23 | 3.16 | ND | 4.01 |
| PIGR | 0.94 | 1.13 | 1.20 | ND | 0.84 | 1.04 | 1.08 | ND | 1.03 | 0.91 | 1.02 |
| PK | 1.00 | 0.92 | 0.92 | 0.94 | 0.85 | 0.93 | 0.97 | 0.82 | 0.94 | 0.90 | 0.92 |
| WFDC2 | 0.87 | 1.53 | 2.20 | 1.28 | 2.00 | 2.13 | 1.65 | 0.98 | ND | ND | 1.73 |
| Clusterin | 1.61 | 0.97 | 0.93 | ND | 0.74 | 1.27 | 1.70 | 1.08 | 1.94 | 1.12 | 1.19 |
| Mucin 5B | 0.99 | 1.34 | 1.04 | ND | 1.06 | 1.04 | ND | ND | ND | 1.16 | 1.07 |
| Calgizzarin | 0.50 | 1.03 | NQ | ND | 0.91 | 1.65 | 0.65 | ND | ND | 1.50 | 1.05 |
| Cpn 10 | 0.38 | 0.92 | 0.38 | ND | 0.49 | 1.00 | 1.14 | 0.51 | 0.59 | 0.34 | 0.86 |
| MIF | 1.17 | 1.02 | 0.88 | 0.88 | ND | 0.38 | 1.33 | 1.19 | ND | 1.01 | 1.03 |
| AAT | 1.13 | 0.88 | 1.04 | 1.07 | 0.71 | 1.12 | 0.91 | 0.93 | 2.00 | 0.79 | 1.03 |
| CKB | 1.30 | 1.35 | 1.45 | 1.28 | 1.01 | 1.41 | 1.69 | 0.92 | 1.39 | 1.37 | 1.40 |
| Transgelin | 0.31 | 1.24 | ND | 1.07 | 0.89 | 1.36 | 0.59 | 1.93 | 0.61 | 0.57 | 1.06 |
| Actin | 1.07 | 1.06 | 0.98 | 1.00 | 0.90 | 1.06 | 0.98 | 1.48 | 0.98 | 1.93 | 1.14 |
| Beta-5-tubulin | 1.31 | 0.94 | 0.72 | 1.14 | 1.00 | 1.22 | 1.09 | 0.97 | 0.88 | 0.89 | 1.01 |
| PEBP | 0.56 | 1.01 | 0.69 | 0.76 | 0.95 | 1.11 | 1.20 | 0.50 | 0.44 | 0.76 | 0.84 |
| HnRNP D0 | 0.58 | ND | ND | ND | ND | 1.06 | ND | 0.76 | 0.22 | 0.88 | 0.79 |
| LAP3 | 1.30 | 0.24 | 1.35 | ND | 0.68 | ND | ND | ND | ND | ND | 1.02 |
| CAP-G | 1.09 | 1.31 | 1.05 | ND | ND | ND | 0.25 | 1.31 | 1.35 | 0.89 | 1.11 |

<0.4  <0.5  <0.67  <0.8  >1.25  >1.5  >2.0  >2.5

Type I cancer samples

| Protein Name | I1 | I2 | I3 | I4 | I5 | I6 | I7 | I8 | I9 | I10 | I6b | I10b | Avg |
|---|---|---|---|---|---|---|---|---|---|---|---|---|---|
| PP14 | 0.97 | 1.64 | NQ | 0.89 | 1.28 | 0.96 | ND | 0.86 | 1.26 | ND | 0.87 | ND | 1.09 |
| PIGR | | | ND | 0.98 | 1.06 | 1.34 | ND | 1.22 | | | 1.03 | 2.84 | |
| PK | | 1.47 | 1.55 | 2.40 | | 1.32 | 1.39 | 1.13 | 0.92 | | 1.62 | | |
| WFDC2 | | | | 1.98 | | | | ND | 1.56 | ND | 3.67 | | |
| Clusterin | | | ND | 1.30 | 1.08 | 1.37 | 1.10 | 0.98 | 1.63 | 1.18 | 2.53 | | |
| Mucin 5B | | | ND | | 1.11 | ND | ND | ND | | | 3.97 | | |
| Calgizzarin | 1.33 | 1.82 | NQ | ND | | 1.08 | ND | ND | 1.84 | ND | 2.90 | | |
| Cpn 10 | 1.28 | 1.33 | 1.09 | ND | | 1.41 | | 1.49 | 1.19 | 1.11 | 1.58 | | 1.55 |
| MIF | | 1.48 | 1.63 | 0.90 | ND | 1.32 | 1.39 | 1.83 | ND | 1.09 | | 1.10 | 1.42 |
| AAT | 0.44 | 0.34 | 0.96 | 0.52 | 0.45 | 1.01 | 0.83 | 0.64 | 1.23 | 0.62 | 1.06 | 0.43 | 0.71 |
| CKB | 0.93 | 0.43 | 1.19 | 1.29 | 0.90 | 1.06 | 1.19 | 0.85 | 0.92 | 0.85 | 0.41 | 0.86 | 0.91 |
| Transgelin | 0.48 | 0.47 | ND | 1.23 | 0.53 | 0.49 | 0.47 | 0.59 | 1.58 | 0.51 | 0.43 | 0.66 | 0.63 |
| Actin | 1.39 | 1.22 | 0.96 | 1.35 | 1.20 | 1.16 | 1.38 | 1.03 | 1.08 | 0.96 | 0.63 | | 1.20 |
| Beta-5-tubulin | 0.57 | | | 1.12 | 1.16 | 1.33 | 1.52 | 1.31 | 0.82 | | | 0.80 | 0.97 |
| PEBP | 1.10 | 1.13 | 1.34 | 0.93 | 1.63 | 1.01 | 1.38 | 1.12 | 1.00 | 1.44 | 0.85 | 1.09 | 1.18 |
| HnRNP D0 | 1.22 | ND | ND | ND | ND | 0.89 | ND | 1.20 | 1.44 | 1.04 | 0.81 | 1.36 | 1.16 |
| LAP3 | | 1.38 | 1.31 | ND | 0.59 | ND | ND | ND | | 0.65 | ND | | 1.17 |
| CAP-G | 1.82 | 1.02 | 0.91 | ND | ND | ND | 0.90 | 1.67 | 1.54 | 0.93 | ND | | 1.49 |

Type II cancer samples

| Protein Name | II1 | II2 | II3 | II4 | II5 | II7 | II8 | II9 | Avg |
|---|---|---|---|---|---|---|---|---|---|
| PP14 | 0.85 | 0.85 | NQ | | ND | | 0.91 | 1.23 | 0.88 |
| PIGR | | 0.87 | 1.07 | ND | | | ND | 1.02 | 1.42 |
| PK | | | 1.67 | | 1.22 | 1.09 | 2.23 | 1.89 | 1.86 |
| WFDC2 | 1.48 | 1.51 | 1.67 | | | | | ND | 2.43 |
| Clusterin | 1.03 | 1.41 | | ND | | | 0.95 | 1.63 | 1.49 |
| Mucin 5B | 0.97 | 1.03 | 0.93 | ND | | ND | ND | ND | 1.53 |
| Calgizzarin | 1.33 | 1.56 | | ND | | | ND | ND | 8.06 |
| Cpn 10 | 1.36 | 1.30 | ND | 1.35 | | 1.99 | | 1.44 | 1.94 |
| MIF | 1.30 | 1.32 | 1.83 | | 1.14 | ND | 1.65 | 1.34 | 1.69 |
| AAT | 0.44 | 0.30 | 1.09 | 0.60 | 0.81 | | 0.60 | 0.94 | 0.68 |
| CKB | 0.59 | 0.27 | 0.66 | | 0.55 | | 0.93 | 0.64 | 0.64 |
| Transgelin | 0.25 | 0.32 | ND | 0.59 | 0.41 | 0.44 | 1.32 | 1.15 | 0.64 |
| Actin | 1.38 | 1.15 | 1.26 | 1.19 | 1.09 | 0.97 | 1.32 | | 1.20 |
| Beta-5-tubulin | 1.33 | 0.93 | 1.35 | 1.63 | 0.81 | 1.18 | 1.38 | 0.65 | 1.19 |
| PEBP | 0.65 | 0.94 | 1.28 | 1.32 | 1.28 | 1.01 | 1.02 | 0.41 | 0.91 |
| HnRNP D0 | 0.94 | ND | ND | ND | ND | ND | 1.22 | 1.89 | 1.62 |
| LAP3 | 1.36 | 1.30 | 1.46 | ND | 1.38 | ND | ND | ND | 2.27 |
| CAP-G | 1.82 | 2.41 | ND | ND | ND | 0.89 | 1.32 | 2.33 | 2.33 |

<0.4  <0.5  <0.67  <0.8  >1.25  >1.5  >2.0  >2.5

TABLE 4

| Run number | S1 (S:P) | S2 (S:P) | S3 (S:P) | S4 (S:P) | S5 (S:P) | S6 (S:P) | S7 (S:P) | S8 (S:P) | S9 (S:P) | S10 (S:P) |
|---|---|---|---|---|---|---|---|---|---|---|
| R1 | 0.81 | 1.00 | 1.00 | 0.84 | 0.80 | 1.02 | 1.04 | 1.04 | 0.76 | 1.03 |
| R2 | 0.80 | 0.91 | 0.89 | 0.82 | 0.96 | 1.09 | ND | 0.93 | 0.83 | 1.11 |
| R3 | 0.91 | 0.91 | 0.89 | 0.79 | 0.88 |  | 1.05 | 0.85 | 0.75 |  |
| Avg | 0.84 | 0.94 | 0.93 | 0.82 | 0.88 | 1.06 | 1.05 | 0.94 | 0.78 | 1.07 |
| SD | 0.06 | 0.05 | 0.06 | 0.03 | 0.08 | 0.05 | 0.01 | 0.10 | 0.04 | 0.06 |

|  | S1 (I:P) | S2 (I:P) | S3 (I:P) | S4 (I:P) | S5 (I:P) | S6 (I:P) | S7 (I:P) | S8 (I:P) | S9 (I:P) | S10 (I:P) | S6 (I:P) | S10 (I:P) |
|---|---|---|---|---|---|---|---|---|---|---|---|---|
| R1 | 1.79 | 1.45 | 1.78 | 2.47 | 2.31 | 2.19 | 1.54 | 1.67 | 1.04 | 1.38 | 1.16 | 1.99 |
| R2 | 2.24 | 1.60 | 1.57 | 2.30 | 1.83 | 2.17 | ND | 1.51 | 1.39 | 1.30 | 0.93 | 1.85 |
| R3 | 1.80 | 1.45 | 1.33 | 1.69 | 1.59 |  | 1.80 | 1.37 | 1.02 |  |  |  |
| Avg | 1.94 | 1.50 | 1.56 | 2.15 | 1.91 | 2.18 | 1.67 | 1.52 | 1.15 | 1.34 | 1.05 | 1.92 |
| SD | 0.26 | 0.09 | 0.23 | 0.41 | 0.37 | 0.01 | 0.18 | 0.15 | 0.21 | 0.06 | 0.16 | 0.10 |

|  | S1 (II:P) | S2 (II:P) | S3 (II:P) | S4 (II:P) | S5 (II:P) | S7 (II:P) | S8 (II:P) | S9 (II:P) |
|---|---|---|---|---|---|---|---|---|
| R1 | 1.90 | 2.75 | 3.47 | 1.51 | 1.41 | 1.12 | 2.19 | 1.15 |
| R2 | 2.31 | 2.96 | 2.24 | 1.51 | 1.23 | ND | 1.79 | 1.54 |
| R3 | 1.79 | 2.12 | 2.11 | 1.33 | 1.13 | 1.23 | 1.99 | 1.32 |
| Avg | 2.00 | 2.61 | 2.61 | 1.45 | 1.26 | 1.18 | 1.99 | 1.34 |
| SD | 0.27 | 0.44 | 0.75 | 0.10 | 0.14 | 0.08 | 0.20 | 0.20 |

TABLE 5

|  | split 1 | split 2 | split 3 | split 4 | split 5 | split 6 | split 7 | split 8 | split 9 | split 10 |
|---|---|---|---|---|---|---|---|---|---|---|
| Training Set |  |  |  |  |  |  |  |  |  |  |
| true pos | 12 | 11 | 12 | 11 | 12 | 12 | 12 | 12 | 12 | 12 |
| false pos | 0 | 1 | 0 | 1 | 0 | 2 | 1 | 1 | 1 | 1 |
| true negs | 13 | 12 | 13 | 12 | 13 | 11 | 12 | 12 | 12 | 12 |
| false negs | 1 | 2 | 1 | 2 | 1 | 1 | 1 | 1 | 1 | 1 |
| Test Set |  |  |  |  |  |  |  |  |  |  |
| true pos | 6 | 7 | 6 | 7 | 6 | 7 | 7 | 7 | 7 | 7 |
| false pos | 1 | 0 | 1 | 0 | 1 | 1 | 1 | 0 | 0 | 0 |
| true negs | 6 | 7 | 6 | 7 | 6 | 6 | 6 | 7 | 7 | 7 |
| false negs | 1 | 0 | 1 | 0 | 1 | 0 | 0 | 0 | 0 | 0 |

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the antibodies, methodologies etc. which are reported therein which might be used in connection with the invention. Nothing herein is to be construed as an admission that the invention is not entitled to antedate such disclosure by virtue of prior invention.

Below full citations are set out for references.

FULL CITATIONS FOR REFERENCES

1. Gygi, S. P., Rist, B., Gerber, S. A., Turecek, F., Gelb, M. H., and Aebersold R. (1999) Quantitative analysis of complex protein mixtures using isotope-coded affinity tags. Nat. Biotechnol. 17, 994-999.
2. DeSouza, L., Diehl, G., Yang, E. C. C., Guo, J., Rodrigues, M. J., Romaschin, A. D., Colgan, T. J., and Siu K. W. M. (2005) Proteomic Analysis of the Proliferative and Secretory Phases of the Human Endometrium: Protein Identification and Differential Protein Expression. Proteomics. 5, 270-281.
3. DeSouza, L., Diehl, G., Rodrigues, M. J., Guo, J., Romaschin, A. D., Colgan, T. J., and Siu, K. W. M. (2005) Search for cancer markers from endometrial tissues using differentially labeled tags iTRAQ and cICAT with multidimensional liquid chromatography and tandem mass spectrometry. J. Proteome Res. 4, 377-386.
4. National. Cancer Institute of Canada: Canadian Cancer Statistics 2006, Toronto, Canada, 2006 [Serial online] April 2006.
5. Guo, J., Colgan, T. J., DeSouza, L. V., Rodrigues, M. J., Romaschin, A. D., and Siu, K. W. M. (2005) Direct analysis of laser capture microdissected endometrial carcinoma and epithelium by matrix-assisted laser desorption/ionization mass spectrometry. *Rapid Commun. Mass Spectrom.* 19, 2762-2766.
6. Buckley, C. H. (2003) Normal endometrium and non-proliferative conditions of the endometrium. In *Obstetrical and Gynaecological Pathology*, 5th Ed., pp 391-442, Fox H, Wells M, editors. London: Churchill-Livingstone.
7. Cao, Q. J., Belbin, T., Socci, N., Balan, R., Prystowsky, M. B., Childs, G., Jones, J. G. (2004) Distinctive gene expression profiles by cDNA microarrays in endometrioid and serous carcinomas of the endometrium. *Int. J. Gynecol. Pathol.* 23, 321-329.
8. Craig, R., Cortens, J. P., and Beavis, R. C. (2005) The use of proteotypic peptide libraries for protein identification. *Rapid Commun. Mass Spectrom.* 19, 1844-1850.
9. Kuster, B., Schirle, M., Mallick, P., and Aebersold. R. (2005) Scoring proteomes with proteotypic peptide probes. *Nat. Rev. Mol. Cell. Biol.* 6, 577-583.
10. Motulsky, H. (1995) *Intuitive Biostatistics*, Oxford University Press, NY.
11. Pepe, M. S. (2003) *The statistical evaluation of medical tests for classification and prediction*. Oxford University Press, NY.
12. Pepe, M. S. (2005) Evaluating technologies for classification and prediction in medicine. *Statist. Med.* 24, 3687-3696.
13. Bell, S. C., Keyte, J. W., and Waites, G. T. (1987) Pregnancy-associated endometrial alpha 2-globulin, the major secretory protein of the luteal phase and first trimester pregnancy endometrium, is not glycosylated prolactin but related to betalactoglobulins. *J. Clin. Endocrinol. Metab.* 65, 1067-1071.
14. Lalitkumar, P. G., Sengupta, J., Karande, A. A., and Ghosh, D. (1998) Placental protein 14 in endometrium during menstrual cycle and effect of early luteal phase mifepristone administration on its expression in implantation stage endometrium in the rhesus monkey. *Hum. Reprod.* 13, 3478-3486.
15. Norderhaug, I. N., Johansen, F. E., Schjerven, H., and Brandtzaeg, P. (1999) Regulation of the formation and external transport of secretory immunoglobulins. *Crit. Rev. Immunol.* 19, 481-508.
16. Ugurel, S., Bell, N., Sucker, A., Zimpfer, A., Rittgen, W., and Schadendorf, D. (2005) Tumor type M2 pyruvate kinase (TuM2-PK) as a novel plasma tumor marker in melanoma. *Int. J. Cancer.* 117, 825-830.
17. Mazurek, S., Boschek, C. B., Hugo, F., and Eigenbrodt, E. (2005) Pyruvate kinase type M2 and its role in tumor growth and spreading. *Semin. Cancer Biol.* 15, 300-308.
18. Dombrauckas, J. D., Santarsiero, B. D., and Mesecar, A. D. (2005) Structural basis for tumor pyruvate kinase M2 allosteric regulation and catalysis. *Biochemistry.* 44, 9417-9429.
19. Schneider, J., Bitterlich, N., and Schulze, G. (2005) Improved sensitivity in the diagnosis of gastro-intestinal tumors by fuzzy logic-based tumor marker profiles including the tumor M2-PK. *Anticancer Res.* 25, 1507-1515.
20. Hempen, P. M., Phillips, K. M., Conway, P. S., Sandoval, K. H., Schneeman, T. A., Wu, H-J., and Kaetzel, C. S. (2002) Transcriptional regulation of the human polymeric Ig receptor gene: Analysis of basal promoter elements. *J. Immunol.* 169, 1912-1921.
21. Schjerven, H., Brandtzaeg, P., and Johansen F-E. (2000) Mechanism of IL-4-mediated up-regulation of the polymeric Ig receptor: Role of STAT6 in cell typespecific delayed transcriptional response. *J. Immunol.* 165, 3898-3906.
22. Pilette, C., Ouadrhiri, Y., Dimanche, F., Vaerman, J. P., and Sibille, Y. (2003) Secretory component is cleaved by neutrophil serine proteinases but its epithelial production is increased by neutrophils through NF-kappa B- and p38 mitogenactivated protein kinase-dependent mechanisms. *Am. J. Respir. Cell Mol. Biol.* 28, 485-498.
23. Di Carlo, E., Forni, G., Lollini, P., Colombo, M. P., Modesti, A., and Musiani P. (2001) The intriguing role of polymorphonuclear neutrophils in antitumor reactions. *Blood.* 97, 339-345.
24. Dong, C., Slattery, M. J., Liang, S., and Peng, H. H. (2005) Melanoma cell extravasation under flow conditions is modulated by leukocytes and endogenously produced interleukin 8. *Mol Cell Biomech.* 2, 145-159.
25. Shamamian, P., Schwartz, J. D., Pocock, B. J., Monea, S., Whiting, D., Marcus, S. G., and Mignatti, P. (2001) Activation of progelatinase A (MMP-2) by neutrophil elastase, cathepsin G, and proteinase-3: a role for inflammatory cells in tumor invasion and angiogenesis. *J. Cell Physiol.* 189, 197-206.
26. Condeelis, J., and Pollard, J. W. (2006) Macrophages: Obligate Partners for Tumor Cell Migration, Invasion, and Metastasis. *Cell.* 124 (2): 263-266.
27. Takenouchi-Ohkubo, N., Takahashi, T., and Tsuchiya, M. (2000) Role of nuclear factor-κB in the expression by tumor necrosis factor-α of the human polymeric immunoglobulin receptor (pIgR) gene. *Immunogenetics.* 51, 289-295.
28. Rincheval-Arnold, A., Belair, L., Cencic, A., and Djiane, J. (2002) Up-regulation of polymeric immunoglobulin receptor mRNA in mammalian epithelial cells by IFN-γ. *Mol. Cell. Endocrinol.* 194, 95-105.
29. Sarkar, J., Gangopadhyay, N. N., Moldoveanu, Z., Mestecky, J., and Stephensen, C. B. (1998) Vitamin A is required for regulation of polymeric immunoglobulin receptor (pIgR) expression by interleukin-4 and interferon-gamma in a human intestinal epithelial cell line. *J. Nutr.* 128, 1063-1069.
30. Pallares, J., Martinez-Guitarte, J. L., Dolcet, X., Llobet, D., Rue, M., Palacios, J., Prat, J., and Matias-Guiu, X. (2004) Abnormalities in the NF-kappaB family and related proteins in endometrial carcinoma. *J. Pathol.* 204, 569-577.
31. Davies, S., Dai, D., Feldman, I., Pickett, G., and Leslie, K. K. (2004) Identification of a novel mechanism of NF-kappaB inactivation by progesterone through progesterone receptors in Hec50co poorly differentiated endometrial cancer cells: induction of A20 and ABIN-2. *Gynecol. Oncol.* 94, 463-470.
32. Ace, C. I., and Okulicz, W. C. (2004) Microarray profiling of progesterone-regulated endometrial genes during the rhesus monkey secretory phase. *Reprod. Biol. Endocrinol.* 2, 54.
33. Hellstrom, I., Raycraft, J., Hayden-Ledbetter, M., Ledbetter, J. A., Schummer, M., McIntosh, M., Drescher, C., Urban, N., and Hellstrom, K. E. (2003) The HE4 (WFDC2) protein is a biomarker for ovarian carcinoma. *Cancer Res.* 63, 3695-3700.
34. Galgano, M. T., Hampton, G. M., and Frierson, H. F. (2006) Comprehensive analysis of HE4 expression in normal and malignant human tissues. *Mod. Pathol.* Epub ahead of print.
35. Bouchard, D., Morriset, D., Bourbonnais, Y., and Tremblay, G. M. (2006) Proteins with whey-acidic-protein motifs and cancer. *Lancet Oncol.* 7, 167-174.
36. Zorn, K. K., Bonome, T., Gangi, L., Chandramouli, G. V., Awtrey, C. S., Gardner, G. J., Barrett, J. C., Boyd, J., and Birrer, M. J. (2005) Gene expression profiles of serous, endometroid and clear cell subtypes of ovarian and endometrial cancer. *Clin. Cancer Res.* 11, 6422-6430.
37. Yu, C. J., Yang, P. C., Shun, C. T., Lee, Y. C., Kuo, S. H., and Luh, K. T. (1996) Overexpression of MUC5 genes is associated with early post-operative metastasis in non-small-cell lung cancer. *Int. J. Cancer.* 69, 457-465.
38. Chen, Y., Zhao, Y. H., Di, Y. P., and Wu, R. (2001) Characterization of human mucin 5B gene expression in airway epithelium and the genomic clone of the aminoterminal and 5'-flanking region. *Am. J. Respir. Cell Mol. Biol.* 25, 542-553.
39. Huang, H., Campbell, S. C., and Nelius, T. (2004) Alpha1-antitrypsin inhibits angiogenesis and tumor growth. *Int. J. Cancer.* 112, 1042-1048.
40. Gleave, M. E., Miyake, H., Zellweger, T., Chi, K., July, L., Nelson, C., and Rennie P. (2001) Use of antisense oligonucleotides targeting the antiapoptotic gene, clusterin/testosterone-repressed prostate message 2, to enhance androgen sensitivity and chemosensitivity in prostate cancer. *Urology.* 58 (2 Suppl 1), 39-49.
41. Human Protein Atlas web site: http://www.proteinatlas.org/
42. Kang, Y. K., Hong, S. W., Lee, H., and Kim, W. H. (2004) Overexpression of clusterin in human hepatocellular carcinoma. *Hum. Pathol.* 35, 1340-1346.
43. So, A., Sinnemann, S., Huntsman, D., Fazli, L., and Gleave, M. (2005) Knockdown of the cytoprotective chaperone, clusterin, chemosensitizes human breast cancer cells both in vitro and in vivo. *Mol. Cancer Ther.* 4, 1837-1849.
44. Ronquist, K. G., Carlsson, L., Ronquist, G., Nilsson, S., and Larsson, A. (2006) Prostasome-derived proteins capable of eliciting an immune response in prostate cancer patients. *Int. J. Cancer.* Epub ahead of print.
45. Kruger, S., Mahnken, A., Kausch, I., and Feller, A. C. (2006) Value of clusterin immunoreactivity as a predictive factor in muscle-invasive urothelial bladder carcinoma. *Urology.* 67, 105-109.
46. Zierau, O., O'Sullivan, J., Morrissey, C., McDonald, D., Wunsche, W., Schneider, M. R., Tenniswood, M. P., and Vollmer G. (2004) Tamoxifen exerts agonistic effects on clusterin and complement C3 gene expression in RUCA-I primary xenografts and metastases but not normal uterus. *Endocr. Relat. Cancer.* 11, 823-830.
47. Byrjalsen, I., Larsen, P. M., Fey, S. J., and Christiansen, C. (1995) Human endometrial proteins with cyclic changes in the expression during the normal menstrual cycle: characterization by protein sequence analysis. *Hum. Reprod.* 10, 2760-2766.
48. Satyaswaroop, P. G., and Mortel, R. (1983) Creatine kinase activity in human endometrium: relative distribution in isolated glands and stroma. *Am. J. Obstet. Gynecol.* 146, 159-162.
49. Joseph, J., Cardesa, A., and Carreras, J. (1997) Creatine kinase activity and isoenzymes in lung, colon and liver carcinomas. *Br. J. Cancer.* 76, 600-605.
50. Yang, E. C., Guo, J., Diehl, G., DeSouza, L., Rodrigues, M. J., Romaschin, A. D., Colgan, T. J., and Siu, K. W. (2004) Protein expression profiling of endometrial malignancies reveals a new tumor marker: chaperonin 10. *J. Proteome Res.* 3, 636-643.
51. Young, C. L., Feierstein, A., and Southwick, F. S. (1994) Calcium regulation of actin filament capping and monomer binding by macrophage capping protein. *J. Biol. Chem.* 269, 13997-14002.
52. Shibata, K., Kikkawa, F., Kondo, C., Mizokami, Y., Kajiyama, H., Ino, K., Nomura, S., and Mizutani, S. (2004) Placental leucine aminopeptidase (P-LAP) expression is associated with chemosensitivity in human endometrial carcinoma. *Gynecol. Oncol.* 95, 307-313.
53. Hardardottir, I., Kunitake, S. T., and Moser, A. H. (1994) Endotoxin and cytokines increase hepatic messenger RNA levels and serum concentrations of apolipoprotein J (clusterin) in Syrian hamsters. *J. Clin. Invest.* 94, 1304-1309.

We claim:

1. A method for diagnosing an endometrial disease or an endometrial phase in a mammalian subject by detecting one or more endometrial markers associated with the endometrial disease or the endometrial phase, the method comprising:
   (a) measuring the amount of the endometrial market Muc5B in a biological sample obtained from the subject, wherein the measuring step comprises:
   (i) contacting the sample with at least one binding agent that specifically binds to the endometrial marker or a part thereof; and
   (ii) measuring the amount of the endometrial marker that binds to the at least one binding agent; and
   (b) comparing the measured amount of the marker with a standard amount;
   wherein a difference in the measured amount relative to the standard amount is indicative of the presence of endometrial disease or of the endometrium phase.

2. The method of claim 1, wherein the standard amount is an amount of the marker measured in non-disease tissue and a higher measured amount relative to the standard amount is indicative of endometrial disease in the biological sample.

3. The method according to claim 1 wherein the at least one binding agent is an antibody.

4. The method according to claim 1, wherein the endometrial disease is endometrial cancer.

5. The method according to claim 2, wherein the endometrial disease is endometrial cancer.

6. The method according to claim 1, wherein the biological sample is obtained from tissues, tumor tissue, extracts, cell cultures, cell lysates, lavage fluid, or physiological fluids.

7. The method of claim 1, for diagnosing and monitoring endometrial cancer, monitoring the progression or metastasis of endometrial cancer, or assessing the aggressiveness or indolence of endometrial cancer.

8. The method of claim 1, wherein the biological sample is a serum, uterine fluid or endometrial biopsy sample.

9. The method of claim 1 wherein the measured amount of the marker is 1.5 to 6 times higher or lower than the standard amount.

10. The method of claim 1, wherein one or more of steps (a) and (b) are repeated at multiple points in time.

11. A method for assessing the aggressiveness or indolence of endometrial cancer in a mammalian subject by detecting one or more endometrial markers associated with the endometrial cancer, the method comprising:
   (a) measuring the amount of the endometrial marker Muc5B, in a biological sample obtained from the subject, wherein the measuring step comprises:
   (i) contacting the sample with at least one binding agent that specifically binds to the endometrial marker or a part thereof; and
   (ii) measuring the amount of the endometrial marker that binds to the at least one binding agent; and
   (b) comparing the measured amount of the markers with a standard amount;
   wherein a difference in the measured amount relative to the standard amount is indicative that the cancer is aggressive or indolent.

* * * * *

SEQUENCE LISTING

```
<160> NUMBER OF SEQ ID NOS: 68

<210> SEQ ID NO 1
<211> LENGTH: 124
<212> TYPE: PRT
<213> ORGANISM: Homo sapiens
<220> FEATURE:
<221> NAME/KEY: MISC_FEATURE
<223> OTHER INFORMATION: WAP four-disulfide core domain 2; isoform 1;
      precursor; NP_006094

<400> SEQUENCE: 1

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
```

```
                        85                  90                  95

Cys Gln Val Asp Ser Gln Cys Pro Gly Gln Met Lys Cys Cys Arg Asn
                100                 105                 110

Gly Cys Gly Lys Val Ser Cys Val Thr Pro Asn Phe
            115                 120

<210> SEQ ID NO 2
<211> LENGTH: 76
<212> TYPE: PRT
<213> ORGANISM: Homo sapiens
<220> FEATURE:
<221> NAME/KEY: MISC_FEATURE
<223> OTHER INFORMATION: WAP four-disulfide core domain 2; isoform 4;
      precursor; NP_542772

<400> SEQUENCE: 2

Met Pro Ala Cys Arg Leu Gly Pro Leu Ala Ala Leu Leu Leu Leu Ser
1               5                   10                  15

Leu Leu Leu Phe Gly Phe Thr Leu Val Ser Asp Lys Glu Gly Ser Cys
            20                  25                  30

Pro Gln Val Asn Ile Asn Phe Pro Gln Leu Gly Leu Cys Arg Asp Gln
            35                  40                  45

Cys Gln Val Asp Ser Gln Cys Pro Gly Gln Met Lys Cys Cys Arg Asn
50                  55                  60

Gly Cys Gly Lys Val Ser Cys Val Thr Pro Asn Phe
65                  70                  75

<210> SEQ ID NO 3
<211> LENGTH: 73
<212> TYPE: PRT
<213> ORGANISM: Homo sapiens
<220> FEATURE:
<221> NAME/KEY: MISC_FEATURE
<223> OTHER INFORMATION: WAP four-disulfide core domain 2 ; isoform 5;
      NP_542773

<400> SEQUENCE: 3

Met Leu Gln Val Gln Val Asn Leu Pro Val Ser Pro Leu Pro Thr Tyr
1               5                   10                  15

Pro Tyr Ser Phe Phe Tyr Pro Asp Lys Glu Gly Ser Cys Pro Gln Val
            20                  25                  30

Asn Ile Asn Phe Pro Gln Leu Gly Leu Cys Arg Asp Gln Cys Gln Val
            35                  40                  45

Asp Ser Gln Cys Pro Gly Gln Met Lys Cys Cys Arg Asn Gly Cys Gly
        50                  55                  60

Lys Val Ser Cys Val Thr Pro Asn Phe
65                  70

<210> SEQ ID NO 4
<211> LENGTH: 102
<212> TYPE: PRT
<213> ORGANISM: Homo sapiens
<220> FEATURE:
<221> NAME/KEY: MISC_FEATURE
<223> OTHER INFORMATION: WAP four-disulfide core domain 2; isoform 2
      precursor; NP_542774

<400> SEQUENCE: 4

Met Pro Ala Cys Arg Leu Gly Pro Leu Ala Ala Leu Leu Leu Leu Ser
1               5                   10                  15

Leu Leu Leu Phe Gly Phe Thr Leu Val Ser Gly Thr Gly Ala Glu Lys
            20                  25                  30
```

-continued

```
Thr Gly Val Cys Pro Glu Leu Gln Ala Asp Gln Asn Cys Thr Gln Glu
         35                  40                  45
Cys Val Ser Asp Ser Glu Cys Ala Asp Asn Leu Lys Cys Cys Ser Ala
     50                  55                  60
Gly Cys Ala Thr Phe Cys Ser Leu Pro Asn Ala Leu Phe His Trp His
65                  70                  75                  80
Leu Lys Thr Arg Arg Leu Trp Glu Ile Ser Gly Pro Arg Pro Arg Arg
             85                  90                  95
Pro Thr Trp Asp Ser Ser
100

<210> SEQ ID NO 5
<211> LENGTH: 570
<212> TYPE: DNA
<213> ORGANISM: Homo sapiens
<220> FEATURE:
<221> NAME/KEY: misc_feature
<223> OTHER INFORMATION: WAP four-disulfide core domain 2 (WFDC2);
      transcript variant 1; mRNA; NM_006103

<400> SEQUENCE: 5
cacctgcacc cgcccgggc atagcaccat gcctgcttgt cgcctaggcc cgctagccgc      60
cgccctcctc ctcagcctgc tgctgttcgg cttcacccta gtctcaggca caggagcaga    120
gaagactggc gtgtgccccg agctccaggc tgaccagaac tgcacgcaag agtgcgtctc    180
ggacagcgaa tgcgccgaca acctcaagtg ctgcagcgcg ggctgtgcca ccttctgctc    240
tctgcccaat gataaggagg ttcctgcccc ccaggtgaac attaactttc ccagctcgg    300 cctctgtcgg gaccagtgcc aggtggacag ccagtgtcct ggccagatga aatgctgccg    360
caatggctgt gggaaggtgt cctgtgtcac tcccaattc tgagctccag ccaccaccag    420
gctgagcagt gaggagagaa agtttctgcc tggccctgca tctggttcca gcccacctgc    480 cctcccttt tcgggactc tgtattccct cttgggctga ccacagcttc tcccttccc     540 aaccaataaa gtaaccactt tcagcaaaaa                                     570

<210> SEQ ID NO 6
<211> LENGTH: 421
<212> TYPE: DNA
<213> ORGANISM: Homo sapiens
<220> FEATURE:
<221> NAME/KEY: misc_feature
<223> OTHER INFORMATION: WAP four-disulfide core domain 2 (WFDC2);
      transcript variant 4; mRNA; NM_080734

<400> SEQUENCE: 6
cacctgcacc cgcccgggc atagcaccat gcctgcttgt cgcctaggcc cgctagccgc      60
cgccctcctc ctcagcctgc tgctgttcgg cttcacccta gtctcagata aggagggttc    120
ctgcccccag gtgaacatta ctttcccca gctcggcctc tgtcgggacc agtgccaggt    180
ggacagccag tgtcctggcc agatgaaatg ctgccgcaat ggctgtggga aggtgtcctg    240
tgtcactccc aatttctgag gtccagccac caccaggctg agcagtgagg agagaaagtt    300
tctgcctggc cctgcatctg gttccagccc acctgccctc ccttttcg ggactctgta     360 ttccctcttg gctgaccac agcttctccc tttcccaacc aataaagtaa ccactttcag    420
c                                                                    421

<210> SEQ ID NO 7
<211> LENGTH: 411
<212> TYPE: DNA
<213> ORGANISM: Homo sapiens
```

```
<220> FEATURE:
<221> NAME/KEY: misc_feature
<223> OTHER INFORMATION: WAP four-disulfide core domain 2 (WFDC2);
      transcript variant 5; mRNA; NM_080735

<400> SEQUENCE: 7
agcccagtga gggggcagtgg gggggccatg ctgcaggtac aagttaatct ccctgtatcg      60
cctctgccca cttacccta ctcctttttc tacccagata aggagggttc ctgcccccag      120
gtgaacatta actttcccca gctcggcctc tgtcgggacc agtgccaggt ggacagccag      180
tgtcctggcc agatgaaatg ctgccgcaat ggctgtggga aggtgtcctg tgtcactccc      240
aatttctgag gtccagccac caccaggctg agcagtgagg agagaaagtt tctgcctggc      300
cctgcatctg gttccagccc acctgccctc ccctttttcg ggactctgta ttccctcttg      360
ggctgaccac agcttctccc tttcccaacc aataaagtaa ccactttcag c              411

<210> SEQ ID NO 8
<211> LENGTH: 358
<212> TYPE: DNA
<213> ORGANISM: Homo sapiens
<220> FEATURE:
<221> NAME/KEY: misc_feature
<223> OTHER INFORMATION: WAP four-disulfide core domain 2 (WFDC2);
      transcript variant 2; mRNA
<220> FEATURE:
<221> NAME/KEY: misc_feature
<223> OTHER INFORMATION: WAP four-disulfide core domain 2 (WFDC2);
      transcript variant 2; mRNA; NM_080736

<400> SEQUENCE: 8
cacctgcacc ccgcccgggc atagcaccat gcctgcttgt cgcctaggcc cgctagccgc      60
cgccctcctc ctcagcctgc tgctgttcgg cttcaccta gtctcaggca caggagcaga      120
gaagactggc gtgtgccccg agctccaggc tgaccagaac tgcacgcaag agtgcgtctc      180
ggacagcgaa tgcgccgaca acctcaagtg ctgcagcgcg gctgtgcca ccttctgctc      240 tctgcccaat gcactgttcc actggcacct aaagacacgg aggctctggg agatttctgg      300
ccctaggcca cgaaggccca cttgggactc aagctgaggt cctgtgattc catttggg       358

<210> SEQ ID NO 9
<211> LENGTH: 124
<212> TYPE: PRT
<213> ORGANISM: Homo sapiens
<220> FEATURE:
<221> NAME/KEY: MISC_FEATURE
<223> OTHER INFORMATION: WFDC2; CAG33258

<400> SEQUENCE: 9

Met Pro Ala Cys Arg Leu Gly Pro Leu Ala Ala Leu Leu Ser
1               5                   10                  15

Leu Leu Leu Phe Gly Phe Thr Leu Val Ser Gly Thr Gly Ala Glu Lys
                20                  25                  30

Thr Gly Val Cys Pro Glu Leu Gln Ala Asp Gln Asn Cys Thr Gln Glu
            35                  40                  45

Cys Val Ser Asp Ser Glu Cys Ala Asp Asn Leu Lys Cys Cys Ser Ala
        50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110
```

-continued

```
Gly Cys Gly Lys Val Ser Cys Val Thr Pro Asn Phe
            115                 120

<210> SEQ ID NO 10
<211> LENGTH: 501
<212> TYPE: PRT
<213> ORGANISM: Homo sapiens
<220> FEATURE:
<221> NAME/KEY: MISC_FEATURE
<223> OTHER INFORMATION: clusterin; isoform 1; NP_001822

<400> SEQUENCE: 10

Met Gln Val Cys Ser Gln Pro Gln Arg Gly Cys Val Arg Glu Gln Ser
1               5                   10                  15

Ala Ile Asn Thr Ala Pro Pro Ser Ala His Asn Ala Ala Ser Pro Gly
            20                  25                  30

Gly Ala Arg Gly His Arg Val Pro Leu Thr Glu Ala Cys Lys Asp Ser
        35                  40                  45

Arg Ile Gly Gly Met Met Lys Thr Leu Leu Leu Phe Val Gly Leu Leu
    50                  55                  60

Leu Thr Trp Glu Ser Gly Gln Val Leu Gly Asp Gln Thr Val Ser Asp
65                  70                  75                  80

Asn Glu Leu Gln Glu Met Ser Asn Gln Gly Ser Lys Tyr Val Asn Lys
                85                  90                  95

Glu Ile Gln Asn Ala Val Asn Gly Val Lys Gln Ile Lys Thr Leu Ile
            100                 105                 110

Glu Lys Thr Asn Glu Glu Arg Lys Thr Leu Leu Ser Asn Leu Glu Glu
        115                 120                 125

Ala Lys Lys Lys Lys Glu Asp Ala Leu Asn Glu Thr Arg Glu Ser Glu
    130                 135                 140

Thr Lys Leu Lys Glu Leu Pro Gly Val Cys Asn Glu Thr Met Met Ala
145                 150                 155                 160

Leu Trp Glu Glu Cys Lys Pro Cys Leu Lys Gln Thr Cys Met Lys Phe
                165                 170                 175

Tyr Ala Arg Val Cys Arg Ser Gly Ser Gly Leu Val Gly Arg Gln Leu
            180                 185                 190

Glu Glu Phe Leu Asn Gln Ser Ser Pro Phe Tyr Phe Trp Met Asn Gly
        195                 200                 205

Asp Arg Ile Asp Ser Leu Leu Glu Asn Asp Arg Gln Gln Thr His Met
    210                 215                 220

Leu Asp Val Met Gln Asp His Phe Ser Arg Ala Ser Ser Ile Ile Asp
225                 230                 235                 240

Glu Leu Phe Gln Asp Arg Phe Phe Thr Arg Glu Pro Gln Asp Thr Tyr
                245                 250                 255

His Tyr Leu Pro Phe Ser Leu Pro His Arg Arg Pro His Phe Phe Phe
            260                 265                 270

Pro Lys Ser Arg Ile Val Arg Ser Leu Met Pro Phe Ser Pro Tyr Glu
        275                 280                 285

Pro Leu Asn Phe His Ala Met Phe Gln Pro Phe Leu Glu Met Ile His
    290                 295                 300

Glu Ala Gln Gln Ala Met Asp Ile His Phe His Ser Pro Ala Phe Gln
305                 310                 315                 320

His Pro Pro Thr Glu Phe Ile Arg Glu Gly Asp Asp Asp Arg Thr Val
                325                 330                 335

Cys Arg Glu Ile Arg His Asn Ser Thr Gly Cys Leu Arg Met Lys Asp
            340                 345                 350
```

```
Gln Cys Asp Lys Cys Arg Glu Ile Leu Ser Val Asp Cys Ser Thr Asn
        355                 360                 365

Asn Pro Ser Gln Ala Lys Leu Arg Arg Glu Leu Asp Glu Ser Leu Gln
        370                 375                 380

Val Ala Glu Arg Leu Thr Arg Lys Tyr Asn Glu Leu Leu Lys Ser Tyr
385                 390                 395                 400

Gln Trp Lys Met Leu Asn Thr Ser Ser Leu Leu Glu Gln Leu Asn Glu
                    405                 410                 415

Gln Phe Asn Trp Val Ser Arg Leu Ala Asn Leu Thr Gln Gly Glu Asp
                420                 425                 430

Gln Tyr Tyr Leu Arg Val Thr Thr Val Ala Ser His Thr Ser Asp Ser
            435                 440                 445

Asp Val Pro Ser Gly Val Thr Glu Val Val Val Lys Leu Phe Asp Ser
        450                 455                 460

Asp Pro Ile Thr Val Thr Val Pro Val Glu Val Ser Arg Lys Asn Pro
465                 470                 475                 480

Lys Phe Met Glu Thr Val Ala Glu Lys Ala Leu Gln Glu Tyr Arg Lys
                    485                 490                 495

Lys His Arg Glu Glu
                500

<210> SEQ ID NO 11
<211> LENGTH: 449
<212> TYPE: PRT
<213> ORGANISM: Homo sapiens
<220> FEATURE:
<221> NAME/KEY: MISC_FEATURE
<223> OTHER INFORMATION: clusterin; isoform 2; NP_976084

<400> SEQUENCE: 11

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
        50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                    85                  90                  95

Glu Leu Pro Gly Val Cys Asn Glu Thr Met Met Ala Leu Trp Glu Glu
                100                 105                 110

Cys Lys Pro Cys Leu Lys Gln Thr Cys Met Lys Phe Tyr Ala Arg Val
            115                 120                 125

Cys Arg Ser Gly Ser Gly Leu Val Gly Arg Gln Leu Glu Glu Phe Leu
        130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                    165                 170                 175

Gln Asp His Phe Ser Arg Ala Ser Ser Ile Ile Asp Glu Leu Phe Gln
                180                 185                 190

Asp Arg Phe Phe Thr Arg Glu Pro Gln Asp Thr Tyr His Tyr Leu Pro
            195                 200                 205
```

Phe Ser Leu Pro His Arg Arg Pro His Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
    370                 375                 380

Arg Val Thr Thr Val Ala Ser His Thr Ser Asp Ser Asp Val Pro Ser
385                 390                 395                 400

Gly Val Thr Glu Val Val Val Lys Leu Phe Asp Ser Asp Pro Ile Thr
                405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
        435                 440                 445

Glu

<210> SEQ ID NO 12
<211> LENGTH: 2859
<212> TYPE: DNA
<213> ORGANISM: Homo sapiens
<220> FEATURE:
<221> NAME/KEY: misc_feature
<223> OTHER INFORMATION: clusterin (CLU); transcript variant 1; mRNA;
      NM_001831

<400> SEQUENCE: 12
ctttccgcgg cattctttgg gcgtgagtca tgcaggtttg cagccagccc caaaggggt      60 gtgtgcgcga gcagagcgct ataaatacgg cgcctcccag tgcccacaac gcggcgtcgc    120
caggaggagc gcgcgggcac agggtgccgc tgaccgaggc gtgcaaagac tccagaattg    180
gaggcatgat gaagactctg ctgctgtttg tgggctgct gctgacctgg gagagtgggc     240
aggtcctggg ggaccagacg gtctcagaca tgagctcca ggaaatgtcc aatcagggaa     300
gtaagtacgt caataaggaa attcaaaatg ctgtcaacgg ggtgaaacag ataaagactc    360
tcatagaaaa aacaaacgaa gagcgcaaga cactgctcag caacctagaa gaagccaaga    420
agaagaaaga ggatgcccta aatgagacca gggaatcaga caaagctg aaggagctcc      480 caggagtgtg caatgagacc atgatggccc tctgggaaga gtaagcccc tgcctgaaac     540 agacctgcat gaagttctac gcacgcgtct gcagaagtgg ctcaggcctg gttggccgcc    600

```
agcttgagga gttcctgaac cagagctcgc ccttctactt ctggatgaat ggtgaccgca    660
tcgactccct gctggagaac gaccggcagc agacgcacat gctggatgtc atgcaggacc    720
acttcagccg cgcgtccagc atcatagacg agctcttcca ggacaggttc ttcacccggg    780
agccccagga tacctaccac tacctgccct tcagcctgcc ccaccggagg cctcacttct    840
tcttcccaa gtcccgcatc gtccgcagct tgatgccctt ctctccgtac gagcccctga    900
acttccacgc catgttccag cccttccttg agatgataca cgaggctcag caggccatgg    960
acatccactt ccatagcccg gccttccagc acccgccaac agaattcata cgagaaggcg   1020
acgatgaccg gactgtgtgc cgggagatcc gccacaactc cacgggctgc ctgcggatga   1080
aggaccagtg tgacaagtgc cgggagatct tgtctgtgga ctgttccacc aacaacccct   1140
cccaggctaa gctgcggcgg gagctcgacg aatccctcca ggtcgctgag aggttgacca   1200
ggaaatacaa cgagctgcta aagtcctacc agtggaagat gctcaacacc tcctccttgc   1260
tggagcagct gaacgagcag tttaactggg tgtcccggct ggcaaacctc acgcaaggcg   1320
aagaccagta ctatctgcgg gtcaccacgg tggcttccca cacttctgac tcggacgttc   1380
cttccggtgt cactgaggtg gtcgtgaagc tctttgactc tgatcccatc actgtgacgg   1440
tccctgtaga agtctccagg aagaacccta aatttatgga gaccgtggcg gagaaagcgc   1500
tgcaggaata ccgcaaaaag caccgggagg agtgagatgt ggatgttgct tttgcaccta   1560
cgggggcatc tgagtccagc tcccccaag atgagctgca gccccccaga gagagctctg   1620
cacgtcacca gtaaccagg ccccagcctc caggcccca actccgccca gcctctcccc   1680
gctctggatc ctgcactcta acactcgact ctgctgctca tgggaagaac agaattgctc   1740
ctgcatgcaa ctaattcaat aaaactgtct tgtgagctga tcgcttggag ggtcctcttt   1800
ttatgttgag ttgctgcttc ccggcatgcc ttcattttgc tatgggggc aggcaggggg   1860
gatggaaaat aagtagaaac aaaaagcag tggctaagat ggtataggga ctgtcatacc   1920
agtgaagaat aaaagggtga agaataaaag ggatatgatg acaaggttga tccacttcaa   1980
gaattgcttg ctttcaggaa gagagatgtg tttcaacaag ccaactaaaa tatattgctg   2040
caaatggaag ctttttctgtt ctattataaa actgtcgatg tattctgacc aaggtgcgac   2100
aatctcctaa aggaatacac tgaaagttaa ggagaagaat cagtaagtgt aaggtgtact   2160
tggtattata atgcataatt gatgttttcg ttatgaaaac atttggtgcc cagaagtcca   2220
aattatcagt tttatttgta agagctattg cttttgcagc ggtttatttt gtaaaagctg   2280
ttgattcga gttgtaagag ctcagcatcc caggggcatc ttcttgactg tggcatttcc   2340
tgtccaccgc cggtttatat gatcttcata ccttttccctg gaccacaggc gtttctcggc   2400
ttttagtctg aaccatagct gggctgcagt accctacgct gccagcaggt ggccatgact   2460
acccgtggta ccaatctcag tcttaaagct caggcttttc gttcattaac attctctgat   2520
agaattctgg tcatcagatg tactgcaatg gaacaaaact catctggctg catcccaggt   2580
gtgtagcaaa gtccacatgt aaatttatag cttagaatat tcttaagtca ctgtcccttg   2640
tctctctttg aagttataaa caacaaactt aaagcttagc ttatgtccaa ggtaagtatt   2700
ttagcatggc tgtcaaggaa attcagagta aagtcagtgt gattcactta atgatataca   2760
ttaattagaa ttatggggtc agaggtattt gcttaagtga tcataattgt aaagtatatg   2820
tcacattgtc acattaatgt caaaaaaaaa aaaaaaaaa                           2859
```

<210> SEQ ID NO 13
<211> LENGTH: 2979
<212> TYPE: DNA

<213> ORGANISM: Homo sapiens
<220> FEATURE:
<221> NAME/KEY: misc_feature
<223> OTHER INFORMATION: clusterin (CLU); transcript variant 2; mRNA; NM_203339

<400> SEQUENCE: 13

| | | | | | |
|---|---|---|---|---|---|
| gggcagcctg | ctgtcggctt | agaggggatg | ggcagtgtgg | agggcctggc | agagcaagag | 60 |
| gactcatcct | tccaaaggga | ctttctctgg | gaagcctgct | cctcgggcca | ctgcgaaccc | 120 |
| tctctactct | ccgaagggaa | ttgtccttcc | tggcttccac | tacttccacc | cctgaatgca | 180 |
| caggcagccc | ggcccaagtc | tcccactagg | gatgcagatg | gattcggtgt | gaagggctgg | 240 |
| ctgctgttgc | ctccggctct | tgaaagtcaa | gttcagaggc | gtgcaaagac | tccagaattg | 300 |
| gaggcatgat | gaagactctg | ctgctgtttg | tggggctgct | gctgacctgg | gagagtgggc | 360 |
| aggtcctggg | ggaccagacg | gtctcagaca | atgagctcca | ggaaatgtcc | aatcagggaa | 420 |
| gtaagtacgt | caataaggaa | attcaaaatg | ctgtcaacgg | ggtgaaacag | ataaagactc | 480 |
| tcatagaaaa | aacaaacgaa | gagcgcaaga | cactgctcag | caacctagaa | gagccaaga | 540 |
| agaagaaaga | ggatgcccta | aatgagacca | gggaatcaga | gacaaagctg | aaggagctcc | 600 |
| caggagtgtg | caatgagacc | atgatggccc | tctgggaaga | gtgtaagccc | tgcctgaaac | 660 |
| agacctgcat | gaagttctac | gcacgcgtct | gcagaagtgg | ctcaggcctg | gttggccgcc | 720 |
| agcttgagga | gttcctgaac | cagagctcgc | ccttctactt | ctggatgaat | ggtgaccgca | 780 |
| tcgactccct | gctggagaac | gaccggcagc | agacgcacat | gctggatgtc | atgcaggacc | 840 |
| acttcagccg | cgcgtccagc | atcatagacg | agctcttcca | ggacaggttc | ttcacccggg | 900 |
| agccccagga | tacctaccac | tacctgccct | tcagcctgcc | ccaccggagg | cctcacttct | 960 |
| tctttcccaa | gtcccgcatc | gtccgcagct | tgatgcccct | tctctccgtac | gagcccctga | 1020 |
| acttccacgc | catgttccag | cccttccttg | agatgataca | cgaggctcag | caggccatgg | 1080 |
| acatccactt | ccatagcccg | gccttccagc | acccgccaac | agaattcata | cgagaaggcg | 1140 |
| acgatgaccg | gactgtgtgc | cgggagatcc | gccacaactc | cacgggctgc | ctgcggatga | 1200 |
| aggaccagtg | tgacaagtgc | cgggagatct | tgtctgtgga | ctgttccacc | aacaacccct | 1260 |
| cccaggctaa | gctgcggcgg | gagctcgacg | aatccctcca | ggtcgctgag | aggttgacca | 1320 |
| ggaaatacaa | cgagctgcta | aagtcctacc | agtggaagat | gctcaacacc | tcctccttgc | 1380 |
| tggagcagct | gaacgagcag | tttaactggg | tgtcccggct | ggcaaacctc | acgcaaggcg | 1440 |
| aagaccagta | ctatctgcgg | gtcaccacgg | tggcttccca | cacttctgac | tcggacgttc | 1500 |
| cttccggtgt | cactgaggtg | gtcgtgaagc | tctttgactc | tgatcccatc | actgtgacgg | 1560 |
| tccctgtaga | agtctccagg | aagaacccta | aatttatgga | gaccgtggcg | gagaaagcgc | 1620 |
| tgcaggaata | ccgcaaaaag | caccgggagg | agtgagatgt | ggatgttgct | tttgcaccta | 1680 |
| cgggggcatc | tgagtccagc | tcccccaag | atgagctgca | gccccccaga | gagagctctg | 1740 |
| cacgtcacca | agtaaccagg | ccccagcctc | caggccccca | actccgccca | gcctctcccc | 1800 |
| gctctggatc | ctgcactcta | acactcgact | ctgctgctca | tgggaagaac | agaattgctc | 1860 |
| ctgcatgcaa | ctaattcaat | aaaactgtct | tgtgagctga | tcgcttggag | ggtcctcttt | 1920 |
| ttatgttgag | ttgctgcttc | ccggcatgcc | ttcattttgc | tatgggggc | aggcagggg | 1980 |
| gatggaaaat | aagtagaaac | aaaaaagcag | tggctaagat | ggtatagga | ctgtcatacc | 2040 |
| agtgaagaat | aaaagggtga | agaataaaag | ggatatgatg | acaaggttga | tccacttcaa | 2100 |
| gaattgcttg | ctttcaggaa | gagagatgtg | tttcaacaag | ccaactaaaa | tatattgctg | 2160 |

-continued

```
caaatggaag cttttctgtt ctattataaa actgtcgatg tattctgacc aaggtgcgac    2220
aatctcctaa aggaatacac tgaaagttaa ggagaagaat cagtaagtgt aaggtgtact    2280
tggtattata atgcataatt gatgttttcg ttatgaaaac atttggtgcc cagaagtcca    2340
aattatcagt tttatttgta agagctattg cttttgcagc ggttttattt gtaaaagctg    2400
ttgatttcga gttgtaagag ctcagcatcc caggggcatc ttcttgactg tggcatttcc    2460
tgtccaccgc cggtttatat gatcttcata ccttccctg gaccacaggc gtttctcggc     2520
ttttagtctg aaccatagct gggctgcagt accctacgct gccagcaggt ggccatgact    2580
acccgtggta ccaatctcag tcttaaagct caggcttttc gttcattaac attctctgat    2640
agaattctgg tcatcagatg tactgcaatg gaacaaaact catctggctg catcccaggt    2700
gtgtagcaaa gtccacatgt aaatttatag cttagaatat tcttaagtca ctgtcccttg    2760
tctctctttg aagttataaa caacaaactt aaagcttagc ttatgtccaa ggtaagtatt    2820
ttagcatggc tgtcaaggaa attcagagta aagtcagtgt gattcactta atgatataca    2880
ttaattagaa ttatggggtc agaggtattt gcttaagtga tcataattgt aaagtatatg    2940
tcacattgtc acattaatgt caaaaaaaaa aaaaaaaa                            2979
```

<210> SEQ ID NO 14
<211> LENGTH: 1594
<212> TYPE: PRT
<213> ORGANISM: Homo sapiens
<220> FEATURE:
<221> NAME/KEY: MISC_FEATURE
<223> OTHER INFORMATION: mucin 5B; AAG33673

<400> SEQUENCE: 14

```
Met Gly Ala Pro Ser Ala Cys Arg Thr Leu Val Leu Ala Leu Ala Ala
1               5                   10                  15

Met Leu Val Val Pro Gln Ala Glu Thr Gln Gly Pro Val Glu Pro Ser
                20                  25                  30

Trp Gly Asn Ala Gly His Thr Met Asp Gly Gly Ala Pro Thr Ser Ser
            35                  40                  45

Pro Thr Arg Arg Val Ser Phe Val Pro Val Thr Val Phe Pro Ser
        50                  55                  60

Leu Ser Pro Leu Asn Pro Ala His Asn Gly Arg Val Cys Ser Thr Trp
65                  70                  75                  80

Gly Asp Phe His Tyr Lys Thr Phe Asp Gly Asp Val Phe Arg Phe Pro
                85                  90                  95

Gly Leu Cys Asn Tyr Val Phe Ser Glu His Cys Arg Ala Ala Tyr Glu
            100                 105                 110

Asp Phe Asn Val Gln Leu Arg Arg Gly Leu Val Gly Ser Arg Pro Val
        115                 120                 125

Val Thr Arg Val Ile Lys Ala Gln Gly Leu Val Leu Lys Ala Ser
    130                 135                 140

Asn Gly Ser Val Leu Ile Asn Gly Gln Arg Glu Glu Leu Pro Tyr Ser
145                 150                 155                 160

Arg Thr Gly Leu Leu Val Glu Gln Ser Gly Asp Tyr Ile Lys Val Ser
                165                 170                 175

Ile Arg Leu Val Leu Thr Phe Leu Trp Asn Gly Glu Asp Ser Ala Leu
            180                 185                 190

Leu Glu Leu Asp Pro Lys Tyr Ala Asn Gln Thr Cys Gly Leu Cys Gly
        195                 200                 205

Asp Phe Asn Gly Leu Pro Ala Phe Asn Glu Phe Tyr Ala His Asn Ala
    210                 215                 220
```

```
Arg Leu Thr Pro Leu Gln Phe Gly Asn Leu Gln Lys Leu Asp Gly Pro
225                 230                 235                 240

Thr Glu Gln Cys Pro Asp Pro Leu Pro Leu Pro Ala Gly Asn Cys Thr
            245                 250                 255

Asp Glu Glu Gly Ile Cys His Arg Thr Leu Leu Gly Pro Ala Phe Ala
            260                 265                 270

Glu Cys His Ala Leu Val Asp Ser Thr Ala Tyr Leu Ala Ala Cys Ala
        275                 280                 285

Gln Asp Leu Cys Arg Cys Pro Thr Cys Pro Cys Ala Thr Phe Val Glu
        290                 295                 300

Tyr Ser Arg Gln Cys Ala His Ala Gly Gly Gln Pro Arg Asn Trp Arg
305                 310                 315                 320

Cys Pro Glu Leu Cys Pro Arg Thr Cys Pro Leu Asn Met Gln His Gln
                325                 330                 335

Glu Cys Gly Ser Pro Cys Thr Asp Thr Cys Ser Asn Pro Gln Arg Ala
            340                 345                 350

Gln Leu Cys Glu Asp His Cys Val Asp Gly Cys Phe Cys Pro Pro Gly
        355                 360                 365

Ser Thr Val Leu Asp Asp Ile Thr His Ser Gly Cys Leu Pro Leu Gly
        370                 375                 380

Gln Cys Pro Cys Thr His Gly Gly Arg Thr Tyr Ser Pro Gly Thr Ser
385                 390                 395                 400

Phe Asn Thr Thr Cys Ser Ser Cys Thr Cys Ser Gly Gly Leu Trp Gln
                405                 410                 415

Cys Gln Asp Leu Pro Cys Pro Gly Thr Cys Ser Val Gln Gly Gly Ala
                420                 425                 430

His Ile Ser Thr Tyr Asp Glu Lys Leu Tyr Asp Leu His Gly Asp Cys
            435                 440                 445

Ser Tyr Val Leu Ser Lys Lys Cys Ala Asp Ser Ser Phe Thr Val Leu
450                 455                 460

Ala Glu Leu Arg Lys Cys Gly Leu Thr Asp Asn Glu Asn Cys Leu Lys
465                 470                 475                 480

Ala Val Thr Leu Ser Leu Asp Gly Gly Asp Thr Ala Ile Arg Val Gln
                485                 490                 495

Ala Asp Gly Gly Val Phe Leu Asn Ser Ile Tyr Thr Gln Leu Pro Leu
            500                 505                 510

Ser Ala Ala Asn Ile Thr Leu Phe Thr Pro Ser Ser Phe Phe Ile Val
        515                 520                 525

Val Gln Thr Gly Leu Gly Leu Gln Leu Leu Val Gln Leu Val Pro Leu
        530                 535                 540

Met Gln Val Phe Val Arg Leu Asp Pro Ala His Gln Gly Gln Met Cys
545                 550                 555                 560

Gly Leu Cys Gly Asn Phe Asn Gln Asn Gln Ala Asp Asp Phe Thr Ala
                565                 570                 575

Leu Ser Gly Val Val Glu Ala Thr Gly Ala Ala Phe Ala Asn Thr Trp
            580                 585                 590

Lys Ala Gln Ala Ala Cys Ala Asn Ala Arg Asn Ser Phe Glu Asp Pro
        595                 600                 605

Cys Ser Leu Ser Val Glu Asn Glu Asn Tyr Ala Arg His Trp Cys Ser
        610                 615                 620

Arg Leu Thr Asp Pro Asn Ser Ala Phe Ser Arg Cys His Ser Ile Ile
625                 630                 635                 640

Asn Pro Lys Pro Phe His Ser Asn Cys Met Phe Asp Thr Cys Asn Cys
```

-continued

```
                645                 650                 655
Glu Arg Ser Glu Asp Cys Leu Cys Ala Ala Leu Ser Ser Tyr Val His
            660                 665                 670
Ala Cys Ala Ala Lys Gly Val Gln Leu Ser Asp Trp Arg Asp Gly Val
        675                 680                 685
Cys Thr Lys Tyr Met Gln Asn Cys Pro Lys Ser Gln Arg Tyr Ala Tyr
    690                 695                 700
Val Val Asp Ala Cys Gln Pro Thr Cys Arg Gly Leu Ser Glu Ala Asp
705                 710                 715                 720
Val Thr Cys Ser Val Ser Phe Val Pro Val Asp Gly Cys Thr Cys Pro
                725                 730                 735
Ala Gly Thr Phe Leu Asn Asp Ala Gly Ala Cys Val Pro Ala Gln Glu
            740                 745                 750
Cys Pro Cys Tyr Ala His Gly Thr Val Leu Ala Pro Gly Glu Val Val
        755                 760                 765
His Asp Glu Gly Ala Val Cys Ser Cys Thr Gly Gly Lys Leu Ser Cys
    770                 775                 780
Leu Gly Ala Ser Leu Gln Lys Ser Thr Gly Cys Ala Ala Pro Met Val
785                 790                 795                 800
Tyr Leu Asp Cys Ser Asn Ser Ser Ala Gly Thr Pro Gly Ala Glu Cys
                805                 810                 815
Leu Arg Ser Cys His Thr Leu Asp Val Gly Cys Phe Ser Thr His Cys
            820                 825                 830
Val Ser Gly Cys Val Cys Pro Pro Gly Leu Val Ser Asp Gly Ser Gly
        835                 840                 845
Gly Cys Ile Ala Glu Glu Asp Cys Pro Cys Val His Asn Glu Ala Thr
    850                 855                 860
Tyr Lys Pro Gly Glu Thr Ile Arg Val Asp Cys Asn Thr Cys Thr Cys
865                 870                 875                 880
Arg Asn Arg Arg Trp Glu Cys Ser His Arg Leu Cys Leu Gly Thr Cys
                885                 890                 895
Val Ala Tyr Gly Asp Gly His Phe Ile Thr Phe Asp Gly Asp Arg Tyr
            900                 905                 910
Ser Phe Glu Gly Ser Cys Glu Tyr Ile Leu Ala Gln Asp Tyr Cys Gly
        915                 920                 925
Asp Asn Thr Thr His Gly Thr Phe Arg Ile Val Thr Glu Asn Ile Pro
    930                 935                 940
Cys Gly Thr Thr Gly Thr Thr Cys Ser Lys Ala Ile Lys Leu Phe Val
945                 950                 955                 960
Glu Ser Tyr Glu Leu Ile Leu Gln Glu Gly Thr Phe Lys Ala Val Ala
                965                 970                 975
Arg Gly Pro Gly Gly Asp Pro Pro Tyr Lys Ile Arg Tyr Met Gly Ile
            980                 985                 990
Phe Leu Val Ile Glu Thr His Gly  Met Ala Val Ser Trp Asp Arg Lys
        995                 1000                1005
Thr Ser  Val Phe Ile Arg Leu  His Gln Asp Tyr Lys  Gly Arg Val
    1010                1015                1020
Cys Gly  Leu Cys Gly Asn Phe  Asp Asp Asn Ala Ile  Asn Asp Phe
    1025                1030                1035
Ala Thr  Arg Ser Arg Ser Val  Val Gly Asp Ala Leu  Glu Phe Gly
    1040                1045                1050
Asn Ser  Trp Lys Leu Ser Pro  Ser Cys Pro Asp Ala  Leu Ala Pro
    1055                1060                1065
```

-continued

```
Lys Asp Pro Cys Thr Ala Asn Pro Phe Arg Lys Ser Trp Ala Gln
    1070                1075                1080

Lys Gln Cys Ser Ile Leu His Gly Pro Thr Phe Ala Ala Cys Arg
    1085                1090                1095

Ser Gln Val Asp Ser Thr Lys Tyr Tyr Glu Ala Cys Val Asn Asp
    1100                1105                1110

Ala Cys Ala Cys Asp Ser Gly Gly Asp Cys Glu Cys Phe Cys Thr
    1115                1120                1125

Ala Val Ala Ala Tyr Ala Gln Ala Cys His Asp Ala Gly Leu Cys
    1130                1135                1140

Val Ser Trp Arg Thr Pro Asp Thr Cys Pro Leu Phe Cys Asp Phe
    1145                1150                1155

Tyr Asn Pro His Gly Gly Cys Glu Trp His Tyr Gln Pro Cys Gly
    1160                1165                1170

Ala Pro Cys Leu Lys Thr Cys Arg Asn Pro Ser Gly His Cys Leu
    1175                1180                1185

Val Asp Leu Pro Gly Leu Glu Gly Cys Tyr Pro Lys Cys Pro Pro
    1190                1195                1200

Ser Gln Pro Phe Phe Asn Glu Asp Gln Met Lys Cys Val Ala Gln
    1205                1210                1215

Cys Gly Cys Tyr Asp Lys Asp Gly Asn Tyr Tyr Asp Val Gly Ala
    1220                1225                1230

Arg Val Pro Thr Ala Glu Asn Cys Gln Ser Cys Asn Cys Thr Pro
    1235                1240                1245

Ser Gly Ile Gln Cys Ala His Ser Leu Glu Ala Cys Thr Cys Thr
    1250                1255                1260

Tyr Glu Asp Arg Thr Tyr Ser Tyr Gln Asp Val Ile Tyr Asn Thr
    1265                1270                1275

Thr Asp Gly Leu Gly Ala Cys Leu Ile Ala Ile Cys Gly Ser Asn
    1280                1285                1290

Gly Thr Ile Ile Arg Lys Ala Val Ala Cys Pro Gly Thr Pro Ala
    1295                1300                1305

Thr Thr Pro Phe Thr Phe Thr Thr Ala Trp Val Pro His Ser Thr
    1310                1315                1320

Thr Ser Pro Ala Leu Pro Val Ser Thr Val Cys Val Arg Glu Val
    1325                1330                1335

Cys Arg Trp Ser Ser Trp Tyr Asn Gly His Arg Pro Glu Pro Gly
    1340                1345                1350

Leu Gly Gly Gly Asp Phe Glu Thr Phe Glu Asn Leu Arg Gln Arg
    1355                1360                1365

Gly Tyr Gln Val Cys Pro Val Leu Ala Asp Ile Glu Cys Arg Ala
    1370                1375                1380

Ala Gln Leu Pro Asp Met Pro Leu Glu Glu Leu Gly Gln Gln Val
    1385                1390                1395

Asp Cys Asp Arg Met Arg Gly Leu Met Cys Ala Asn Ser Gln Gln
    1400                1405                1410

Ser Pro Pro Leu Cys His Asp Tyr Glu Leu Arg Val Leu Cys Cys
    1415                1420                1425

Glu Tyr Val Pro Cys Gly Pro Ser Pro Ala Pro Gly Thr Ser Pro
    1430                1435                1440

Gln Pro Ser Leu Ser Ala Ser Thr Glu Pro Ala Val Pro Thr Pro
    1445                1450                1455

Thr Gln Thr Thr Ala Thr Glu Lys Thr Thr Leu Trp Val Thr Pro
    1460                1465                1470
```

Ser Ile Arg Ser Thr Ala Ala Leu Thr Ser Gln Thr Gly Ser Ser
    1475                1480                1485

Ser Gly Pro Val Thr Val Thr Pro Ser Ala Pro Gly Thr Thr Thr
    1490                1495                1500

Cys Gln Pro Arg Cys Gln Trp Thr Glu Trp Phe Asp Glu Asp Tyr
    1505                1510                1515

Pro Lys Ser Glu Gln Leu Gly Gly Asp Val Glu Ser Tyr Asp Lys
    1520                1525                1530

Ile Arg Ala Ala Gly Gly His Leu Cys Gln Gln Pro Lys Asp Ile
    1535                1540                1545

Glu Cys Gln Ala Glu Ser Phe Pro Asn Trp Thr Leu Ala Gln Val
    1550                1555                1560

Gly Gln Lys Val His Cys Asp Val His Phe Gly Leu Val Cys Arg
    1565                1570                1575

Asn Trp Glu Gln Glu Gly Val Phe Lys Met Cys Tyr Asn Tyr Arg
    1580                1585                1590

Ile

<210> SEQ ID NO 15
<211> LENGTH: 519
<212> TYPE: PRT
<213> ORGANISM: Homo sapiens
<220> FEATURE:
<221> NAME/KEY: MISC_FEATURE
<223> OTHER INFORMATION: NP_056991; leucine aminopeptidase 3

<400> SEQUENCE: 15

Met Phe Leu Leu Pro Leu Pro Ala Ala Gly Arg Val Val Arg Arg
1               5                   10                  15

Leu Ala Val Arg Arg Phe Gly Ser Arg Ser Leu Ser Thr Ala Asp Met
            20                  25                  30

Thr Lys Gly Leu Val Leu Gly Ile Tyr Ser Lys Glu Lys Glu Asp Asp
        35                  40                  45

Val Pro Gln Phe Thr Ser Ala Gly Glu Asn Phe Asp Lys Leu Leu Ala
    50                  55                  60

Gly Lys Leu Arg Glu Thr Leu Asn Ile Ser Gly Pro Pro Leu Lys Ala
65                  70                  75                  80

Gly Lys Thr Arg Thr Phe Tyr Gly Leu His Gln Asp Phe Pro Ser Val
                85                  90                  95

Val Leu Val Gly Leu Gly Lys Lys Ala Ala Gly Ile Asp Glu Gln Glu
            100                 105                 110

Asn Trp His Glu Gly Lys Glu Asn Ile Arg Ala Ala Val Ala Ala Gly
        115                 120                 125

Cys Arg Gln Ile Gln Asp Leu Glu Leu Ser Ser Val Glu Val Asp Pro
    130                 135                 140

Cys Gly Asp Ala Gln Ala Ala Ala Glu Gly Ala Val Leu Gly Leu Tyr
145                 150                 155                 160

Glu Tyr Asp Asp Leu Lys Gln Lys Lys Lys Met Ala Val Ser Ala Lys
                165                 170                 175

Leu Tyr Gly Ser Gly Asp Gln Glu Ala Trp Gln Lys Gly Val Leu Phe
            180                 185                 190

Ala Ser Gly Gln Asn Leu Ala Arg Gln Leu Met Glu Thr Pro Ala Asn
        195                 200                 205

Glu Met Thr Pro Thr Arg Phe Ala Glu Ile Ile Glu Lys Asn Leu Lys
    210                 215                 220

```
Ser Ala Ser Ser Lys Thr Glu Val His Ile Arg Pro Lys Ser Trp Ile
225                 230                 235                 240

Glu Glu Gln Ala Met Gly Ser Phe Leu Ser Val Ala Lys Gly Ser Asp
            245                 250                 255

Glu Pro Pro Val Phe Leu Glu Ile His Tyr Lys Gly Ser Pro Asn Ala
        260                 265                 270

Asn Glu Pro Pro Leu Val Phe Val Gly Lys Gly Ile Thr Phe Asp Ser
    275                 280                 285

Gly Gly Ile Ser Ile Lys Ala Ser Ala Asn Met Asp Leu Met Arg Ala
290                 295                 300

Asp Met Gly Gly Ala Ala Thr Ile Cys Ser Ala Ile Val Ser Ala Ala
305                 310                 315                 320

Lys Leu Asn Leu Pro Ile Asn Ile Ile Gly Leu Ala Pro Leu Cys Glu
            325                 330                 335

Asn Met Pro Ser Gly Lys Ala Asn Lys Pro Gly Asp Val Val Arg Ala
        340                 345                 350

Lys Asn Gly Lys Thr Ile Gln Val Asp Asn Thr Asp Ala Glu Gly Arg
    355                 360                 365

Leu Ile Leu Ala Asp Ala Leu Cys Tyr Ala His Thr Phe Asn Pro Lys
370                 375                 380

Val Ile Leu Asn Ala Ala Thr Leu Thr Gly Ala Met Asp Val Ala Leu
385                 390                 395                 400

Gly Ser Gly Ala Thr Gly Val Phe Thr Asn Ser Ser Trp Leu Trp Asn
            405                 410                 415

Lys Leu Phe Glu Ala Ser Ile Glu Thr Gly Asp Arg Val Trp Arg Met
        420                 425                 430

Pro Leu Phe Glu His Tyr Thr Arg Gln Val Val Asp Cys Gln Leu Ala
    435                 440                 445

Asp Val Asn Asn Ile Gly Lys Tyr Arg Ser Ala Gly Ala Cys Thr Ala
450                 455                 460

Ala Ala Phe Leu Lys Glu Phe Val Thr His Pro Lys Trp Ala His Leu
465                 470                 475                 480

Asp Ile Ala Gly Val Met Thr Asn Lys Asp Glu Val Pro Tyr Leu Arg
            485                 490                 495

Lys Gly Met Thr Gly Arg Pro Thr Arg Thr Leu Ile Glu Phe Leu Leu
        500                 505                 510

Arg Phe Ser Gln Asp Asn Ala
    515

<210> SEQ ID NO 16
<211> LENGTH: 2100
<212> TYPE: DNA
<213> ORGANISM: Homo sapiens
<220> FEATURE:
<221> NAME/KEY: misc_feature
<223> OTHER INFORMATION: NM_015907; leucine aminopeptidase 3 (LAP3);
      mRNA

<400> SEQUENCE: 16
ctgcccatcc gtcccgcccc ctagacgcac gtccgctcgc ccggcgcccg agccagtccg      60
cgcgcacgcc gtctgcgccc cgaaagcccc gccccaaggc gcgcccgccc accgctctcc     120
acgtgctcgc tggagggcgg tgcgaggggc cgagccgaca gatgttcttt gctgcctctt     180
ccggctgcgg ggcgagtagt cgtccgacgt ctggccgtga cgtttcgg gagccggagt       240 ctctccaccg cagacatgac gaagggcctt gttttaggaa tctattccaa agaaaaagaa     300
gatgatgtgc cacagttcac aagtgcagga gagaattttg ataaaattgtt agctggaaag    360
```

```
ctgagagaga ctttgaacat atctggacca cctctgaagg cagggaagac tcgaacctttt    420 tatggtctgc atcaggactt ccccagcgtg gtgctagttg gcctcggcaa aaaggcagct    480
ggaatcgacg aacaggaaaa ctggcatgaa ggcaaagaaa acatcagagc tgctgttgca    540
gcggggtgca ggcagattca agacctggag ctctcgtctg tggaggtgga tccctgtgga    600
gacgctcagg ctgctgcgga gggagcggtg cttggtctct atgaatacga tgacctaaag    660
caaaaaaaga agatggctgt gtcggcaaag ctctatggaa gtggggatca ggaggcctgg    720
cagaaaggag tcctgtttgc ttctgggcag aacttggcac gccaattgat ggagacgcca    780
gccaatgaga tgacgccaac cagatttgct gaaattattg aagaatct caaaagtgct    840 agtagtaaaa ccgaggtcca tatcagaccc aagtcttgga ttgaggaaca ggcaatggga    900
tcattcctca gtgtggccaa aggatctgac gagcccccag tcttcttgga aattcactac    960
aaaggcagcc ccaatgcaaa cgaaccaccc ctggtgtttg ttgggaaagg aattaccttt   1020
gacagtggtg gtatctccat caaggcttct gcaaatatgg acctcatgag ggctgacatg   1080
ggaggagctg caactatatg ctcagccatc gtgtctgctg caaagcttaa tttgcccatt   1140
aatattatag gtctggcccc tctttgtgaa aatatgccca gcggcaaggc caacaagccg   1200
ggggatgttg ttagagccaa aaacgggaag accatccagg ttgataacac tgatgctgag   1260
gggaggctca tactggctga tgcgctctgt tacgcacaca cgtttaaccc gaaggtcatc   1320
ctcaatgccg ccaccttaac aggtgccatg gatgtagctt gggatcagg tgccactggg   1380 gtctttacca attcatcctg gctctggaac aaactcttcg aggccagcat tgaaacaggg   1440
gaccgtgtct ggaggatgcc tctcttcgaa cattatacaa gacaggttgt agattgccag   1500
cttgctgatg ttaacaacat ggaaaatac agatctgcag gagcatgtac agctgcagca   1560
ttcctgaaag aattcgtaac tcatcctaag tgggcacatt tagacatagc aggcgtgatg   1620
accaacaaag atgaagttcc ctatctacgg aaaggcatga ctgggaggcc cacaaggact   1680
ctcattgagt tcttacttcg tttcagtcaa gacaatgctt agttcagata tcaaaaatg   1740 tcttcactct gtcttaaatt ggacagttga acttaaaagg tttttgaata atggatgaa   1800 aatcttttaa cggagacaaa ggatggtatt taaaaatgta gaacacaatg aaatttgtat   1860
gccttgattt tttttttcatt tcacacaaag atttataaag gtaaagttaa tatcttacttt   1920 gataaggatt tttaagatac tctataatg attaaaattt ttagaacttc ctaatcactt   1980
ttcagagtat atgttttttca ttgagaagca aaattgtaac tcagatttgt gatgctagga   2040
acatgagcaa actgaaaatt actatgcact tgtcagaaac aataaatgca acttgttgtg   2100
```

<210> SEQ ID NO 17
<211> LENGTH: 348
<212> TYPE: PRT
<213> ORGANISM: Homo sapiens
<220> FEATURE:
<221> NAME/KEY: MISC_FEATURE
<223> OTHER INFORMATION: NP_001738; gelsolin-like capping protein

<400> SEQUENCE: 17

```
Met Tyr Thr Ala Ile Pro Gln Ser Gly Ser Pro Phe Pro Gly Ser Val
1               5                   10                  15

Gln Asp Pro Gly Leu His Val Trp Arg Val Glu Lys Leu Lys Pro Val
                20                  25                  30

Pro Val Ala Gln Glu Asn Gln Gly Val Phe Phe Ser Gly Asp Ser Tyr
            35                  40                  45

Leu Val Leu His Asn Gly Pro Glu Glu Val Ser His Leu His Leu Trp
```

```
                50                      55                      60
Ile Gly Gln Gln Ser Ser Arg Asp Glu Gln Gly Ala Cys Ala Val Leu
 65                      70                      75                      80

Ala Val His Leu Asn Thr Leu Leu Gly Glu Arg Pro Val Gln His Arg
                        85                      90                      95

Glu Val Gln Gly Asn Glu Ser Asp Leu Phe Met Ser Tyr Phe Pro Arg
                100                     105                     110

Gly Leu Lys Tyr Gln Glu Gly Gly Val Glu Ser Ala Phe His Lys Thr
                115                     120                     125

Ser Thr Gly Ala Pro Ala Ala Ile Lys Lys Leu Tyr Gln Val Lys Gly
            130                     135                     140

Lys Lys Asn Ile Arg Ala Thr Glu Arg Ala Leu Asn Trp Asp Ser Phe
145                     150                     155                     160

Asn Thr Gly Asp Cys Phe Ile Leu Asp Leu Gly Gln Asn Ile Phe Ala
                        165                     170                     175

Trp Cys Gly Gly Lys Ser Asn Ile Leu Glu Arg Asn Lys Ala Arg Asp
                180                     185                     190

Leu Ala Leu Ala Ile Arg Asp Ser Glu Arg Gln Gly Lys Ala Gln Val
                195                     200                     205

Glu Ile Val Thr Asp Gly Glu Glu Pro Ala Glu Met Ile Gln Val Leu
        210                     215                     220

Gly Pro Lys Pro Ala Leu Lys Glu Gly Asn Pro Glu Glu Asp Leu Thr
225                     230                     235                     240

Ala Asp Lys Ala Asn Ala Gln Ala Ala Leu Tyr Lys Val Ser Asp
                        245                     250                     255

Ala Thr Gly Gln Met Asn Leu Thr Lys Val Ala Asp Ser Ser Pro Phe
                        260                     265                     270

Ala Leu Glu Leu Leu Ile Ser Asp Asp Cys Phe Val Leu Asp Asn Gly
                275                     280                     285

Leu Cys Gly Lys Ile Tyr Ile Trp Lys Gly Arg Lys Ala Asn Glu Lys
        290                     295                     300

Glu Arg Gln Ala Ala Leu Gln Val Ala Glu Gly Phe Ile Ser Arg Met
305                     310                     315                     320

Gln Tyr Ala Pro Asn Thr Gln Val Glu Ile Leu Pro Gln Gly His Glu
                        325                     330                     335

Ser Pro Ile Phe Lys Gln Phe Phe Lys Asp Trp Lys
                340                     345

<210> SEQ ID NO 18
<211> LENGTH: 1460
<212> TYPE: DNA
<213> ORGANISM: Homo sapiens
<220> FEATURE:
<221> NAME/KEY: misc_feature
<223> OTHER INFORMATION: NM_001747; capping protein (actin filament);
      gelsolin-like CAPG; mRNA.

<400> SEQUENCE: 18
gacggcctgg catacccact gcccacccca gtgactgctc ttctgcttca ggcctgctgg      60
cctcccagca ctgcctgccc ctccctgtcg ggggacatcg cctccacacc ggctggggaa     120
ggagcccagg ggtggggctg gtgggtgggg ctggtggttg gggcagccag agaagtaaga     180
gggaagtgag aagccgggtg gggcaggctg gaaggaagac gaacctacga agcagagatc     240
tgaagacagc atgtacacag ccattcccca gagtggctct ccattcccag gctcagtgca     300
ggatccaggc ctgcatgtgt ggcgggtgga gaagctgaag ccggtgcctg tggcgcaaga     360
```

-continued

```
gaaccagggc gtcttcttct cggggggactc ctacctagtg ctgcacaatg cccagaaga    420 ggtttcccat ctgcacctgt ggataggcca gcagtcatcc cgggatgagc agggggcctg    480
tgccgtgctg gctgtgcacc tcaacacgct gctgggagag cggcctgtgc agcaccgcga    540
ggtgcagggc aatgagtctg acctcttcat gagctacttc ccacggggcc tcaagtacca    600
ggaaggtggt gtggagtcag catttcacaa gacctccaca ggagccccag ctgccatcaa    660
gaaactctac caggtgaagg ggaagaagaa catccgtgcc accgagcggg cactgaactg    720
ggacagcttc aacactgggg actgcttcat cctggacctg gccagaaca tcttcgcctg     780 gtgtggtgga aagtccaaca tcctggaacg caacaaggcg agggacctgg ccctggccat    840
ccgggacagt gagcgacagg gcaaggccca ggtggagatt gtcactgatg gggaggagcc    900
tgctgagatg atccaggtcc tgggcccaa gcctgctctg aaggagggca accctgagga    960
agacctcaca gctgacaagg caaatgccca ggccgcagct ctgtataagg tctctgatgc   1020
cactggacag atgaacctga ccaaggtggc tgactccagc ccatttgccc ttgaactgct   1080
gatatctgat gactgctttg tgctggacaa cgggctctgt ggcaagatct atatctggaa   1140
ggggcgaaaa gcgaatgaga aggagcggca ggcagccctg caggtggccg agggcttcat   1200
ctcgcgcatg cagtacgccc cgaacactca ggtggagatt ctgcctcagg ccatgagag    1260 tcccatcttc aagcaattt tcaaggactg gaaatgaggg tgggcgtctt cctgccccat    1320
gctcccctgc cccccaccac ctgcctgctt gcttctctgg ctgcctggtc agtgcagagg   1380
tgccccctgc agatgttcaa taaggagac aagtgctttc ccagctcttt tcctgcacca    1440
ccaaaaaaaa aaaaaaaaa                                                1460
```

<210> SEQ ID NO 19
<211> LENGTH: 180
<212> TYPE: PRT
<213> ORGANISM: Homo sapiens
<220> FEATURE:
<221> NAME/KEY: MISC_FEATURE
<223> OTHER INFORMATION: glycodelin precursor (PP14); NP_002562 and
      NP_001018059

<400> SEQUENCE: 19

```
Met Leu Cys Leu Leu Leu Thr Leu Gly Val Ala Leu Val Cys Gly Val
1               5                  10                 15

Pro Ala Met Asp Ile Pro Gln Thr Lys Gln Asp Leu Glu Leu Pro Lys
            20                  25                  30

Leu Ala Gly Thr Trp His Ser Met Ala Met Ala Thr Asn Asn Ile Ser
        35                  40                  45

Leu Met Ala Thr Leu Lys Ala Pro Leu Arg Val His Ile Thr Ser Leu
    50                  55                  60

Leu Pro Thr Pro Glu Asp Asn Leu Glu Ile Val Leu His Arg Trp Glu
65                  70                  75                  80

Asn Asn Ser Cys Val Glu Lys Lys Val Leu Gly Glu Lys Thr Glu Asn
                85                  90                  95

Pro Lys Lys Phe Lys Ile Asn Tyr Thr Val Ala Asn Glu Ala Thr Leu
            100                 105                 110

Leu Asp Thr Asp Tyr Asp Asn Phe Leu Phe Leu Cys Leu Gln Asp Thr
        115                 120                 125

Thr Thr Pro Ile Gln Ser Met Met Cys Gln Tyr Leu Ala Arg Val Leu
    130                 135                 140

Val Glu Asp Asp Glu Ile Met Gln Gly Phe Ile Arg Ala Phe Arg Pro
145                 150                 155                 160
```

Leu Pro Arg His Leu Trp Tyr Leu Leu Asp Leu Lys Gln Met Glu Glu
            165                 170                 175

Pro Cys Arg Phe
        180

<210> SEQ ID NO 20
<211> LENGTH: 857
<212> TYPE: DNA
<213> ORGANISM: Homo sapiens
<220> FEATURE:
<221> NAME/KEY: misc_feature
<223> OTHER INFORMATION: progestagen-associated endometrial protein
      (placental protein 14, pregnancy-associated endometrial alpha-2-
      globulin, alpha uterine protein) (PAEP); transcript variant 1;
      mRNA; NM_001018049

<400> SEQUENCE: 20
catccctctg gctccagagc tcagagccac ccacagccgc agccatgctg tgcctcctgc      60
tcaccctggg cgtggccctg gtctgtggtg tcccggccat ggacatcccc cagaccaagc     120
aggacctgga gctcccaaag ttggcaggga cctggcactc catggccatg gcgaccaaca     180
acatctccct catggcgaca ctgaaggccc tctgagggt ccacatcacc tcactgttgc      240 ccaccccga ggacaacctg gagatcgttc tgcacagatg ggagaacaac agctgtgttg      300
agaagaaggt ccttggagag aagactgaga atccaaagaa gttcaagatc aactatacgg     360
tggcgaacga ggccacgctg ctcgatactg actacgacaa tttcctgttt ctctgcctac     420
aggacaccac caccccatc cagagcatga tgtgccagta cctggccaga gtcctggtgg      480
aggacgatga gatcatgcag ggattcatca gggctttcag gcccctgccc aggcacctat     540
ggtacttgct ggacttgaaa cagatggaag agccgtgccg tttctaggtg agctcctgcc     600
tggtcctgcc tcctggctca cctccgcctc caggaagacc agactccac ccttccacac      660 ctccagagca gtgggacttc ctcctgccct ttcaaagaat aaccacagct cagaagacga     720
tgacgtggtc atctgtgtcg ccatccctt cctgctgcac acctgcacca cggccatggg     780
gaggctgctc cctgggggca gagtctctgg cagaggttat taataaaccc ttggagcatg     840
aaaaaaaaaa aaaaaaa                                                    857

<210> SEQ ID NO 21
<211> LENGTH: 828
<212> TYPE: PRT
<213> ORGANISM: Homo sapiens
<220> FEATURE:
<221> NAME/KEY: MISC_FEATURE
<223> OTHER INFORMATION: NM_002571; progestagen-associated endometrial
      protein (placental protein 14, pregnancy-associated endometrial
      alpha-2-globulin, alpha uterine protein) (PAEP); transcript
      variant 2; mRNA.

<400> SEQUENCE: 21

Cys Ala Thr Cys Cys Cys Thr Cys Thr Gly Gly Cys Thr Cys Cys Ala
1               5                   10                  15

Gly Ala Gly Cys Thr Cys Ala Gly Ala Gly Cys Cys Ala Cys Cys Cys
            20                  25                  30

Ala Cys Ala Gly Cys Cys Gly Cys Ala Gly Cys Cys Ala Thr Gly Cys
        35                  40                  45

Thr Gly Thr Gly Cys Cys Thr Cys Cys Thr Gly Cys Thr Cys Ala Cys
    50                  55                  60

Cys Cys Thr Gly Gly Gly Cys Gly Thr Gly Cys Cys Cys Thr Gly
65                  70                  75                  80

Gly Thr Cys Thr Gly Thr Gly Gly Thr Gly Thr Cys Cys Cys Gly Gly

-continued

```
                85                  90                  95
Cys Cys Ala Thr Gly Gly Ala Cys Ala Thr Cys Cys Cys Cys Ala
            100                 105                 110
Gly Ala Cys Cys Ala Ala Gly Cys Ala Gly Ala Cys Cys Thr Gly
            115                 120                 125
Gly Ala Gly Cys Thr Cys Cys Ala Ala Gly Thr Thr Gly Gly
            130                 135                 140
Cys Ala Gly Gly Ala Cys Cys Thr Gly Gly Cys Ala Cys Thr Cys
145                 150                 155                 160
Cys Ala Thr Gly Gly Cys Cys Ala Thr Gly Gly Cys Gly Ala Cys Cys
            165                 170                 175
Ala Ala Cys Ala Ala Cys Ala Thr Thr Cys Cys Cys Thr Cys Ala
            180                 185                 190
Thr Gly Gly Cys Gly Ala Cys Ala Cys Thr Gly Ala Ala Gly Gly Cys
            195                 200                 205
Cys Cys Cys Thr Cys Thr Gly Ala Gly Gly Thr Cys Cys Ala Cys
            210                 215                 220
Ala Thr Cys Ala Cys Cys Thr Cys Ala Cys Thr Gly Thr Thr Gly Cys
225                 230                 235                 240
Cys Cys Ala Cys Cys Cys Cys Gly Ala Gly Ala Cys Ala Ala
            245                 250                 255
Cys Cys Thr Gly Gly Ala Gly Ala Cys Gly Thr Thr Cys Thr Gly
            260                 265                 270
Cys Ala Cys Ala Gly Ala Thr Gly Gly Ala Gly Ala Ala Cys Ala
            275                 280                 285
Ala Cys Ala Gly Cys Thr Gly Thr Gly Thr Thr Gly Ala Gly Ala Ala
            290                 295                 300
Gly Ala Ala Gly Gly Thr Cys Cys Thr Thr Gly Gly Ala Gly Ala Gly
305                 310                 315                 320
Ala Ala Gly Ala Cys Thr Gly Ala Gly Ala Ala Thr Cys Cys Ala Ala
            325                 330                 335
Ala Gly Ala Ala Gly Thr Thr Cys Ala Ala Gly Ala Thr Cys Ala Ala
            340                 345                 350
Cys Thr Ala Thr Ala Cys Gly Gly Thr Gly Gly Cys Gly Ala Ala Cys
            355                 360                 365
Gly Ala Gly Gly Cys Cys Ala Cys Gly Cys Thr Cys Thr Cys Gly
            370                 375                 380
Ala Thr Ala Cys Thr Gly Ala Cys Thr Ala Cys Gly Ala Cys Ala Ala
385                 390                 395                 400
Thr Thr Thr Cys Cys Thr Gly Thr Thr Cys Thr Cys Thr Gly Cys
            405                 410                 415
Cys Thr Ala Cys Ala Gly Gly Ala Cys Ala Cys Cys Ala Cys Cys Ala
            420                 425                 430
Cys Cys Cys Cys Cys Ala Thr Cys Cys Gly Ala Gly Cys Ala Thr
            435                 440                 445
Gly Ala Thr Gly Thr Gly Cys Cys Ala Gly Thr Ala Cys Cys Thr Gly
            450                 455                 460
Gly Cys Cys Ala Gly Ala Gly Thr Cys Thr Gly Gly Thr Gly Gly
465                 470                 475                 480
Ala Gly Gly Ala Cys Gly Ala Thr Gly Ala Thr Cys Ala Thr
            485                 490                 495
Gly Cys Ala Gly Gly Gly Ala Thr Thr Cys Ala Thr Cys Ala Gly Gly
            500                 505                 510
```

```
Gly Cys Thr Thr Thr Cys Ala Gly Gly Cys Cys Cys Thr Gly Cys
        515                 520                 525

Cys Cys Ala Gly Gly Cys Ala Cys Cys Thr Ala Thr Gly Gly Thr Ala
530                 535                 540

Cys Thr Thr Gly Cys Thr Gly Gly Ala Cys Thr Thr Gly Ala Ala Ala
545                 550                 555                 560

Cys Ala Gly Ala Thr Gly Gly Ala Ala Gly Ala Gly Cys Cys Gly Thr
                565                 570                 575

Gly Cys Cys Gly Thr Thr Thr Cys Thr Ala Gly Cys Thr Cys Ala Cys
                580                 585                 590

Cys Thr Cys Cys Gly Cys Cys Thr Cys Cys Ala Gly Gly Ala Ala Gly
        595                 600                 605

Ala Cys Cys Ala Gly Ala Cys Thr Cys Cys Ala Cys Cys Cys Cys Thr
    610                 615                 620

Thr Cys Cys Ala Cys Ala Cys Cys Thr Cys Cys Ala Gly Ala Gly Cys
625                 630                 635                 640

Ala Gly Thr Gly Gly Ala Cys Thr Thr Cys Cys Thr Cys Cys Thr
                645                 650                 655

Gly Cys Cys Cys Thr Thr Thr Cys Ala Ala Gly Ala Ala Thr Ala
        660                 665                 670

Ala Cys Cys Ala Cys Ala Gly Cys Thr Cys Ala Gly Ala Ala Gly Ala
        675                 680                 685

Cys Gly Ala Thr Gly Ala Cys Gly Thr Gly Gly Thr Cys Ala Thr Cys
    690                 695                 700

Thr Gly Thr Gly Thr Cys Gly Cys Ala Thr Cys Cys Cys Thr
705                 710                 715                 720

Thr Cys Cys Thr Gly Cys Thr Gly Cys Ala Cys Ala Cys Cys Thr Gly
                725                 730                 735

Cys Ala Cys Cys Ala Cys Gly Gly Cys Cys Ala Thr Gly Gly Gly Gly
                740                 745                 750

Ala Gly Gly Cys Thr Gly Cys Thr Cys Cys Thr Gly Gly Gly Gly
        755                 760                 765

Gly Cys Ala Gly Ala Gly Thr Cys Thr Cys Thr Gly Gly Cys Ala Gly
770                 775                 780

Ala Gly Gly Thr Thr Ala Thr Thr Ala Ala Thr Ala Ala Cys Cys
785                 790                 795                 800

Cys Thr Thr Gly Gly Ala Gly Cys Ala Thr Gly Ala Ala Ala Ala
    805                 810                 815

Ala Ala Ala Ala Ala Ala Ala Ala Ala Ala
            820                 825

<210> SEQ ID NO 22
<211> LENGTH: 290
<212> TYPE: PRT
<213> ORGANISM: Homo sapiens
<220> FEATURE:
<221> NAME/KEY: MISC_FEATURE
<223> OTHER INFORMATION: RNA binding protein (autoantigenic, hnRNP-
      associated with lethal yellow); short isoform; NP_031393

<400> SEQUENCE: 22

Met Ser Leu Lys Leu Gln Ala Ser Asn Val Thr Asn Lys Asn Asp Pro
1               5                   10                  15

Lys Ser Ile Asn Ser Arg Val Phe Ile Gly Asn Leu Asn Thr Ala Leu
            20                  25                  30

Val Lys Lys Ser Asp Val Glu Thr Ile Phe Ser Lys Tyr Gly Arg Val
        35                  40                  45
```

```
Ala Gly Cys Ser Val His Lys Gly Tyr Ala Phe Val Gln Tyr Ser Asn
         50                  55                  60

Glu Arg His Ala Arg Ala Ala Val Leu Gly Glu Asn Gly Arg Val Leu
 65                  70                  75                  80

Ala Gly Gln Thr Leu Asp Ile Asn Met Ala Gly Glu Pro Lys Pro Asp
                 85                  90                  95

Arg Pro Lys Gly Leu Lys Arg Ala Ala Ser Ala Ile Tyr Arg Leu Phe
                100                 105                 110

Asp Tyr Arg Gly Arg Leu Ser Pro Val Pro Val Pro Arg Ala Val Pro
            115                 120                 125

Val Lys Arg Pro Arg Val Thr Val Pro Leu Val Arg Arg Val Lys Thr
        130                 135                 140

Asn Val Pro Val Lys Leu Phe Ala Arg Ser Thr Ala Val Thr Thr Ser
145                 150                 155                 160

Ser Ala Lys Ile Lys Leu Lys Ser Ser Glu Leu Gln Ala Ile Lys Thr
                165                 170                 175

Glu Leu Thr Gln Ile Lys Ser Asn Ile Asp Ala Leu Leu Ser Arg Leu
                180                 185                 190

Glu Gln Ile Ala Ala Glu Gln Lys Ala Asn Pro Asp Gly Lys Lys Lys
            195                 200                 205

Gly Asp Gly Gly Ala Gly Gly Gly Gly Gly Gly Ser Gly
210                 215                 220

Gly Gly Ser Gly Gly Gly Gly Gly Ser Ser Arg Pro Pro
225                 230                 235                 240

Ala Pro Gln Glu Asn Thr Thr Ser Glu Ala Gly Leu Pro Gln Gly Glu
                245                 250                 255

Ala Arg Thr Arg Asp Asp Gly Asp Glu Glu Gly Leu Leu Thr His Ser
            260                 265                 270

Glu Glu Glu Leu Glu His Ser Gln Asp Thr Asp Ala Asp Asp Gly Ala
        275                 280                 285

Leu Gln
    290

<210> SEQ ID NO 23
<211> LENGTH: 306
<212> TYPE: PRT
<213> ORGANISM: Homo sapiens
<220> FEATURE:
<221> NAME/KEY: MISC_FEATURE
<223> OTHER INFORMATION: RNA binding protein (autoantigenic, hnRNP-
      associated with lethal yellow); long isoform; NP_057951

<400> SEQUENCE: 23

Met Ser Leu Lys Leu Gln Ala Ser Asn Val Thr Asn Lys Asn Asp Pro
 1               5                  10                  15

Lys Ser Ile Asn Ser Arg Val Phe Ile Gly Asn Leu Asn Thr Ala Leu
             20                  25                  30

Val Lys Lys Ser Asp Val Glu Thr Ile Phe Ser Lys Tyr Gly Arg Val
         35                  40                  45

Ala Gly Cys Ser Val His Lys Gly Tyr Ala Phe Val Gln Tyr Ser Asn
         50                  55                  60

Glu Arg His Ala Arg Ala Ala Val Leu Gly Glu Asn Gly Arg Val Leu
 65                  70                  75                  80

Ala Gly Gln Thr Leu Asp Ile Asn Met Ala Gly Glu Pro Lys Pro Asp
                 85                  90                  95

Arg Pro Lys Gly Leu Lys Arg Ala Ala Ser Ala Ile Tyr Ser Gly Tyr
```

```
                100                 105                 110
Ile Phe Asp Tyr Asp Tyr Tyr Arg Asp Asp Phe Tyr Asp Arg Leu Phe
            115                 120                 125

Asp Tyr Arg Gly Arg Leu Ser Pro Val Pro Val Pro Arg Ala Val Pro
        130                 135                 140

Val Lys Arg Pro Arg Val Thr Val Pro Leu Val Arg Arg Val Lys Thr
145                 150                 155                 160

Asn Val Pro Val Lys Leu Phe Ala Arg Ser Thr Ala Val Thr Thr Ser
                165                 170                 175

Ser Ala Lys Ile Lys Leu Lys Ser Ser Glu Leu Gln Ala Ile Lys Thr
            180                 185                 190

Glu Leu Thr Gln Ile Lys Ser Asn Ile Asp Ala Leu Leu Ser Arg Leu
        195                 200                 205

Glu Gln Ile Ala Ala Glu Gln Lys Ala Asn Pro Asp Gly Lys Lys Lys
    210                 215                 220

Gly Asp Gly Gly Gly Ala Gly Gly Gly Gly Gly Gly Gly Ser Gly
225                 230                 235                 240

Gly Gly Gly Ser Gly Gly Gly Gly Gly Gly Ser Ser Arg Pro Pro
                245                 250                 255

Ala Pro Gln Glu Asn Thr Thr Ser Glu Ala Gly Leu Pro Gln Gly Glu
            260                 265                 270

Ala Arg Thr Arg Asp Asp Gly Asp Glu Glu Gly Leu Leu Thr His Ser
        275                 280                 285

Glu Glu Glu Leu Glu His Ser Gln Asp Thr Asp Ala Asp Asp Gly Ala
    290                 295                 300

Leu Gln
305
```

<210> SEQ ID NO 24
<211> LENGTH: 1541
<212> TYPE: DNA
<213> ORGANISM: Homo sapiens
<220> FEATURE:
<221> NAME/KEY: misc_feature
<223> OTHER INFORMATION: RNA binding protein, autoantigenic (hnRNP-
      associated with lethal yellow homolog (mouse)) (RALY); transcript
      variant 2; mRNA; NM_007367

<400> SEQUENCE: 24

```
cgcgcgagcg gcgccagctc ggggcagcgg aacccagaga agctgagggg gcggtagcgg      60
cggcgacggc gacgacgacg actcccgcgc gtgtgcccag cctcttcccg ccgcagccgc     120
ccttttcctc cctcccttac gtccccgagt gcggcagtac cgcctccttc ccagccgcgc     180
ggcttcctcc agacctctcg gcgcgggtga gccctattcc cagaggcagg tggtgctgac     240
cctgtaaccc aaaggaggaa acagctggct aagctcatca ttgttactgg tgggcaccat     300
gtccttgaag cttcaggcaa gcaatgtaac caacaagaat gaccccaagt ccatcaactc     360
tcgagtcttc attggaaacc tcaacacagc tctggtgaag aaatcagatg tggagaccat     420
cttctctaag tatggccgtg tggccggctg ttctgtgcac aagggctatg cctttgttca     480
gtactccaat gagcgccatg cccgggcagc tgtgctggga gagaatgggc gggtgctggc     540
cgggcagacc ctggacatca acatggctgg agagcctaag cctgacagac ccaaggggct     600
aaagagagca gcatctgcca tatacaggct cttcgactac cggggccgtc tgtcgcccgt     660
gccagtgccc agggcggtcc ctgtgaagcg acccgggtc acagtcccct tggtccggcg     720
tgtcaaaact aacgtacctg tcaagctctt tgcccgctcc acagctgtca ccaccagctc     780
```

-continued

| | |
|---|---|
| agccaagatc aagttaaaga gcagtgagct gcaggccatc aagacggagc tgacacagat | 840 |
| caagtccaat atcgatgccc tgctgagccg cttggagcag atcgctgcgg agcaaaaggc | 900 |
| caatccagat ggcaagaaga agggtgatgg aggtggcgcc ggcggcggcg cggtggtgg | 960 |
| tggcagcggt ggcggtggca gtggtggtgg cgtggcggt gcagcagcc ggccaccagc | 1020 |
| cccccaagag aacacaactt ctgaggcagg cctgccccag ggggaagcac ggacccgaga | 1080 |
| cgacggcgat gaggaaggc tcctgacaca cagcgaggaa gagctggaac acagccagga | 1140 |
| cacagacgcg gatgatgggg ccttgcagta agcagcctga caggagcaat ggccaccagc | 1200 |
| aggtgaaggg catcgctgcc ccaggcctca agccgggcac ccaaccctgg atgccacccc | 1260 |
| ccagcgggta ccagaggaaa gctggcagca ggcgcctcct ccccaacgc atcccagcca | 1320 |
| gtgccatgtc ctctgcaggt ggagttactg gcctactcct tccccatgag ccctccctgt | 1380 |
| ctgcactgcc caggccagag ggtagagcac aggggtttcc ccatactacc tcccctcccc | 1440 |
| aggacactcc caggcttggg ttttttctat aggtttggcg gggggccaca gggaggggac | 1500 |
| cctgacaata aagagattgg atcccaaaaa aaaaaaaaa a | 1541 |

<210> SEQ ID NO 25
<211> LENGTH: 1589
<212> TYPE: DNA
<213> ORGANISM: Homo sapiens
<220> FEATURE:
<221> NAME/KEY: misc_feature
<223> OTHER INFORMATION: RNA binding protein; autoantigenic (hnRNP-
    associated with lethal yellow homolog (mouse)) (RALY); transcript
    variant 1; mRNA

<400> SEQUENCE: 25

| | |
|---|---|
| cgcgcgagcg gcgccagctc ggggcagcgg aacccagaga agctgaggg gcggtagcgg | 60 |
| cggcgacggc gacgacgacg actcccgcgc gtgtgcccag cctcttcccg ccgcagccgc | 120 |
| ccttttcctc cctcccttac gtccccgagt gcggcagtac cgcctccttc ccagccgcgc | 180 |
| ggcttcctcc agacctctcg gcgcgggtga gccctattcc cagaggcagg tggtgctgac | 240 |
| cctgtaaccc aaaggaggaa acagctggct aagctcatca ttgttactgg tgggcaccat | 300 |
| gtccttgaag cttcaggcaa gcaatgtaac caacaagaat gaccccaagt ccatcaactc | 360 |
| tcgagtcttc attggaaacc tcaacacagc tctggtgaag aaatcagatg tggagaccat | 420 |
| cttctctaag tatggccgtg tggccggctg ttctgtgcac aagggctatg cctttgttca | 480 |
| gtactccaat gagcgccatg cccgggcagc tgtgctggga gagaatgggc gggtgctggc | 540 |
| cgggcagacc ctggacatca acatggctgg agagcctaag cctgacagac caaggggct | 600 |
| aaagagagca gcatctgcca tatacagtgg ctacatcttt gactatgatt actaccggga | 660 |
| cgacttctac gacaggctct tcgactaccg gggccgtctg tcgcccgtgc cagtgcccag | 720 |
| ggcggtccct gtgaagcgac cccgggtcac agtccctttg gtccggcgtg tcaaaactaa | 780 |
| cgtacctgtc aagctctttg cccgctccac agctgtcacc accagctcag ccaagatcaa | 840 |
| gttaaagagc agtgagctgc aggccatcaa gacggagctg acacagatca agtccaatat | 900 |
| cgatgccctg ctgagccgct tggagcagat cgctgcggga caaaaggcca atccagatgg | 960 |
| caagaagaag ggtgatggag gtggcgccgg cggcggcggc ggtggtggtg gcagcggtgg | 1020 |
| cggtggcagt ggtggtggcg gtggcggtgg cagcagccgg ccaccagccc cccaagagaa | 1080 |
| cacaacttct gaggcaggcc tgccccaggg ggaagcacgg acccgagacg acggcgatga | 1140 |
| ggaagggctc ctgacacaca gcgaggaaga gctggaacac agccaggaca cagacgcgga | 1200 |
| tgatggggcc ttgcagtaag cagcctgaca ggagcaatgg ccaccagcag gtgaagggca | 1260 |

-continued

```
tcgctgcccc aggcctcaag ccgggcaccc aaccctggat gccacccccc agcgggtacc    1320
agaggaaagc tggcagcagg cgcctcctcc cccaacgcat cccagccagt gccatgtcct    1380
ctgcaggtgg agttactggc ctactccttc cccatgagcc ctccctgtct gcactgccca    1440
ggccagaggg tagagcacag gggtttcccc atactacctc ccctcccag dacactccca    1500 ggcttgggtt ttttctatag gtttggcggg gggccacagg gagggaccc tgacaataaa    1560 gagattggat cccaaaaaaa aaaaaaaaa                                      1589
```

<210> SEQ ID NO 26
<211> LENGTH: 444
<212> TYPE: PRT
<213> ORGANISM: Homo sapiens
<220> FEATURE:
<221> NAME/KEY: MISC_FEATURE
<223> OTHER INFORMATION: NP_821133; Amino acid; tubulin; beta
      polypeptide

<400> SEQUENCE: 26

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
```

```
                290                 295                 300
Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
                340                 345                 350

Val Cys Asp Ile Pro Pro Arg Gly Leu Lys Met Ala Val Thr Phe Ile
                355                 360                 365

Gly Asn Ser Thr Ala Ile Gln Glu Leu Phe Lys Arg Ile Ser Glu Gln
                370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
                420                 425                 430

Glu Glu Asp Phe Gly Glu Glu Ala Glu Glu Ala
                435                 440

<210> SEQ ID NO 27
<211> LENGTH: 2510
<212> TYPE: DNA
<213> ORGANISM: Homo sapiens
<220> FEATURE:
<221> NAME/KEY: misc_feature
<223> OTHER INFORMATION: NM_178014; mRNA; tubulin; beta (TUBB); mRNA
<220> FEATURE:
<221> NAME/KEY: misc_feature
<223> OTHER INFORMATION: NM_178014; mRNA; tubulin, beta (TUBB); mRNA

<400> SEQUENCE: 27
gcacctcgct gctccagcct ctggggcgca ttccaacctt ccagcctgcg acctgcggag      60
aaaaaaaatt acttattttc ttgccccata catatccttga ggcgagcaaa aaaattaaat    120
tttaaccatg agggaaatcg tgcacatcca ggctggtcag tgtggcaacc agatcggtgc    180
caagttctgg gaggtgatca gtgatgaaca tggcatcgac cccaccggca cctaccacgg    240
ggacagcgac ctgcagctgg accgcatctc tgtgtactac aatgaagcca caggtggcaa    300
atatgttcct cgtgccatcc tggtggatct agaacctggg accatggact ctgttcgctc    360
aggtcctttt ggccagatct ttagaccaga caactttgta tttggtcagt ctggggcagg    420
taacaactgg gccaaaggcc actacacaga gggcgccgag ctggttgatt ctgtcctgga    480
tgtggtacgg aaggaggcag agagctgtga ctgcctgcag gcttccagc tgacccactc     540 actgggcggg ggcacaggct ctggaatggg cactctcctt atcagcaaga tccgagaaga    600 atacccctgat cgcatcatga ataccttcag tgtggtgcct tcacccaaag tgtctgacac    660
cgtggtcgag ccctacaatg ccaccctctc cgtccatcag ttggtagaga atactgatga    720
gacctattgc attgacaacg aggccctcta tgatatctgc ttccgcactc tgaagctgac    780
cacaccaacc tacgggggatc tgaaccacct tgtctcagcc accatgagtg gtgtcaccac    840
ctgcctccgt ttccctggcc agctcaatgc tgacctccgc aagttggcag tcaacatggt    900
ccccttccca cgtctccatt tctttatgcc tggctttgcc cctctcacca gccgtggaag    960
ccagcagtat cgagctctca cagtgccgga actcacccag caggtcttcg atgccaagaa   1020
catgatggct gcctgtgacc cccgccacgg ccgatacctc accgtggctg ctgtcttccg   1080
tggtcggatg tccatgaagg aggtcgatga gcagatgctt aacgtgcaga acaagaacag   1140
```

```
cagctacttt gtggaatgga tccccaacaa tgtcaagaca gccgtctgtg acatcccacc    1200
tcgtggcctc aagatggcag tcaccttcat tggcaatagc acagccatcc aggagctctt    1260
caagcgcatc tcggagcagt tcactgccat gttccgccgg aaggccttcc tccactggta    1320
cacaggcgag ggcatggacg agatggagtt caccgaggct gagagcaaca tgaacgacct    1380
cgtctctgag tatcagcagt accaggatgc caccgcagaa gaggaggagg atttcggtga    1440
ggaggccgaa gaggaggcct aaggcagagc ccccatcacc tcaggcttct cagttccctt    1500
agccgtctta ctcaactgcc cctttcctct ccctcagaat ttgtgtttgc tgcctctatc    1560
ttgttttttg ttttttcttc tggggggggt ctagaacagt gcctggcaca tagtaggcgc    1620
tcaataaata cttgtttgtt gaatgtctcc tctctctttc cactctggga aacctaggtt    1680
tctgccattc tgggtgaccc tgtatttctt tctggtgccc attccatttg tccagttaat    1740
acttcctctt aaaaatctcc aagaagctgg gtctccagat cccatttaga accaaccagg    1800
tgctgaaaac acatgtagat aatggccatc atcctaagcc caaagtagaa aatggtagaa    1860
ggtagtgggt agaagtcact atataaggaa ggggatggga ttttccattc taaaagtttt    1920
ggagagggaa atccaggcta ttaaagtcac taaatttcta agtatgtcca tttcccatct    1980
cagcttcaag ggaggtgtca gcagtattat ctccactttc aatctccctc caagctctac    2040
tctggaggag tctgtcccac tctgtcaagt ggaatccttc cctttccaac tctacctccc    2100
tcactcagct ccctttcccct gatcagagaa agggatcaag ggggttggga gggggaaag    2160 agaccagcct tggtccctaa gcctccagaa acgtcttctt aatccccacc ttttcttact    2220
cccaaaaaag aatgaacacc cctgactctg gagtggtgta tactgccaca tcagtgtttg    2280
agtcagtccc cagaggagag gggaaccctc ctccatcttt tttgcaacat ctcatttctt    2340 cctttttgctg ttgcttcccc cctcacacac ttggttttgt tctatcctac atttgagatt    2400
tctattttat gttgaacttg ctgcttttt tcatattgaa aagatgacat cgccccaaga    2460
gccaaaaata aatgggaatt gaaaaaaaaa aaaaaaaaa aaaaaaaaa               2510
```

<210> SEQ ID NO 28
<211> LENGTH: 375
<212> TYPE: PRT
<213> ORGANISM: Homo sapiens
<220> FEATURE:
<221> NAME/KEY: MISC_FEATURE
<223> OTHER INFORMATION: NP_001605; Amino acid; actin; gamma 1
      propeptide
<220> FEATURE:
<221> NAME/KEY: MISC_FEATURE
<223> OTHER INFORMATION: NP_001605; Amino acid; actin, gamma 1
      propeptide

<400> SEQUENCE: 28

```
Met Glu Glu Glu Ile Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95
```

```
Ala Pro Glu Glu His Pro Val Leu Leu Thr Glu Ala Pro Leu Asn Pro
            100                 105                 110
Lys Ala Asn Arg Glu Lys Met Thr Gln Ile Met Phe Glu Thr Phe Asn
        115                 120                 125
Thr Pro Ala Met Tyr Val Ala Ile Gln Ala Val Leu Ser Leu Tyr Ala
    130                 135                 140
Ser Gly Arg Thr Thr Gly Ile Val Met Asp Ser Gly Asp Gly Val Thr
145                 150                 155                 160
His Thr Val Pro Ile Tyr Glu Gly Tyr Ala Leu Pro His Ala Ile Leu
                165                 170                 175
Arg Leu Asp Leu Ala Gly Arg Asp Leu Thr Asp Tyr Leu Met Lys Ile
            180                 185                 190
Leu Thr Glu Arg Gly Tyr Ser Phe Thr Thr Thr Ala Glu Arg Glu Ile
        195                 200                 205
Val Arg Asp Ile Lys Glu Lys Leu Cys Tyr Val Ala Leu Asp Phe Glu
210                 215                 220
Gln Glu Met Ala Thr Ala Ala Ser Ser Ser Ser Leu Glu Lys Ser Tyr
225                 230                 235                 240
Glu Leu Pro Asp Gly Gln Val Ile Thr Ile Gly Asn Glu Arg Phe Arg
                245                 250                 255
Cys Pro Glu Ala Leu Phe Gln Pro Ser Phe Leu Gly Met Glu Ser Cys
            260                 265                 270
Gly Ile His Glu Thr Thr Phe Asn Ser Ile Met Lys Cys Asp Val Asp
        275                 280                 285
Ile Arg Lys Asp Leu Tyr Ala Asn Thr Val Leu Ser Gly Gly Thr Thr
290                 295                 300
Met Tyr Pro Gly Ile Ala Asp Arg Met Gln Lys Glu Ile Thr Ala Leu
305                 310                 315                 320
Ala Pro Ser Thr Met Lys Ile Lys Ile Ile Ala Pro Pro Glu Arg Lys
                325                 330                 335
Tyr Ser Val Trp Ile Gly Gly Ser Ile Leu Ala Ser Leu Ser Thr Phe
            340                 345                 350
Gln Gln Met Trp Ile Ser Lys Gln Glu Tyr Asp Glu Ser Gly Pro Ser
        355                 360                 365
Ile Val His Arg Lys Cys Phe
    370                 375

<210> SEQ ID NO 29
<211> LENGTH: 1919
<212> TYPE: DNA
<213> ORGANISM: Homo sapiens
<220> FEATURE:
<221> NAME/KEY: misc_feature
<223> OTHER INFORMATION: NM_001614; actin, gamma 1 (ACTG1); mRNA.

<400> SEQUENCE: 29
gtctcagtcg ccgctgccag ctctcgcact ctgttcttcc gccgctccgc cgtcgcgttt     60
ctctgccggt cgcaatggaa gaagagatcg ccgcgctggt cattgacaat ggctccggca    120
tgtgcaaagc tggttttgct ggggacgacg ctccccgagc cgtgtttcct tccatcgtcg    180
ggcgccccag acaccagggc gtcatggtgg gcatgggcca gaaggactcc tacgtgggcg    240
acgaggccca gagcaagcgt ggcatcctga ccctgaagta ccccattgag catggcatcg    300
tcaccaactg ggacgacatg gagaagatct ggcaccacac cttctacaac gagctgcgcg    360
tggccccgga ggagcaccca gtgctgctga ccgaggcccc cctgaacccc aaggccaaca    420
```

| | |
|---|---|
| gagagaagat gactcagatt atgtttgaga ccttcaacac cccggccatg tacgtggcca | 480 |
| tccaggccgt gctgtccctc tacgcctctg ggcgcaccag tggcattgtc atggactctg | 540 |
| gagacggggt cacccacacg gtgcccatct acgagggcta cgccctcccc cacgccatcc | 600 |
| tgcgtctgga cctggctggc cgggacctga ccgactacct catgaagatc ctcactgagc | 660 |
| gaggctacag cttcaccacc acggccgagc gggaaatcgt gcgcgacatc aaggagaagc | 720 |
| tgtgctacgt cgccctggac ttcgagcagg agatggccac cgccgcatcc tcctcttctc | 780 |
| tggagaagag ctacgagctg cccgatggcc aggtcatcac cattggcaat gagcggttcc | 840 |
| ggtgtccgga ggcgctgttc cagccttcct tcctgggtat ggaatcttgc ggcatccacg | 900 |
| agaccacctt caactccatc atgaagtgtg acgtggacat ccgcaaagac ctgtacgcca | 960 |
| acacggtgct gtcgggcggc accaccatgt acccgggcat tgccgacagg atgcagaagg | 1020 |
| agatcaccgc cctggcgccc agcaccatga agatcaagat catcgcaccc ccagagcgca | 1080 |
| agtactcggt gtggatcggt ggctccatcc tggcctcact gtccaccttc cagcagatgt | 1140 |
| ggattagcaa gcaggagtac gacgagtcgg gcccctccat cgtccaccgc aaatgcttct | 1200 |
| aaacggactc agcagatgcg tagcatttgc tgcatgggtt aattgagaat agaaatttgc | 1260 |
| ccctggcaaa tgcacacacc tcatgctagc ctcacgaaac tggaataagc cttcgaaaag | 1320 |
| aaattgtcct tgaagcttgt atctgatatc agcactggat tgtagaactt gttgctgatt | 1380 |
| ttgaccttgt attgaagtta actgttcccc ttggtatttg tttaataccc tgtacatatc | 1440 |
| tttgagttca acctttagta cgtgtggctt ggtcacttcg tggctaaggt aagaacgtgc | 1500 |
| ttgtggaaga caagtctgtg gcttggtgag tctgtgtggc cagcagcctc tgatctgtgc | 1560 |
| agggtattaa cgtgtcaggg ctgagtgttc tgggatttct ctagaggctg gcaagaacca | 1620 |
| gttgttttgt cttgcgggtc tgtcagggtt ggaaagtcca agccgtagga cccagtttcc | 1680 |
| tttcttagct gatgtctttg gccagaacac cgtgggctgt tacttgcttt gagttggaag | 1740 |
| cggttttgcat ttacgcctgt aaatgtattc attcttaatt tatgtaaggt ttttttttgta | 1800 |
| cgcaattctc gattctttga agagatgaca acaaattttg gttttctact gttatgtgag | 1860 |
| aacattaggc cccagcaaca cgtcattgtg taaggaaaaa taaaagtgct gccgtaacc | 1919 |

<210> SEQ ID NO 30
<211> LENGTH: 1345
<212> TYPE: DNA
<213> ORGANISM: Homo sapiens
<220> FEATURE:
<221> NAME/KEY: misc_feature
<223> OTHER INFORMATION: NM_001615; actin, gamma 2, smooth muscle,
enteric (ACTG2); mRNA

<400> SEQUENCE: 30

| | |
|---|---|
| gcctctgggg ttttatattg ctctggtatt catgccaaag acacaccagc cctcagtcac | 60 |
| tgggagaaga acctctcata ccctcggtgc tccagtcccc agctcactca gccacacaca | 120 |
| ccatgtgtga agaggagacc accgcgctcg tgtgtgacaa tggctctggc ctgtgcaagg | 180 |
| caggcttcgc aggagatgat gcccccgggg ctgtcttccc ctccattgtg gccgccctc | 240 |
| gccaccaggg tgtgatggtg ggaatgggcc agaaagacag ctatgtgggg gatgaggctc | 300 |
| agagcaagcg agggatccta actctcaaat accccattga acacggcatc atcaccaact | 360 |
| gggatgacat ggagaagatc tggcaccact ccttctacaa tgagctgcgt gtagcacctg | 420 |
| aagagcaccc caccctgctc acagaggctc cctaaatcc caaggccaac agggaaaaga | 480 |
| tgacccagat catgtttgaa accttcaatg tccctgccat gtacgtcgcc attcaagctg | 540 |

```
tgctctccct ctatgcctct ggccgcacga caggcatcgt cctggattca ggtgatggcg      600
tcacccacaa tgtccccatc tatgaaggct atgccctgcc ccatgccatc atgcgcctgg      660
acttggctgg ccgtgacctc acggactacc tcatgaagat cctcacagag agaggctatt      720
cctttgtgac cacagctgag agagaaattg tgcgagacat caaggagaag ctgtgctatg      780
tggccctgga ttttgagaat gagatggcca cagcagcttc ctcttcctcc ctggagaaga      840
gctatgagct gccagatggg caggttatca ccattggcaa tgagcgcttc cgctgccctg      900
agaccctctt ccagccttcc tttattggca tggagtccgc tggaattcat gagacaacct      960
acaattccat catgaagtgt gacattgaca tccgtaagga cttatatgcc aacaatgtcc     1020
tctctggggg caccaccatg taccctggca ttgctgacag gatgcagaag gagatcacag     1080
ccctggcccc cagcaccatg aagatcaaga ttattgctcc cccagagcgg aagtactcag     1140
tctggatcgg gggctctatc ctggcctctc tctccaccct ccagcagatg tggatcagca     1200
agcctgagta tgatgaggca gggccctcca ttgtccacag gaagtgcttc taaagtcaga     1260
acaggttctc caaggatccc ctcgagacta ctctgttacc agtcatgaaa cattaaaacc     1320
tacaagcctt aaaaaaaaaa aaaaa                                           1345
```

<210> SEQ ID NO 31
<211> LENGTH: 376
<212> TYPE: PRT
<213> ORGANISM: Homo sapiens
<220> FEATURE:
<221> NAME/KEY: MISC_FEATURE
<223> OTHER INFORMATION: NP_001606; actin, gamma 2 propeptide

<400> SEQUENCE: 31

```
Met Cys Glu Glu Glu Thr Thr Ala Leu Val Cys Asp Asn Gly Ser Gly
1               5                   10                  15

Leu Cys Lys Ala Gly Phe Ala Gly Asp Asp Ala Pro Arg Ala Val Phe
            20                  25                  30

Pro Ser Ile Val Gly Arg Pro Arg His Gln Gly Val Met Val Gly Met
        35                  40                  45

Gly Gln Lys Asp Ser Tyr Val Gly Asp Glu Ala Gln Ser Lys Arg Gly
    50                  55                  60

Ile Leu Thr Leu Lys Tyr Pro Ile Glu His Gly Ile Ile Thr Asn Trp
65                  70                  75                  80

Asp Asp Met Glu Lys Ile Trp His His Ser Phe Tyr Asn Glu Leu Arg
                85                  90                  95

Val Ala Pro Glu Glu His Pro Thr Leu Leu Thr Glu Ala Pro Leu Asn
            100                 105                 110

Pro Lys Ala Asn Arg Glu Lys Met Thr Gln Ile Met Phe Glu Thr Phe
        115                 120                 125

Asn Val Pro Ala Met Tyr Val Ala Ile Gln Ala Val Leu Ser Leu Tyr
    130                 135                 140

Ala Ser Gly Arg Thr Thr Gly Ile Val Leu Asp Ser Gly Asp Gly Val
145                 150                 155                 160

Thr His Asn Val Pro Ile Tyr Glu Gly Tyr Ala Leu Pro His Ala Ile
                165                 170                 175

Met Arg Leu Asp Leu Ala Gly Arg Asp Leu Thr Asp Tyr Leu Met Lys
            180                 185                 190

Ile Leu Thr Glu Arg Gly Tyr Ser Phe Val Thr Thr Ala Glu Arg Glu
        195                 200                 205

Ile Val Arg Asp Ile Lys Glu Lys Leu Cys Tyr Val Ala Leu Asp Phe
    210                 215                 220
```

Glu Asn Glu Met Ala Thr Ala Ala Ser Ser Ser Leu Lys Ser
225                 230                 235                 240

Tyr Glu Leu Pro Asp Gly Gln Val Ile Thr Ile Gly Asn Glu Arg Phe
            245                 250                 255

Arg Cys Pro Glu Thr Leu Phe Gln Pro Ser Phe Ile Gly Met Glu Ser
                260                 265                 270

Ala Gly Ile His Glu Thr Thr Tyr Asn Ser Ile Met Lys Cys Asp Ile
            275                 280                 285

Asp Ile Arg Lys Asp Leu Tyr Ala Asn Asn Val Leu Ser Gly Gly Thr
        290                 295                 300

Thr Met Tyr Pro Gly Ile Ala Asp Arg Met Gln Lys Glu Ile Thr Ala
305                 310                 315                 320

Leu Ala Pro Ser Thr Met Lys Ile Lys Ile Ile Ala Pro Pro Glu Arg
                325                 330                 335

Lys Tyr Ser Val Trp Ile Gly Gly Ser Ile Leu Ala Ser Leu Ser Thr
            340                 345                 350

Phe Gln Gln Met Trp Ile Ser Lys Pro Glu Tyr Asp Glu Ala Gly Pro
        355                 360                 365

Ser Ile Val His Arg Lys Cys Phe
    370                 375

<210> SEQ ID NO 32
<211> LENGTH: 102
<212> TYPE: PRT
<213> ORGANISM: Homo sapiens
<220> FEATURE:
<221> NAME/KEY: MISC_FEATURE
<223> OTHER INFORMATION: Q04984 and AAH23518; Chaperonin 10

<400> SEQUENCE: 32

Met Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 33
<211> LENGTH: 538
<212> TYPE: DNA
<213> ORGANISM: Homo sapiens
<220> FEATURE:
<221> NAME/KEY: misc_feature
<223> OTHER INFORMATION: NM_002157 and U07550; chaperonin 10 mRNA,
      complete cds

<400> SEQUENCE: 33
gctacactag agcagagtac gagtctgagg cggagggagt aatggcagga caagcgttta      60
gaaagtttct tccactcttt gaccgagtat tggttgaaag gagtgctgct gaaactgtaa     120
ccaaaggagg cattatgctt ccagaaaaat ctcaaggaaa agtattgcaa gcaacagtag     180

```
tcgctgttgg atcgggttct aaaggaaagg gtggagagat tcaaccagtt agcgtgaaag      240
ttggagataa agttcttctc ccagaatatg gaggcaccaa agtagttcta gatgacaagg      300
attatttcct atttagagat ggtgacattc ttggaaagta cgtagactga ataagtcac      360 tattgaaatg gcatcaacat gatgctgccc attccactga agttctgaaa tctttcgtca      420
tgtaaataat ttccatattt ctcttttata ataaactaat gataactaat gacatccagt      480
gtctccaaaa ttgtttcctt gtactgatat aaacacttcc aaataaaaat atgtaaat       538
```

<210> SEQ ID NO 34
<211> LENGTH: 93
<212> TYPE: PRT
<213> ORGANISM: Homo sapiens
<220> FEATURE:
<221> NAME/KEY: MISC_FEATURE
<223> OTHER INFORMATION: P05109; Calgranulin A

<400> SEQUENCE: 34

```
Met Leu Thr Glu Leu Glu Lys Ala Leu Asn Ser Ile Ile Asp Val Tyr
 1               5                  10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90
```

<210> SEQ ID NO 35
<211> LENGTH: 4205
<212> TYPE: PRT
<213> ORGANISM: Homo sapiens
<220> FEATURE:
<221> NAME/KEY: MISC_FEATURE
<223> OTHER INFORMATION: A12027; Macrophage migration inhibition factor
      (MRP-14); cDNA from Human placenta (formula v)

<400> SEQUENCE: 35

```
Cys Thr Thr Gly Gly Gly Thr Gly Cys Thr Thr Cys Cys Ala Cys
 1               5                  10                  15

Cys Thr Thr Thr Thr Gly Gly Cys Thr Cys Thr Gly Thr Ala Ala
            20                  25                  30

Ala Thr Ala Ala Thr Gly Cys Thr Gly Cys Thr Ala Thr Gly Ala Ala
        35                  40                  45

Cys Ala Thr Gly Ala Ala Thr Gly Thr Ala Cys Ala Ala Cys Ala
    50                  55                  60

Thr Cys Thr Gly Thr Thr Gly Ala Ala Thr Cys Cys Cys Thr Gly
65                  70                  75                  80

Cys Ala Thr Thr Cys Ala Ala Thr Thr Cys Thr Thr Thr Gly Cys
                85                  90                  95

Ala Thr Ala Thr Ala Thr Ala Cys Cys Cys Ala Gly Gly Ala Gly Cys
                100                 105                 110

Ala Gly Ala Ala Thr Gly Ala Thr Gly Ala Thr Cys Ala Thr Ala
        115                 120                 125

Thr Gly Gly Thr Ala Ala Thr Cys Thr Gly Thr Gly Thr Thr Thr
        130                 135                 140
```

-continued

```
Ala Thr Thr Thr Ala Thr Thr Thr Gly Ala Gly Gly Ala Ala Cys Ala
145                 150                 155                 160

Ala Ala Cys Thr Thr Gly Cys Cys Gly Thr Thr Thr Thr Cys Cys Ala
                165                 170                 175

Thr Ala Ala Cys Ala Gly Cys Thr Gly Cys Ala Cys Thr Ala Thr Thr
            180                 185                 190

Thr Thr Ala Cys Ala Thr Thr Cys Cys Cys Ala Cys Thr Ala Ala Cys
        195                 200                 205

Ala Gly Thr Gly Cys Ala Thr Thr Ala Gly Gly Cys Thr Thr Cys Cys
    210                 215                 220

Ala Ala Thr Thr Cys Thr Cys Thr Ala Thr Gly Cys Cys Cys Thr Cys
225                 230                 235                 240

Ala Cys Cys Ala Ala Cys Ala Cys Thr Thr Gly Thr Thr Thr Thr Cys
                245                 250                 255

Thr Gly Gly Gly Thr Thr Thr Thr Ala Ala Ala Ala Gly Ala Ala Gly
            260                 265                 270

Thr Ala Gly Thr Ala Gly Thr Cys Ala Thr Cys Cys Thr Thr Gly Thr
        275                 280                 285

Ala Gly Gly Thr Gly Thr Cys Ala Gly Gly Thr Gly Gly Thr Ala Thr
    290                 295                 300

Cys Thr Cys Ala Thr Thr Gly Thr Cys Gly Thr Thr Thr Thr Gly Cys
305                 310                 315                 320

Thr Thr Cys Ala Thr Gly Thr Thr Thr Thr Cys Cys Thr Ala Ala Ala
                325                 330                 335

Gly Ala Thr Thr Ala Gly Thr Ala Ala Thr Thr Thr Thr Cys Ala Thr
            340                 345                 350

Ala Thr Gly Cys Thr Thr Ala Thr Thr Gly Ala Cys Cys Ala Thr Thr
        355                 360                 365

Thr Gly Thr Ala Thr Ala Thr Cys Thr Thr Cys Thr Thr Cys Gly Gly
    370                 375                 380

Ala Gly Ala Ala Gly Thr Gly Thr Cys Thr Ala Thr Thr Thr Gly Ala
385                 390                 395                 400

Gly Thr Cys Thr Thr Thr Cys Cys Cys Cys Ala Ala Thr Thr Thr Thr
                405                 410                 415

Gly Ala Thr Thr Gly Gly Thr Thr Thr Gly Thr Thr Thr Gly Thr Thr
            420                 425                 430

Thr Thr Thr Thr Gly Thr Thr Gly Thr Thr Gly Ala Gly Thr Thr Gly
        435                 440                 445

Thr Ala Gly Gly Gly Ala Thr Thr Cys Thr Thr Thr Thr Ala Thr Ala
    450                 455                 460

Thr Thr Cys Thr Gly Gly Ala Thr Ala Thr Thr Ala Ala Thr Cys Cys
465                 470                 475                 480

Cys Thr Thr Ala Thr Cys Ala Gly Ala Thr Ala Thr Thr Thr Gly Thr
                485                 490                 495

Thr Thr Thr Ala Cys Ala Ala Ala Thr Ala Thr Thr Thr Thr Cys Thr
            500                 505                 510

Thr Thr Gly Thr Ala Ala Cys Ala Ala Cys Ala Gly Ala Ala Ala Cys
        515                 520                 525

Ala Cys Ala Cys Cys Ala Cys Ala Gly Thr Cys Thr Thr Cys Ala Ala
    530                 535                 540

Gly Gly Thr Thr Gly Gly Ala Ala Gly Cys Cys Ala Gly Thr Thr Ala
545                 550                 555                 560

Ala Thr Cys Thr Gly Ala Gly Thr Ala Gly Cys Ala Thr Thr Thr Thr
```

```
                565                 570                 575
Gly Thr Thr Ala Gly Thr Gly Thr Gly Gly Gly Ala Gly Ala
            580                 585                 590
Gly Gly Ala Thr Thr Thr Gly Thr Thr Cys Cys Thr Cys Cys Thr Gly
        595                 600                 605
Ala Ala Ala Thr Cys Cys Thr Gly Gly Gly Ala Ala Thr Thr Gly
        610                 615                 620
Gly Cys Cys Ala Cys Cys Thr Cys Cys Thr Cys Thr Cys Thr Cys
625                 630                 635                 640
Cys Thr Cys Thr Thr Ala Gly Gly Cys Ala Thr Gly Ala Ala Gly Cys
            645                 650                 655
Gly Cys Gly Thr Cys Thr Gly Gly Cys Thr Thr Cys Thr Cys Cys Ala
            660                 665                 670
Ala Ala Gly Ala Ala Cys Thr Cys Thr Thr Cys Cys Cys Thr Cys
        675                 680                 685
Cys Ala Cys Thr Ala Cys Cys Thr Cys Ala Gly Ala Gly Thr Thr Ala
            690                 695                 700
Gly Cys Thr Thr Cys Cys Thr Cys Thr Cys Thr Thr Cys Ala Gly Cys
705                 710                 715                 720
Cys Ala Gly Thr Gly Ala Thr Cys Cys Thr Gly Gly Gly Thr Cys
            725                 730                 735
Cys Cys Ala Gly Ala Cys Ala Cys Ala Ala Thr Ala Ala Thr Ala
            740                 745                 750
Ala Cys Cys Ala Ala Gly Ala Gly Ala Gly Gly Thr Gly Ala Ala
            755                 760                 765
Ala Gly Gly Cys Thr Cys Cys Cys Thr Gly Cys Thr Gly Thr Gly Thr
            770                 775                 780
Thr Thr Ala Thr Gly Cys Ala Ala Thr Gly Gly Cys Thr Cys Ala Gly
785                 790                 795                 800
Gly Cys Cys Cys Thr Thr Gly Thr Gly Ala Ala Gly Thr Gly Cys Cys
            805                 810                 815
Gly Ala Gly Gly Gly Ala Cys Cys Cys Ala Ala Gly Cys Ala Gly
            820                 825                 830
Cys Cys Thr Cys Cys Ala Thr Cys Thr Cys Cys Ala Gly Gly Gly
            835                 840                 845
Cys Ala Thr Gly Gly Thr Cys Cys Ala Thr Cys Cys Cys Ala Gly
            850                 855                 860
Cys Thr Thr Thr Cys Ala Cys Ala Gly Ala Ala Cys Ala Gly Gly Ala
865                 870                 875                 880
Ala Ala Gly Cys Thr Gly Thr Gly Gly Ala Gly Gly Ala Gly Thr Gly
            885                 890                 895
Thr Gly Gly Gly Cys Ala Gly Cys Ala Gly Gly Thr Ala Gly Gly
        900                 905                 910
Ala Ala Thr Gly Gly Ala Thr Ala Thr Ala Gly Cys Cys Cys Thr Thr
            915                 920                 925
Gly Gly Cys Ala Ala Cys Ala Ala Cys Ala Thr Thr Thr Cys
            930                 935                 940
Cys Cys Cys Ala Cys Ala Ala Ala Gly Cys Ala Cys Cys Cys Ala Cys
945                 950                 955                 960
Cys Cys Ala Ala Ala Gly Ala Ala Cys Ala Ala Cys Ala Ala Cys
            965                 970                 975
Gly Ala Thr Ala Gly Thr Thr Thr Thr Ala Gly Thr Thr Thr Thr
            980                 985                 990
```

-continued

Ala Gly Thr Ala Ala Thr Gly Ala Gly Ala Ala Cys Ala Ala Thr Ala
            995                 1000                1005

Gly Thr Thr Cys Thr Cys Ala Thr Gly Ala Cys Thr Ala Ala Ala
    1010                1015                1020

Ala Gly Cys Cys Ala Thr Cys Ala Gly Cys Cys Ala Gly Gly Ala
    1025                1030                1035

Cys Ala Cys Thr Gly Thr Thr Cys Thr Cys Ala Ala Cys Cys Cys
    1040                1045                1050

Thr Thr Thr Thr Gly Cys Gly Gly Thr Cys Thr Thr Thr Gly Gly
    1055                1060                1065

Ala Cys Cys Cys Thr Thr Thr Gly Ala Ala Ala Cys Thr Cys Thr
    1070                1075                1080

Gly Ala Cys Ala Gly Ala Ala Gly Cys Cys Ala Thr Gly Gly Ala
    1085                1090                1095

Gly Gly Ala Ala Thr Gly Thr Thr Cys Thr Cys Ala Cys Thr Gly
    1100                1105                1110

Ala Gly Thr Gly Cys Ala Thr Gly Cys Ala Cys Thr Cys Ala Ala
    1115                1120                1125

Ala Ala Thr Gly Ala Thr Gly Cys Ala Thr Thr Cys Ala Ala Cys
    1130                1135                1140

Thr Thr Cys Ala Ala Thr Thr Cys Ala Gly Thr Thr Thr Cys Ala
    1145                1150                1155

Gly Gly Gly Ala Thr Gly Thr Ala Thr Gly Gly Cys Cys Thr Gly
    1160                1165                1170

Ala Cys Cys Ala Cys Cys Ala Ala Thr Gly Cys Ala Gly Gly Gly
    1175                1180                1185

Gly Ala Thr Thr Ala Gly Cys Ala Ala Thr Cys Gly Cys Ala Ala
    1190                1195                1200

Thr Ala Gly Thr Gly Gly Ala Gly Ala Gly Gly Gly Cys Ala Thr
    1205                1210                1215

Gly Gly Gly Ala Gly Thr Gly Gly Gly Ala Ala Thr Cys Thr Gly
    1220                1225                1230

Gly Cys Thr Gly Gly Ala Thr Cys Ala Ala Gly Cys Ala Ala Gly
    1235                1240                1245

Thr Gly Gly Ala Thr Gly Cys Cys Ala Gly Cys Ala Gly Cys Cys
    1250                1255                1260

Cys Ala Gly Ala Ala Ala Ala Gly Ala Gly Cys Cys Cys Cys
    1265                1270                1275

Cys Cys Thr Ala Cys Cys Thr Gly Cys Thr Thr Thr Thr Thr Cys
    1280                1285                1290

Cys Thr Thr Cys Cys Thr Gly Gly Gly Cys Ala Cys Thr Ala Thr
    1295                1300                1305

Thr Gly Cys Cys Cys Ala Gly Cys Ala Ala Thr Gly Cys Cys
    1310                1315                1320

Thr Thr Cys Cys Thr Cys Thr Thr Thr Cys Cys Gly Cys Thr Thr
    1325                1330                1335

Cys Thr Cys Cys Thr Ala Cys Cys Thr Cys Cys Cys Ala Cys
    1340                1345                1350

Cys Cys Ala Ala Ala Ala Thr Thr Thr Cys Ala Thr Thr Cys
    1355                1360                1365

Thr Gly Cys Ala Cys Ala Gly Thr Gly Ala Thr Thr Gly Cys Cys
    1370                1375                1380

Ala Cys Ala Thr Thr Cys Ala Cys Thr Gly Gly Thr Thr Gly Ala
    1385                1390                1395

```
Gly Ala Ala Ala Cys Ala Gly Ala Gly Ala Cys Thr Gly Thr Ala
    1400            1405                1410
Gly Cys Ala Ala Cys Thr Cys Thr Gly Gly Cys Ala Gly Gly Gly
    1415            1420                1425
Ala Gly Ala Ala Gly Cys Thr Gly Thr Cys Thr Cys Thr Gly Ala
    1430            1435                1440
Thr Gly Gly Cys Cys Thr Gly Ala Ala Gly Cys Thr Gly Thr Gly
    1445            1450                1455
Gly Gly Cys Ala Gly Cys Thr Gly Gly Cys Cys Ala Ala Gly Cys
    1460            1465                1470
Cys Thr Ala Ala Cys Cys Gly Cys Thr Ala Thr Ala Ala Ala Ala
    1475            1480                1485
Ala Gly Gly Ala Gly Cys Thr Gly Cys Cys Thr Cys Thr Cys Ala
    1490            1495                1500
Gly Cys Cys Cys Thr Gly Cys Ala Thr Gly Thr Cys Thr Cys Thr
    1505            1510                1515
Thr Gly Thr Cys Ala Gly Cys Thr Gly Thr Cys Thr Thr Thr Cys
    1520            1525                1530
Ala Gly Ala Ala Gly Ala Cys Cys Thr Gly Gly Thr Ala Ala Gly
    1535            1540                1545
Thr Gly Gly Gly Ala Cys Thr Gly Thr Cys Thr Gly Gly Gly Thr
    1550            1555                1560
Thr Gly Gly Cys Cys Cys Gly Cys Ala Cys Thr Thr Thr Thr Gly
    1565            1570                1575
Gly Gly Cys Thr Thr Cys Thr Cys Thr Thr Gly Gly Gly Gly Ala
    1580            1585                1590
Gly Gly Gly Thr Cys Ala Gly Gly Gly Ala Ala Gly Thr Gly Gly
    1595            1600                1605
Ala Gly Cys Ala Gly Cys Cys Thr Thr Cys Cys Thr Gly Ala Gly
    1610            1615                1620
Ala Gly Ala Gly Gly Ala Gly Ala Gly Ala Gly Ala Ala Ala Gly
    1625            1630                1635
Cys Thr Cys Ala Gly Gly Ala Gly Gly Thr Cys Thr Gly Gly
    1640            1645                1650
Ala Gly Cys Ala Ala Ala Gly Ala Thr Ala Cys Thr Cys Cys Thr
    1655            1660                1665
Gly Gly Ala Gly Gly Thr Gly Gly Gly Ala Gly Thr Gly Ala
    1670            1675                1680
Gly Gly Cys Ala Gly Gly Ala Thr Ala Ala Gly Gly Ala Ala
    1685            1690                1695
Gly Gly Ala Gly Ala Gly Thr Ala Thr Cys Cys Thr Cys Cys Ala
    1700            1705                1710
Gly Cys Ala Cys Cys Thr Thr Cys Cys Ala Gly Thr Gly Gly Gly
    1715            1720                1725
Thr Ala Ala Gly Gly Gly Cys Ala Cys Ala Thr Thr Gly Thr Cys
    1730            1735                1740
Thr Cys Cys Thr Ala Gly Gly Cys Thr Gly Gly Ala Cys Thr Thr
    1745            1750                1755
Thr Thr Cys Thr Thr Gly Ala Gly Cys Ala Gly Ala Gly Gly Gly
    1760            1765                1770
Thr Gly Gly Gly Gly Thr Gly Thr Ala Ala Gly Gly Ala Ala
    1775            1780                1785
Ala Gly Thr Cys Thr Ala Cys Gly Gly Gly Cys Cys Cys Cys Cys
```

1790 1795 1800

Gly Thr Gly Thr Gly Thr Gly Thr Gly Cys Ala Cys Ala Thr Gly
1805 1810 1815

Thr Cys Thr Cys Thr Gly Thr Gly Thr Gly Ala Ala Thr Gly Gly
1820 1825 1830

Ala Cys Cys Cys Thr Thr Cys Cys Cys Cys Thr Thr Cys Cys Cys
1835 1840 1845

Ala Cys Ala Cys Gly Thr Gly Thr Ala Thr Cys Cys Cys Thr Ala
1850 1855 1860

Thr Cys Ala Thr Cys Cys Cys Ala Cys Cys Cys Thr Thr Cys Cys
1865 1870 1875

Cys Ala Cys Cys Ala Gly Ala Gly Gly Cys Cys Ala Thr Ala Gly
1880 1885 1890

Cys Cys Ala Thr Cys Thr Gly Cys Thr Gly Gly Thr Thr Thr Gly
1895 1900 1905

Gly Thr Thr Ala Thr Thr Thr Gly Ala Gly Ala Gly Thr Gly Cys
1910 1915 1920

Ala Gly Gly Cys Cys Ala Gly Gly Ala Cys Ala Ala Gly Gly Cys
1925 1930 1935

Cys Ala Thr Cys Gly Cys Thr Thr Gly Gly Gly Gly Cys Ala Thr
1940 1945 1950

Gly Ala Ala Thr Cys Cys Thr Cys Thr Gly Cys Gly Thr Ala Cys
1955 1960 1965

Thr Gly Cys Cys Cys Thr Gly Gly Cys Cys Ala Gly Ala Thr Gly
1970 1975 1980

Cys Ala Ala Ala Thr Thr Cys Cys Cys Thr Gly Cys Cys Ala Thr
1985 1990 1995

Gly Gly Gly Ala Thr Thr Cys Cys Cys Cys Ala Gly Ala Ala Gly
2000 2005 2010

Gly Thr Thr Cys Thr Gly Thr Thr Thr Thr Thr Cys Ala Gly Gly
2015 2020 2025

Thr Gly Gly Gly Gly Cys Ala Ala Gly Thr Thr Cys Cys Gly Thr
2030 2035 2040

Gly Gly Gly Cys Ala Thr Cys Ala Thr Gly Thr Thr Gly Ala Cys
2045 2050 2055

Cys Gly Ala Gly Cys Thr Gly Gly Ala Gly Ala Ala Ala Gly Cys
2060 2065 2070

Cys Thr Thr Gly Ala Ala Cys Thr Cys Thr Ala Thr Cys Ala Thr
2075 2080 2085

Cys Gly Ala Cys Gly Thr Cys Thr Ala Cys Cys Ala Cys Ala Ala
2090 2095 2100

Gly Thr Ala Cys Thr Cys Cys Cys Thr Gly Ala Thr Ala Ala Ala
2105 2110 2115

Gly Gly Gly Gly Ala Ala Thr Thr Thr Cys Cys Ala Thr Gly Cys
2120 2125 2130

Cys Gly Thr Cys Thr Ala Cys Ala Gly Gly Gly Ala Thr Gly Ala
2135 2140 2145

Cys Cys Thr Gly Ala Ala Gly Ala Ala Ala Thr Thr Gly Cys Thr
2150 2155 2160

Ala Gly Ala Gly Ala Cys Cys Gly Ala Gly Thr Gly Thr Cys Cys
2165 2170 2175

Thr Cys Ala Gly Thr Ala Thr Ala Thr Cys Ala Gly Gly Gly Thr
2180 2185 2190

-continued

```
Gly Ala Gly Gly Ala Gly Gly Gly Cys Thr Gly Gly Thr
2195                2200                2205

Gly Thr Gly Gly Cys Gly Gly Gly Gly Cys Thr Cys Thr Cys
2210                2215                2220

Thr Gly Cys Cys Thr Gly Gly Thr Cys Cys Thr Gly Gly Gly
2225                2230                2235

Cys Thr Gly Cys Cys Thr Gly Gly Cys Cys Ala Gly Cys
2240                2245                2250

Gly Gly Thr Cys Cys Thr Cys Cys Cys Thr Gly Cys Cys Ala Cys
2255                2260                2265

Cys Cys Thr Thr Cys Ala Thr Ala Gly Ala Thr Gly Cys Thr Ala
2270                2275                2280

Thr Gly Cys Cys Thr Cys Gly Gly Cys Thr Cys Thr Cys Thr Cys
2285                2290                2295

Thr Gly Ala Gly Ala Thr Cys Thr Thr Ala Ala Ala Cys Thr
2300                2305                2310

Cys Thr Gly Gly Cys Thr Thr Cys Thr Thr Cys Cys Thr Cys Cys
2315                2320                2325

Thr Cys Ala Ala Thr Cys Thr Thr Gly Ala Cys Ala Gly Ala Ala
2330                2335                2340

Ala Ala Ala Gly Gly Gly Thr Gly Cys Ala Gly Ala Cys Gly Thr
2345                2350                2355

Cys Thr Gly Gly Thr Thr Cys Ala Ala Ala Gly Ala Gly Thr Thr
2360                2365                2370

Gly Gly Ala Thr Ala Thr Cys Ala Ala Cys Ala Cys Thr Gly Ala
2375                2380                2385

Thr Gly Gly Thr Gly Cys Ala Gly Thr Thr Ala Ala Cys Thr Thr
2390                2395                2400

Cys Cys Ala Gly Gly Ala Gly Thr Thr Cys Cys Thr Cys Ala Thr
2405                2410                2415

Thr Cys Thr Gly Gly Thr Gly Ala Thr Ala Ala Ala Gly Ala Thr
2420                2425                2430

Gly Gly Gly Cys Gly Thr Gly Gly Cys Ala Gly Cys Cys Cys Ala
2435                2440                2445

Cys Ala Ala Ala Ala Ala Ala Gly Cys Cys Ala Thr Gly Ala
2450                2455                2460

Ala Gly Ala Ala Ala Gly Cys Cys Ala Cys Ala Ala Ala Gly Ala
2465                2470                2475

Gly Thr Ala Gly Cys Thr Gly Ala Gly Thr Thr Ala Cys Thr Gly
2480                2485                2490

Gly Gly Cys Cys Cys Ala Gly Ala Gly Gly Cys Thr Gly Gly Gly
2495                2500                2505

Cys Cys Cys Cys Thr Gly Gly Ala Cys Ala Thr Gly Thr Ala Cys
2510                2515                2520

Cys Thr Gly Cys Ala Gly Ala Ala Thr Ala Ala Thr Ala Ala Ala
2525                2530                2535

Gly Thr Cys Ala Thr Cys Ala Ala Thr Ala Cys Cys Thr Cys Ala
2540                2545                2550

Thr Gly Cys Cys Thr Cys Thr Cys Thr Cys Thr Thr Ala Thr Gly
2555                2560                2565

Cys Thr Thr Thr Gly Thr Gly Gly Ala Ala Thr Gly Ala Gly
2570                2575                2580

Gly Thr Thr Cys Cys Thr Cys Gly Gly Thr Gly Thr Gly Gly Ala
2585                2590                2595
```

Gly Gly Gly Ala Gly Gly Thr Thr Gly Gly Ala Ala Ala Ala
2600            2605            2610

Cys Cys Cys Ala Ala Ala Gly Gly Ala Ala Gly Ala Ala Ala Ala
2615            2620            2625

Ala Gly Ala Ala Ala Thr Cys Thr Ala Thr Gly Thr Thr Ala Thr
2630            2635            2640

Cys Cys Cys Ala Cys Cys Thr Ala Cys Cys Thr Cys Thr Cys
2645            2650            2655

Ala Cys Ala Ala Gly Cys Cys Thr Thr Thr Cys Cys Thr Gly Cys
2660            2665            2670

Thr Thr Thr Ala Cys Cys Cys Thr Cys Ala Cys Cys Thr Gly
2675            2680            2685

Gly Cys Cys Thr Cys Thr Gly Cys Cys Cys Cys Ala Cys Ala Thr
2690            2695            2700

Thr Cys Cys Thr Thr Cys Ala Gly Cys Cys Cys Thr Cys Ala
2705            2710            2715

Thr Thr Thr Cys Gly Ala Gly Cys Ala Thr Thr Gly Gly Ala Thr
2720            2725            2730

Thr Thr Gly Ala Gly Gly Cys Thr Thr Ala Ala Gly Ala Thr
2735            2740            2745

Thr Cys Ala Ala Ala Ala Ala Gly Thr Cys Gly Thr Cys Ala Thr
2750            2755            2760

Gly Ala Ala Thr Ala Thr Ala Gly Cys Thr Gly Ala Thr Gly Ala
2765            2770            2775

Thr Thr Thr Thr Ala Thr Ala Gly Thr Gly Gly Thr Thr Cys Thr
2780            2785            2790

Gly Ala Ala Ala Thr Gly Gly Gly Thr Cys Gly Gly Gly Gly Ala
2795            2800            2805

Thr Thr Thr Gly Gly Gly Ala Ala Cys Ala Gly Gly Thr Gly
2810            2815            2820

Gly Thr Ala Gly Thr Ala Thr Ala Ala Gly Ala Ala Cys Ala Ala
2825            2830            2835

Cys Thr Gly Ala Thr Ala Cys Thr Gly Thr Thr Cys Thr Cys Thr
2840            2845            2850

Ala Ala Gly Cys Thr Ala Ala Ala Thr Cys Thr Thr Ala Gly Cys
2855            2860            2865

Thr Thr Cys Cys Ala Gly Cys Thr Ala Cys Cys Thr Gly Thr Cys
2870            2875            2880

Thr Thr Ala Gly Ala Thr Gly Thr Gly Gly Cys Thr Cys Thr Thr
2885            2890            2895

Gly Gly Gly Ala Ala Cys Cys Thr Thr Ala Gly Ala Gly Thr Gly
2900            2905            2910

Ala Thr Ala Gly Cys Thr Ala Cys Ala Thr Ala Gly Ala Ala Gly
2915            2920            2925

Thr Gly Thr Gly Thr Gly Gly Gly Thr Gly Thr Gly Thr Gly Thr
2930            2935            2940

Gly Thr Gly Thr Gly Thr Gly Thr Cys Thr Gly Thr Gly Thr Gly
2945            2950            2955

Thr Gly Thr Gly Thr Gly Thr Gly Thr Gly Ala Gly Ala Gly Ala
2960            2965            2970

Gly Ala Gly Ala Cys Ala Gly Ala Cys Ala Gly Ala Ala Ala Gly
2975            2980            2985

Ala Gly Ala Gly Cys Ala Ala Gly Ala Gly Ala Gly Gly Gly Ala 2990 2995 3000

Ala Gly Gly Gly Gly Gly Gly Ala Gly Ala Gly Gly Cys Thr Gly
3005 3010 3015

Ala Thr Thr Gly Thr Gly Thr Gly Thr Gly Thr Gly Gly Thr Gly
3020 3025 3030

Thr Gly Ala Thr Gly Thr Ala Gly Gly Thr Gly Gly Ala Cys Ala
3035 3040 3045

Ala Thr Gly Thr Thr Cys Ala Gly Ala Gly Thr Cys Cys Thr Cys
3050 3055 3060

Cys Ala Thr Thr Ala Ala Cys Ala Gly Gly Ala Thr Ala Ala Thr
3065 3070 3075

Cys Cys Thr Cys Ala Cys Ala Cys Cys Thr Gly Thr Cys Cys Ala
3080 3085 3090

Cys Ala Thr Ala Cys Cys Thr Gly Thr Ala Gly Thr Thr Thr Gly
3095 3100 3105

Thr Cys Cys Thr Thr Gly Gly Gly Gly Ala Thr Thr Thr Thr Gly
3110 3115 3120

Ala Ala Ala Ala Thr Thr Thr Thr Thr Cys Cys Thr Cys Cys Cys
3125 3130 3135

Thr Cys Thr Cys Cys Ala Cys Thr Cys Cys Cys Ala Ala Ala Cys
3140 3145 3150

Thr Cys Cys Cys Ala Ala Cys Thr Cys Ala Ala Thr Thr Ala Ala
3155 3160 3165

Ala Thr Gly Ala Thr Ala Ala Ala Gly Gly Ala Ala Thr Ala Gly
3170 3175 3180

Gly Cys Ala Ala Ala Thr Ala Gly Gly Ala Ala Ala Ala Thr Ala
3185 3190 3195

Ala Ala Thr Thr Ala Gly Thr Ala Ala Ala Ala Cys Thr Thr Ala
3200 3205 3210

Ala Gly Thr Cys Ala Ala Ala Gly Ala Ala Thr Ala Gly Gly Thr
3215 3220 3225

Thr Ala Thr Thr Cys Ala Thr Ala Cys Gly Cys Thr Gly Cys Cys
3230 3235 3240

Thr Ala Thr Gly Gly Gly Ala Thr Thr Cys Thr Ala Thr Gly Cys
3245 3250 3255

Thr Thr Thr Gly Thr Gly Ala Thr Cys Ala Gly Ala Ala Ala Ala
3260 3265 3270

Thr Thr Ala Thr Cys Thr Ala Ala Ala Ala Ala Ala Thr Ala Cys
3275 3280 3285

Thr Thr Cys Cys Cys Ala Ala Gly Gly Gly Cys Thr Gly Gly Thr
3290 3295 3300

Ala Cys Ala Ala Gly Gly Gly Ala Gly Gly Cys Cys Ala Gly Ala
3305 3310 3315

Ala Gly Ala Cys Gly Ala Gly Thr Gly Gly Thr Thr Cys Thr Thr
3320 3325 3330

Cys Thr Cys Thr Gly Ala Gly Gly Thr Gly Gly Ala Cys Ala Thr
3335 3340 3345

Thr Ala Ala Ala Ala Ala Ala Ala Gly Ala Ala Gly Ala Ala Ala
3350 3355 3360

Ala Thr Gly Ala Ala Gly Gly Gly Gly Ala Ala Cys Cys Thr Thr
3365 3370 3375

Thr Thr Gly Ala Cys Ala Ala Gly Ala Ala Thr Gly Thr Cys Ala
3380 3385 3390

```
Cys Cys Cys Cys Ala Ala Ala Cys Thr Gly Gly Ala Thr Thr Thr
3395             3400                 3405

Thr Cys Ala Thr Gly Cys Thr Gly Thr Gly Gly Thr Gly Thr Gly
3410             3415                 3420

Gly Gly Gly Ala Ala Thr Thr Thr Thr Cys Thr Gly Thr Thr Gly
3425             3430                 3435

Thr Cys Cys Thr Cys Ala Cys Thr Thr Ala Gly Gly Thr Gly Cys
3440             3445                 3450

Thr Gly Gly Gly Gly Cys Ala Gly Thr Gly Gly Thr Gly Thr Thr
3455             3460                 3465

Ala Gly Thr Gly Ala Thr Gly Gly Thr Ala Ala Ala Ala Ala
3470             3475                 3480

Gly Gly Thr Ala Gly Gly Ala Ala Gly Cys Thr Gly Thr Cys Ala
3485             3490                 3495

Cys Ala Gly Ala Ala Thr Cys Ala Cys Thr Ala Ala Ala Cys Cys
3500             3505                 3510

Ala Gly Gly Thr Thr Cys Thr Thr Ala Ala Cys Thr Thr Gly
3515             3520                 3525

Thr Cys Thr Gly Thr Cys Thr Ala Thr Ala Cys Ala Thr Cys Thr
3530             3535                 3540

Cys Thr Gly Ala Ala Ala Thr Thr Gly Gly Gly Thr Thr Gly Ala
3545             3550                 3555

Ala Gly Thr Thr Gly Thr Gly Thr Gly Cys Ala Thr Cys Ala Thr
3560             3565                 3570

Thr Thr Thr Gly Ala Gly Thr Gly Ala Cys Gly Cys Ala Cys Thr
3575             3580                 3585

Gly Ala Gly Ala Ala Cys Ala Thr Thr Cys Cys Thr Cys Cys Ala
3590             3595                 3600

Cys Gly Gly Cys Thr Thr Cys Cys Ala Thr Cys Gly Ala Gly Ala
3605             3610                 3615

Gly Thr Cys Thr Cys Gly Ala Ala Ala Ala Gly Gly Cys Cys Cys
3620             3625                 3630

Ala Ala Cys Ala Cys Cys Thr Cys Ala Ala Ala Ala Gly Gly
3635             3640                 3645

Thr Thr Ala Ala Gly Ala Ala Cys Ala Cys Thr Thr Gly Thr Cys
3650             3655                 3660

Cys Thr Gly Cys Thr Thr Ala Cys Thr Gly Gly Thr Thr Thr Thr
3665             3670                 3675

Thr Ala Gly Thr Ala Ala Cys Ala Ala Thr Gly Gly Cys Ala
3680             3685                 3690

Gly Ala Gly Thr Ala Thr Thr Cys Thr Cys Thr Cys Thr Gly
3695             3700                 3705

Thr Cys Thr Cys Thr Cys Thr Cys Thr Cys Thr Thr Thr Thr Thr
3710             3715                 3720

Thr Thr Thr Thr Thr Thr Thr Thr Thr Thr Thr Thr Thr Thr Gly
3725             3730                 3735

Ala Gly Ala Cys Ala Cys Ala Gly Gly Gly Thr Cys Thr Thr Gly
3740             3745                 3750

Thr Cys Thr Gly Thr Cys Ala Cys Gly Thr Gly Gly Ala Cys Thr
3755             3760                 3765

Ala Gly Ala Gly Thr Ala Cys Ala Ala Thr Gly Gly Gly Cys Ala
3770             3775                 3780

Thr Gly Ala Thr Cys Ala Thr Gly Gly Gly Cys Thr Cys Ala Cys
3785             3790                 3795
```

```
Thr Gly Thr Ala Gly Cys Cys Thr Cys Gly Ala Ala   Cys Ala Cys
    3800            3805                3810

Cys Thr Gly Gly Gly Cys Thr Cys Ala Ala Gly Thr   Ala Ala Thr
    3815            3820                3825

Cys Cys Thr Cys Cys Cys Ala Cys Cys Thr Cys Ala   Gly Cys Cys
    3830            3835                3840

Thr Cys Thr Thr Thr Ala Gly Thr Ala Gly Cys Thr   Gly Gly Gly
    3845            3850                3855

Ala Cys Thr Ala Cys Ala Gly Cys Ala Thr Gly Ala   Gly Cys Cys
    3860            3865                3870

Ala Cys Thr Gly Cys Cys Cys Thr Thr Gly Gly Cys   Thr Ala Ala
    3875            3880                3885

Thr Thr Thr Thr Thr Ala Ala Ala Thr Thr Ala Thr   Thr Thr Thr
    3890            3895                3900

Thr Thr Thr Gly Thr Ala Gly Ala Gly Ala Thr Gly   Gly Ala Ala
    3905            3910                3915

Ala Cys Thr Thr Gly Cys Thr Ala Thr Gly Thr Thr   Gly Cys Cys
    3920            3925                3930

Cys Ala Gly Gly Cys Thr Ala Gly Thr Cys Thr Cys   Ala Ala Ala
    3935            3940                3945

Cys Thr Cys Cys Thr Gly Gly Ala Cys Thr Cys Ala   Ala Gly Cys
    3950            3955                3960

Gly Ala Thr Cys Cys Thr Cys Cys Thr Ala Cys Cys   Thr Thr Gly
    3965            3970                3975

Gly Cys Cys Thr Cys Cys Cys Ala Ala Ala Gly Thr   Gly Cys Thr
    3980            3985                3990

Gly Ala Gly Ala Thr Thr Ala Cys Ala Gly Thr Gly   Thr Gly Ala
    3995            4000                4005

Thr Cys Cys Ala Cys Ala Cys Ala Cys Ala Cys Cys   Cys Thr Gly
    4010            4015                4020

Gly Cys Cys Ala Ala Ala Gly Ala Thr Thr Gly Gly   Ala Gly Thr
    4025            4030                4035

Ala Thr Thr Thr Thr Thr Ala Thr Thr Gly Cys Thr   Ala Thr Thr
    4040            4045                4050

Gly Thr Thr Gly Thr Gly Cys Thr Gly Gly Gly Thr   Gly Gly Gly
    4055            4060                4065

Thr Gly Gly Gly Thr Gly Gly Gly Thr Gly Thr Ala   Thr Gly Cys
    4070            4075                4080

Thr Thr Thr Gly Thr Gly Gly Gly Gly Ala Cys Gly   Thr Gly Thr
    4085            4090                4095

Gly Thr Thr Gly Thr Thr Gly Cys Cys Ala Ala Gly   Gly Gly Cys
    4100            4105                4110

Thr Ala Ala Ala Thr Cys Ala Gly Thr Cys Cys Thr   Ala Cys Cys
    4115            4120                4125

Cys Cys Thr Gly Cys Thr Gly Cys Cys Cys Ala Cys   Ala Gly Thr
    4130            4135                4140

Cys Cys Thr Cys Cys Ala Cys Ala Gly Cys Thr Thr   Thr Cys Cys
    4145            4150                4155

Thr Gly Cys Thr Cys Thr Gly Thr Gly Ala Ala Gly   Cys Thr Ala
    4160            4165                4170

Ala Gly Gly Ala Thr Ala Cys Ala Cys Cys Cys Gly   Ala Thr
    4175            4180                4185

Gly Ala Thr Ala Ala Gly Cys Thr Gly Thr Cys Ala   Ala Cys Ala
```

<210> SEQ ID NO 36
<211> LENGTH: 428
<212> TYPE: DNA
<213> ORGANISM: Homo sapiens
<220> FEATURE:
<221> NAME/KEY: misc_feature
<223> OTHER INFORMATION: NM_002964; S100 calcium binding protein A8
    (calgranulin A); S100A8; mRNA

<400> SEQUENCE: 36
atgtctcttg tcagctgtct ttcagaagac ctggtggggc aagtccgtgg gcatcatgtt      60
gaccgagctg gagaaagcct tgaactctat catcgacgtc taccacaagt actccctgat     120 aaagggaat  ttccatgccg tctacaggga tgacctgaag aaattgctag agaccgagtg     180
tcctcagtat atcaggaaaa agggtgcaga cgtctggttc aaagagttgg atatcaacac     240
tgatggtgca gttaacttcc aggagttcct cattctggtg ataaagatgg gcgtggcagc     300
ccacaaaaaa agccatgaag aaagccacaa agagtagctg agttactggg cccagaggct     360
gggcccctgg acatgtacct gcagaataat aaagtcatca atacctcaaa aaaaaaaaa     420 aaaaaaaa                                                              428

<210> SEQ ID NO 37
<211> LENGTH: 114
<212> TYPE: PRT
<213> ORGANISM: Homo sapiens
<220> FEATURE:
<221> NAME/KEY: MISC_FEATURE
<223> OTHER INFORMATION: P06702; Calgranulin B/MRP-14

<400> SEQUENCE: 37

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro

<210> SEQ ID NO 38
<211> LENGTH: 462
<212> TYPE: DNA
<213> ORGANISM: Homo sapiens
<220> FEATURE:
<221> NAME/KEY: misc_feature
<223> OTHER INFORMATION: X06233; Human mRNA for calcium-binding protein
    in macrophages (MRP-14); macrophage migration inhibitory factor
    (MIF)-related protein

<400> SEQUENCE: 38

| | |
|---|---|
| aaaacactct gtgtggctcc tcggctttga cagagtgcaa gacgatgact tgcaaaatgt | 60 |
| cgcagctgga acgcaacata gagaccatca tcaacacctt ccaccaatac tctgtgaagc | 120 |
| tggggcaccc agacaccctg aaccagggggg aattcaaaga gctggtgcga aagatctgc | 180 |
| aaaattttct caagaaggag aataagaatg aaaaggtcat agaacacatc atggaggacc | 240 |
| tggacacaaa tgcagacaag cagctgagct tcgaggagtt catcatgctg atggcgaggc | 300 |
| taacctgggc ctcccacgag aagatgcacg agggtgacga gggccctggc caccaccata | 360 |
| agccaggcct cggggagggc accccctaag accacagtgg ccaagatcac agtggccacg | 420 |
| gccacggcca cagtcatggt ggccacggcc acagccaccc at | 462 |

<210> SEQ ID NO 39
<211> LENGTH: 4439
<212> TYPE: DNA
<213> ORGANISM: Homo sapiens
<220> FEATURE:
<221> NAME/KEY: misc_feature
<223> OTHER INFORMATION: M21064; Human migration inhibitory factor-
      related protein 14 (MRP14) gene; complete cds

<400> SEQUENCE: 39

| | |
|---|---|
| atcactgtgg agtaggggaa gggcactcct ggggtggcaa ggtgggaggt gggccctgtg | 60 |
| ttcccacagt gggcagggag gtagtgaaag ggaagctggc cggacaggaa gggccattcc | 120 |
| aagagggctt tgtgcgcagg gctaagccaa gctttctcca taggcaatgg ggagcaactg | 180 |
| gaggttcgta gcaggagaag gacacatcaa gcccaccagg aggctaagta aaaacagttg | 240 |
| tctcccaagt tataagttcc tggaacccct gctgggagca ggatttagaa aaatgatgct | 300 |
| gagagatgct agaaacatat tcgccctgag gctctctcac tcagactgca agaggaaggt | 360 |
| atcatcagaa ttgcccttaa ccaggaacca gaatagctgg gtcccccttcc tgccaagtca | 420 |
| gcaaccagct atgtgacctt gctcaggtcc atctccgggt gtcagtttct tcatctacaa | 480 |
| tgcaagaggg ttgcccacct ctgagaaccc ttctaacccc aaatctcacc ctatgaatct | 540 |
| aagaacacaa cccctcgcca tcctaagtat cacagagcca ggcaagcatg ggtgagagct | 600 |
| cagaccatcc ttgttggact aaaaggaagg ggcagactgc catgggggc agccgagagg | 660 |
| gtcaggcccc cataggtcct cagcctgctt caacctcaaa ggggatgggg ggctgagtgg | 720 |
| tgccagagga gcagcaggct cgctcgggga gagtagggcc ttaggataga agggaaatga | 780 |
| actaaacaac cagcttcctg caaaccagtt tcaggccagg gctgggaatt tcacaaaaaa | 840 |
| gcagaaggcg ctctgtgaac atttcctgcc ccgcccagc ccccttcctg gcagcattag | 900 |
| cacactgctc acctgtgaag caatcttccg gagacagggc caagggcaa gtgccccagt | 960 |
| caggagctgc ctataaatgc cgagcctgca cagctctggc aaaacactctg tgtggctcct | 1020 |
| cggctttggt aagtgagctg ccagcttccc caggcagaag cctgcctgcc gattccttct | 1080 |
| ttccttccct gacccaactt ccttccaaat cctcctccta gaagccctcc ttggttggcc | 1140 |
| ctgcctactt taaagcttct ttcacatttt cttaggtcat gttcccctgg ggcctcctgc | 1200 |
| cctcaaatgc tttgcttttt ggcactctgt agatattcta aaaaatcatt ttgtacatgt | 1260 |
| gtgtgacagg ccatctccca gttaagttgc agcctgtgct ttcttttat tttgcacttc | 1320 |
| ccccactatt tctgtgagtg cttagtagga agtgtcaaag aagcttgaca gcattttctt | 1380 |
| ctaagtgtcc caactcttgg ttttccatta cacagacaga gtgcaagacg atgacttgca | 1440 |
| aaatgtcgca gctggaacgc aacatagaga ccatcatcaa caccttccac caatactctg | 1500 |
| tgaagctggg gcacccagac accctgaacc agggggaatt caaagagctg gtgcgaaaag | 1560 |

```
atctgcaaaa ttttctcaag gtagggctgg actctggcag gtctgaccca gcctcaccgc   1620
agtttgggtt gacaagggag gatgggagta tgggctacag caatcaaggg gaagatttga   1680
gctcctggag cccagcccca agacgcagcg agtgtcctgt tatacagggc aggtgctcac   1740
agttacacag gacgacaggg tcaagaaatt gctcaattga acacctgcta tttgtcgggc   1800
cctgttctgg gcagagggat gtagtggtaa atgggagccc actattccat gaggagacac   1860
acagtaaagt tgttggccaa taaagagcac agataaagcc aaatgccaat aagtgcctgg   1920
aagaaaatga gatagagtgc gctgtgggca atggggctgg gtggggtgga ggtgaccagt   1980
tagggtacat gagaagggcc tctttgagga ggtaacattt gagctgagcc ccgaatgttg   2040
gggagggaag cccctgagga tgacacttgg cacaaagctg aggagaccct aagcctcagg   2100
gcgaacttgg ggtggaagac ttgggggctt ttctaatcct aagggtctgc ggtggaaaat   2160
gaatgcataa agagcacatg gagagcacct gcacagcact cagggaactg ggaggttttt   2220
cccccgctcc aaaaatgatt aggcagttct aagaaaaagg ctgagcactt ccaacagcct   2280
ttttgttttc ttttcaaatt tggggaaagt cgggaaacag aggcctgcat taagaagggt   2340
ggaacacatg ggtctcagtc tcagttccag tcccggagcc agacatcctg gggtaggtcc   2400
ccagccctcc cagtgcccct ccctccgcct tggtaaggtg gagaattgca gccttcagag   2460
ttaggggccc tgacagctct ccataggtgg aggcctcagg caggcaggat gctgggtggg   2520
gtaggcaaga aagggcccag cagagaggcc gcatcggaaa actatcctcc atgtgaccc   2580 ctatgcccgc ttcacccccc acctgacatc ccccaccaga agcaaagcga tgctgtggga   2640
aaggaagcag agcctcatgg atgggctgca caggagagtg ctcgcattgg ctgggtaccc   2700
cacaggttct gggaggggac ttagcgaggt gactcagtgc ctcggcctcc caaagtgctg   2760
ggattacaag catgagccac cctgtccgac catctcccct tttatacttt atcacaccct   2820
tgaggtcagc ggagcacata ctctgctctc tgaccctcca tctcccctgc ccacacctag   2880 gttttttctag tgtttccccg ttgtattggt tgaaataagt ttcactaatt ggtaacctcc   2940
agagggaagg gaagggaggg caggggaagg agtgaagtgc agaggggtag cagagtggaa   3000
ctggcctcta agtcagatct gaatttgcat gccctcaata gtcaagcctg tgaaaactaa   3060
tgaccctctc taggactggt ttcaagtctt cctccaggaa gataccattc ctagctgtta   3120
aagttgttat aaggaccaaa tgaggtgaca tttccaggct tactcatgcc atgaccaggg   3180
caagaccctg gaactcagct tcctcttcta taaatagaga atcagcaccc aagtcacagg   3240
gtcatggagg gaataaactg gagagcgttt ggtatgtgct cagtgtctgc tccattgtgc   3300
gcactcagcc tatggtcatt tttaatttt aaatccagcc ccagggtcga ggcttccttg   3360
tacatttgcc agctggtcat ttactgtgct cccagtcccc acctctggcc acacccagct   3420
ctcacagcct tctctcccca cccgcagaag gagaataaga atgaaaaggt catagaacac   3480
atcatggagg acctggacac aaatgcagac aagcagctga gcttcgagga gttcatcatg   3540
ctgatggcga ggctaacctg gcctcccac gagaagatgc acgagggtga cgagggccct   3600
ggccaccacc ataagccagg cctcggggag ggcacccccct aagaccacag tggccaagat   3660
cacagtggcc acggccacgg ccacagtcat ggtggccacg gccacaggcc actaatcagg   3720
aggccaggcc accctgcctc tacccaacca gggccccggg gctgttatgt caaactgtct   3780
tggctgtggg gctaggggct ggggcaaata agtctcttcc tccaagtcag tgctctgtgt   3840
gcttcttcca cctcttctcc aaccctgcct tcccagggct ctggcattta gacagccctg   3900
tccttatctg tgactcagcc ccctcattca gtattaacaa aatgagaagc agcaaaacat   3960
```

-continued

```
gggtctgtgc tgggcccctt ggctcacctc cctgaccatg tcctcacctc tgacttcagg    4020
ccccactgtt cagatcccag gctccctgcc ccatctcaga cacccctgtcc agcctgtcca    4080 gcctgacaaa tggcccttgt cactgtacac tgtagaaagc aaaaaggcat atctctaccc    4140
cttgatatgc ctgctacctc accaaccagc cccaagcctg tcttcaccca tcactgtcta    4200
cacagccctc tctctctcct aacagaattc tattcctctg aaagtcttca gaaactggac    4260
ctagatagtg ccatgtctgg ggaggaatat ggcaccaggc agtggaaaca aggacagatc    4320
ggtgtgttat ctcacatttg atcagagagc atgatctctc ttaacagacc tgccaccctα    4380 atcaacggga gtgctcacac aagtgggagt ctgagagctt agccctatgc ccaccctgg     4439
```

<210> SEQ ID NO 40
<211> LENGTH: 764
<212> TYPE: PRT
<213> ORGANISM: Homo sapiens
<220> FEATURE:
<221> NAME/KEY: MISC_FEATURE
<223> OTHER INFORMATION: P01833 and Q8IZY7; Polymeric-immunoglobulin receptor (precursor)

<400> SEQUENCE: 40

```
Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
```

```
                275                 280                 285
Arg Ala Pro Ala Phe Glu Gly Arg Ile Leu Leu Asn Pro Gln Asp Lys
290                 295                 300
Asp Gly Ser Phe Ser Val Val Ile Thr Gly Leu Arg Lys Glu Asp Ala
305                 310                 315                 320
Gly Arg Tyr Leu Cys Gly Ala His Ser Asp Gly Gln Leu Gln Glu Gly
                325                 330                 335
Ser Pro Ile Gln Ala Trp Gln Leu Phe Val Asn Glu Glu Ser Thr Ile
                340                 345                 350
Pro Arg Ser Pro Thr Val Val Lys Gly Val Ala Gly Ser Ser Val Ala
                355                 360                 365
Val Leu Cys Pro Tyr Asn Arg Lys Glu Ser Lys Ser Ile Lys Tyr Trp
370                 375                 380
Cys Leu Trp Glu Gly Ala Gln Asn Gly Arg Cys Pro Leu Leu Val Asp
385                 390                 395                 400
Ser Glu Gly Trp Val Lys Ala Gln Tyr Glu Gly Arg Leu Ser Leu Leu
                405                 410                 415
Glu Glu Pro Gly Asn Gly Thr Phe Thr Val Ile Leu Asn Gln Leu Thr
                420                 425                 430
Ser Arg Asp Ala Gly Phe Tyr Trp Cys Leu Thr Asn Gly Asp Thr Leu
                435                 440                 445
Trp Arg Thr Thr Val Glu Ile Lys Ile Ile Glu Gly Glu Pro Asn Leu
450                 455                 460
Lys Val Pro Gly Asn Val Thr Ala Val Leu Gly Glu Thr Leu Lys Val
465                 470                 475                 480
Pro Cys His Phe Pro Cys Lys Phe Ser Ser Tyr Glu Lys Tyr Trp Cys
                485                 490                 495
Lys Trp Asn Asn Thr Gly Cys Gln Ala Leu Pro Ser Gln Asp Glu Gly
                500                 505                 510
Pro Ser Lys Ala Phe Val Asn Cys Asp Glu Asn Ser Arg Leu Val Ser
                515                 520                 525
Leu Thr Leu Asn Leu Val Thr Arg Ala Asp Glu Gly Trp Tyr Trp Cys
530                 535                 540
Gly Val Lys Gln Gly His Phe Tyr Gly Glu Thr Ala Ala Val Tyr Val
545                 550                 555                 560
Ala Val Glu Glu Arg Lys Ala Ala Gly Ser Arg Asp Val Ser Leu Ala
                565                 570                 575
Lys Ala Asp Ala Ala Pro Asp Glu Lys Val Leu Asp Ser Gly Phe Arg
                580                 585                 590
Glu Ile Glu Asn Lys Ala Ile Gln Asp Pro Arg Leu Phe Ala Glu Glu
                595                 600                 605
Lys Ala Val Ala Asp Thr Arg Asp Gln Ala Asp Gly Ser Arg Ala Ser
610                 615                 620
Val Asp Ser Gly Ser Ser Glu Glu Gln Gly Gly Ser Ser Arg Ala Leu
625                 630                 635                 640
Val Ser Thr Leu Val Pro Leu Gly Leu Val Leu Ala Val Gly Ala Val
                645                 650                 655
Ala Val Gly Val Ala Arg Ala Arg His Arg Lys Asn Val Asp Arg Val
                660                 665                 670
Ser Ile Arg Ser Tyr Arg Thr Asp Ile Ser Met Ser Asp Phe Glu Asn
                675                 680                 685
Ser Arg Glu Phe Gly Ala Asn Asp Asn Met Gly Ala Ser Ser Ile Thr
                690                 695                 700
```

```
Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
        755                 760

<210> SEQ ID NO 41
<211> LENGTH: 4266
<212> TYPE: DNA
<213> ORGANISM: Homo sapiens
<220> FEATURE:
<221> NAME/KEY: misc_feature
<223> OTHER INFORMATION: NM_002644; polymeric immunoglobulin receptor
      (PIGR); mRNA

<400> SEQUENCE: 41
```

| | | | | | |
|---|---|---|---|---|---|
| agagtttcag | ttttggcagc | agcgtccagt | gccctgccag | tagctcctag | agaggcaggg | 60 |
| gttaccaact | ggccagcagg | ctgtgtccct | gaagtcagat | caacgggaga | gaaggaagtg | 120 |
| gctaaaacat | tgcacaggag | aagtcggcct | gagtggtgcg | gcgctcggga | cccaccagca | 180 |
| atgctgctct | tcgtgctcac | ctgcctgctg | gcggtcttcc | cagccatctc | cacgaagagt | 240 |
| cccatatttg | gtcccgagga | ggtgaatagt | gtggaaggta | actcagtgtc | catcacgtgc | 300 |
| tactacccac | ccacctctgt | caaccggcac | acccggaagt | actggtgccg | gcagggagct | 360 |
| agaggtggct | gcataaccct | catctcctcg | gagggctacg | tctccagcaa | atatgcaggc | 420 |
| agggctaacc | tcaccaactt | cccggagaac | ggcacatttg | tggtgaacat | tgcccagctg | 480 |
| agccaggatg | actccgggcg | ctacaagtgt | ggcctgggca | tcaatagccg | aggcctgtcc | 540 |
| tttgatgtca | gcctggaggt | cagccagggt | cctgggctcc | taaatgacac | taaagtctac | 600 |
| acagtggacc | tgggcagaac | ggtgaccatc | aactgccctt | tcaagactga | aatgctcaa | 660 |
| aagaggaagt | ccttgtacaa | gcagataggc | ctgtaccctg | tgctggtcat | cgactccagt | 720 |
| ggttatgtaa | atcccaacta | tacaggaaga | atacgccttg | atattcaggg | tactggccag | 780 |
| ttactgttca | gcgttgtcat | caaccaactc | aggctcagcg | atgctgggca | gtatctctgc | 840 |
| caggctgggg | atgattccaa | tagtaataag | aagaatgctg | acctccaagt | gctaaagccc | 900 |
| gagcccgagc | tggtttatga | agacctgagg | ggctcagtga | ccttccactg | tgccctgggc | 960 |
| cctgaggtgg | caaacgtggc | caaatttctg | tgccgacaga | gcagtgggga | aaactgtgac | 1020 |
| gtggtcgtca | cacccctggg | gaagaggggcc | ccagcctttg | agggcaggat | cctgctcaac | 1080 |
| ccccaggaca | aggatggctc | attcagtgtg | gtgatcacag | gcctgaggaa | ggaggatgca | 1140 |
| gggcgctacc | tgtgtggagc | ccattcggat | ggtcagctgc | aggaaggctc | gcctatccag | 1200 |
| gcctggcaac | tcttcgtcaa | tgaggagtcc | acgattcccc | gcagcccac | tgtggtgaag | 1260 |
| ggggtggcag | gaggctctgt | ggccgtgctc | tgcccctaca | accgtaagga | aagcaaaagc | 1320 |
| atcaagtact | ggtgtctctg | gaaggggccc | cagaatggcc | gctgccccct | gctggtggac | 1380 |
| agcgagggt | gggttaaggc | ccagtacgag | ggccgcctct | ccctgctgga | ggagccaggc | 1440 |
| aacggcacct | tcactgtcat | cctcaaccag | ctcaccagcc | gggacgccgg | cttctactgg | 1500 |
| tgtctgacca | acgcgatac | tctctggagg | accaccgtgg | agatcaagat | tatcgaagga | 1560 |
| gaaccaaacc | tcaaggtacc | agggaatgtc | acggctgtgc | tgggagagac | tctcaaggtc | 1620 |
| ccctgtcact | ttccatgcaa | attctctcg | tacgagaaat | actggtgcaa | gtggaataac | 1680 |

```
acgggctgcc aggccctgcc cagccaagac gaaggcccca gcaaggcctt cgtgaactgt    1740
gacgagaaca gccggcttgt ctccctgacc ctgaacctgg tgaccagggc tgatgagggc    1800
tggtactggt gtggagtgaa gcagggccac ttctatggag agactgcagc cgtctatgtg    1860
gcagttgaag agaggaaggc agcggggtcc cgcgatgtca gcctagcgaa ggcagacgct    1920
gctcctgatg agaaggtgct agactctggt tttcgggaga ttgagaacaa agccattcag    1980
gatcccaggc ttttttgcaga ggaaaaggcg gtggcagata caagagatca agccgatggg    2040
agcagagcat ctgtggattc cggcagctct gaggaacaag gtggaagctc cagagcgctg    2100
gtctccaccc tggtgcccct gggcctggtg ctggcagtgg gagccgtggc tgtggggtg    2160 gccagagccc ggcacaggaa gaacgtcgac cgagtttcaa tcagaagcta caggacagac    2220
attagcatgt cagacttcga gaactccagg gaatttggag ccaatgacaa catgggagcc    2280
tcttcgatca ctcaggagac atccctcgga ggaaaagaag agtttgttgc caccactgag    2340
agcaccacag agaccaaaga acccaagaag gcaaaaaggt catccaagga ggaagccgag    2400
atggcctaca aagacttcct gctccagtcc agcaccgtgg ccgccgaggc ccaggacggc    2460
ccccaggaag cctagacggt gtcgccgcct gctccctgca cccatgacaa tcaccttcag    2520
aatcatgtcg atcctggggc cctcagctcc tggggacccc actccctgct ctaacacctg    2580
cctaggtttt tcctactgtc ctcagaggcg tgctggtccc ctcctcagtg acatcaaagc    2640
ctggcctaat tgttcctatt ggggatgagg gtggcatgag gaggtccac ttgcaacttc    2700 tttctgttga gagaacctca ggtacggaga agaatagagg tcctcatggg tcccttgaag    2760
gaagagggac cagggtggga gagctgattg cagaaaggag agacgtgcag cgcccctctg    2820 caccccttatc atgggatgtc aacagaattt ttccctccac tccatccctc cctcccgtcc    2880
ttcccctctt cttctttcct tccatcaaaa gatgtatttg aattcatact agaattcagg    2940
tgctttgcta gatgctgtga caggtatgcc accaacactg ctcacagcct ttctgaggac    3000
accagtgaaa gaagccacag ctcttcttgg cgtatttata ctcactgagt cttaactttt    3060
caccaggggt gctcacctct gcccctattg ggagaggtca taaatgtct cgagtcctaa    3120 ggccttaggg gtcatgtatg atgagcatac acacaggtaa ttataaaccc acattcttac    3180
catttcacac ataagaaaat tgaggtttgg aagagtgaag cgttttttctt tttctttttt    3240 tttttgaga cggagtctct cactgtcgcc caggctggag tgcagtggcg caatctcggc    3300
tcactgcaac ctccgcctcc caggttgaca ccattctcct gcctcaccct cccaagtagc    3360
tgggactaca ggcgcctgcc agcacgcctg gctaatttt tgtatttta gtagagacag    3420 ggtttcaccg tgttagccag gatggtctcg atctcctgac ctcgtgatcc gcctgcctct    3480
gcctcccaaa gtgctgggat tacaggcgtg agccaccgcg tccggcctct ttttttcttt    3540 tcttttttttt gagacaaagt ctcactgtgt cacccagact ggaatgcagt gacacaatct    3600
cggctcactg aaacctctgc cttccaggtt caagctattc tcatgcctca gcctctcaag    3660
tagctgggac tacagatgtg ggccaccatg tctggctaat tttttttttt ttttttttt    3720 tttgtagaga cagggtttcg ccatgttgac gagactggtc tcgaactcct ggcctcaagt    3780
gatctgccgc ctcagcttct caaagtactg ggattatata ggcatgagcc actgagcctg    3840
gccctgaagc gttttctca aaggccctca gtgagataaa ttagatttgg catctcctgt    3900
cctgggccag ggatctctct acaagagccc ctgcccctct gttggaggca cagttttaga    3960
ataaggagga ggagggagaa gagaaaatgt aaaggaggga gatctttccc aggccgcacc    4020
atttctgtca ctcacatgga cccaagataa aagaatggcc aaaccctcac aacccctgat    4080
```

```
gtttgaagag ttccaagttg aagggaaaca aagaagtgtt tgatggtgcc agagaggggc    4140
tgctctccag aaagctaaaa tttaatttct tttttcctct gagttctgta cttcaaccag    4200
cctacaagct ggcacttgct aacaaatcag aaatatgaca attaatgatt aaagactgtg    4260
attgcc                                                                4266
```

```
<210> SEQ ID NO 42
<211> LENGTH: 187
<212> TYPE: PRT
<213> ORGANISM: Homo sapiens
<220> FEATURE:
<221> NAME/KEY: MISC_FEATURE
<223> OTHER INFORMATION: P30086; Phosphatidylethanolamine binding
      protein (PEBP)

<400> SEQUENCE: 42

Met Pro Val Asp Leu Ser Lys Trp Ser Gly Pro Leu Ser Leu Gln Glu
1               5                   10                  15

Val Asp Glu Gln Pro Gln His Pro Leu His Val Thr Tyr Ala Gly Ala
            20                  25                  30

Ala Val Asp Glu Leu Gly Lys Val Leu Thr Pro Thr Gln Val Lys Asn
        35                  40                  45

Arg Pro Thr Ser Ile Ser Trp Asp Gly Leu Asp Ser Gly Lys Leu Tyr
50                  55                  60

Thr Leu Val Leu Thr Asp Pro Asp Ala Pro Ser Arg Lys Asp Pro Lys
65                  70                  75                  80

Tyr Arg Glu Trp His His Phe Leu Val Val Asn Met Lys Gly Asn Asp
                85                  90                  95

Ile Ser Ser Gly Thr Val Leu Ser Asp Tyr Val Gly Ser Gly Pro Pro
            100                 105                 110

Lys Gly Thr Gly Leu His Arg Tyr Val Trp Leu Val Tyr Glu Gln Asp
        115                 120                 125

Arg Pro Leu Lys Cys Asp Glu Pro Ile Leu Ser Asn Arg Ser Gly Asp
130                 135                 140

His Arg Gly Lys Phe Lys Val Ala Ser Phe Arg Lys Lys Tyr Glu Leu
145                 150                 155                 160

Arg Ala Pro Val Ala Gly Thr Cys Tyr Gln Ala Glu Trp Asp Asp Tyr
                165                 170                 175

Val Pro Lys Leu Tyr Glu Gln Leu Ser Gly Lys
            180                 185
```

```
<210> SEQ ID NO 43
<211> LENGTH: 1507
<212> TYPE: DNA
<213> ORGANISM: Homo sapiens
<220> FEATURE:
<221> NAME/KEY: misc_feature
<223> OTHER INFORMATION: NM_002567; prostatic binding protein (PBP);
      mRNA

<400> SEQUENCE: 43
tgggcggcgg ctgaggcgcg tgctctcgcg tggtcgctgg gtctgcgtct tcccgagcca      60
gtgtgctgag ctctccgcgt cgcctctgtc gcccgcgcct ggcctaccgc ggcactcccg     120
gctgcacgct ctgcttggcc tcgccatgcc ggtggacctc agcaagtggt ccggcccctt     180
gagcctgcaa gaagtggacg agcagccgca gcaccgctg catgtcacct acgccggggc     240
ggcggtggac gagctgggca aagtgctgac gcccacccag gttaagaata gacccaccag     300
catttcgtgg gatggtcttg attcagggaa gctctacacc ttggtcctga cagacccgga     360
```

```
tgctcccagc aggaaggatc ccaaatacag agaatggcat catttcctgg tggtcaacat    420
gaagggcaat gacatcagca gtggcacagt cctctccgat tatgtgggct cggggcctcc    480
caagggcaca ggcctccacc gctatgtctg gctggtttac gagcaggaca ggccgctaaa    540
gtgtgacgag cccatcctca gcaaccgatc tggagaccac cgtggcaaat tcaaggtggc    600
gtccttccgt aaaaagtatg agctcagggc cccggtggct ggcacgtgtt accaggccga    660
gtgggatgac tatgtgccca aactgtacga gcagctgtct ggaagtaggg ggttagctt    720 ggggacctga actgtcctgg aggccccaag ccatgttccc cagttcagtg ttgcatgtat    780
aatagatttc tcctcttcct gccccccttg gcatgggtga cctgacca gtcagatggt    840 agttgagggt gacttttcct gctgcctggc ctttataatt ttactcactc actctgattt    900
atgttttgat caaatttgaa cttcattttg gggggtattt tggtactgtg atggggtcat    960
caaattatta atctgaaaat agcaacccag aatgtaaaaa agaaaaaact ggggggaaaa   1020
agaccaggtc tacagtgata gagcaaagca tcaaagaatc tttaagggag gtttaaaaaa   1080
aaaaaaaaaa aaaaagattg gttgcctctg cctttgtgat cctgagtcca gaatggtaca   1140
caatgtgatt ttatggtgat gtcactcacc tagacaacca gaggctggca ttgaggctaa   1200
cctccaacac agtgcatctc agatgcctca gtaggcatca gtatgtcact ctggtccctt   1260
taaagagcaa tcctggaaga agcaggaggg agggtggctt tgctgttgtt gggacatggc   1320
aatctagacc ggtagcagcg ctcgctgaca gcttgggagg aaacctgaga tctgtgtttt   1380
ttaaattgat cgttcttcat gggggtaaga aaagctggtc tggagttgct gaatgttgca   1440
ttaattgtgc tgtttgcttg tagttgaata aaaatagaaa cctgaatgaa gaaaaaaaaa   1500
aaaaaaa                                                            1507
```

<210> SEQ ID NO 44
<211> LENGTH: 249
<212> TYPE: PRT
<213> ORGANISM: Homo sapiens
<220> FEATURE:
<221> NAME/KEY: MISC_FEATURE
<223> OTHER INFORMATION: P39687 ; Acidic leucine-rich nuclear
      phosphoprotein 32 family member A

<400> SEQUENCE: 44

```
Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
            20                  25                  30

Lys Leu Glu Gly Leu Thr Asp Glu Phe Glu Glu Leu Glu Phe Leu Ser
        35                  40                  45

Thr Ile Asn Val Gly Leu Thr Ser Ile Ala Asn Leu Pro Lys Leu Asn
    50                  55                  60

Lys Leu Lys Lys Leu Glu Leu Ser Asp Asn Arg Val Ser Gly Gly Leu
65                  70                  75                  80

Glu Val Leu Ala Glu Lys Cys Pro Asn Leu Thr His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Gln Leu Thr Tyr
    130                 135                 140

Leu Asp Gly Tyr Asp Arg Asp Asp Lys Glu Ala Pro Asp Ser Asp Ala
```

```
                145                 150                 155                 160
Glu Gly Tyr Val Glu Gly Leu Asp Asp Glu Glu Asp Glu Asp Glu
                    165                 170                 175

Glu Glu Tyr Asp Glu Asp Ala Gln Val Val Glu Asp Glu Glu Asp Glu
            180                 185                 190

Asp Glu Glu Glu Gly Glu Glu Asp Val Ser Gly Glu Glu Glu
        195                 200                 205

Glu Asp Glu Glu Gly Tyr Asn Asp Gly Glu Val Asp Glu Glu Asp
    210                 215                 220

Glu Glu Glu Leu Gly Glu Glu Arg Gly Gln Lys Arg Lys Arg Glu
225                 230                 235                 240

Pro Glu Asp Glu Gly Glu Asp Asp Asp
            245

<210> SEQ ID NO 45
<211> LENGTH: 1136
<212> TYPE: DNA
<213> ORGANISM: Homo sapiens
<220> FEATURE:
<221> NAME/KEY: misc_feature
<223> OTHER INFORMATION: NM_006305; acidic (leucine-rich) nuclear
      phosphoprotein 32 family member A (ANP32A); mRNA

<400> SEQUENCE: 45
cgggtgctgg gggctcgaga accgagcgga gctggttgag ccttcaaagt cctaaaacgc     60
gcggccgtgg gttcgggggtt tattgattga attccgccgg cgcgggagcc tctgcagaga   120
gagagcgcga gagatggaga tgggcagacg gattcattta gagctgcgga acaggacgcc   180
ctctgatgtg aaagaacttg tcctggacaa cagtcggtcg aatgaaggca aactcgaagg   240
cctcacagat gaatttgaag aactggaatt cttaagtaca atcaacgtag gcctcacctc   300
aatcgcaaac ttaccaaagt taaacaaact taagaagctt gaactaagcg ataacagagt   360 ctcaggggggc ctggaagtat tggcagaaaa gtgtccgaac ctcacgcatc taaatttaag   420
tggcaacaaa attaaagacc tcagcacaat agagccactg aaaaagttag aaaacctcaa   480
gagcttagac cttttcaatt gcgaggtaac caacctgaac gactaccgag aaaatgtgtt   540
caagctcctc ccgcaactca catatctcga cggctatgac cgggacgaca aggaggcccc   600
tgactcggat gctgagggct acgtggaggg cctggatgat gaggaggagg atgaggatga   660
ggaggagtat gatgaagatg ctcaggtagt ggaagacgag gaggacgagg atgaggagga   720
ggaaggtgaa gaggaggacg tgagtggaga ggaggaggag gatgaagaag gttataacga   780
tggagaggta gatgacgagg aagatgaaga agagcttggt gaagaagaaa ggggtcagaa   840
gcgaaaacga gaacctgaag atgagggaga agatgatgac taagtggaat aacctatttt   900
gaaaaattcc tattgtgatt tgactgtttt tacccatatc ccctctcccc cccccctcca   960
atcctgcccc ctgaaactta tttttttctg attgtaacgt tgctgtggga acgagagggg  1020
aagagtgtac tgggggttgc ggggggaggg atggcgggtg ggggtggaat aaaatactat  1080
ttttactgcc actctttaaa aaaaaaaaa aaaaaaaaa aaaaaaaaa aaaaaa        1136

<210> SEQ ID NO 46
<211> LENGTH: 643
<212> TYPE: PRT
<213> ORGANISM: Homo sapiens
<220> FEATURE:
<221> NAME/KEY: MISC_FEATURE
<223> OTHER INFORMATION: P17066; Heat shock 70kDa protein

<400> SEQUENCE: 46
```

```
Met Gln Ala Pro Arg Glu Leu Ala Val Gly Ile Asp Leu Gly Thr Thr
1               5                   10                  15

Tyr Ser Cys Val Gly Val Phe Gln Gln Gly Arg Val Glu Ile Leu Ala
            20                  25                  30

Asn Asp Gln Gly Asn Arg Thr Thr Pro Ser Tyr Val Ala Phe Thr Asp
                35                  40                  45

Thr Glu Arg Leu Val Gly Asp Ala Ala Lys Ser Gln Ala Ala Leu Asn
    50                  55                  60

Pro His Asn Thr Val Phe Asp Ala Lys Arg Leu Ile Gly Arg Lys Phe
65                  70                  75                  80

Ala Asp Thr Thr Val Gln Ser Asp Met Lys His Trp Pro Phe Arg Val
                85                  90                  95

Val Ser Glu Gly Gly Lys Pro Lys Val Arg Val Cys Tyr Arg Gly Glu
            100                 105                 110

Asp Lys Thr Phe Tyr Pro Glu Glu Ile Ser Ser Met Val Leu Ser Lys
        115                 120                 125

Met Lys Glu Thr Ala Glu Ala Tyr Leu Gly Gln Pro Val Lys His Ala
    130                 135                 140

Val Ile Thr Val Pro Ala Tyr Phe Asn Asp Ser Gln Arg Gln Ala Thr
145                 150                 155                 160

Lys Asp Ala Gly Ala Ile Ala Gly Leu Asn Val Leu Arg Ile Ile Asn
                165                 170                 175

Glu Pro Thr Ala Ala Ala Ile Ala Tyr Gly Leu Asp Arg Arg Gly Ala
                180                 185                 190

Gly Glu Arg Asn Val Leu Ile Phe Asp Leu Gly Gly Gly Thr Phe Asp
    195                 200                 205

Val Ser Val Leu Ser Ile Asp Ala Gly Val Phe Glu Val Lys Ala Thr
    210                 215                 220

Ala Gly Asp Thr His Leu Gly Gly Glu Asp Phe Asp Asn Arg Leu Val
225                 230                 235                 240

Asn His Phe Met Glu Glu Phe Arg Arg Lys His Gly Lys Asp Leu Ser
                245                 250                 255

Gly Asn Lys Arg Ala Leu Arg Arg Leu Arg Thr Ala Cys Glu Arg Ala
            260                 265                 270

Lys Arg Thr Leu Ser Ser Ser Thr Gln Ala Thr Leu Glu Ile Asp Ser
        275                 280                 285

Leu Phe Glu Gly Val Asp Phe Tyr Thr Ser Ile Thr Arg Ala Arg Phe
    290                 295                 300

Glu Glu Leu Cys Ser Asp Leu Phe Arg Ser Thr Leu Glu Pro Val Glu
305                 310                 315                 320

Lys Ala Leu Arg Asp Ala Lys Leu Asp Lys Ala Gln Ile His Asp Val
                325                 330                 335

Val Leu Val Gly Gly Ser Thr Arg Ile Pro Lys Val Gln Lys Leu Leu
            340                 345                 350

Gln Asp Phe Phe Asn Gly Lys Glu Leu Asn Lys Ser Ile Asn Pro Asp
        355                 360                 365

Glu Ala Val Ala Tyr Gly Ala Ala Val Gln Ala Ala Val Leu Met Gly
    370                 375                 380

Asp Lys Cys Glu Lys Val Gln Asp Leu Leu Leu Leu Asp Val Ala Pro
385                 390                 395                 400

Leu Ser Leu Gly Leu Glu Thr Ala Gly Gly Val Met Thr Thr Leu Ile
                405                 410                 415

Gln Arg Asn Ala Thr Ile Pro Thr Lys Gln Thr Gln Thr Phe Thr Thr
```

|   |   |   | 420 |   |   |   | 425 |   |   |   | 430 |   |
|---|---|---|---|---|---|---|---|---|---|---|---|---|
Tyr Ser Asp Asn Gln Pro Gly Val Phe Ile Gln Val Tyr Glu Gly Glu
        435              440              445

Arg Ala Met Thr Lys Asp Asn Asn Leu Leu Gly Arg Phe Glu Leu Ser
 450                   455              460

Gly Ile Pro Pro Ala Pro Arg Gly Val Pro Gln Ile Glu Val Thr Phe
465               470              475              480

Asp Ile Asp Ala Asn Gly Ile Leu Ser Val Thr Ala Thr Asp Arg Ser
             485              490              495

Thr Gly Lys Ala Asn Lys Ile Thr Ile Thr Asn Asp Lys Gly Arg Leu
 500                   505              510

Ser Lys Glu Glu Val Glu Arg Met Val His Glu Ala Glu Gln Tyr Lys
         515               520              525

Ala Glu Asp Glu Ala Gln Arg Asp Arg Val Ala Ala Lys Asn Ser Leu
      530              535              540

Glu Ala His Val Phe His Val Lys Gly Ser Leu Gln Glu Glu Ser Leu
545               550              555              560

Arg Asp Lys Ile Pro Glu Glu Asp Arg Arg Lys Met Gln Asp Lys Cys
             565              570              575

Arg Glu Val Leu Ala Trp Leu Glu His Asn Gln Leu Ala Glu Lys Glu
        580               585              590

Glu Tyr Glu His Gln Lys Arg Glu Leu Glu Gln Ile Cys Arg Pro Ile
     595               600              605

Phe Ser Arg Leu Tyr Gly Gly Pro Gly Val Pro Gly Gly Ser Ser Cys
 610                  615              620

Gly Thr Gln Ala Arg Gln Gly Asp Pro Ser Thr Gly Pro Ile Ile Glu
625               630              635              640

Glu Val Asp

```
<210> SEQ ID NO 47
<211> LENGTH: 2664
<212> TYPE: DNA
<213> ORGANISM: Homo sapiens
<220> FEATURE:
<221> NAME/KEY: misc_feature
<223> OTHER INFORMATION: NM_002155; heat shock 70kDa protein 6 (HSP70B')
      (HSPA6); mRNA

<400> SEQUENCE: 47
agagccagcc cggaggagct agaaccttcc ccgcatttct ttcagcagcc tgagtcagag      60
gcgggctggc ctggcgtagc cgcccagcct cgcggctcat gccccgatct gcccgaacct     120
tctcccgggg tcagcgccgc gccgcgccac ccggctgagt cagcccgggc gggcgagagg     180
ctctcaactg ggcgggaagg tgcgggaagg tgcggaaagg ttcgcgaaag ttcgcggcgg     240
cgggggtcgg gtgaggcgca aaaggataaa aagcccgtgg aagcggagct gagcagatcc     300
gagccgggct ggctgcagag aaaccgcagg gagagcctca ctgctgagcg ccctcgacg     360 gcggagcggc agcagcctcc gtggcctcca gcatccgaca agaagcttca gccatgcagg     420
ccccacggga gctcgcggtg ggcatcgacc tgggcaccac ctactcgtgc gtgggcgtgt     480
ttcagcaggg ccgcgtggag atcctggcca acgaccaggg caaccgcacc acgcccagct     540
acgtggcctt caccgacacc gagcggctgg tcggggacgc ggccaagagc aggcggccc     600 tgaaccccca aacaccgtg ttcgatgcca gcggctgat cgggcgcaag ttcgcggaca     660
ccacggtgca gtcggacatg aagcactggc ccttccgggt ggtgagcgag ggcggcaagc     720
ccaaggtgcg cgtatgctac cgcggggagg acaagacgtt ctaccccgag gagatctcgt     780
```

```
ccatggtgct gagcaagatg aaggagacgg ccgaggcgta cctgggccag cccgtgaagc      840
acgcagtgat caccgtgccc gcctatttca atgactcgca gcgccaggcc accaaggacg      900
cgggggccat cgcggggctc aacgtgttgc ggatcatcaa tgagcccacg gcagctgcca      960
tcgcctatgg gctggaccgg cggggcgcgg gagagcgcaa cgtgctcatt tttgacctgg     1020
gtggggcac cttcgatgtg tcggttctct ccattgacgc tggtgtcttt gaggtgaaag      1080
ccactgctgg agatacccac ctgggaggag aggacttcga caaccggctc gtgaaccact     1140
tcatggaaga attccggcgg aagcatggga aggacctgag cgggaacaag cgtgccctgc     1200
gcaggctgcg cacagcctgt gagcgcgcca agcgcaccct gtcctccagc acccaggcca     1260
ccctggagat agactccctg ttcgagggcg tggacttcta cacgtccatc actcgtgccc     1320
gctttgagga actgtgctca gacctcttcc gcagcaccct ggagccggtg gagaaggccc     1380
tgcgggatgc caagctggac aaggcccaga ttcatgacgt cgtcctggtg ggggctcca      1440
ctcgcatccc caaggtgcag aagttgctgc aggacttctt caacggcaag gagctgaaca     1500
agagcatcaa ccctgatgag gctgtggcct atgggctgc tgtgcaggcg gccgtgttga      1560
tggggacaa atgtgagaaa gtgcaggatc tcctgctgct ggatgtggct cccctgtctc      1620
tggggctgga gacagcaggt ggggtgatga ccacgctgat ccagaggaac gccactatcc     1680
ccaccaagca gacccagact ttcaccacct actcggacaa ccagcctggg gtcttcatcc     1740
aggtgtatga gggtgagagg gccatgacca aggacaacaa cctgctgggg cgttttgaac     1800
tcagtggcat ccctcctgcc ccacgtggag tcccccagat agaggtgacc tttgacattg     1860
atgctaatgg catcctgagc gtgacagcca ctgacaggag cacaggtaag gctaacaaga     1920
tcaccatcac caatgacaag ggccggctga gcaaggagga ggtggagagg atggttcatg     1980
aagccgagca gtacaaggct gaggatgagg cccagaggga cagagtggct gccaaaaact     2040
cgctggagc ccatgtcttc catgtgaaag gttctttgca agaggaaagc cttagggaca     2100
agattcccga agaggacagg cgcaaaatgc aagacaagtg tcgggaagtc cttgcctggc     2160
tggagcacaa ccagctggca gagaaggagg agtatgagca tcagaagagg gagctggagc     2220
aaatctgtcg ccccatcttc tccaggctct atggggggcc tggtgtccct gggggcagca     2280
gttgtggcac tcaagcccgc caggggggacc ccagcaccgg ccccatcatt gaggaggttg     2340
attgaatggc ccttcgtgat aagtcagctg tgactgtcag ggctatgcta tgggccttct     2400
agactgtctt ctatgatcct gcccttcaga gatgaacttt ccctccaaag ctagaacttt     2460
cttcccagga taactgaagt cttttgactt tttgggggga gggcggttca tcctcttctg     2520
cttcaaataa aaagtcatta atttattaaa acttgtgtgg cactttaaca ttgctttcac     2580
ctatattttg tgtactttgt tacttgcatg tatgaatttt gttatgtaaa atatagttat     2640
agacctaaat aaaaaaaaaa aaaa                                            2664
```

<210> SEQ ID NO 48
<211> LENGTH: 2492
<212> TYPE: DNA
<213> ORGANISM: Homo sapiens
<220> FEATURE:
<221> NAME/KEY: misc_feature
<223> OTHER INFORMATION: X51757; heat-shock protein HSP70B gene

<400> SEQUENCE: 48

```
cccgggcggg cgagaggctc tcaactgggg gggaaggtgc gggaaggtgc ggaaaggttc       60
gcgaaagttc gcggcggcgg gggtcgggtg aggcgcaaaa ggataaaaag cccgtggaag      120
```

```
cggagctgag cagatccgag ccgggctggc tgcagagaca ccgcagggag agcctcactg    180
ctgagcgccc ctcgacggcg gacgggcagc agcctccgtg gcctccagca tccgacaaga    240
agcttcagcc atgcaggccc acgggagct cgcggtgggc atcgacctgg caccaccta     300 ctcgtgcgtg ggcgtgtttc agcagggccg cgtggagatc ctggccaacg accagggcaa    360
ccgcaccacg cccagctacg tggccttcac cgacaccgag cggctggtcg gggacgcggc    420
caagagccag gcggccctga acccccacaa caccgtgttc gatgccaagc ggctgatcgg    480
gcgcaagttc gcggacacca cggtgcagtc ggacatgaag cactggccct ccgggtggt     540 gagcgagggc ggcaagccca aggtgccggt atcgtaccgc ggggaggaca agacgttcta    600
ccccgaggag atctcgtcca tggtgctgag caagatgaag gagacggccg aggcgtacct    660
gggccagccc gtgaagcacg cagtgatcac cgtgcccgcc tatttcaatg actcgcagcg    720
ccaggccacc aaggacgcgg gggccatcgc ggggctcaac gtgttgcgga tcatcaatga    780
gcccacggca gctgccatcg cctatgggct ggaccggcgg ggcgcgggag agcgcaacgt    840 gctcatttttt gacctgggtg ggggcacctt cgatgtgtcg gttctctcca ttgacgctgg    900 tgtcttttgag gtgaaagcca ctgctggaga tacccacctg ggaggagagg acttcgacaa    960
ccggctcgtg aaccacttca tggaagaatt ccggcggaag catgggaagg acctgagcgg   1020
gaacaagcgt gccctcggca ggctgcgcac agcctgtgag cgcgccaagc gcaccctgtc   1080
ctccagcacc caggccaccc tggagataga ctccctgttc gagggcgtgg acttctacac   1140
gtccatcact cgtgcccgct ttgaggaact gtgctcagac ctcttccgca gcaccctgga   1200
gccggtggag aaggccctgc gggatgccaa gctggacaag gcccagattc atgacgtcgt   1260
cctggtgggg ggctccactc gcatccccaa ggtgcagaag ttgctgcagg acttcttcaa   1320
cggcaaggag ctgaacaaga gcatcaaccc tgatgaggct gtggcctatg gggctgctgt   1380
gcaggcggcc gtgttgatgg gggacaaatg tgagaaagtg caggatctcc tgctgctgga   1440
tgtggctccc ctgtctctgg ggctggagac agcaggtggg gtgatgacca cgctgatcca   1500
gaggaacgcc actatccccca ccaagcagac ccagactttc accacctact cggacaacca   1560
gcctggggtc ttcatccagg tgtatgaggg tgagaggggcc atgaccaagg acaacaacct   1620 gctgggggcgt tttgaactca gtggcatccc tcctgcccca cgtggagtcc cccagataga   1680
ggtgaccttt gacattgatg ctaatggcat cctgagcgtg acagccactg acaggagcac   1740
aggtaaggct aacaagatca ccatcaccaa tgacaagggc cggctgagca aggaggaggt   1800
ggagaggatg gttcatgaag ccgagcagta caaggctgag gatgaggccc agaggacag   1860 agtggctgcc aaaaactcgc tggaggccca tgtcttccat gtgaaaggtt ctttgcaaga   1920
ggaaagcctt agggacaaga ttcccgaaga ggacaggcgc aaaatgcaag acaagtgtcg   1980
ggaagtcctt gcctggctgg agcacaacca gctggcagag aaggaggagt atgagcatca   2040
gaagagggag ctggagcaaa tctgtcgccc catcttctcc aggctctatg gggggcctgg   2100
tgtccctggg ggcagcagtt gtggcactca agcccgccag ggggacccca gcaccggccc   2160
catcattgag gaggttgatt gaatggccct tcgtgataag tcagctgtga ctgtcagggc   2220
tatgctatgg gccttctaga ctgtcttcta tgatcctgcc cttcagagat gaactttccc   2280
tccaaagcta gaactttctt ccaggataa ctgaagtctt ttgactttttt gcggggaggg   2340 cggttcatcc tcttctgctt caaataaaaa gtcattaatt tattaaaact tgtgtggcac   2400
tttaacattg ctttcaccta tatttttgtgt acttttgttac ttgcatgtat gaattttgtt   2460
atgtaaaata tagttataga cctaaataag ct                                  2492
```

<210> SEQ ID NO 49
<211> LENGTH: 115
<212> TYPE: PRT
<213> ORGANISM: Homo sapiens
<220> FEATURE:
<221> NAME/KEY: MISC_FEATURE
<223> OTHER INFORMATION: P14174; macrophage migration inhibitory factor

<400> SEQUENCE: 49

```
Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115
```

<210> SEQ ID NO 50
<211> LENGTH: 561
<212> TYPE: DNA
<213> ORGANISM: Homo sapiens
<220> FEATURE:
<221> NAME/KEY: misc_feature
<223> OTHER INFORMATION: NM_002415; macrophage migration inhibitory factor (glycosylation-inhibiting factor) (MIF); mRNA

<400> SEQUENCE: 50

```
accacagtgg tgtccgagaa gtcaggcacg tagctcagcg gcggccgcgg cgcgtgcgtc      60
tgtgcctctg cgcgggtctc ctggtccttc tgccatcatg ccgatgttca tcgtaaacac     120
caacgtgccc cgcgcctccg tgccggacgg gttcctctcc gagctcaccc agcagctggc     180
gcaggccacc ggcaagcccc cccagtacat cgcggtgcac gtggtcccgg accagctcat     240
ggccttcggc ggctccagcg agccgtgcgc gctctgcagc ctgcacagca tcggcaagat     300
cggcggcgcg cagaaccgct cctacagcaa gctgctgtgc ggcctgctgg ccgagcgcct     360
gcgcatcagc ccggacaggg tctacatcaa ctattacgac atgaacgcgg ccaatgtggg     420
ctggaacaac tccaccttcg cctaagagcc gcagggaccc acgctgtctg cgctggctcc     480
acccgggaac ccgccgcacg ctgtgttcta ggcccgccca ccccaacctt ctggtgggga     540
gaaataaacg gtttagagac t                                               561
```

<210> SEQ ID NO 51
<211> LENGTH: 2167
<212> TYPE: DNA
<213> ORGANISM: Homo sapiens
<220> FEATURE:
<221> NAME/KEY: misc_feature
<223> OTHER INFORMATION: L19686; macrophage migration inhibitory factor (MIF) gene; complete cds

<400> SEQUENCE: 51

```
ctgcaggaac caatacccat aggctatttg tataaatggg ccatggggcc tcccagctgg      60
```

```
aggctggctg gtgccacgag ggtcccacag gcatgggtgt ccttcctata tcacatggcc    120
ttcactgaga ctggtatatg gattgcacct atcagagacc aaggacagga cctccctgga    180
aatctctgag gacctggcct gtgatccagt tgctgccttg tcctcttcct gctatgtcat    240
ggcttatctt ctttcaccca ttcattcatt cattcattca ttcagcagta ttagtcaatg    300
tctcttgata tgcctggcac ctgctagatg gtccccgagt ttaccattag tggaaaagac    360
atttaagaaa ttcaccaagg gctctatgag aggccataca cggtggacct gactagggtg    420
tggcttccct gaggagctga agttgccag aggcccagag aaggggagct gagcacgttt      480
gaaccactga acctgctctg gacctcgcct ccttccttcg gtgcctccca gcatcctatc    540
ctctttaaag agcaggggtt cagggaagtt ccctggatgg tgattcgcag gggcagctcc    600
cctctcacct gccgcatgac tacccccgccc catctcaaac acacaagctc acgcatgcgg    660
gactggagcc cttgaggaca tgtggcccaa agacaggagg tacaggggct cagtgcgtgc    720
agtggaatga actgggcttc atctctggaa gggtaagggg ccatcttccg ggttcaccgc    780
cgcatcccca cccccggcac agcgcctcct ggcgactaac atcggtgact tagtgaaagg    840
actaagaaag acccgaggcg aggccggaac aggccgattt ctagccgcca agtggagaac    900
aggttggagc ggtgcgccgg gcttagcggc ggttgctgga ggaacgggcg gagtcgccca    960
gggtcctgcc ctgcggggt cgagccgagg caggcggtga cttccccact cggggcggag     1020
ccgcagcctc gcggggggcgg ggcctggcgc cggcggtggc gtcacaaaag gcgggaccac   1080
agtggtgtcc gagaagtcag gcacgtagct cagcggcggc cgcggcgcgt gcgtctgtgc    1140
ctctgcgcgg gtctcctggt ccttctgcca tcatgccgat gttcatcgta aacaccaacg    1200
tgccccgcgc ctccgtgccg gacgggttcc tctccgagct cacccagcag ctggcgcagg    1260
ccaccggcaa gccccccag gtttgccggg aggggacagg aagaggggg tgcccaccgg       1320 acgaggggtt ccgcgctggg agctggggag gcgactcctg aacggagctg ggggggcgggg   1380 cgggggggagg acggtggctc gggcccgaag tggacgttcg gggcccgacg aggtcgctgg   1440
ggcgggctga ccgcgccctt tcctcgcagt acatcgcggt gcacgtggtc ccggaccagc    1500
tcatggcctt cggcggctcc agcgagccgt gcgcgctctg cagcctgcac agcatcggca    1560
agatcggcgg cgcgcagaac cgctcctaca gcaagctgct gtgcggcctg ctggccgagc    1620
gcctgcgcat cagcccggac aggtacgcgg agtcgcggag gggcggggga ggggcggcgg    1680
cgcgcggcca gcccgggac tgagccaccc gctgagtccg gcctcctccc cccgcagggt     1740
ctacatcaac tattacgaca tgaacgcggc caatgtgggc tggaacaact ccaccttcgc    1800
ctaagagccg cagggaccca cgctgtctgc gctggctcca cccgggaacc cgccgcacgc    1860
tgtgttctag gcccgcccac cccaaccttc tggtggggag aaataaacgg tttagagact    1920
aggagtgcct cggggttcct tggcttgcgg gaggaattgg tgcagagccg ggacattggg    1980
gagcgaggtc gggaaacggt gttggggcg ggggtcaggg ccgggttgct ctcctcgaac      2040
ctgctgttcg ggagcccttt tgtccagcct gtccctccta cgctcctaac agaggagccc    2100
cagtgtcttt ccattctatg gcgtacgaag ggatgaggag aagttggcac tctgccctgg    2160
gctgcag                                                              2167
```

<210> SEQ ID NO 52
<211> LENGTH: 105
<212> TYPE: PRT
<213> ORGANISM: Homo sapiens
<220> FEATURE:
<221> NAME/KEY: MISC_FEATURE -continued
<223> OTHER INFORMATION: P31949; Calgizzarin

<400> SEQUENCE: 52

Met Ala Lys Ile Ser Ser Pro Thr Glu Thr Glu Arg Cys Ile Glu Ser
1               5                   10                  15

Leu Ile Ala Val Phe Gln Lys Tyr Ala Gly Lys Asp Gly Tyr Asn Tyr
            20                  25                  30

Thr Leu Ser Lys Thr Glu Phe Leu Ser Phe Met Asn Thr Glu Leu Ala
        35                  40                  45

Ala Phe Thr Lys Asn Gln Lys Asp Pro Gly Val Leu Asp Arg Met Met
    50                  55                  60

Lys Lys Leu Asp Thr Asn Ser Asp Gly Gln Leu Asp Phe Ser Glu Phe
65                  70                  75                  80

Leu Asn Leu Ile Gly Gly Leu Ala Met Ala Cys His Asp Ser Phe Leu
                85                  90                  95

Lys Ala Val Pro Ser Gln Lys Arg Thr
            100                 105

<210> SEQ ID NO 53
<211> LENGTH: 595
<212> TYPE: DNA
<213> ORGANISM: Homo sapiens
<220> FEATURE:
<221> NAME/KEY: misc_feature
<223> OTHER INFORMATION: NM_005620 and D38583; S100 calcium binding
      protein A11 (calgizzarin)(S100A11); mRNA

<400> SEQUENCE: 53
gggcaaggct gggccgggaa gggcgtgggt tgaggagagg ctccagaccc gcacgccgcg      60
cgcacagagc tctcagcgcc gctcccagcc acagcctccc gcgcctcgct cagctccaac     120
atggcaaaaa tctccagccc tacagagact gagcggtgca tcgagtccct gattgctgtc     180
ttccagaagt atgctggaaa ggatggttat aactacactc tctccaagac agagttccta     240
agcttcatga atacagaact agctgccttc acaaagaacc agaaggaccc tggtgtcctt     300
gaccgcatga tgaagaaact ggacaccaac agtgatggtc agctagattt ctcagaattt     360
cttaatctga ttggtggcct agctatggct tgccatgact ccttcctcaa ggctgtccct     420
tcccagaagc ggacctgagg acccttggc cctggccttc aaaccacccc ctttccttc      480 cagcctttct gtcatcatct ccacagccca cccatccct gagcacacta accacctcat     540
gcaggcccca cctgccaata gtaataaagc aatgtcactt ttttaaaaca tgaaa          595

<210> SEQ ID NO 54
<211> LENGTH: 249
<212> TYPE: PRT
<213> ORGANISM: Homo sapiens
<220> FEATURE:
<221> NAME/KEY: MISC_FEATURE
<223> OTHER INFORMATION: P00938 and NP_000356; Triosephosphate isomerase

<400> SEQUENCE: 54

Met Ala Pro Ser Arg Lys Phe Phe Val Gly Gly Asn Trp Lys Met Asn
1               5                   10                  15

Gly Arg Lys Gln Ser Leu Gly Glu Leu Ile Gly Thr Leu Asn Ala Ala
            20                  25                  30

Lys Val Pro Ala Asp Thr Glu Val Val Cys Ala Pro Pro Thr Ala Tyr
        35                  40                  45

Ile Asp Phe Ala Arg Gln Lys Leu Asp Pro Lys Ile Ala Val Ala Ala
    50                  55                  60

```
Gln Asn Cys Tyr Lys Val Thr Asn Gly Ala Phe Thr Gly Glu Ile Ser
 65                  70                  75                  80

Pro Gly Met Ile Lys Asp Cys Gly Ala Thr Trp Val Val Leu Gly His
                 85                  90                  95

Ser Glu Arg Arg His Val Phe Gly Glu Ser Asp Glu Leu Ile Gly Gln
            100                 105                 110

Lys Val Ala His Ala Leu Ala Glu Gly Leu Gly Val Ile Ala Cys Ile
        115                 120                 125

Gly Glu Lys Leu Asp Glu Arg Glu Ala Gly Ile Thr Glu Lys Val Val
130                 135                 140

Phe Glu Gln Thr Lys Val Ile Ala Asp Asn Val Lys Asp Trp Ser Lys
145                 150                 155                 160

Val Val Leu Ala Tyr Glu Pro Val Trp Ala Ile Gly Thr Gly Lys Thr
                165                 170                 175

Ala Thr Pro Gln Gln Ala Gln Glu Val His Glu Lys Leu Arg Gly Trp
            180                 185                 190

Leu Lys Ser Asn Val Ser Asp Ala Val Ala Gln Ser Thr Arg Ile Ile
        195                 200                 205

Tyr Gly Gly Ser Val Thr Gly Ala Thr Cys Lys Glu Leu Ala Ser Gln
    210                 215                 220

Pro Asp Val Asp Gly Phe Leu Val Gly Gly Ala Ser Leu Lys Pro Glu
225                 230                 235                 240

Phe Val Asp Ile Ile Asn Ala Lys Gln
                245
```

<210> SEQ ID NO 55
<211> LENGTH: 1254
<212> TYPE: DNA
<213> ORGANISM: Homo sapiens
<220> FEATURE:
<221> NAME/KEY: misc_feature
<223> OTHER INFORMATION: NM_000365; triosephosphate isomerase 1 (TPI1);
    mRNA

<400> SEQUENCE: 55

```
ccttcagcgc ctcggctcca gcgccatggc gccctccagg aagttcttcg ttggggaaa     60 ctggaagatg aacgggcgga agcagagtct gggggagctc atcggcactc tgaacgcggc    120
caaggtgccg gccgacaccg aggtggtttg tgctccccct actgcctata tcgacttcgc    180
ccggcagaag ctagatccca agattgctgt ggctgcgcag aactgctaca agtgactaa     240 tggggctttt actggggaga tcagccctgg catgatcaaa gactgcggag ccacgtgggt    300
ggtcctgggg cactcagaga aaggcatgt cttggggag tcagatgagc tgattgggca     360
gaaagtggcc catgctctgg cagagggact cggagtaatc gcctgcattg gggagaagct    420
agatgaaagg gaagctggca tcactgagaa ggttgttttc gagcagacaa aggtcatcgc    480
agataacgtg aaggactgga gcaaggtcgt cctggcctat gagcctgtgt gggccattgg    540
tactggcaag actgcaacac cccaacaggc ccaggaagta cacgagaagc tccgaggatg    600
gctgaagtcc aacgtctctg atgcggtggc tcagagcacc cgtatcattt atggaggctc    660
tgtgactggg gcaacctgca aggagctggc cagccagcct gatgtggatg gcttccttgt    720
gggtggtgct tccctcaagc ccgaattcgt ggacatcatc aatgccaaac aatgagcccc    780
atccatcttc cctacccttc tgccaagcc agggactaag cagcccagaa gcccagtaac    840 tgcccttttcc ctgcatatgc ttctgatggt gtcatctgct ccttcctgtg gcctcatcca    900
aactgtatct tccttttactg tttatatctt caccctgtaa tggttgggac caggccaatc    960
```

-continued

| | |
|---|---|
| ccttctccac ttactataat ggttggaact aaacgtcacc aaggtggctt ctccttggct | 1020 |
| gagagatgga aggcgtggtg ggatttgctc ctgggttccc taggccctag tgagggcaga | 1080 |
| agagaaacca tcctctccct tcttacaccg tgaggccaag atcccctcag aaggcaggag | 1140 |
| tgctgccctc tcccatggtg cccgtgcctc tgtgctgtgt atgtgaacca cccatgtgag | 1200 |
| ggaataaacc tggcactagg aaaaaaaaaa aaaaaaaaa aaaaaaaaa aaaa | 1254 |

<210> SEQ ID NO 56
<211> LENGTH: 5005
<212> TYPE: DNA
<213> ORGANISM: Homo sapiens
<220> FEATURE:
<221> NAME/KEY: misc_feature
<223> OTHER INFORMATION: X69723; TPI1 gene for triosephosphate isomerase

<400> SEQUENCE: 56

| | |
|---|---|
| ctgcagttcc tgccaggcct tgccagccgg ggcgagggtt gggatgatcc tggcggccta | 60 |
| tgcctgtgtg ggctgcccct cccgctgtga accctgcatt tgtcccgcaa gttttcactc | 120 |
| aggtagactc cctgggtaca agggtgcctg ctcagcagtc gggcatgagc tgctccgatg | 180 |
| ggcgaaggag gttgtctatt ccacagttgg agaggggccc tctctgcccc agtgggcgat | 240 |
| ctgggctacg gccaagttgc caccagctag ttccgcttga aaaccacttc tggccccgtg | 300 |
| ggggactcaa gtcgccaagc gagggttccc ctgagcgccg gagctcacag gtctcgcctt | 360 |
| gtcccgaaag ccccgcaatc gaggcggagg cgaccgagcc cccgactctc ctagaacgtt | 420 |
| gccacaagaa gggggaacgt cggaacagtg catcatcggg cggcggccgg ggcggcggca | 480 |
| ggagggcggg cgggggggcag ggctccgggg gactgggcgg gccatggcgg aggacggcga | 540 |
| ggaggcggag ttccacttcg cggcgctcta tataagtggg cagtgccgc gactgcgcgc | 600 |
| agacactgac cttcagcgcc tcggctccag cgccatggcg ccctccagga agttcttcgt | 660 |
| tggggggaaac tggaagatga acgggcggaa gcagagtctg ggggagctca tcggcactct | 720 |
| gaacgcggcc aaggtgccgg ccgacaccgg taagccctcg ccgaggaggg gtctggccgg | 780 |
| gccggggccg ggccggggca ggagtggcag cgcctctccc gaggcccgag gtccgggccg | 840 |
| gtatccgcgc ggacctgatg cagggctgtg ggacgagggc cgctggggtc cgggcagggg | 900 |
| cctcgcagcc gcagcccgt cggtgcgtcg aggggcagg gcggagcaca tgatgccct | 960 |
| tggactacgg ggcaggtaag gacgttttgg gtctcctgga ggaaggcggc cccggggcgc | 1020 |
| gcactggctg tgcccgccag gcgacggggt taggagccga gcccgaggct tgcgggaga | 1080 |
| ccgggggagg ctgggccgcg tgggcttccg ctccctgccc tggcctccgc gtgcgcgccg | 1140 |
| ccgcacgtag ccccagactc ctcccccctcc tcgccggcgt cgtcccgcgc cgagctgctg | 1200 |
| ctgccctgag ccccccagatc tgaaccccctt cccttcggca acctgagcga ctcccgcctt | 1260 |
| ccacggaagg gaccgagccc gtgccaaaca ggctgagcga tttgggagtg aggagccatc | 1320 |
| ctaccgcttt ccccaacctg gaaacagcaa agcgcaaggc ctctgagtca gttaggtctc | 1380 |
| tgccacccac gggcaaagga tgctctcctc catcctcctt cctccctcca ccgaaatcgg | 1440 |
| agagccgcgg gcctgatcca agaggcatc cccttctcgt tcattcccca gaggcctcaa | 1500 |
| tacaaacccc aggagttggc ccctctcctt ttgctacaaa tccttgcctt gcaaagggga | 1560 |
| ggtgaggatg ggctatttta gaagggaagc agggttgctc cctggagaat gctgagtctg | 1620 |
| tgaggtgcct atgccgagaa tagctcgagg aaattggagc cccagctgtt aaaagagcag | 1680 |
| agggcagggt gagggccgtg gctctcaggg gtatctggaa ggctcttcga gttgagtgca | 1740 |
| gacccagcct tgggctggaa aatggacaaa ggtcatcttg ctggggtgaa aaggggggaga | 1800 |

```
gcagaaccaa gaagaagagg gtgagggctg gggggctcca gggcactggt taggaattgt    1860
ggggaatgaa ggctttcttt agtctcatcc ccctgtggta ccatcttgtc ctcagaggtg    1920
gtttgtgctc cccctactgc ctatatcgac ttcgcccggc agaagctaga tcccaagatt    1980
gctgtggctg cgcagaactg ctacaaagtg actaatgggg cttttactgg ggagatcagg    2040
tgagatcgag gtggagaggg gtgtgtggga cccttccctc actttcctcg ttgaggggaa    2100
agccacaggg tgggctccct gctgaacctt ggcttcatct cttcctttag ccctggcatg    2160
atcaaagact gcggagccac gtgggtggtc ctggggcact cagagagaag gcatgtcttt    2220
ggggagtcag atgaggttag tagccaagag agaagataag ggatgtcttt ttccaagaag    2280
gatgtctcac caagtctgtt tctcaacagc tgattgggca gaaagtggcc catgctctgg    2340
cagagggact cggagtaatc gcctgcattg gggagaagct agatgaaagg gaagctggca    2400
tcactgagaa ggttgttttc gagcagacaa aggtcatcgc aggtatctct ggagaaaggg    2460
acctttgagc ctatccaggg ccacagagac tcagagggta gggtcaggcc ctggagcctg    2520
tcttggtccc catgctgatc agaaaaggaa aaaggggag ggggagtgac aatctttgct    2580
tggggcctat gacttctcca gccccaaggt agatgccacc tggaaatccc caatgtcca    2640 ctaggggca gtaggccacc gttcttcgta ctccggagaa cctggctgga gagctctttc    2700
ttgttcaccc ttccctccat ctgtatctct gccctgcaga taacgtgaag gactggagca    2760
aggtcgtcct ggcctatgag cctgtgtggg ccattggtac tggcaagact gcaacacccc    2820
aacaggtaac cgggcccagg agccctgccc tcatcccagc ctgcctcaat aggtttggac    2880
agacacagcc cacatggagc aaccccttat ttcaaagaca cagagacctt gaacccagag    2940
acagtgactt gtccaagggc atccagtcca gggcctggct tggatcagag ccctggtact    3000
ctgactcagt cagaaaccac actaagtgtc cactggtgcc agtgattttt cctcttagag    3060
aggcagaaaa ggtcttactt aggccagctt cttgttctag gcccaggaag tacacgagaa    3120
gctccgagga tggctgaagt ccaacgtctc tgatgcggtg gctcagagca cccgtatcat    3180
ttatggaggt gagtggcttt ggttccggc tgaggtggag tgggctgagg actagactga    3240
gccctcggac atggaggtgg ggatggggca gactcatccc attcttgacc aagcccttgt    3300
tctgctccct tccaggctc tgtgactggg gcaacctgca aggagctggc cagccagcct    3360
gatgtggatg gcttccttgt gggtggtgct tccctcaagc ccgaattcgt ggacatcatc    3420
aatgccaaac aatgagcccc atccatcttc cctaccctttc ctgccaagcc agggactaag    3480
cagcccagaa gcccagtaac tgcccttttcc ctgcatatgc ttctgatggt gtcatctgct    3540
ccttcctgtg gcctcatcca aactgtatct tcctttactg tttatatctt cacccctgtaa    3600 tggttgggac caggccaatc ccttctccac ttactataat ggttggaact aaacgtcacc    3660
aaggtggctt ctccttggct gagagatgga aggcgtggtg ggatttgctc ctgggttccc    3720
taggccctag tgagggcaga agagaaacca tcctctccct tcttacaccg tgaggccaag    3780
atcccctcag aaggcaggag tgctgccctc tccatggtg cccgtgcctc tgtgctgtgt    3840
atgtgaacca cccatgtgag ggaataaacc tggcactagg tcttgtggtt tgtctgcctt    3900
cactggactt gcccagataa tcttccttttt tgaggcagct atataaatga tcatttgtgc    3960
aagaaaaaaa aaaaacaag aacaggtttc tataacaaca tctcttacta ttttttacttg    4020 aaaaaatgtt ttgcgtagca gactgtcata gccttgaacg ccggctccct ttcttcctcc    4080
ctccaagtgg ctctggggct gttgatttcc cgagagcttg ggttggggta gggctcagcc    4140
tcaccagctt tcagcagctg gtctaggcca gcagtgcctc cccacctccc caagggaggg    4200
```

-continued

```
tggtggcaag acctcagcac agtctgtggt atcacaggct cactggtaga gcagtagcgc    4260
ttcatgcagg gggcaagggc agggcagaca cctggccgag cggtatcccc aggttgtggc    4320
gcacacacag gcggctcagg tgcagaaggg agtgtggctc cgctgggaga gagaaggagg    4380
ggaatgtaag tatgggtgca gccaccagcc agatgtcctc aaactacggg gtcctcatca    4440
gatgcctttc tgcttcctg cttcgagtgt gcccacctgg ctgaaagggg aatttgagat     4500
acccggaagt tctgcctccc agataagatt tcacacatcc ctagtcagag ctgggggtga    4560
agagctggct aaggccctct aaacaacagg ccaaggtggc tctgacagtg gtggagctgg    4620
cccaggcttt gactccagag gcttgggagc tggggctgag gtgaggaggg atggccctcc    4680
actctacagc ccaacacaac tgcagagagc agctccaagc cctggaccca gtcagttcct    4740
ggggaggctc ctcccctgct gccccaccct aaggcctgcc tcctccactg ctctcctcct    4800
ccctggtgcc cagggcccca gtgtctccat cctgaggtgt ggctgaggaa ggaagtaggt    4860
atgtggcaca gagacaggtt agagcccagg gaatccggta tacagcctgg gtacctcgtc    4920
tgcccatcct tcttttggac ctgtacatca aacccagtac ctaaccgttt gcacctcttg    4980
cctaggggtg attactcctg aattc                                          5005
```

<210> SEQ ID NO 57
<211> LENGTH: 418
<212> TYPE: PRT
<213> ORGANISM: Homo sapiens
<220> FEATURE:
<221> NAME/KEY: MISC_FEATURE
<223> OTHER INFORMATION: ITHU and P01009; alpha -1-antitrypsin precursor

<400> SEQUENCE: 57

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
```

```
                210             215             220
Lys Asp Thr Glu Glu Asp Phe His Val Asp Gln Val Thr Val
225             230             235             240

Lys Val Pro Met Met Lys Arg Leu Gly Met Phe Asn Ile Gln His Cys
            245             250             255

Lys Lys Leu Ser Ser Trp Val Leu Leu Met Lys Tyr Leu Gly Asn Ala
            260             265             270

Thr Ala Ile Phe Phe Leu Pro Asp Glu Gly Lys Leu Gln His Leu Glu
            275             280             285

Asn Glu Leu Thr His Asp Ile Ile Thr Lys Phe Leu Glu Asn Glu Asp
            290             295             300

Arg Arg Ser Ala Ser Leu His Leu Pro Lys Leu Ser Ile Thr Gly Thr
305             310             315             320

Tyr Asp Leu Lys Ser Val Leu Gly Gln Leu Gly Ile Thr Lys Val Phe
            325             330             335

Ser Asn Gly Ala Asp Leu Ser Gly Val Thr Glu Glu Ala Pro Leu Lys
            340             345             350

Leu Ser Lys Ala Val His Lys Ala Val Leu Thr Ile Asp Glu Lys Gly
            355             360             365

Thr Glu Ala Ala Gly Ala Met Phe Leu Glu Ala Ile Pro Met Ser Ile
370             375             380

Pro Pro Glu Val Lys Phe Asn Lys Pro Phe Val Phe Leu Met Ile Glu
385             390             395             400

Gln Asn Thr Lys Ser Pro Leu Phe Met Gly Lys Val Val Asn Pro Thr
            405             410             415

Gln Lys

<210> SEQ ID NO 58
<211> LENGTH: 1607
<212> TYPE: PRT
<213> ORGANISM: Homo sapiens
<220> FEATURE:
<221> NAME/KEY: MISC_FEATURE
<223> OTHER INFORMATION: NM_000295; serine (or cysteine) proteinase
      inhibitor, clade A (alpha-1 antiproteinase, antitrypsin), member
      1 (SERPINA1); transcript variant 1; mRNA

<400> SEQUENCE: 58

Ala Ala Thr Gly Ala Cys Thr Cys Cys Thr Thr Thr Cys Gly Gly Thr
1               5               10              15

Ala Ala Gly Thr Gly Cys Ala Cys Thr Gly Gly Ala Ala Gly Cys Thr
            20              25              30

Gly Thr Ala Cys Ala Cys Thr Gly Cys Cys Ala Gly Gly Cys Gly Ala
            35              40              45

Ala Ala Gly Cys Gly Thr Cys Cys Gly Gly Gly Cys Ala Gly Cys Gly
            50              55              60

Thr Ala Gly Gly Cys Gly Gly Cys Gly Ala Cys Thr Cys Ala Gly Ala
65              70              75              80

Ala Thr Cys Cys Cys Ala Gly Cys Cys Ala Gly Thr Gly Gly Ala Cys
            85              90              95

Thr Thr Ala Gly Cys Cys Cys Cys Thr Gly Thr Thr Thr Gly Cys Thr
            100             105             110

Cys Cys Thr Cys Cys Gly Ala Thr Ala Ala Cys Thr Gly Gly Gly Gly
            115             120             125

Thr Gly Ala Cys Cys Thr Thr Gly Gly Thr Thr Ala Ala Thr Ala Thr
            130             135             140
```

```
Thr Cys Ala Cys Cys Ala Gly Cys Ala Gly Cys Cys Thr Cys Cys Cys
145                 150                 155                 160

Cys Cys Gly Thr Thr Gly Cys Cys Cys Cys Thr Cys Thr Gly Gly Ala
                165                 170                 175

Thr Cys Cys Ala Cys Thr Gly Cys Thr Thr Ala Ala Ala Thr Ala Cys
            180                 185                 190

Gly Gly Ala Cys Gly Ala Gly Gly Ala Cys Ala Gly Gly Gly Cys Cys
        195                 200                 205

Cys Thr Gly Thr Cys Thr Cys Cys Thr Cys Ala Gly Cys Thr Thr Cys
    210                 215                 220

Ala Gly Gly Cys Ala Cys Cys Ala Cys Cys Ala Cys Thr Gly Ala Cys
225                 230                 235                 240

Cys Thr Gly Gly Gly Ala Cys Ala Gly Thr Gly Ala Ala Thr Cys Gly
                245                 250                 255

Ala Cys Ala Ala Thr Gly Cys Cys Gly Thr Cys Thr Thr Cys Thr Gly
            260                 265                 270

Thr Cys Thr Cys Gly Thr Gly Gly Gly Gly Cys Ala Thr Cys Cys Thr
        275                 280                 285

Cys Cys Thr Gly Cys Thr Gly Gly Cys Ala Gly Gly Cys Cys Thr Gly
    290                 295                 300

Thr Gly Cys Thr Gly Cys Cys Thr Gly Gly Thr Cys Cys Cys Thr Gly
305                 310                 315                 320

Thr Cys Thr Cys Cys Cys Thr Gly Gly Cys Thr Gly Ala Gly Gly Ala
                325                 330                 335

Thr Cys Cys Cys Cys Ala Gly Gly Gly Ala Gly Ala Thr Gly Cys Thr
            340                 345                 350

Gly Cys Cys Cys Ala Gly Ala Ala Gly Ala Cys Ala Gly Ala Thr Ala
        355                 360                 365

Cys Ala Thr Cys Cys Cys Ala Cys Cys Ala Thr Gly Ala Thr Cys Ala
    370                 375                 380

Gly Gly Ala Thr Cys Ala Cys Cys Cys Ala Ala Cys Cys Thr Thr Cys
385                 390                 395                 400

Ala Ala Cys Ala Ala Gly Ala Thr Cys Ala Cys Cys Cys Cys Cys Ala
                405                 410                 415

Ala Cys Cys Thr Gly Gly Cys Thr Gly Ala Gly Thr Thr Cys Gly Cys
            420                 425                 430

Cys Thr Thr Cys Ala Gly Cys Cys Thr Ala Thr Ala Cys Cys Gly Cys
        435                 440                 445

Cys Ala Gly Cys Thr Gly Gly Cys Ala Cys Ala Cys Cys Ala Gly Thr
    450                 455                 460

Cys Cys Ala Ala Cys Ala Gly Cys Ala Cys Cys Ala Ala Thr Ala Thr
465                 470                 475                 480

Cys Thr Thr Cys Thr Thr Cys Thr Cys Cys Cys Cys Ala Gly Thr Gly
                485                 490                 495

Ala Gly Cys Ala Thr Cys Gly Cys Thr Ala Cys Ala Gly Cys Cys Thr
            500                 505                 510

Thr Thr Gly Cys Ala Ala Thr Gly Cys Thr Cys Thr Cys Cys Cys Thr
        515                 520                 525

Gly Gly Gly Gly Ala Cys Cys Ala Ala Gly Gly Cys Thr Gly Ala Cys
    530                 535                 540

Ala Cys Thr Cys Ala Cys Gly Ala Thr Gly Ala Ala Ala Thr Cys Cys
545                 550                 555                 560

Thr Gly Gly Ala Gly Gly Gly Cys Cys Thr Gly Ala Ala Thr Thr Thr
                565                 570                 575
```

```
Cys Ala Ala Cys Cys Thr Cys Ala Cys Gly Ala Gly Ala Thr Thr
                580                 585                 590
Cys Cys Gly Gly Ala Gly Gly Cys Thr Cys Ala Gly Ala Thr Cys Cys
        595                 600                 605
Ala Thr Gly Ala Ala Gly Gly Cys Thr Thr Cys Cys Ala Gly Gly Ala
        610                 615                 620
Ala Cys Thr Cys Thr Cys Cys Gly Thr Ala Cys Cys Thr Cys
625                 630                 635                 640
Ala Ala Cys Cys Ala Gly Cys Cys Ala Gly Ala Cys Ala Gly Cys Cys
            645                 650                 655
Ala Gly Cys Thr Cys Cys Ala Gly Cys Thr Gly Ala Cys Cys Ala Cys
            660                 665                 670
Cys Gly Gly Cys Ala Ala Thr Gly Gly Cys Cys Thr Gly Thr Thr Cys
            675                 680                 685
Cys Thr Cys Ala Gly Cys Gly Ala Gly Gly Cys Cys Thr Gly Ala
        690                 695                 700
Ala Gly Cys Thr Ala Gly Thr Gly Gly Ala Thr Ala Ala Gly Thr Thr
705                 710                 715                 720
Thr Thr Thr Gly Gly Ala Gly Gly Ala Thr Gly Thr Ala Ala Ala
            725                 730                 735
Ala Ala Gly Thr Thr Gly Thr Ala Cys Cys Ala Cys Thr Cys Ala Gly
            740                 745                 750
Ala Ala Gly Cys Cys Thr Thr Cys Ala Cys Thr Gly Thr Cys Ala Ala
            755                 760                 765
Cys Thr Thr Cys Gly Gly Gly Ala Cys Ala Cys Cys Gly Ala Ala
        770                 775                 780
Gly Ala Gly Gly Cys Cys Ala Ala Gly Ala Ala Cys Ala Gly Ala
785                 790                 795                 800
Thr Cys Ala Ala Cys Gly Ala Thr Thr Ala Cys Gly Thr Gly Gly Ala
            805                 810                 815
Gly Ala Ala Gly Gly Gly Thr Ala Cys Thr Cys Ala Ala Gly Gly Gly
            820                 825                 830
Ala Ala Ala Ala Thr Thr Gly Thr Gly Gly Ala Thr Thr Gly Gly
            835                 840                 845
Thr Cys Ala Ala Gly Gly Ala Gly Cys Thr Thr Gly Ala Cys Ala Gly
        850                 855                 860
Ala Gly Ala Cys Ala Cys Ala Gly Thr Thr Thr Thr Gly Cys Thr
865                 870                 875                 880
Cys Thr Gly Gly Thr Gly Ala Ala Thr Thr Ala Cys Ala Thr Cys Thr
            885                 890                 895
Thr Cys Thr Thr Thr Ala Ala Gly Gly Cys Ala Ala Thr Gly
        900                 905                 910
Gly Gly Ala Gly Ala Gly Ala Cys Cys Thr Thr Gly Ala Ala
            915                 920                 925
Gly Thr Cys Ala Ala Gly Gly Ala Cys Ala Cys Gly Ala Gly Gly
        930                 935                 940
Ala Ala Gly Ala Gly Gly Ala Cys Thr Thr Cys Ala Cys Gly Thr
945                 950                 955                 960
Gly Gly Ala Cys Cys Ala Gly Gly Thr Gly Ala Cys Ala Cys Cys
            965                 970                 975
Gly Thr Gly Ala Ala Gly Gly Thr Gly Cys Thr Ala Thr Gly Ala
        980                 985                 990
Thr Gly Ala Ala Gly Cys Gly Thr  Thr Thr Ala Gly Gly  Cys Ala Thr
```

-continued

```
                995                 1000                1005
Gly Thr  Thr Thr Ala Ala  Cys Ala Thr Cys  Cys Ala Gly Cys Ala
    1010             1015             1020

Cys Thr  Gly Thr Ala Ala  Gly Ala Ala Gly  Cys Thr Gly Thr Cys
    1025             1030             1035

Cys Ala  Gly Cys Thr Gly  Gly Thr Gly Cys  Thr Gly Cys Thr
    1040             1045             1050

Gly Ala  Thr Gly Ala Ala  Ala Thr Ala Cys  Cys Thr Gly Gly
    1055             1060             1065

Cys Ala  Ala Thr Gly Cys  Cys Ala Cys Gly  Cys Cys Ala Thr
    1070             1075             1080

Cys Thr  Thr Cys Thr Thr  Cys Thr Gly Cys  Cys Thr Gly Ala
    1085             1090             1095

Thr Gly  Ala Gly Gly Gly  Ala Ala Cys Thr  Ala Cys Ala
    1100             1105             1110

Gly Cys  Ala Cys Cys Thr  Gly Ala Ala Ala  Thr Gly Ala
    1115             1120             1125

Ala Cys  Thr Cys Ala Cys  Cys Ala Cys Gly Ala  Thr Ala Thr
    1130             1135             1140

Cys Ala  Thr Cys Ala Cys  Cys Ala Ala Gly Thr  Thr Cys Cys Thr
    1145             1150             1155

Gly Gly  Ala Ala Ala Ala  Thr Gly Ala Ala Gly  Ala Cys Ala Gly
    1160             1165             1170

Ala Ala  Gly Gly Thr Cys  Thr Gly Cys Cys Ala  Gly Cys Thr Thr
    1175             1180             1185

Ala Cys  Ala Thr Thr Thr Ala  Cys Cys Ala Ala  Ala Cys Thr
    1190             1195             1200

Gly Thr  Cys Cys Ala Thr Thr  Ala Cys Thr Gly  Ala Ala Cys
    1205             1210             1215

Cys Thr  Ala Thr Gly Ala Thr  Cys Thr Gly Ala Ala  Gly Ala Gly
    1220             1225             1230

Cys Gly  Thr Cys Cys Thr Gly  Gly Gly Thr Cys Ala  Ala Cys Thr
    1235             1240             1245

Gly Gly  Gly Cys Ala Thr Cys  Ala Cys Thr Ala Ala  Gly Gly Thr
    1250             1255             1260

Cys Thr  Thr Cys Ala Gly Cys  Ala Ala Thr Gly Gly  Gly Gly Cys
    1265             1270             1275

Thr Gly  Ala Cys Cys Thr Cys  Thr Cys Cys Gly Gly  Gly Gly Thr
    1280             1285             1290

Cys Ala  Cys Ala Gly Ala Gly Gly  Ala Gly Gly Cys  Ala Cys Cys
    1295             1300             1305

Cys Cys  Thr Gly Ala Ala Gly  Cys Thr Cys Thr Cys  Cys Ala Ala
    1310             1315             1320

Gly Gly  Cys Cys Gly Thr Gly  Cys Ala Thr Ala Ala  Gly Gly Cys
    1325             1330             1335

Thr Gly  Thr Gly Cys Thr Gly  Ala Cys Cys Ala Thr  Cys Gly Ala
    1340             1345             1350

Cys Gly  Ala Gly Ala Ala Ala  Gly Gly Gly Ala Cys  Thr Gly Ala
    1355             1360             1365

Ala Gly  Cys Thr Gly Cys Thr  Gly Gly Gly Gly Cys  Cys Ala Thr
    1370             1375             1380

Gly Thr  Thr Thr Thr Thr Ala  Gly Ala Gly Gly Cys  Cys Ala Thr
    1385             1390             1395
```

```
Ala Cys Cys Cys Ala Thr Gly Thr Cys Thr Ala Thr Cys Cys Cys
    1400                1405                1410

Cys Cys Cys Cys Gly Ala Gly Gly Thr Cys Ala Ala Gly Thr Thr
    1415                1420                1425

Cys Ala Ala Cys Ala Ala Ala Cys Cys Cys Thr Thr Thr Gly Thr
    1430                1435                1440

Cys Thr Thr Cys Thr Thr Ala Ala Thr Gly Ala Thr Thr Gly Ala
    1445                1450                1455

Ala Cys Ala Ala Ala Ala Thr Ala Cys Cys Ala Ala Gly Thr Cys
    1460                1465                1470

Thr Cys Cys Cys Thr Cys Thr Thr Cys Ala Thr Gly Gly Gly
    1475                1480                1485

Ala Ala Ala Gly Thr Gly Gly Thr Gly Ala Ala Thr Cys Cys
    1490                1495                1500

Cys Ala Cys Cys Cys Ala Ala Ala Ala Thr Ala Ala Cys Thr
    1505                1510                1515

Gly Cys Cys Thr Cys Thr Cys Gly Cys Thr Cys Thr Cys Ala
    1520                1525                1530

Ala Cys Cys Cys Cys Thr Cys Cys Cys Cys Thr Cys Cys Ala Thr
    1535                1540                1545

Cys Cys Cys Thr Gly Gly Cys Cys Cys Cys Cys Thr Cys Cys Cys
    1550                1555                1560

Thr Gly Gly Ala Thr Gly Ala Cys Ala Thr Thr Ala Ala Ala Gly
    1565                1570                1575

Ala Ala Gly Gly Gly Thr Thr Gly Ala Gly Cys Thr Gly Gly Thr
    1580                1585                1590

Cys Cys Cys Thr Gly Cys Cys Thr Gly Cys Ala Ala Ala Ala
    1595                1600                1605

<210> SEQ ID NO 59
<211> LENGTH: 12222
<212> TYPE: DNA
<213> ORGANISM: Homo sapiens
<220> FEATURE:
<221> NAME/KEY: misc_feature
<223> OTHER INFORMATION: K02212; Human alpha-1-antitrypsin gene
      (S variant); complete cds

<400> SEQUENCE: 59
gaattccagg ttggaggggc ggcaacctcc tgccagcctt caggccactc tcctgtgcct      60
gccagaagag acagagcttg aggagagctt gaggagagca ggaaaggtgg aacattgctg    120
ctgctgctca ctcagttcca caggtgggag gaacagcagg gcttagagtg ggggtcattg    180
tgcagatggg aaaacaaagg cccagagagg ggaagaaatg cctaggagct accgagggca    240
ggcgacctca accacagccc agtgctggag ctgtgagtgg atgtagagca gcggaatatc    300
cattcagcca gctcagggga aggacagggg ccctgaagcc aggggatgga gctgcaggga    360
agggagctca gagagaaggg gaggggagtc tgagctcagt ttcccgctgc ctgaaaggag    420
ggtggtacct actcccttca cagggtaact gaatgagaga ctgcctggag gaaagctctt    480
caagtgtggc ccaccccacc ccagtgacac cagcccctga cacgggggag ggagggcagc    540
atcaggaggg gctttctggg cacacccagt acccgtctct gagctttcct tgaactgttg    600
cattttaatc ctcacagcag ctcaacaagg tacataccgt caccatcccc attttacaga    660
tagggaaatt gaggctcgga gcggttaaac aactcacctg aggcctcaca gccagtaagt    720
gggttccctg gtctgaatgt gtgtgctgga ggatcctgtg ggtcactcgc ctggtagagc    780
```

```
cccaaggtgg aggcataaat gggactggtg aatgacagaa ggggcaaaaa tgcactcatc    840
cattcactct gcaagtatct acggcacgta cgccagctcc caagcaggtt tgcgggttgc    900
acagcggagc gatgcaatct gatttaggct tttaaaggat tgcaatcaag tgggacccac    960
tagcctcaac cctgtacctc ccctcccctc caccccagc agtctccaaa ggcctccaac    1020
aaccccagag tgggggccat gtatccaaag aaactccaag ctgtatacgg atcacactgg    1080
ttttccagga gcaaaaacag aaacagcctg aggctggtca aaattgaacc tcctcctgct    1140
ctgagcagcc tagggggcag actaagcaga gggctgtgca gacccacata aagagcctac    1200
tgtgtgccag gcacttcacc cgaggcactt cacaagcatg cttgggaatg aaacttccaa    1260
ctctttggga tgcaggtgaa acagttcctg gttcagagag gtgaagcggc ctgcctgagg    1320
cagcacagct cttctttaca gatgtgcttc cccacctcta ccctgtctca cggcccccca    1380
tgccagcctg acggttgtgt ctgcctcagt catgctccat ttttccatcg ggaccatcaa    1440
gagggtgttt gtgtctaagg ctgactgggt aactttggat gagcggtctc tccgctccga    1500
gcctgtttcc tcatctgtca acgggctct aacccactct gatctcccag gcggcagta    1560 agtcttcagc atcaggcatt tgggggtgac tcagtaaatg gtagatcttg ctaccagtgg    1620
aacagccact aaggattctg cagtgagagc agagggccag ctaagtggta ctctcccaga    1680
gactgtctga ctcacgccac cccctccacc ttggacacag gacgctgtgg tttctgagcc    1740
aggtacaatg actcctttcg gtaagtgcag tggaagctgt acactgccca ggcaaagcgt    1800
ccgggcagcg taggcgggcg actcagatcc cagccagtgg acttagcccc tgtttgctcc    1860
tccgataact ggggtgacct tggttaatat tcaccagcag cctcccccgt tgcccctctg    1920
gatccactgc ttaaatacgg acgaggacag ggcctgtctc cctcagcttc aggcaccacc    1980
actgacctgg gacagtgaat cgtaagtatg cctttcactg cgagggttc tggagaggct    2040 tccgagctcc ccatggccca ggcaggcagc aggtctgggg caggaggggg gttgtggagt    2100
gggtatccgc ctgctgaggt gcagggcaga tggagaggct gcagctgagc tcctatttc    2160 ataataacag cagccatgag ggttgtgtcc tgtttcccag tcctgcccgg tcccccctcg    2220
gtacctcctg gtggatacac tggttcctgt aagcagaagt ggatgagggt gtctaggtct    2280
gcagtcctgg caccccagga tgggggacac cagccaagat acagcaacag caacaaagcg    2340
cagccatttc tttctgtttg cacagctcct ctgtctgtcg ggggctcctg tctgttgtct    2400
cctataagcc tcaccacctc tcctactgct tgggcatgca tctttctccc cttctataga    2460
tgaggaggtt aaggttcaga gagggtggg gaggaacgcc ggctcacatt ctccatcccc    2520
tccagatatg accaggaaca gacctgtgcc agcctcagcc ttacatcaaa atgggcctcc    2580
ccatgcaccg tggacctctg ggccctcctg tcccagtgga ggacaggaag ctgtgagggg    2640
cactgtcacc cagggctcaa gctggcattc ctgaataatc gctctgcacc aggccacggc    2700
taagctcagt gcgtgattaa gcctcataac cctccaaggc agttactagt gtgattccca    2760
ttttacagat gaggaagatg gggacagaga ggtgaataac tggccccaaa tcacacacca    2820
tccataattc gggctcaggc acctggctcc agtcccaaa ctcttgaacc tggccctagt    2880
gtcactgttt ctcttgggtc tcaggcgctg gatgggaac aggaaacctg gctgaactt    2940 gaggcctctc tgatgctcgg tgacttcaga cagttgctca acctctctgt tctcttgggc    3000
aaaacatgat aacctttgac ttctgtcccc tcccctcacc ccacccgacc ttgatctctg    3060
aagtgttgga aggatttaat ttttcctgca ctgagttttg gagacaggtc aaaaagatga    3120
ccaaggccaa ggtggccagt ttcctataga acgcctctaa aagacctgca gcaatagcag    3180
```

```
caagaactgg tattctcgag aacttgctgc gcagcaggca cttcttggca ttttatgtgt   3240
atttaatttc acaatagctc tatgacaaag tccacctttc tcatctccag gaaactgagg   3300
ttcagagagg ttaagtaact tgtccaaggt cacacagcta atagcaagtt gacgtggagc   3360
aatctggcct cagagccttt aattttagcc acagactgat gctcccctct tcatttagcc   3420
aggctgcctc tgaagttttc tgattcaaga cttctggctt cagctttgta cacagagatg   3480
attcaatgtc aggttttgga gcgaaatctg tttaatccca gacaaaacat ttaggattac   3540
atctcagttt tgtaagcaag tagctctgtg attttagtg agttatttaa tgctctttgg    3600
ggctcaattt ttctatctat aaatagggc taataatttg cacctatag ggtaagcttt     3660 gaggacagat tagatgatac ggtgcctgta aaacaccagg tgttagtaag tgtggcaatg   3720
atggtgacgc tgaggctgtg tttgcttagc atagggttag gcagctggca ggcagtaaac   3780
agttggataa tttaatggaa aatttgccaa actcagatgc tgttcactgc tgagcaggag   3840 cccccttcctg ctgaaatggt cctggggagt gcagcaggct ctccgggaag aaatctacca  3900
tctctcgggc aggagctcaa cctgtgtgca ggtacaggga gggcttcctc acctggtgcc   3960
cactcatgca ttacgtcagt tattcctcat ccctgtccaa aggattcttt tctccattgt   4020
acagctatga agctagtgct caaagaagtg aagtcattta ccccaggccc cctgccagta   4080
agtgacaggg cctggtcaca cttgggttta tttattgccc agttcaacag gttgtttgac   4140
cataggcgag attctcttcc ctgcaccctg ccgggttgct cttggtccct tattttatgc   4200
tcctgggtag aaatggtgcg agattaggca gggagtggac gcttcctgt ccctggcccc    4260 gcaaagagtg ctcccacctg ccccgatccc agaaatgtca ccatgaagcc ttcattcttt   4320
tggtttaaag cttggcctca gtgtccgtac accatgggt ccttggccag atggcgactt    4380
tctcctctcc agtcgccctc ccaggcacta gcttttagga gtgcagggtg ctgcctctga   4440
tagaagggcc aggagagagc aggttttgga gacctgatgt tataaggaac agcttgggag   4500
gcataatgaa cccaacatga tgcttgagac caatgtcaca gcccaattct gacattcatc   4560
atctgagatc tgaggacaca gctgtctcag ttcatgatct gagtgctggg aaagccaaga   4620
cttgttccag ctttgtcact gacttgctgt atagcctcaa caaggccctg accctctctg   4680
ggcttcaaac tcttcactgt gaaaggagga aaccagagta ggtgatgtga caccaggaaa   4740
gatggatggg tgtgggggaa tgtgctcctc ccagctgtca ccccctcgcc accctccctg   4800
caccagcctc tccacctcct ttgagcccag aattcccctg tctaggaggg cacctgtctc   4860
gtgcctagcc atgggaattc tccatctgtt ttgctacatt gaaccagat gccattctaa    4920 ccaagaatcc tggctgggtg caggggctct cgcctgtaac cccagcactt tgggaggcca   4980
aggcaggcga atcaagaggt caggagttca agacctgcct ggccaacacg gtgaaacctc   5040
agctctacta aaaatacaaa aattagccag gcgtggtggc acacgcctgt aatcccagct   5100
atttgggaag ctgagacaga agaatttctt gaacccggga ggtggaggtt tcagtgagcc   5160
gagatcacgc cactgcactc caccctggcg gataaagcga gactctgtct caaaaaaaac   5220
ccaaaaacct atgttagtgt acagagggcc ccagtgaagt cttctcccag ccccactttg   5280
cacaactggg gagagtgagg ccccaggacc agaggattct tgctaaaggc caagtggata   5340
gtgatggccc tgccaggcta gaagcccaca ccctctggcc tgaggccact cagcatattt   5400
agtgtcccca ccctgcagag gcccaactcc ctcctgacca ctgagccctg taatgatggg   5460
ggaatttcca taagccatga aggactgcac aaagttcagt tgggagtgaa agagaaatta   5520
aagggagatg gaaatataca gcactaattt tagcaccgtc ttcagttcta acaacactag   5580
```

```
ctagctgaag aaaatacaaa catgtattat gtaatgtgtg gtctgttcca tttggattac   5640
ttagaggcac gagggccaag gagaaaggtg gtggagagaa accagctttg cacttcattt   5700
gttgctttat tggaaggaaa cttttaaaag tccaagggg ttgaagaatc tcaatatttg    5760
ttatttccag ctttttttct ccagttttc atttcccaaa ttcaaggaca ccttttctt     5820 tgtattttgt taagatgatg gttttggttt tgtgactagt agttaacaat gtggctgccg   5880
ggcatattct cctcagctag gacctcagtt ttcccatctg tgaagacggc aggttctacc   5940 taggggctg caggcaggtg gtccgaagcc tgggcatatc tggagtagaa ggatcactgt    6000
ggggcagggc aggttctgtg ttgctgtgga tgacgttgac tttgaccatt gctcggcaga   6060
gcctgctctc gctggttcag ccacaggccc caccactccc tattgtctca gccccgggta   6120
tgaaacatgt attcctcact ggcctatcac ctgaagcctt tgaatttgca acacctgcca   6180
acccctccct caaaagagtt gccctctcta gatccttttg atgtaaggtt tggtgttgag   6240
acttatttca ctaaattctc atacataaac atcactttat gtatgaggca aaatgaggac   6300
cagggagatg aatgacttgt cctggctcat acacctggaa agtgacagag tcagattaga   6360
tcctaggtct atctgaagtt aaaagaggtg tcttttcact tcccacctcc tccatctact   6420
ttaaagcagc acaaacccct gctttcaagg agagatgagc gtctctaaag cccctgacag   6480
caagagccca gaactgggac accattagtg acccagacgg caggtaagct gactgcagga   6540
gcatcagcct attcttgtgt ctgggaccac agagcattgt ggggacagcc ccgtctcttg   6600
ggaaaaaaac cctaagggct gaggatcctt gtgagtgttg ggtgggaaca gctcccagga   6660
ggtttaatca cagcccctcc atgctctcta gctgttgcca ttgtgcaaga tgcatttccc   6720
ttctgtgcag cagtttccct ggccactaaa tagtgggatt agatagaagc cctccaaggg   6780
ctccagcttg acatgattct tgattctgat ctgacccgat tctgataatc gtgggcaggc   6840
ccattcctct tcttgtgcct cattttcttc ttttgtaaaa caatggctgt accatttgca   6900
tcttagggtc attgcagatg aaagtgttgc tgtccagagc ctgggtgcag gacctagatg   6960
taggattctg gttctgctac ttcctcagtg acattgaata gctgacctaa tctctctggc   7020 tttggttct tcatctgtaa aagaaggata ttagcattag cacctcacgg gattgttaca    7080
agaaagcaat gaattaacac atgtgagcac ggagaacagt gcttggcata tggtaagcac   7140
tacgtacatt ttgctattct tctgattctt tcagtgttac tgatgtcggc aagtacttgg   7200
cacaggctgg tttaataatc cctaggcact ttcacgtggt gtcaatccct gatcactggg   7260
agtcatcatg tgccttgact cgggcctggc cccccatct ctgtcttgca ggacaatgcc    7320
gtcttctgtc tcgtggggca tcctcctgct ggcaggcctg tgctgcctgg tccctgtctc   7380
cctggctgag gatccccagg gagatgctgc ccagaagaca gatacatccc accatgatca   7440
ggatcaccca accttcaaca agatcacccc caacctggct gagttcgcct tcagcctata   7500
ccgccagctg gcacaccagt ccaacagcac caatatcttc ttctccccag tgagcatcgc   7560
tacagccttt gcaatgctct ccctggggac caaggctgac actcacgatg aaatcctgga   7620
gggcctgaat ttcaacctca cggagattcc ggaggctcag atccatgaag gcttccagga   7680
actcctccgt accctcaacc agccagacag ccagctccag ctgaccaccg gcaatggcct   7740
gttcctcagc gagggcctga agctagtgga taagttttg gaggatgtta aaagttgta    7800 ccactcagaa gccttcactg tcaacttcgg ggacaccgaa gaggccaaga acagatcaa    7860 cgattacgtg gagaagggta tcaagggaa aattgtggat ttggtcaagg agcttgacag    7920
agacacagtt tttgctctgg tgaattacat cttcttaaa ggtaaggttg ctcaaccagc    7980
```

```
ctgagctgtt tcccatagaa acaagcaaaa atatttctca aaccatcagt tcttgaactc    8040
tccttggcaa tgcattatgg gccatagcaa tgcttttcag cgtggattct tcagttttct    8100
acacacaaac actaaaatgt tttccatcat tgagtaattt gaggaaataa tagattaaac    8160
tgtcaaaact actgacgctc tgcagaactt ttcagagcct ttaatgtcct tgtgtatact    8220
gtatatgtag aatatataat gcttagaact atagaacaaa ttgtaataca ctgcataaag    8280
ggatagtttc atggaacata ctttacacga ctcagtgtc ccagaatcag tatcagtttt     8340
gcaatctgaa agacctgggt tcaaatcctg cctctaacac aattagcttt tgacaaaaac    8400
aatgcattct acctctttga ggtgctaatt tctcatctta gcatggacaa aataccattc    8460
ttgctgtcag gttttttag gattaaacaa atgacaaaga ctgtggggat ggtgtgtggc     8520
atacagcagg tgatggactc ttctgtatct caggctgcct tcctgcccct gaggggttaa    8580
aatgccaggg tcctggggggc cccagggcat tctaagccag ctcccactgt cccaggaaaa   8640
cagcataggg gaggggaggt gggaggcaag gccagggct gcttcctcca ctctgaggct     8700
cccttgctct tgaggcaaag gagggcagtg gaggcaagcc aggctgcagt cagcacagct    8760
aaagtcctgg ctctgctgtg gccttagtgg gggcccaggt ccctctccag ccccagtctc    8820
ctccttctgt ccaatgagaa agctgggatc aggggtccct gaggcccctg tccactctgc    8880
atgcctcgat ggtgaagctc tgttggtatg gcagagggga ggctgctcag gcatctgcat    8940
ttcccctgcc aatctagagg atgaggaaag ctctcaggaa tagtaagcag aatgtttgcc    9000
ctggatgaat aactgagctg ccaattaaca aggggcaggg agccttagac agaaggtacc    9060
aaatatgcct gatgctccaa cattttattt gtaatatcca agacaccctc aaataaacat    9120
atgattccaa taaaaatgca cagccacgat ggcatctctt agcctgacat cgccacgatg    9180
tagaaattct gcatcttcct ctagttttga attatcccca cacaatcttt ttcggcagct    9240
tggatggtca gtttcagcac cttttacaga tgatgaagct gagcctcgag ggatgtgtgt    9300
cgtcaagggg gctcagggct tctcagggag gggactcatg gtttcttatt ctgctacact    9360
cttccaaacc ttcactcacc cctggtgatg cccaccttcc cctctctcca ggcaaatggg    9420
agagacccctt tgaagtcaag gacaccgagg aagaggactt ccacgtggac caggtgacca    9480
ccgtgaaggt gcctatgatg aagcgtttag gcatgtttaa catccagcac tgtaagaagc    9540
tgtccagctg ggtgctgctg atgaaatacc tgggcaatgc caccgccatc ttcttcctgc    9600
ctgatgaggg gaaactacag cacctggtaa atgaactcac ccacgatatc atcaccaagt    9660
tcctggaaaa tgaagacaga aggtgattcc ccaacctgag ggtgaccaag aagctgccca    9720
cacctcttag ccatgttggg actgaggccc atcaggactg ccagagggc tgaggagggt     9780
gaacccccaca tccctgggtc actgctactc tgtataaact tggcttccag aatgaggcca    9840
ccactgagtt caggcagcgc cgtccatgct ccatgaggag aacagtaccc agggtgagga    9900
ggtaaaggtc tcgtccctgg gaacttccca ctccagtgtg gacactgtcc cttcccaata    9960
tccagtgccc aaggcaggga cagcagcacc accacacgtt ctggcagaac caaaaaggaa   10020
cagatggct tcctggcaaa ggcagcagtg gagtgtggaa ttcaagggta gaatgtccct    10080
ggggggacgg gggaagagcc tgtgtggcaa ggcccagaaa agcaaggttc ggaattggaa   10140
cagccaggcc atgttcgcag aaggcttgcg tttctctgtc actttatcgg tgctgttaga   10200
ttgggtgtcc tgtagtaagt gatacttaaa catgagccac acattagtgt atgtgtgtgc   10260
attcgtgatt atgcccatgc cctgctgatc tagttcgttt tgtacactgt aaaaccaaga   10320
tgaaaataca aaggtgtcg ggttcataat aggaatcgag gctggaattt ctctgttcca   10380
```

```
tgccagcacc tcctgaggtc tctgctccag gggttgagaa agaacaaaga ggctgagagg     10440
gtaacggatc agagagccca gagccagctg ccgctcacac cagaccctgc tcagggtggc     10500
attgtctccc catggaaaac cagagaggag cactcagcct ggtgtggtca ctcttctctt     10560
atccactaaa cggttgtcac tgggcactgc caccagcccc gtgtttctct gggtgtaggg     10620
ccctggggat gttacaggct gggggccagg tgacccaaca ctacagggca agatgagaca     10680
ggcttccagg acacctagaa tatcagagga ggtggcattt caagcttttg tgattcattc     10740
gatgttaaca ttctttgact caatgtagaa gagctaaaag tagaacaaac caaagccgag     10800
ttcccatctt agtgtgggtg gaggacacag gagtaagtgg cagaaataat cagaaaagaa     10860
aacacttgca ctgtggtggg tcccagaaga acaagaggaa tgctgtgcca tgccttgaat     10920
ttcttttctg cacgacaggt ctgccagctt acatttaccc aaactgtcca ttactggaac     10980
ctatgatctg aagagcgtcc tgggtcaact gggcatcact aaggtcttca gcaatggggc     11040
tgacctctcc ggggtcacag aggaggcacc cctgaagctc tccaaggtga gatcaccctg     11100
acgaccttgt tgcaccatgg tatctgtagg gaagaatgtg tggggctgc agcactgtcc       11160 tgaggctgag gaaggggccg agggaaacaa atgaagaccc aggctgagct cctgaagatg     11220
cccgtgattc actgacacgg gacggtgggc aaacagcaaa gccaggcagg ggctgctgtg     11280
cagctggcac tttcggggcc tcccttgagg ttgtgtcact gaccctgaat ttcaactttg     11340
cccaagacct tctagacatt gggccttgat ttatccatac tgacacagaa aggtttgggc     11400
taagttgttt caaaggaatt tctgactcct tcgatctgtg agatttggtg tctgaattaa     11460
tgaatgattt cagctaaagt gacacttatt ttggaaaact aaaggcgacc aatgaacaac     11520
ctgcagttcc atgaatggct gcattatctt ggggtctggg cactgtgaag gtcactgcca     11580
gggtccgtgt cctcaaggag cttcaagccg tgtactagaa aggagagagc cctggaggca     11640
gacgtggagt gacgatgctc ttccctgttc tgagttgtgg gtgcacctga gcaggggag      11700 aggcgcttgt caggaagatg gacagagggg agccagcccc atcagccaaa gccttgagga     11760
ggagcaaggc ctatgtgaca gggagggaga ggatgtgcag ggccagggcc gtccagggg     11820 agtgagcgct tcctgggagg tgtccacgtg agccttgctc gaggcctggg atcagcctta     11880
caacgtgtct ctgcttctct cccctccagg ccgtgcataa ggctgtgctg accatcgacg     11940
agaaagggac tgaagctgct ggggccatgt ttttagaggc cataccgatg tctatccccc     12000
ccgaggtcaa gttcaacaaa ccctttgtct tcttaatgat tgaacaaaat accaagtctc     12060
ccctcttcat gggaaaagtg gtgaatccca cccaaaaata actgcctctc gctcctcaac     12120
ccctcccctc catccctggc cccctccctg gatgacatta agaagggtt gagctggtcc       12180 ctgcctgcat gtgatctgta aatccctggg atgttttctc tg                         12222
```

<210> SEQ ID NO 60
<211> LENGTH: 381
<212> TYPE: PRT
<213> ORGANISM: Homo sapiens
<220> FEATURE:
<221> NAME/KEY: MISC_FEATURE
<223> OTHER INFORMATION: gi/125294, P12277; Creatine kinase, B chain (B-CK)

<400> SEQUENCE: 60

Met Pro Phe Ser Asn Ser His Asn Ala Leu Lys Leu Arg Phe Pro Ala
1               5                   10                  15

Glu Asp Glu Phe Pro Asp Leu Ser Ala His Asn Asn His Met Ala Lys
            20                  25                  30

Val Leu Thr Pro Glu Leu Tyr Ala Glu Leu Arg Ala Lys Ser Thr Pro
            35                  40                  45

Ser Gly Phe Thr Leu Asp Asp Val Ile Gln Thr Gly Val Asp Asn Pro
 50                  55                  60

Gly His Pro Tyr Ile Met Thr Val Gly Cys Val Ala Gly Asp Glu Glu
 65                  70                  75                  80

Ser Tyr Glu Val Phe Lys Asp Leu Phe Asp Pro Ile Ile Glu Asp Arg
                85                  90                  95

His Gly Gly Tyr Lys Pro Ser Asp Glu His Lys Thr Asp Leu Asn Pro
               100                 105                 110

Asp Asn Leu Gln Gly Gly Asp Asp Leu Asp Pro Asn Tyr Val Leu Ser
           115                 120                 125

Ser Arg Val Arg Thr Gly Arg Ser Ile Arg Gly Phe Cys Leu Pro Pro
       130                 135                 140

His Cys Ser Arg Gly Glu Arg Arg Ala Ile Glu Lys Leu Ala Val Glu
145                 150                 155                 160

Ala Leu Ser Ser Leu Asp Gly Asp Leu Ala Gly Arg Tyr Tyr Ala Leu
                165                 170                 175

Lys Ser Met Thr Glu Ala Glu Gln Gln Gln Leu Ile Asp Asp His Phe
                180                 185                 190

Leu Phe Asp Lys Pro Val Ser Pro Leu Leu Leu Ala Ser Gly Met Ala
            195                 200                 205

Arg Asp Trp Pro Asp Ala Arg Gly Ile Trp His Asn Asp Asn Lys Thr
        210                 215                 220

Phe Leu Val Trp Val Asn Glu Glu Asp His Leu Arg Val Ile Ser Met
225                 230                 235                 240

Gln Lys Gly Gly Asn Met Lys Glu Val Phe Thr Arg Phe Cys Thr Gly
                245                 250                 255

Leu Thr Gln Ile Glu Thr Leu Phe Lys Ser Lys Asp Tyr Glu Phe Met
            260                 265                 270

Trp Asn Pro His Leu Gly Tyr Ile Leu Thr Cys Pro Ser Asn Leu Gly
        275                 280                 285

Thr Gly Leu Arg Ala Gly Val His Ile Lys Leu Pro Asn Leu Gly Lys
    290                 295                 300

His Glu Lys Phe Ser Glu Val Leu Lys Arg Leu Arg Leu Gln Lys Arg
305                 310                 315                 320

Gly Thr Gly Gly Val Asp Thr Ala Ala Val Gly Gly Val Phe Asp Val
                325                 330                 335

Ser Asn Ala Asp Arg Leu Gly Phe Ser Glu Val Glu Leu Val Gln Met
            340                 345                 350

Val Val Asp Gly Val Lys Leu Leu Ile Glu Met Glu Gln Arg Leu Glu
        355                 360                 365

Gln Gly Gln Ala Ile Asp Asp Leu Met Pro Ala Gln Lys
    370                 375                 380

<210> SEQ ID NO 61
<211> LENGTH: 1431
<212> TYPE: DNA
<213> ORGANISM: Homo sapiens
<220> FEATURE:
<221> NAME/KEY: misc_feature
<223> OTHER INFORMATION: NM_001823; creatine kinase, brain (CKB); mRNA;
      Creatine kinase, B chain (B-CK)

<400> SEQUENCE: 61
gctgttcgcc tgcgtcgctc cgggagctgc cgacggacgg agcgcccccg cccccgcccg    60

| | |
|---|---|
| gccgcccgcc cgccgccgcc atgcccttct ccaacagcca caacgcactg aagctgcgct | 120 |
| tcccggccga ggacgagttc cccgacctga gcgcccacaa caaccacatg gccaaggtgc | 180 |
| tgaccccccga gctgtacgcg gagctgcgcg ccaagagcac gccgagcggc ttcacgctgg | 240 |
| acgacgtcat ccagacaggc gtggacaacc cgggccaccc gtacatcatg accgtgggct | 300 |
| gcgtggcggg cgacgaggag tcctacgaag tgttcaagga tctcttcgac cccatcatcg | 360 |
| aggaccggca cggcggctac aagcccagcg atgagcacaa gaccgacctc aaccccgaca | 420 |
| acctgcaggg cggcgacgac ctggacccca actacgtgct gagctcgcgg gtgcgcacgg | 480 |
| gccgcagcat ccgtggcttc tgcctccccc cgcactgcag ccgcggggag cgccgcgcca | 540 |
| tcgagaagct cgcggtggaa gccctgtcca gcctggacgg cgacctggcg ggccgatact | 600 |
| acgcgctcaa gagcatgacg gaggcggagc agcagcagct catcgacgac cacttcctct | 660 |
| tcgacaagcc cgtgtcgccc ctgctgctgg cctcgggcat ggcccgcgac tggcccgacg | 720 |
| cccgcggtat ctggcacaat gacaataaga ccttcctggt gtgggtcaac gaggaggacc | 780 |
| acctgcgggt catctccatg cagaagggggg gcaacatgaa ggaggtgttc acccgcttct | 840 |
| gcaccggcct cacccagatt gaaactctct tcaagtctaa ggactatgag ttcatgtgga | 900 |
| accctcacct gggctacatc ctcacctgcc catccaacct gggcaccggg ctgcgggcag | 960 |
| gtgtgcatat caagctgccc aacctgggca agcatgagaa gttctcggag gtgcttaagc | 1020 |
| ggctgcgact tcagaagcga ggcacaggcg gtgtggacac ggctgcggtg ggcggggtct | 1080 |
| tcgacgtctc caacgctgac cgcctgggct tctcagaggt ggagctggtg cagatggtgg | 1140 |
| tggacggagt gaagctgctc atcgagatgg agcagcggct ggagcagggc caggccatcg | 1200 |
| acgacctcat gcctgcccag aaatgaagcc cggcccacac ccgacaccag ccctgctgct | 1260 |
| tcctaactta ttgcctgggc agtgcccacc atgcacccct gatgttcgcc gtctggcgag | 1320 |
| cccttagcct tgctgtagag acttccgtca cccttggtag agtttatttt tttgatggct | 1380 |
| aagatactgc tgatgctgaa ataaactagg gttttggcct gcctgcgtct g | 1431 |

<210> SEQ ID NO 62
<211> LENGTH: 4200
<212> TYPE: DNA
<213> ORGANISM: Homo sapiens
<220> FEATURE:
<221> NAME/KEY: misc_feature
<223> OTHER INFORMATION: X15334; Human gene for creatine kinase B
      (EC 2.7.3.2)

<400> SEQUENCE: 62

| | |
|---|---|
| gatcagtttt ttttttttaat cgcacttatg cttattgttt attagcgttt cctcccatct | 60 |
| ttgcctgaag tctccgggga ctgcctttgg gggtcgggta aacttgtccc ctgcgaagag | 120 |
| ggcccagggt tggggtctgg aaactccgag gctgcacttg ccagcggcct cttaaggcca | 180 |
| cagcgtcccc gtggtttctg gctcgcagcc ccccgagacc caggacttgt ccaaggtcag | 240 |
| ggcaccgcgg gtgccccccgg gctgggccgc agcagactgc gcttcccgcg cgccttcgct | 300 |
| ttgcaccagg atcgcccagg aaatgcctgc gggcaccttg aggaaggtcg gcggctccgg | 360 |
| gccagctcgc actggccggg gtggggcggg ggccgtacct gctgcggaag ccccgaaagc | 420 |
| tttcgccccgg cccctcgccg ccgccgcggg ggctggctgg actaggcggg caggctcgag | 480 |
| gatgcggatg aacccaagcg tcctcgagtg cccggaggct ctccgcctca gtttcccgcc | 540 |
| cagaggcaag ggcgtgcgag gggatccaga tatccaagga cctgaggttt cggcctcgag | 600 |
| gtcttgggcg ggggactggg caggctgcgc ggggtcccag cgaggggaca gctcgggtgg | 660 |

-continued

```
gcggccaggg tgttgggggc tgcgggcggc ggacaaagcg gcggcaccac cccgcggcgc    720
gggccaatgg aatgaatggg ctataaatag ccgccaatgg gcggcccgcg ttgtgcccct    780
taagagccgc gggagcgcgg agcggccgct gttcgcctgc gtcgctccgg gagctgccga    840
cggacggagc gcccccgccc ccgcccgccc gcccggtgag tgggcccggg ggccgggggc    900
gtccgcgccc gggctagggg cgctgcgagc aaaggggggcg cgtcgcctgg agcgcgcgcc    960
ggaccggccg ggggtccccg gcgatgatgg cgctccccgc gcgcgctgcg gaccccgctg   1020
accttggccg cgtcccgggg ggcgccgggg ggcccggcgg cggggggcctg agtggtacgc   1080 gggagcccgg gaaccccggc gtgccggtcc cctctgaccc cgcgtctccc cgcagcccgc   1140
cgccgccatg cccttctcca acagccacaa cgcactgaag ctgcgcttcc cggccgagga   1200
cgagttcccc gacctgagcg cccacaacaa ccacatggcc aaggtgctga ccccccgagct   1260 gtacgcggag ctgcgcgcca agagcacgcc gagcggcttc acgctggacg acgtcatcca   1320
gacaggcgtg gacaacccgg gtacgcgacc cctcggggcc ggggtcccgg cccccccctcc   1380 ccccgcgcag ccgcagggtc ctcagcagcg cgctcggggcc cggcagtgac gtcactgtcc   1440
ccgtcccgcg cccccctcccc caggccaccc gtacatcatg accgtgggct gcgtggcggg   1500
cgacgaggag tcctacgaag tgttcaagga tctcttcgac cccatcatcg aggaccggca   1560
cggcggctac aagcccagcg atgagcacaa gaccgacctc aaccccgaca acctgcaggt   1620
gcggggctgc gggcgggccg ggcgggcggg gccggggtct tcgggcgctc actcccgtct   1680
cgcctcccag ggcggcgacg acctggaccc caactacgtg ctgagctcgc gggtgcgcac   1740
gggccgcagc atccgtggct tctgcctccc cccgcactgc agccgcgggg agcgccgagc   1800
catcgagaag ctcgcggtgg aaggtagggg ccggggcggg gcgaggggcgg cggcggccgc   1860 gtccccctcc cggcgcggtc cccgcccgct tttgtttacg tcgcccggga gcggcagccg   1920
ccgtcgcgct cttatctgcg cgcgcccggg ttcagttttcc cggacccacc gagggacgga   1980
ggcccagccc ccgcgcccac agcggcctgg ggcccaggga gggcgggtcc tggcgcgggg   2040
tcaccgcctg ggaccgtcgc ccggggccgtg aggactggac gcccgcagat ccgggcgggt   2100 ggggcccctct gacgtccccc gaggtggggc acggggggcgg gcgggtccgc gctgcgggct   2160
ggaggggcgg gcgcgggagc ccagcgtcct gagcgcaccc ctcgcagccc tgtccagcct   2220
ggacggcgac ctggcggggcc gatactacgc gctcaagagc atgacggagg cggagcagca   2280
gcagctcatc gacgaccact tcctcttcga caagcccgtg tcgcccctgc tgctggcctc   2340
gggcatggcc cgcgactggc ccgacgcccg cggtatctgg tgcgtgtccc tctgcgccct   2400
ctcgcggcgt cctccctccc cgctacctcc gctttccctc tcgcccccct cgcgggggtg   2460 gggccctcg cggcgaggag gaggaggagg aggaggggagg ggccggccgc gctccgggtc   2520
tgggttccgt gccgcgcctc ctcctgcgcc ggtgaccttg gccgagcagg tgcgttaagg   2580
gactgggccc cggcccgtgg gggctcagga ctcagcaaca cctccccacc ccgagacgtg   2640
aggtgggggc ggggctctct ggcgcctctc cccgacggcc ctgggagctg gagctctttg   2700 ttttctttctc tcactcctcc gccgctggga ttctaccagg ggctggtgac gccaaagctt   2760 ctccagggggc agggctccta ccccccactgt gggggggcggg tcgggctgtc ctggcggtcc   2820
ctggccccgc ccacctcgg gccacagcgc atgatggcag ctggggttct cctgctgtga   2880 ggcgtccgg ttcccccgcc cgccccgtgt tggcgggtgg agtcttggca gcagcctcca   2940
ctcctgggca tggcagggag cagcacctca gggacttggg aagttccttt ggtctggggg   3000
cggcctgggg cttttttctg ggtatgccct gagaccagcc ctcccgcagg cacaatgaca   3060
```

```
ataagacctt cctggtgtgg gtcaacgagg aggaccacct gcgggtcatc tccatgcaga   3120 agggggggcaa catgaaggag gtgttcaccc gcttctgcac cggcctcacc caggtgccag   3180
ggacggggca ggcccagacc ccagggcccc agcagggatg tgggtgcccc agcatcagtc   3240 cccccgggg atttccggca ctggggagtc tcagggcctg taggggtttc aggcaggcct   3300
tctccctcat accctcttct ccgtctgcag attgaaactc tcttcaagtc taaggactat   3360
gagttcatgt ggaaccctca cctgggctac atcctcacct gcccatccaa cctgggcacc   3420
gggctgcggg caggtgtgca tatcaagctg cccaacctgg gcaagcatga aagttctcg   3480 gaggtgctta agcggctgcg acttcagaag cgaggcacag gtgagcaggg caggtgctgc   3540
ggcttcccgt ggcctttggg cagccctgtt cctccgccc tgacttgctg tctccccagg   3600
cggtgtggac acggctgcgg tgggcggggt cttcgacgtc tccaacgctg accgcctggg   3660
cttctcagag gtggagctgg tgcagatggt ggtggacgga gtgaagctgc tcatcgagat   3720
ggaacagcgg ctggagcagg gccaggccat cgacgacctc atgcctgccc agaaatgaag   3780
cccggcccac acccgacacc agccctgctg cttcctaact tattgcctgg gcagtgccca   3840
ccatgcaccc ctgatgttcg ccgtctggcg agcccttagc cttgctgtag agacttccgt   3900 caccttggt agagtttatt tttttgatgg ctaagatact gctgatgctg aaataaacta   3960
gggttttggc ctgcctgcgt ctgagtggtg cctctccttt cccaggggggg agggggaagg   4020 gcagcagcca ggcccagga gtcttgagtc ctgggcctgc tgtgggcctc gccttctgtg   4080
agatgggaca agagccagga ggtggccact ctgttctgcc tgccctacct agtccatggg   4140 cccctccct cgtgtctatc gggctgtgca ggcaggaaca tgggagagag cgagggagga   4200
```

<210> SEQ ID NO 63
<211> LENGTH: 531
<212> TYPE: PRT
<213> ORGANISM: Homo sapiens
<220> FEATURE:
<221> NAME/KEY: MISC_FEATURE
<223> OTHER INFORMATION: P14618; Pyruvate kinase M1 or M2 isozyme

<400> SEQUENCE: 63

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val

```
                165                 170                 175
Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
            195                 200                 205

Val Asn Leu Pro Gly Ala Ala Val Asp Leu Pro Ala Val Ser Glu Lys
            210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
            275                 280                 285

Gly Ile Met Val Ala Arg Gly Asp Leu Gly Ile Glu Ile Pro Ala Glu
            290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
            355                 360                 365

Asp Tyr Pro Leu Glu Ala Val Arg Met Gln His Leu Ile Ala Arg Glu
            370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
                405                 410                 415

Val Glu Ala Ser Phe Lys Cys Cys Ser Gly Ala Ile Ile Val Leu Thr
            420                 425                 430

Lys Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
            450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
            515                 520                 525

Pro Val Pro
        530

<210> SEQ ID NO 64
<211> LENGTH: 10368
<212> TYPE: DNA
<213> ORGANISM: Homo sapiens
<220> FEATURE:
<221> NAME/KEY: misc_feature
<223> OTHER INFORMATION: X56494; M gene for M1-type and M2-type pyruvate
      kinase
```

```
<400> SEQUENCE: 64
ggtcttcaca ttttgaatgc gcaacattgt atctgtgaat gaaggcaaga gttaacagct      60
gtttaattga taactgctcg catcattagt tgctggctaa caactgggaa atcagaaaat     120
gtcttgtaga aaatgtaag aaaagttcca acaatactga cttaaacacg agcaaaggtg     180
aaaacagaaa tgctgactcc tgcataggtt atcggccta atgttctgac ttgatatttc     240
cagatgccca gctctgcgct aatatcaaca ccgtctattt actttctact ctgaggcatt    300
cgctctgcag gattccagac cctactaaat tattcacatg ccccaaccg gtccttcctt     360
gttccgcggt cctaacacaa tgaatggtcc taagaggaaa acggcctcgg ctcccgctcc    420
aggcccactt cgcagtccct agttctccct actgccgctc cagtgccaga gcccctccga    480
aggcggccag gacctccaac cacgcacaag tctgcagctc tccccaactt tccgttcagc    540
tcagtctccg agggtgcgcc agagcagaca cccggaggag tggggagtgg cagggcgggg    600
ccgggagaat gctgccccgg aacccataaa ttcggccctg cccaggtagg ccgggacagc    660
tggggtggcc tgggccgaga gccaagaaaa gagacccat ctggacgccc aacttggcgg    720
caacaggtgg ccggcgcccg ggggtctggg aggaaagtcg ctccgggcgg gccccgttgc    780
cccgccgcgt ccccattggt catcaggttt cttaaaatgt gactctgaat ctgtgtcctt    840
ccgccgcaga atttagtccc accgaaaggg caacctgccc gcgcgttccg ccaccgccgc    900
cgcgcttcct cctgaaggtg actcgagccc gcggggacgc aggggcggg gcccgggtcg    960
cccggagccg ggattgggca gagggcgggg cggcggaggg attgcggcgg cccgcagcgg   1020
gataaccttg aggctgaggc agtggctcct tgcacagcag ctgcacgcgc cgtggctccg   1080
gatctcttcg tctttgcagc gtagcccgag tcggtcagca gccggaggtg agcggtgcag   1140
gcagtacgcc atcagtcccc accaagggcc agtcgcccgg ctagtgcgga atcccggcgc   1200
gccgccggc cccgggcacg caggcagggc ggcgcaggat ccctgtgcta aatggtatat    1260
taaccacttc tcagtcttac cactctcttt caatttgtct cgacccagga cctcagcagc   1320
catgtcgaag ccccatagtg aagccgggac tgccttcatt cagacccagc agctgcacgc   1380
agccatggct gacacattcc tggagcacat gtgccgcctg gacattgatt caccacccat   1440
cacagcccgg aacactggca tcatctgtac cattggtgag tgggtgtccc ccttcccca    1500
aaaagggctt catgggcagt gacctttctc tcctgaaaag agctccatgc acttttaaa    1560
gacttttgag ctatttggga gaggaaaaat tttcagggaa aaaaattctt taaacttaaa   1620
gcaaacttaa atgttttcc ttggttgaat aattaatact tgtggcttta aaacttttcc   1680
taataggccc agcttcccga tcagtggaga cgttgaagga gatgattaag tctggaatga    1740
atgtggctcg tctgaacttc tctcatggaa ctcatgaggt gagctgtggc tggaccctat    1800
cctggcaggg gaattggagc tggattctag tgtgggagca cgcttgtcat cttccttctt    1860
ttccccagt accatgcgga gaccatcaag aatgtgcgca cagccacgga aagctttgct    1920
tctgacccca tcctctaccg gcccgttgct gtggctctag acactaaagg acctgagatc    1980
cgaactgggc tcatcaaggg cgtgagtatt ctgcggagag cgaggggaag gctcagtagg    2040
caatatgccc cagagacatg attccttccg aggtgatgct gctactggtg tctccagttt    2100
ggactcttcc ttactctctt gtccctagag cggcactgca gaggtggagc tgaagaaggg    2160
agccactctc aaaatcacgc tggataacgc ctacatggaa aagtgtgacg agaacatcct    2220
gtggctggac tacaagaaca tctgcaaggt ggtggaagtg ggcagcaaga tctacgtgga    2280
tgatgggctt atttctctcc aggtgaagca gaaaggtacg tatgggagct ggagtccagt    2340
```

```
tgtctaaaac agtcttttgt ctctaaactt ctcgtctctg cctccccaac ttacccttttt   2400 ttatacaggt gccgacttcc tggtgacgga ggtggaaaat ggtggctcct tgggcagcaa   2460
gaagggtgtg aaccttcctg gggctgctgt ggacttgcct gctgtgtcgg agaaggacat   2520
ccaggatctg aagtttgggg tcgagcagga tgttgatatg gtgtttgcgt cattcatccg   2580
caaggcatct gatgtccatg aagttaggaa ggtcctggga gagaagggaa agaacatcaa   2640
gattatcagc aaaatcgaga atcatgaggg ggttcggagg caagtccccg ttgtccctgg   2700
tctactgcca tacttgtggc ctctgttcta tataacctct ctccccccca ctttgtccat   2760
caggtttgat gaaatcctgg aggccagtga tgggatcatg gtggctcgtg gtgatctagg   2820
cattgagatt cctgcagaga aggtcttcct tgctcagaag atgatgattg gacggtgcaa   2880
ccgagctggg aagcctgtca tctgtgctac tcaggcatgt gcccacccctt ccccacattc   2940 tcatgtgcac actcgcatgt ttgtatggga aagctctgga ggctgtctga tctcttccca   3000
tggaattgtc gcaacgtaac acacagataa tccccttccc ccatgtacct acacaaagcc   3060
atactctgtg tacctactca ctatccagag gatcagcttg ctgtcatttg tctctgaaga   3120
cagctcaagc tacatctcac taatgctctg tcccctccca gatgctggag agcatgatca   3180
agaagccccc gcccactcgg gctgaaggca gtgatgtggc caatgcagtc ctggatggag   3240
ccgactgcat catgctgtct ggagaaacag ccaaagggga ctatcctctg gaggctgtgc   3300
gcatgcagca cctggtgagt tctgggcctg ccccatcccc cagggcttcg gactgggcct   3360
gggatggatg caagctctgg tgcagagctt tttaggtttc tccatcctct tatgcacagc   3420 cttttcattat cctccaagtt acagcagcaa gagggtgggg gtggaagtgg aggtggcttt   3480 tttttttct cctgttcctg cattcctgcc cacacccca cccctctcat ttccttctgc   3540
tctggaggca cctccttcat tggacaccac acagtttatt tcacttctga cttcaaggtt   3600
gtgaattctt cccatggctt aagtcctggg atacttctgc agtgaaagga ggtcttgtac   3660
ctcttcctca gagtcagaag ttctgagtac ctttgcccta ttctgaaaag ggctaggggc   3720
tcctgctccc agctgccctc ttcctttggc ttccaattca gttccctctg ccccgcatcc   3780
tgcagacagg cgctcccgca gggggccctt gtggacctgc actggagtct gttgccttca   3840
ctgagctgcc tgtgctggcc ttgcatggtg cctgtagggg gatttgcttt gctgtgccat   3900
tggggtacag ctgctgctct tactctagac caaaaagtcg ggttgagtga ctggtggcag   3960
ggccaagata gagacagcgg ggagggtggc tgaccctggc ggccctggac tgagcgtctg   4020
gaggagtcgt ggaggctctt tcccttcttt ctcctctgag agctcgttct tcaggctctt   4080
ccagcttgtc atgtcgagtg cctggccact gctcagggtt ggaggctcag tcccttgcc   4140 ctgtctgttc cagctctgga gctaactcag ggatccctga tcagggttac gtaggtttgg   4200
taaaatgagt gctggaaatt aactttctcc cagtagtctt aggtctagct cagtgaactt   4260
aaactttatc cagatatggt ttttccttca gcctttctat tcccttttcta gccagtgaaa   4320 gacccgctgc cctttgacct cagccccctc caagccccca agtttaaaac gccaccccct   4380
gccaccagaa aaacagaaa aaaaaaaaa aaaaaaaact aaaacaccca tctggtctgg   4440
gcatcttcct tccttttttca ctatgtatcc tgttactggg cttaaacagc tttcagagaa   4500
gagatgtcat ttctattaaa tgctcttca gtagcgaact gagttcacac ttgactaagg   4560
atattttccg gactgtctgt catcagcatc cttagtgggt ttcccccatat ttaaattggt   4620 agaggccagg gatggtggct cacacctgta atctcagtac tttgggaggc caaggtaggt   4680
ggattgcttg agctcagaag accagcctgg gcaacctggt gaaaccctgt ctctactaaa   4740
```

```
aattcaagtt agctagctgg gcatggtgat gcacttctgt agtcccagct acttggagag    4800
ggggtggtgc tggggcagca ggatcgctta aacccaggag gttaaggttg cagtcagcca    4860
agatggtacc agcctaggtg acaaagtgac accctgtctc aaaaaagaaa ccaaacaaac    4920
ataaaaaaaa aaacaaaaaa atcggtagag agtgattttct ctcccaggcc cacttaatgt    4980
agactgggcc tggctgacac ctcaccattc gtgtgatgtg attgctgttc tgatgcttag    5040
atactcttgg cgcagtctca caattgccac catggtagga aggtgtccag gagacggtgc    5100
accttgaacc agtcaccact aaagtggctg cctttctggg tctctccaca catcccctct    5160
ctctaatttc cctacttaat cgtgtgactt catggtctca aaggaggaac agaggctgat    5220
cttgacttag atatactgaa ccatgaaatc actgcataga atgtggggac ttgaatgtgt    5280
ctttgggcaa gtcatttaac ctcttaagac ctcatctgta aaatggatta gatatgttta    5340
attatagcct tagcattaaa tattcattgc tgttattatt aagtgtctga taagtctctg    5400
tgtacatgga tgtaatcttc ctaactccca ttacctccat ttatagatga gggttatatg    5460
gccaataaag cctgggtttg aatctaggtc tactgcctcc aaagccagtc ttctctcctg    5520
caacatcatg ctctgtctag caggagatga gaacaggtct ccatttggag cctgtcagtg    5580
gggtcagaga ctaagattca ggctcagggt ctaaattccg tatcctttct tccatacect    5640 ggtgtttcct atgaacagat agatacttta gggctgcaag gtttggattg catggcactg    5700
ctcagaagat aagttacagg tctgggctag gctgtagctg cccctccagg tggctagacc    5760
tttcctttct gtgtcaccag ttaacactgg ccaacagttc cttccattaa ctgttcactg    5820
cttcctcctg tgtctaactg atgcagttta tgacccataa ctaagagcag taccaggtat    5880
ggctctgttt cctgttcatg tccctgtcc tctgggctgc atgcattccg ttcttacaga    5940
aagaatacct ttaacctagt acatcctgcc acacatctgc ttctactgtg aaattgatga    6000
gggggtatta ccgattcttc cctctcccat catttactga gatgctggtg attgcattat    6060
aatcctctta agcttacatt gtctttctga ttcttggtct tatctgagca agtgatctat    6120
aaataactca gtggctttct catgactgtt ttaattatta gattttaatc aagtgtctta    6180
ttaaatatat ctgcatgctt ccacaggcat ctgtctcttc acatggctgt tcagtgtgcc    6240
tctcacaact tagcccaaac tcagttgagc tgccttgctt tggctttgac ccagcttttcc    6300 agcgctgctc aatctgttgc catggcaggc cattggaaag gctcagttca tccccgtgcc    6360
tgaagccaag tgagcgctca ctccatgcat gcatggaggc tgggcaggag cctgcctaat    6420
caaccagcca tgtgaggagg gagggcctgt tccttcctgt aagctatgtc atgaggcagc    6480
gtggtcaagt cctctgccag ggagtggcct ggcccagcct gggcatgttt tcatgccagg    6540
gtgctagagc ctactgccag attgtctccc tccaccccca atgaaaaat ccttccagaa    6600 gggaagagcc aatttcccct gtattggagg ggaagtggca gcacctcctg aagcagttgg    6660
actttcatca ccctacctct gcatctgcct gaaggacaga tttagccaat taacctaagg    6720
ttaccttcct ctctgataaa ttccccattc tgtcttccca tgtgttgtgt ctcgtttttt    6780
tcctcctcct tccctcttcc ttgccccctc ttcccctaaa ccttacagat agctcgtgag    6840
gctgaggcag ccatgttcca ccgcaagctg tttgaagaac ttgtgcgagc ctcaagtcac    6900
tccacagacc tcatggaagc catggccatg gcagcgtgg aggcttctta taagtgttta    6960
gcagcagctt tgatagttct gacggagtct ggcaggtagg gccctaaggg caggtaacac    7020
tgttaggata accagcctct tgctgcacct gccccaggag aagagagaag cccaacctg    7080 gcatctggga acagagcctc ttctcgtctg taggaacacc gccagggagg tcatggcagg    7140
```

```
gcagaccaaa gggtcctgtg gctcagtagg cacagtagat gtcacaggca cttggtgaag    7200
gactggtttc tgtggagtct tgatcttggc tcagctcaga atctccagtg attgggctcc    7260
tcttggcctt tgttcccagg aacatgttcc tcaccagctg tccggtgact cttcccctcc    7320
ctctcctttt gtgacaaagc tctgacaaag ctctgtcccc ctctcgtccc tctggacgga    7380
tgttgctccc ctagattgcc cgtgaggcag aggctgccat ctaccacttg caattatttg    7440
aggaactccg ccgcctggcg cccattacca gcgacccac agaagccacc gccgtgggtg     7500
ccgtggaggc ctccttcaag tgctgcagtg gggccataat cgtcctcacc aagtctggca    7560
ggtaggaggc ggcagcggct ccctggaatg ccctgctcag tggtacctca ccttgggggt    7620
cctgggagca gtccattgaa caatgctcag gtggcactga gccaaggtaa gaccctctg     7680 cctgccacct tgggcctgca gggaaggatt gagcagagcc ccttcccagg gcccaaagga    7740
ctctaggtag cactcataag gaatgtcaga acatttggat caaaagcaaa tttatgctgg    7800
agatttatta cataacagtg cacaggctga ctacaaatgg ttatttgata ttgaaaattt    7860
agtcctctaa aattgtaaaa gataccactt ttgcttattc cagttactat gtgctcttta    7920
aaaatttcag ttgggaaatg aatttattta aatgctgttt actgtgcctc catttggcac    7980
actagtccct gctgttttg agccctaaag acaaattggg ttccagctca ggagaggttg     8040
ctgtgctatc ttggctgaca ttctgtgggc ctggcagcca ggctgaggac tgtgtggcct    8100
atgctgggcc tccaacttgg gatcccttcc ttggcccagg acattgagtt aatgtccttc    8160
actctcctag ttagggagta tgctccttgt ccctgtccac aggggagcaa gggtttcctg    8220
gaagagggga gcaaacaggc agtgcccatg cactgaggag cagcagatgg gcgtgggcag    8280
cccagagaac caggacacaa gctctgtgca gatccctcag cagagggctc cagcctccca    8340
ctcttggctg aacagctcca acccgtaggg ttgaccttc ttaaaaggtc cagttcttgc     8400
tgtttggcta ttttaagctc tagtcttctg gggtttcact cagctggtcc tggcttcagc    8460
aattgcttcc ctctgaaggc cttgcataga ggccaagcgt gaagtgcagg gacttctctg    8520
ctgtgatgtg gcttaagttt ccctgacacc tgttgagtgt cctcataact tcccttctgg    8580 tgccctccc cagctcctga ccagctgc agctacaagt gtgcagtgtc agtgttcaag       8640
aaagtgcctg gcagagggc tttagaaggg tcccctgcct tccaaaggag ctttggcagg    8700
cagacgtgct cctgcagcaa cactcccatt tcctgttctt gcctgctgag tagcacctag    8760
atttctaagc ctcatctaga tactcagatt tgattctggg cctttatagc ccagttgctg    8820
ggactgtttc aggagctagg ggccatgtgg ggcagggaga gggcacaaaa gtagagaagc    8880
ctgatgttga ttcccagggg gctggtcagc tctgctactg ctccttgcag atgtcaagag    8940
tcaggtgcta gtcacgtgct gcttggcttg tcactgtcat tggcagcgag aggaatgggt    9000
gctggtgaca ttgggccagg gctgcctctc tgtgtcagag ttcagggtgt aggagggggtt   9060 ctgccaacca tgggctgtgt ggggtaagtg ggttgaggct gatctttctg ggtcaaggtg    9120
atcctgagcc cttgcctgtg gaatgggggt agagggcaat ggtaacctag ctagcatgct    9180 gtggggata taggatgagg ggctgcccga ccctcgggag gggtcctagg gagcagatgt     9240
tgaagaggcc agagccctca gtgagctgga tgaggggtg agccgtttga actccctgag    9300
ggtacttcct ggggcctcgt gtaatggtct cttctgtatg tccccatcc catctcaggt    9360 ctgctcacca ggtggccaga taccgcccac gtgcccccat cattgctgtg acccggaatc    9420
cccagacagc tcgtcaggcc cacctgtacc gtggcatctt ccctgtgctg tgcaaggacc    9480
cagtccagga ggcctgggct gaggacgtgg acctccgggt gaactttgcc atgaatgttg    9540
```

```
gtacgtggct ggagcagggg ctagagccta gaggagcttg gggatgcttg agcattggcc    9600
accaacctcc cttctcttcc tccaggcaag gcccgaggct tcttcaagaa gggagatgtg    9660
gtcattgtgc tgaccggatg gcgccctggc tccggcttca ccaacaccat gcgtgttgtt    9720
cctgtgccgt gatggacccc agagcccctc ctccagcccc tgtcccaccc ccttccccca    9780
gcccatccat taggccagca acgcttgtag aactcactct gggctgtaac gtggcactgg    9840
taggttggga caccagggaa gaagatcaac gcctcactga acatggctg tgtttgcagc     9900
ctgctctagt gggacagccc agagcctggc tgccccatca tgtggcccca cccaatcaag    9960
ggaagaagga ggaatgctgg actggaggcc cctggagcca gatggcaaga gggtgacagc   10020
ttcctttcct gtgtgtactc tgtccagttc ctttagaaaa aatggatgcc cagaggactc   10080
ccaaccctgg cttggggtca agaaacagcc agcaagagtt aggggtcctt agggcactgg   10140
gctgttgttc cattgaagcc gactctggcc ctggccctta cttgcttctc tagctctcta   10200
ggcctctcca gtttgcacct gtccccaccc tccactcagc tgtcctgcag caaacactcc   10260
accctccacc ttccatttcc cccactactg cagcacctcc aggcctgttg ctatagagcc   10320
tacctgtatg taataaacaa cagctgaagc acctgtttcc tctctttt               10368
```

<210> SEQ ID NO 65
<211> LENGTH: 201
<212> TYPE: PRT
<213> ORGANISM: Homo sapiens
<220> FEATURE:
<221> NAME/KEY: MISC_FEATURE
<223> OTHER INFORMATION: Q01995; Transgelin

<400> SEQUENCE: 65

Met Ala Asn Lys Gly Pro Ser Tyr Gly Met Ser Arg Glu Val Gln Ser
1               5                   10                  15
Lys Ile Glu Lys Lys Tyr Asp Glu Glu Leu Glu Glu Arg Leu Val Glu
            20                  25                  30
Trp Ile Ile Val Gln Cys Gly Pro Asp Val Gly Arg Pro Asp Arg Gly
        35                  40                  45
Arg Leu Gly Phe Gln Val Trp Leu Lys Asn Gly Val Ile Leu Ser Lys
    50                  55                  60
Leu Val Asn Ser Leu Tyr Pro Asp Gly Ser Lys Pro Val Lys Val Pro
65                  70                  75                  80
Glu Asn Pro Pro Ser Met Val Phe Lys Gln Met Glu Gln Val Ala Gln
                85                  90                  95
Phe Leu Lys Ala Ala Glu Asp Tyr Gly Val Ile Lys Thr Asp Met Phe
            100                 105                 110
Gln Thr Val Asp Leu Phe Glu Gly Lys Asp Met Ala Ala Val Gln Arg
        115                 120                 125
Thr Leu Met Ala Leu Gly Ser Leu Ala Val Thr Lys Asn Asp Gly His
    130                 135                 140
Tyr Arg Gly Asp Pro Asn Trp Phe Met Lys Lys Ala Gln Glu His Lys
145                 150                 155                 160
Arg Glu Phe Thr Glu Ser Gln Leu Gln Glu Gly Lys His Val Ile Gly
                165                 170                 175
Leu Gln Met Gly Ser Asn Arg Gly Ala Ser Gln Ala Gly Met Thr Gly
            180                 185                 190
Tyr Gly Arg Pro Arg Gln Ile Ile Ser
        195                 200

```
<210> SEQ ID NO 66
<211> LENGTH: 1822
<212> TYPE: DNA
<213> ORGANISM: Homo sapiens
<220> FEATURE:
<221> NAME/KEY: misc_feature
<223> OTHER INFORMATION: D84342; DNA for SM22 alpha; complete cds

<400> SEQUENCE: 66
ccgggtgaaa gcagagtgct ccctgaccct ctgcccctcc ctcctccacc ctggcctgct      60
ttagctttcc ccagacatgg ccaacaaggg tccttcctat ggcatgagcc gcgaagtgca     120
gtccaaaatc gagaagaagt atgacgagga gctggaggag cggctggtgg agtggatcat     180
agtgcagtgt ggccctgatg tgggccgccc agaccgtggg cgcttgggct tccaggtctg     240
gctgaagaat ggcgtggtga gtggcaccct gggctagggc gctgggggc tggggtgtga     300 cccctgtga gtcctgggcc aatccctgag gactgctaag ctgcgtccta tgccctatgc     360
ctggtagatt ctgagcaagc tggtgaacag cctgtaccct gatggctcca gccggtgaa     420 ggtgcccgag aacccaccct ccatggtctt caagcagatg gagcaggtgg ctcagttcct     480
gaaggcggct gaggactatg gggtcatcaa gactgacatg ttccagactg ttgacctctt     540
tgaaggtaga gaggagaatg ctgggggagg aggtgggcag gaggacaggg tgctgggaca     600
gggagagggt atgaccaaat atgccacaac tagggtgtg ctcgcccgca cacagcaggg     660
atgggatatg ccgagaataa cacgccacgc tcacagggcc cactgagagg cctcccttga     720 attgggaca actcttggcc ctggtttggc catttttttg tgagagacgg gggcaggccc     780
tggcttggag tcttgtttat acgttcttga tgttcatctc ctctctcctg tcttctcaca     840
ggcaaagaca tggcagcagt gcagaggacc ctgatggctt gggcagcttt ggcagtgacc     900
aagaatgatg ggcactaccg tgagatccc aactggttta tgaagtatgt ggcccccagg     960
gagcttgagt ctccgcatgg ggtgggaggt ggcttgttct aaggagcttg cgggaaggat    1020 tagggaagc agatagccaa gaaaggataa agtgagggtc tgggatgggg aataatgggt    1080
ccttaatact ccttgacccc tcccttccca ccctcctgcg ctcagtctcc ctagcctatg    1140
aggcaagcta gattagggaa aaaaagtgca acaggaaggc aatgggattg gctaggacg     1200 taacagaggg atcagaaaac gggtggaaaa cacacagttc taccaagtct ttatcctgct    1260
tcctcctctt ctaggaaagc gcaggagcat aagaggaat tcacagagag ccagctgcag    1320
gagggaaagc atgtcattgg ccttcagatg ggcagcaaca gaggggcctc ccaggccggc    1380
atgacaggct acgacgacc tcggcagatc atcagttaga gcgagagggg ctagccctga    1440
gcccggccct cccccagctc cttggctgca gccatcccgc ttagcctgcc tcacccacac    1500
ccgtgtggta ccttcagccc tggccaagct ttgaggctct gtcactgagc aatggtaact    1560
gcacctgggc agctcctccc tgtgccccca gcctcagccc aacttcttac ccgaaagcat    1620
cactgccttg gccctccct cccggctgcc cccatcacct ctactgtctc ctccctgggc    1680
taagcagggg agaagcgggc tgggggtagc ctggatgtgg gccaagtcca ctgtcctcct    1740
tggcggcaaa agcccattga agaagaacca gcccagcctg cccctatct tgtcctggaa    1800 tatttttggg gttggaactc tc                                            1822

<210> SEQ ID NO 67
<211> LENGTH: 355
<212> TYPE: PRT
<213> ORGANISM: Homo sapiens
<220> FEATURE:
<221> NAME/KEY: MISC_FEATURE
<223> OTHER INFORMATION: Q14103; Heterogeneous nuclear ribonucleoprotein
```

<400> SEQUENCE: 67

```
Met Ser Glu Glu Gln Phe Gly Gly Asp Gly Ala Ala Ala Ala Thr
1               5                   10                  15

Ala Ala Val Gly Gly Ser Ala Gly Glu Gln Glu Gly Ala Met Val Ala
            20                  25                  30

Ala Thr Gln Gly Ala Ala Ala Ala Gly Ser Gly Ala Gly Thr Gly
        35                  40                  45

Gly Gly Thr Ala Ser Gly Gly Thr Glu Gly Gly Ser Ala Glu Ser Glu
    50                  55                  60

Gly Ala Lys Ile Asp Ala Ser Lys Asn Glu Glu Asp Glu Gly His Ser
65                  70                  75                  80

Asn Ser Ser Pro Arg His Ser Glu Ala Ala Thr Ala Gln Arg Glu Glu
                85                  90                  95

Trp Lys Met Phe Ile Gly Gly Leu Ser Trp Asp Thr Thr Lys Lys Asp
                100                 105                 110

Leu Lys Asp Tyr Phe Ser Lys Phe Gly Glu Val Val Asp Cys Thr Leu
            115                 120                 125

Lys Leu Asp Pro Ile Thr Gly Arg Ser Arg Gly Phe Gly Phe Val Leu
130                 135                 140

Phe Lys Glu Ser Glu Ser Val Asp Lys Val Met Asp Gln Lys Glu His
145                 150                 155                 160

Lys Leu Asn Gly Lys Val Ile Asp Pro Lys Arg Ala Lys Ala Met Lys
                165                 170                 175

Thr Lys Glu Pro Val Lys Lys Ile Phe Val Gly Gly Leu Ser Pro Asp
            180                 185                 190

Thr Pro Glu Glu Lys Ile Arg Glu Tyr Phe Gly Gly Phe Gly Glu Val
        195                 200                 205

Glu Ser Ile Glu Leu Pro Met Asp Asn Lys Thr Asn Lys Arg Arg Gly
210                 215                 220

Phe Cys Phe Ile Thr Phe Lys Glu Glu Glu Pro Val Lys Lys Ile Met
225                 230                 235                 240

Glu Lys Lys Tyr His Asn Val Gly Leu Ser Lys Cys Glu Ile Lys Val
                245                 250                 255

Ala Met Ser Lys Glu Gln Tyr Gln Gln Gln Gln Trp Gly Ser Arg
            260                 265                 270

Gly Gly Phe Ala Gly Arg Ala Arg Gly Arg Gly Gly Pro Ser Gln
        275                 280                 285

Asn Trp Asn Gln Gly Tyr Ser Asn Tyr Trp Asn Gln Gly Tyr Gly Asn
290                 295                 300

Tyr Gly Tyr Asn Ser Gln Gly Tyr Gly Gly Tyr Gly Gly Tyr Asp Tyr
305                 310                 315                 320

Thr Gly Tyr Asn Asn Tyr Tyr Gly Tyr Gly Asp Tyr Ser Asn Gln Gln
                325                 330                 335

Ser Gly Tyr Gly Lys Val Ser Arg Arg Gly Gly His Gln Asn Ser Tyr
            340                 345                 350

Lys Pro Tyr
        355
```

<210> SEQ ID NO 68
<211> LENGTH: 14983
<212> TYPE: DNA
<213> ORGANISM: Homo sapiens
<220> FEATURE:
<221> NAME/KEY: misc_feature
<223> OTHER INFORMATION: AF026126; heterogeneous nuclear ribonucleoprotein D (HNRPD) gene; complete cds

<400> SEQUENCE: 68

```
tcgcagaggt gcagccacac cccggcctaa cgtgttgttc cccccgatac tggagtggtg      60
gggagggtga gtggactcca ggaatcctcg gaagggcggg ggcggaggca gggggcccct     120
ctagccgcta cttcgaaaca gcattccttg ttctcgatgg tccccgcgcg actgtcttag     180
ctcacgacac ttccggttcc ttttaaaggc ccccaaggct gtgcaacgcg gagcgtgaga     240
ggaaggtata aagggtagcg agagggcggg accgaggagg aaagggaaaa aaaaaaaact     300
aggggggatag gggtgggggg acgcgcgaag ggcgcgctct cgcgtcacgt gaccgggacg     360
cgccgttctt ccgtcggcca ttttaggtgg tccgcggcgg cgccattaaa gcgaggagga     420
ggcgagagcg gccgccgctg gtgcttattc tttttagtg cagcgggaga gagcgggagt     480
gtgcgccgcg cgagagtggg aggcgaaggg ggcaggccag ggagaggcgc aggagccttt     540
gcagccacgc gcgcgccttc cctgtcttgt gtgcttcgcg aggtagagcg ggcgcgcggc     600
agcgcgggga ttactttgct gctagtttcg gttcgcggca ggcgggtgta gtctcggcgg     660
cagcggcgga gacactagca ctatgtcgga ggagcagttc ggcggggacg gggcggcggc     720
agcggcaacg gcggcggtag gcggctcggc gggcgagcag gagggagcca tggtggcggc     780
gacacagggg gcagcggcgg cggcgggaag cggagccggg accggggggcg gaaccgcgtc     840
tggaggcacc gaagggggca gcgccgagtc ggaggggggcg aagattgacg ccagtaagaa     900
cgaggaggat gaagggtgag taagggggcat cccaggatag tcaggcccaa ctagtccccc     960
tccccctctt tattccccccg ccattagcgc tggttcccgc tctcagcccg ttctccgggc    1020
cccatgcagc ctccttgcac tggtctccct ttttctatgt tgggttcccc ggaccttcat    1080
ttccttcttc ctttgcctgc ttatcgcccc cctcccccat cacacacgtt tccacccttta   1140
gccgtcacca tgctgctcct cggcccgccc tcctttcctc cctcgccatg ggtctcctcc    1200
caccgactta gccgccagat ttttttcccgc ctgtcgtggg gtaccttttt tctttccatg   1260
ctgtcccctc tttttccctt tttctacagt cttgggcata aaacacaga cacaaacagc     1320
ttctctgttt gtattactaa ggtttatttg gtgcttctcc accatcctga aacgatgcga     1380
ttgtttataa gcacatgttt tggggaacgc gtaggctgtc cacctctgcc tctcccttgt    1440
cggccttacg ccgactgttt tcttgggatt ttgaataagt ttcgcctaag gatttactca    1500
ttttctccac catacgctat cgcacaatgg catactcata caggccctac attttgacat    1560
gcagaccaaa ttgggtctgg tgaaatgctc cgagtttctt gttggtacat ggttttgct    1620
ccgcgggctc tggttaagtt cttagtcgat cgggcctgca cttgactgga gctgttccta    1680
tctccggcct agcatctacc cttcccccac cccactgagt tattctaacc gcgcacccctt   1740
ttcgcgccct cagctattgg gttccccaac tgttagtaca gattgtacct tacttttat    1800
gtgcaaccta atttttaca accccccagcc ccctttttt cccggtgccc aggatcctat    1860
tttggtgtct tgatatctgt ttcccgccca ctaagggagg cctgtagtcc tcttaagaga    1920
aacaaatcac tgtattgtgc tatgggatac tttttttttc ttttggtgc aaatttctta    1980
gtattaactt gcttcctcca attgaaataa cagttgtata tactacctaa atctgcattt   2040
agtgtattaa aatgcagcat ttgggattgg gaacataata cggagttag caggagggac    2100
taaatcaggt ttcttggttg agtttctta gctccgatta ctgaccgatg atcgtgggtt    2160
cacgcttcca ttccttttg taatgggag gggtgtgtgt gtgtctgaat ttttttttaa     2220
ctgtaaagag aaaggtgttg gtggatataa caagatgtcg ctttaatcta gtattagaaa   2280
```

```
acacgatttc ttttactgag aaagagccca ggatttggag ggaaagttgg gaggggagaa    2340
gcactttgga atatagggtt tattaagccc agcttaggca gattcttgtc aggctgtttg    2400
atgatagtgc tggttttggg ggagtggtgg tgggaaggga agcaaacttt taaaaattaa    2460
acagaaccaa ctcgaattgt atatagctta tttgagaaag gaagatgtta gatatttgga    2520
aacttaaaac ctttaacatt ttggttttcg tttgctgaat tctgttcttt ggacagaggc    2580
accaaaatga ttaattgtat aacttcctgt tggggcagg cttctgtta gccctgataa      2640 ttcaaatcgc aaagcagctg actttatagt tacctactgt tgaagtgtaa atgaattaaa    2700 gttttttaacc ctaacagtgt caaaaactaa aactagaatt ttgattggtt gctgtaccgg   2760
ttgttaattc cctagccatt caaactcctc cccacgacac tctgaagcag cgacggcaca   2820 gcggaagaa tggtaaatct tttaaatttt atttctgtat tataaaggtt tcagtagtca    2880
taatatgtag aggctgtgta ttggttagtt gcccattgat ccccaggaaa ttctagacca   2940
tagtacatac agtaggtttg tacctgggat atatacccttt tataggcatc atgtgtaatc  3000
tttgggcaaa attgatgccg ttacatggta tttggtctgt ggtaatgcat gtagttgcag   3060
tttggcaatt taagctaaac aattagtaac gatatttta tatcgagcaa gaaaaaatat    3120
taccgtaatc ttcacatttg atttatttta agatgaaaaa tattttgtt ggaatttaag   3180 tttaatggct aaatatgaag actccttgat ataaaatatt gtgtttaaaa tgtcatgcat   3240
gttatactga atattctgg agatgtctga agcagttctt taagcagcac tgtgtattat    3300
ggaaaaatgt ttgtctttta cctagcatat ttgtaaatag acctttaata aaatgtgtgt  3360
gtgtgtgtgt gtgtgtgtgt gtgtatatat atataccatt aaaaggtggg ctaatgtggc  3420
tttccactac agctcttacc agatttttta ttttcagtgt gatttggctg gaatattaat   3480
aacagttggt tgacatgtat tcacaattgc atgacttctc tttggaagct ggtaggttga   3540
gtattgttct ttttatccat cctttcccct cccctaaatg tcagtctttc tgcttttagg   3600
attatatttg aattttcagg ggtttataca ccaccactgg agagtagaag gccactaact   3660
tgcaggcagt taacttatat ctttacaagc tacattctat tttaagagcc tatttagggt   3720
aacatttaaa gatttgctta tcactgtatt ctcatccact gaaatcagtc cagctttacc   3780
ttggagaaaa agcagatggg aaacaggcaa ggggaaaagc aaaaagagg aaaaaaaag    3840 actgggtca cagtttcgat gaatgttatt ccctgtatt ggtgagtggt gggcactagc     3900
agctcaattt cactgctagc taatagtggc aaattaagat taaactataa actatttgac  3960
attactccat tatgtatttt gagtctcatg taattgtttc cagtgatttg aaatgaccat  4020
aaacttaaat ttgaaggtca gtgttttgac tcttcgaagt aattacactt gacctgctac   4080
ctaaaacgat gtaatattac aacttttttg aataatctca ggaaaaatgg agaaatgttt   4140
atattcatag ttaataaaca ttctagatag taaccaactg tcatttactg aaaataaaat   4200
tttacccagg tttatttat ttttgagacg gagtttagct tttgttgccc aggctggagt    4260
gcagtggtgt gatcttggct cagcgcaacc tccacctccc aggttcaagc aattctcctg   4320
cctcagcctc caaagtagtt gggattacag gcatattcca ccatgcctgg ctaatttgt   4380 attttagta gagacagggt ttcttcatgt tggtcaggct ggtctcgaac tcccgacctc    4440
aggtgatccg cctgcctcgg cctccccaag tgctgtaatc acaggcgtga gccactgcgc   4500
ccggcctagc caggttgatt ttaaaattac acttaaaaat aatgttctca ttttaagggg   4560
ctctaatatt tgactttct taactttcca attatgcagc cctatcctgt tccagacgtt    4620
aaggctttct ttttgaatga aaaactttca gactttttc tctctctttt ttttttttt     4680
```

```
tggtgtctgc actccccacc gtatctgtcc cttcctcttt ctcccatttt gagggatatt   4740
ataagggcaa cagttttata gtctcaatat tgagggtaag actggttaat agatagagta   4800
tccaaattga atttattaaa cacagttctg tgtgcatttc cttctgcaaa tctgagaata   4860
aagtgattac agtttcatcc taaaatactt taaaaatcag ttggttttag aaataggttt   4920 ttttccttt gcatgtaaga atggacagct attttagga aggcatgcac ctgttatccc     4980
agctactcag gaggctgagg caggagaatt gcttgaaccc gggaggtgga ggttgcagtg   5040
agcctagatc atgccattgc actccagccc gggcgacaga gtgagactct gtttaaaaag   5100
aaaaaaataa gtatttgtaa atgtatatat atatatatat acacacacac acacacatat   5160
atatataaaa tcattatgcc atcagtttga gggagagcat gtatgccaac attgtaaaga   5220
ctaagtgccc atttatccat aattaagata agcagacttt tccccattgt actataaagt   5280
tagagtttgg ggctgggtat ggtacttccg cctgtaatcc cagcagtttg ggaggctgga   5340
gcgggcggat cacttgaggc caggagttca agaccagcct ggccaacgag ggaaacccc    5400 gtctctacta aaaatgcaaa aatcaagtca ggcgtggtgg tgcagcctgt aatccctccc   5460
acggaggctg aggaatgaga atcactttga acctgggagg cagaggttgc agtgagctga   5520
gattgtgcca ctgcgctcca gcttgggcga cagagtgaga ctgtctcaaa aactaagcaa   5580
ccagaaacag aaaaagatgg aatgaatta atatgttcca tttagtaaag atggaataga   5640
attggtccag tttgtgttca ttgtagcata ttcacctatt tggtctgcaa ccattttttt   5700
ttttttaaag cctaagcata ccctgagaac aacaaccttt tttgattaga acagaagaaa   5760
aagccagaat gttcttgggc tgccaaaata ttaatacgtt tgtctcaaag acgaaccact   5820
taggtgcttg cttagagact tctactttac acagaatttg aaaagtttga cagctggcta   5880
cttactctgc aaaacggaag ggagactttt tagaacagca actggtgatc tggcaaaaat   5940
gaaaagtaga acttgtgaag aaatgagatg gacttggtgt attaatagct aattttagaa   6000
gaccctgtgg atattctaaa tcagcataat agtgatgtct gagccatagt gttaaattat   6060
gattactgta tttgaagtat aagaaggcag aaaagtgtga tgctgttaga aaaaaatctc   6120
atttcaaatg attgaaggtt aaaaacaatt ggggaaagat tagagagggc aggcggtgct   6180
ttaagggagg tggaataata cttggctcct tattctccaa aagtgctgga tagctgaagt   6240
ttttaatatt ctggataatt gatatttgat tattagtttta ggaggggatag catcttcagt   6300 gaacccttgt agctctaagg taggcatatt aaacaactac catactaaag gtggggagta   6360
cgtttggaga gcactttgct gggccagctg atgatatgct taggtgatat ttaagaaaat   6420
ctgcttcttg tctgaaaaac atttgggget tcagaataat accacatacc tcattcttgg   6480
tgttttaatt tatttctttg taattgtttt ctgtttctta ataattttaa attaagggta   6540
ttttcccaat ataaacattg ctttttggtt aaataaaatc aaaactagtt ctgtctccat   6600
atctgaatag accagacaga gaattttctt gcctttcaac agcttaaaaa atgttttgt    6660 tagaactgtt gtgttcaggc tgaaatactt tcaaagtttg ttagttatta ttgagaaatt   6720
tctgtaataa tcatggaaag ggtaatttaa tagttaaatc tcaacttaat tgaagttatt   6780
tctgttgtgg aacttatggt catcttagca agaggtcatt gctttatagt cagttctctt   6840
tctcattaaa aatatagtgt actcaccttt acagggtgaa tgttggtaaa taacttctgt   6900
ctgtgaagga agtattctgg acctgtaagt taaaaataag gtgtttatag caaattatgt   6960
aaataaagat tgtatattag aaggtacaca ctattcaaat ttaaagaaaa tgtatattga   7020 gaaataact caaattcttc catgaaattg gcaagaagta aacatttcaa atacacaaaa    7080
```

```
cattatgggt attttttgttc atttgattat aaaatgccaa agttgtttta taaatgctac    7140
ttcaagcctg gaaactttga ggaagtcctg aacattaagc atataaatgg cccagctcta    7200
gaatacatgt aagttgaaaa gctaacctga agtgggaagc gcagtatata cctaagactt    7260
actctgcact gaaagtttgc tttgtcacta gaagtaaaac aagactgtgg taggatagta    7320
agatcagtaa cacctcagtt aatcaggtat cttggaggaa gtgaagaaag accctaattc    7380
aagggacagt taattggcct tttattccaa gaatgggcct tagtggcagt atcttaaaag    7440
cccacaagat ggagatgttt cctaatgaaa ggcctttaat ttctttatag agctgagtta    7500
gtgtcacatc ccagtcccca cccatgaccc ttccccagtt aaaaagaaga gaaaatgttg    7560
agcaagtctg atttgattcc catggtgaca ttttttagcca ttatgtaaca aattctgaca    7620 gtttacccctt aaaattaaaa acctccagtc ctgtcttttt aaagggtaga agaaggtta    7680 ggtataggat agcttttttat ttatttattt atttatttt gtacaaaggg agcctatgta    7740
aagctgccag atctgaactt tctggtgttt tgctgtaatg ttagtaagat ttcgccttaa    7800
aatattttat tttgagtata tacgtttggt cttagagtgt cttggtggat ttccgcttac    7860
cacccatcac tttctgcatt ttaaaggctt aaatacttta ttgctggtta actgaggttc    7920
tactgtaaac gaatcatcta agttaattag tggattgtac ttcaatggat aattttcact    7980
aaattgttta tattgcacat tactttgtc ttaaggactc ttagcacatc aaaaaaattg    8040
gctcacaact taattgtgag atgtagaatt ttccatttta tgtgctaaga gttttgttaa    8100
tgagagaact gttaaaatag aaaaggagct tcagcataga caccaatgct ggttgctgag    8160
atcagtgggg aactgcatag cattttaaca agtttaatga acatttggaa gagaaatttg    8220
aagctaagat tctggttttt ttgctgttaa cttttaatt ttttaatcta aggaaaactt    8280
ttatgtacag tatttttact ttgggtatat gtttatcttt tagcaagttg aaagacttaa    8340
tttgctgctt gctcactatt ttgtaattat ttgggagcag cagtaataag ccagcttttt    8400
ggaataggat gttcctgatg tgtggttatg taggaagaat gatgttttaa tatactgccc    8460
agtaaactgg tgcagtttgg aaaaggtgtg ttattgatgt ggataatatt taaggcaatt    8520 tttttttaagc atttttaatac tgcttttgt ctttacagga aaatgtttat aggaggcctt    8580
agctgggaca ctacaaagaa agatcctaag gaaaactttt atgtacagta tttttacttt    8640
gggtatatgt ttatctttta gcaagttgaa agacttaatt tgctgcttgc tcactatttt    8700
gtaattattt gggagcagca gtaataagcc agcttttttgg aataggatgt tcctgatgtg    8760
tggttatgta ggaagaatga tgttttaata tactgcccag taaactggtg cagtttggaa    8820
aaggtgtgtt attgatgtgg ataatattta aggcaatttt ttttaagcat tttaatactg    8880
ctttttgtct ttacaggaaa atgtttatag gaggccttag ctgggacact acaaagaaag    8940
atctgaagga ctacttttcc aaatttggtg aagttgtaga ctgcactctg aagttagatc    9000
ctatcacagg gcgatcaagg ggttttggct ttgtgctatt taaagaatcg gagagtgtag    9060
ataaggtagt gtgttacgtg ttctgatcag ttaataatat aaaatattaa catatggata    9120
gtttgataca atgagtttgc ctatttgtgg ttccccattt tgatagtata ggaaggaaga    9180
atagttcttg ccccaatacg ttttatgaag atagaggtag gttcaggaat tatttcctga    9240
ataatttgtg ttccaggctc tgctaaattt tgaaattaac tttaaagata ctatagactt    9300
aaagatgcct agttaaaagg atgtgttta gcaattcaca gaagtccata ttttgaaatt    9360
ttgttaggca agcaacttt aactgaatca ttattttgat cctgggctaa agggaagtag    9420
cagttatgtt tgtatatagt gctaaaggga agtagcagtc atgtttgtat atattgaagg    9480
```

```
taatggttat ctagtaattg gttaaatttg tgtatgtcct accattctta cctttagatt    9540
taaacagtat atgttagttg atgttacatc accaccatga cttgacagtt taatcttgag    9600
caagtcaaca tatgcttggc attatctgta tttatagtta tttttaagta agttaatagt    9660
ctctgaactt cagttaagat atatatttt taaatgaaaa cttcaatttc cttaggtcat     9720
ggatcaaaaa gaacataaat tgaatgggaa ggtgattgat cctaaaaggg ccaaagccat    9780
gaaaacaaaa gagccggtta aaaaaatttt tgttggtggc ctttctccag atacacctga    9840
agagaaaata agggagtact ttggtggttt tggtgaggta tgttataaat gttttgaccc    9900
agtttatgtc aaaattagtg tgaatgtgat tgtcccatta tggactcaga gtcacttggc    9960
ttttcaaagc tgttagggta gattatgtga tctgttttgg aataaggata ttgtaaatac   10020
ttcattagca ggtctttgaa ggttggataa tgtgtttttc tcattgagca cctactctat   10080
gcagagtatt gctggggtag agtataccaa agatgaaata gacaaacatt cttaaataca   10140
gacaattaag aggaagaaat ctagattaga aggagacttt tgttgaaaat aggaaaggaa   10200
ttaagaatag ggtgtagtgc cttatcagtt gaaatgcatg tgtaagtgca aatttaatga   10260
gactaatcat tatagactca ttagtgaggc tggacgcgat ggctcatgct gtagtaatcc   10320
cagcacttgg gaggccgaag tgggtggatt actggagacc aggagatgaa gaccatcctg   10380
gacaacatag tggacccgtc tcaattaaaa gtaaaacaaa cttagactca ttagtgaaat   10440
aggtagataa tagaggtttc ttttatgaat taatgaatta atgaaagttg agaaatttgt   10500
ggccttgggc tccagatacg tcccacagac atttattgct tgattgaaac aataagtgct   10560
tttttagtgt tgaggatttg agatattgcc cacaaaactc agtatctagc ttttaaaaa    10620 atatttgcaa gagcacgcaa catgggaact gacgctgccc tcctgtacgg cagcatctct   10680
caaactgagt agtagcttcc atcttggttt gggcatatgc tctccagttt ttagtagtcc   10740
tcaccaccct acttcctgtt ttctctcaaa tacatttttt ttctgttttt cttagatttg   10800
actgttttct tcttgttctt tgtgggcatt tgaatttgtg acccttgagt taggtagtaa   10860
atgtcagtgc gtggtaaagc ttatttttgt aaatagttgt gaagacctta gatggaatgg   10920
gtgttctaat ttgaagaatt ccttaaaagg attagaataa ataggagaa acaggagact    10980 agaacttcag tgccaaatac atgttttctt tgtgtgtttt ccccctcta aacttgtgtt    11040 tcttttaagg tcaataaaat gcatgttagc atattaaaat ttgttttta ataccaggtg    11100 gaatccatag agctccccat ggacaacaag accaataaga ggcgtgggtt ctgctttatt   11160
acctttaagg aagaagaacc agtgaagaag ataatgaaa agaaatacca caatgttggt    11220
cttagtaaag taagttaagc atccatttac ttgtagagaa aactagctgt tgtaaagagc   11280
ttaaccattt atctttctct gtaaaggctt aagttctttg catgctttaa aaacttctca   11340
ttggttactt accattgacc aactttttgt ggggagcagg atggacacat tgttagtgt    11400 ttttgtctag gctttcacaa aaatagtttt tagaacttga caagtaaaat gaagtaacat   11460
cactagcaag tactcataag tgattactct taagtactaa atattggttt aattaataaa   11520
ctgactgagg aaagtttcaa attagcctac tctatttaaa catgttggct attctggtta   11580
ttagaaactt atttagcaac tttttatttc ttgagtcagt ttaataatgt aatttttctc   11640
ttttagtgtg aaataaaagt agccatgtcg aaggaacaat atcagcaaca gcaacagtgg   11700
ggatctagag gaggatttgc aggaagagct cgtggaagag gtggtggtaa gctagagcct   11760
aagtttactc tatcttaagc ttttctgctt tttaattatc ctgaagtaaa gatctttgct   11820
gatcttctga ctttagtgaa cctattaatg tgctgcaggc cccagtcaaa actggaacca   11880
```

```
gggatatagt aactattgga atcaaggcta tggcaactat ggatataaca gccaaggtta   11940
cggtggttat ggaggatatg actacactgg ttacaacaac tactatggat atggtgatta   12000
tagcagtaag tactatactt tttatattaa ctgctatttg acatttattt tgtacaaatt   12060
tggataggca gaaaggttag tgtagccttg ccaagtgcaa atgtcttcag gtttcaaatt   12120
cctggaaact tgaaactgca gccattttat tgcttggttc ctcccagcct atatcacaca   12180
cacattataa gggtagggtg tatgtgtggt tctatatatg tttgctgggc atttgtttta   12240
cttggattta aaaattttaa gctcagttca gatcttttaa gctcaaggta ttctaaatgt   12300
cacttcttgg accaaccaat aatcttggca tgatgtgtct taatcctata aaactgaata   12360
ataccacatg ttgccagtta aaactaatag tatcctcgct ttaggattat taatgtagaa   12420
actcttaaaa cagatgttga gcttgataga accaaaaaac ttgacttttta gacatggaaa   12480
gccctgactt cattgtgcaa ctaaggtagt tgctctccac ctgatttgta gcaactgttg   12540
agtcgtcagg taaagggttc tactagaagc aatcttacat tttttttggag gagagtggtt   12600
gcattggttg cattgtttta agtggttttt ctttttcctttc cttggttaga ccagttcttg   12660
gagttatatc ctttcttagg tgactaggcc tgctgcacaa taataggtta attaaagtca   12720
gaagaaggtc agcaaagatg gattgggtga gattggggcc cttttcttag aagggcagag   12780
atactaagca ctgattgtgg ttgacaattt gttctaaatt ttaagatatt ttttgctggt   12840
ggttgtgaaa gggtcagctg tccatccttt gaaacttaaa acttttaaac tgtaagggtg   12900
agggattgt ctcccatttt atacaataag tcaagtaatc agctcattct gaatgcctgc   12960
cattgtatgc attcactaca tatttggtaa attatttgat aaatgattgc tcagggtgaa   13020
ttttcacac ttgggaatta agctacccctt aattttttga gattgtttaa aattaggtac   13080
tgttctgatt attagtatgt aaccactacc gttctggttc taacacttgt tttatttttag   13140
accagcagag tggttatggg aaggtatcca ggcgaggtgg tcatcaaaat agctacaaac   13200
cataactaaat tattccattt gcaacttatc cccaacaggt atgttctaaa aatagttttt   13260
ttttgtcatt tacaatagta gtttttataa tctatattgt tcataaaaca atgcttaatt   13320
taagagtttc acagcaccca gaagtgctta ccatattata acatagtgac tttcaaaaga   13380
tatgtaacac aggtgctctt aagcttttgc ctttttgtcc tattattaac aagtcagtaa   13440
agttaacagg taaagtactg ctaatgggta caaattaagg aattgcagca aaaaagtatt   13500
gcctactaac tctgacatta taccttgttt gtaccgccag cgggaacttc attgcaggcc   13560
ctgtgtcgcg ctgacttcag attctcacag gcccgctcaa tgcggacagg taacgagat   13620
gctccacgct ctcgaatgct gccgtttggt atggtctctt ccaacatcct gtatcagcat   13680
tataaaataa aatggatact tcaagctttg ccttcactta tttcttttgct ttttaaaaac   13740
tatttgtaat gtaattttaa tgcatttttt acaggcccag taatggttaa atacgtcagc   13800
ttactgaata attttaacta tttattcttc taaggataca gcttgtctct ggattttcca   13860
gtcttaatttt tatattttat taatctatttt taatgcttgc ttttcccatt tatagacgtt   13920
gtagcagtaa ttgcaagaag ttcttgagct gaattcctgt tgtgacaact tcctataatt   13980
acagtagata acttttttctt ttagtcgtat ataacttttc tataacttgt gatggacaag   14040
agatatgctt atccaataaa ataagcttaa atattagatg ctcttgggtc aaaatgtcct   14100
tttaccaaat tgaccttttt atgagttctt tgggtaaata ctttaaagct ttttatattt   14160
taaagaatac ttgtaaaagc atatcacatc ttaaaccagt ggtgcacatg tggatttaca   14220
gctcatggac tctactgttc agctttaatt tataaaacat atcacacatt taatgttata   14280
```

```
cagtatttac atatagtgga acatagggat aactcagttt tatgtaaatt tttgttaagt    14340
gttgtagcct gcccagagtg acttctattt tttcttcttt gtctccaggt ggtgaagcag    14400
tattttccaa tttgaagatt catttgaagg tggctcctgc cacctgctaa tagcagttca    14460
aactaaattt tttgtatcaa gtccctgaat ggaagtatga cgttgggtcc ctctgaagtt    14520
taattctgag ttctcattaa aagaaatttg ctttcattgt tttatttctt aattgctatg    14580
cttcagaatc aatttgtgtt ttatgccctt tcccccagta ttgtagagca agtcttgtgt    14640
taaaagccca gtgtgacagt gtcatgatgt agtagtgtct tactggtttt ttaataaatc    14700
cttttgtata aaaatgtatt ggctctttta tcatcagaat aggaaaaaat tgtcatggat    14760
tcaagttatt aaaagcataa gtttggaaga caggcttgcc gaaattgagg acatgattaa    14820
aattgcagtg aagtttgaaa tgtttttagc aaaatctaat ttttgccata atgtgtcctc    14880
cctgtccaaa ttgggaatga cttaatgtca atttgtttgt tggttgtttt aataatactt    14940
ccttatgtag ccattaagat ttatatgaat attttcccca atg                     14983
```